US009809653B2

(12) United States Patent
Baudat et al.

(10) Patent No.: US 9,809,653 B2
(45) Date of Patent: Nov. 7, 2017

(54) ANTI-LAMP1 ANTIBODIES AND ANTIBODY DRUG CONJUGATES, AND USES THEREOF

(71) Applicant: SANOFI, Paris (FR)

(72) Inventors: Yves Baudat, Paris (FR); Francis Blanche, Paris (FR); Béatrice Cameron, Paris (FR); Tarik Dabdoubi, Le Coudray Montceaux (FR); Anne-Marie LeFebvre, Le Plessis Pâté (FR); Magali Mathieu, Choisy le Roi (FR); Ana Merino-Trigo, Paris (FR); Manoel Nunes, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/751,598

(22) Filed: Jun. 26, 2015

(65) Prior Publication Data
US 2016/0280793 A1 Sep. 29, 2016

Related U.S. Application Data

(63) Continuation of application No. PCT/EP2013/078017, filed on Dec. 26, 2013.

(30) Foreign Application Priority Data

Dec. 27, 2012 (EP) .................................... 12306691
Dec. 27, 2012 (EP) .................................... 12306694

(51) Int. Cl.
| A61K 39/395 | (2006.01) |
| C07K 16/28 | (2006.01) |
| A61K 47/48 | (2006.01) |
| G01N 33/574 | (2006.01) |
| C07K 16/30 | (2006.01) |
| C12Q 1/68 | (2006.01) |
| A61K 39/00 | (2006.01) |

(52) U.S. Cl.
CPC .... *C07K 16/2896* (2013.01); *A61K 47/48384* (2013.01); *A61K 47/48561* (2013.01); *A61K 47/48569* (2013.01); *A61K 47/48584* (2013.01); *A61K 47/48592* (2013.01); *A61K 47/48615* (2013.01); *C07K 16/30* (2013.01); *C07K 16/3023* (2013.01); *C07K 16/3046* (2013.01); *C07K 16/3069* (2013.01); *C12Q 1/6886* (2013.01); *G01N 33/574* (2013.01); *A61K 2039/505* (2013.01); *C07K 2317/24* (2013.01); *C07K 2317/33* (2013.01); *C07K 2317/34* (2013.01); *C07K 2317/41* (2013.01); *C07K 2317/565* (2013.01); *C07K 2317/73* (2013.01); *C07K 2317/732* (2013.01); *C07K 2317/77* (2013.01); *C07K 2317/92* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 4,179,337 A | 12/1979 | Davis et al. |
| 4,256,746 A | 3/1981 | Miyashita et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,496,689 A | 1/1985 | Mitra |
| 4,640,835 A | 2/1987 | Shimizu et al. |

(Continued)

FOREIGN PATENT DOCUMENTS

| EP | 0125023 A1 | 11/1984 |
| EP | 0173494 A2 | 3/1986 |

(Continued)

OTHER PUBLICATIONS

George et al. (Circulation. 1998; 97: 900-906).*

(Continued)

*Primary Examiner* — Sheela J Huff
(74) *Attorney, Agent, or Firm* — Sandra A. Brockman-Lee

(57) ABSTRACT

Antibodies are provided which specifically bind human and *Macaca fascicularis* lysosomal-associated membrane protein 1 (LAMP1) proteins and immunoconjugates comprising said antibodies conjugated or linked to a growth inhibitory agent. Pharmaceutical compositions comprising antibodies or immunoconjugates of the invention and use of the antibodies or immunoconjugates for the treatment of cancer are also provided, as well as LAMP1 antibodies, isolated nucleic acids, vectors and host cells comprising a sequence encoding said antibodies and the use of said antibody as a diagnostic tool. The application further provides for the detection of LAMP1 gene amplification or gain in cancer cells leading to the determination if patients with cancer are likely to respond to anti-LAMP1 therapy. Anti-LAMP1 therapeutic agent for use for treating cancer in a patient harboring LAMP1 gene copy number gain in cancer cells is further provided.

17 Claims, 47 Drawing Sheets

(56) References Cited

U.S. PATENT DOCUMENTS

| | | |
|---|---|---|
| 4,670,417 A | 6/1987 | Iwasaki et al. |
| 4,791,192 A | 12/1988 | Nakagawa et al. |
| 4,816,567 A | 3/1989 | Cabilly et al. |
| 4,861,719 A | 8/1989 | Miller |
| 4,975,278 A | 12/1990 | Senter et al. |
| 5,202,238 A | 4/1993 | Fell, Jr. et al. |
| 5,204,244 A | 4/1993 | Fell et al. |
| 5,208,020 A | 5/1993 | Chari et al. |
| 5,225,539 A | 7/1993 | Winter |
| 5,278,056 A | 1/1994 | Bank et al. |
| 5,475,092 A | 12/1995 | Chari et al. |
| 5,500,362 A | 3/1996 | Robinson et al. |
| 5,530,101 A | 6/1996 | Queen et al. |
| 5,565,332 A | 10/1996 | Hoogenboom et al. |
| 5,585,089 A | 12/1996 | Queen et al. |
| 5,585,499 A | 12/1996 | Chari et al. |
| 5,821,337 A | 10/1998 | Carter et al. |
| 5,846,545 A | 12/1998 | Chari et al. |
| 5,859,205 A | 1/1999 | Adair et al. |
| 5,882,877 A | 3/1999 | Gregory et al. |
| 5,994,524 A | 11/1999 | Matsushima et al. |
| 6,013,516 A | 1/2000 | Verma et al. |
| 6,018,032 A | 1/2000 | Koike et al. |
| 6,127,175 A | 10/2000 | Vigne et al. |
| 6,180,349 B1 | 1/2001 | Ginzinger et al. |
| 6,333,410 B1 | 12/2001 | Chari et al. |
| 6,464,998 B1 | 10/2002 | Beuzard et al. |
| 2005/0003403 A1 | 1/2005 | Rossi et al. |
| 2011/0123554 A1 | 5/2011 | Osterroth et al. |

FOREIGN PATENT DOCUMENTS

| | | |
|---|---|---|
| EP | 0239400 B1 | 8/1994 |
| EP | 0592106 B1 | 11/2004 |
| EP | 0519596 B1 | 2/2005 |
| EP | 2050764 A1 | 4/2009 |
| WO | 8101145 A1 | 4/1981 |
| WO | 8702671 A1 | 5/1987 |
| WO | 8705330 A1 | 9/1987 |
| WO | 8807378 A1 | 10/1988 |
| WO | 9109967 A1 | 7/1991 |
| WO | 9411026 A2 | 5/1994 |
| WO | 9419478 A1 | 9/1994 |
| WO | 9514785 A1 | 6/1995 |
| WO | 9602576 A1 | 2/1996 |
| WO | 9622378 A1 | 7/1996 |
| WO | 9710354 A1 | 3/1997 |
| WO | 9845322 A2 | 10/1998 |
| WO | 2004016801 A2 | 2/2004 |
| WO | 2004048537 A2 | 6/2004 |
| WO | 2004091668 A1 | 10/2004 |
| WO | 2005012912 A2 | 2/2005 |
| WO | 2008010101 A2 | 1/2008 |
| WO | 2009032661 A1 | 3/2009 |
| WO | 2012078688 A2 | 6/2012 |
| WO | 2012087336 A1 | 6/2012 |
| WO | 2012088254 A1 | 6/2012 |

OTHER PUBLICATIONS

Abba M.C., et al., "Identification of Novel Amplification Gene Targets in Mouse and Human Breast Cancer at a Syntenic Cluster Mapping to Mouse Ch8A1 and Human Ch13Q34," Cancer Research, 2007, vol. 67 (9), pp. 4104-4112.

Al-Lazikani B., et al., "Standard Conformations for the Canonical Structures of Immunoglobulins," Journal of Molecular Biology, 1997, vol. 273 (4), pp. 927-948.

Almagro J.C., et al., "Humanization of Antibodies," Frontiers in Bioscience, 2008, vol. 13, pp. 1619-1633.

Anonymous: #3243 LAMP1 (C54H11) Rabbit mAB, Cell Signalling Technologies, retrieved from http://media.cellsignal.com/pdf/3243.pdf on Jul. 8, 2014.

Anonymous, Anti LAMP1 Human MaxPab (H00003916-B01P), tebu-bio, retrieved from http://www.tebu-bio.com/Product/157H00003916-1301P on Jul. 11, 2014.

Anonymous, APC anti-human CD107a (LAMP-1) Product Data Sheet, retrieved from http://www.biolegend.com/apc-anti-human-cd107a-lamp-1-antibody-5428.html on Oct. 8, 2013.

Anonymous, LAMP1 antibody H00003916-B01P Product Datasheet, Novusbio, retrieved from http://www.novusbio.com/PDFs/H00003916-B01P.pdf on Jul. 11, 2014.

Baskar J.F., et al., "The Enhancer Domain of the Human Cytomegalovirus Major Immediate-Early Promoter Determines Cell Type-Specific Expression in Transgenic Mice," Journal of Virology, 1996, vol. 70 (5), pp. 3207-3214.

Berman H.M., et al., "The Protein Data Bank," Nucleic Acids Research, 2000, vol. 28 (1), pp. 235-242.

Beroukhim R., et al., "Assessing the Significance of Chromosomal Aberrations in Cancer: Methodology and Application to Glioma," Proceedings of the National Academy of Sciences of the United States of America, 2007, vol. 104 (50), pp. 20007-20012.

Beroukhim R., et al., "The Landscape of Somatic Copy-Number Alteration Across Human Cancers," Nature, 2010, vol. 463 (7283), pp. 899-905.

Brady G., et al., "New Cosmid Vectors Developed for Eukaryotic DNA Cloning," Gene, 1984, vol. 27 (2), pp. 223-232.

Cancer Genome Atlas Research Network., "Comprehensive genomic characterization defines human glioblastoma genes and core pathways," Nature, 2008, vol. 455 (7216), pp. 1061-1068.

Carlsson S.R., et al., "The Polylactosaminoglycans of Human Lysosomal Membrane Glycoproteins Lamp-1 and Lamp-2. Localization on the Peptide Backbones," The Journal of Biological Chemistry, 1990, vol. 265 (33), pp. 20488-20495.

Caron P.C., et al., "Engineered Humanized Dimeric Forms of IgG are More Effective Antibodies," The Journal of Experimental Medicine, 1992, vol. 176 (4), pp. 1191-1195.

Cook N.R., et al., "Lysosome Associated Membrane Protein 1 (LAMP1) Traffics Directly from the Tgn to Early Endosomes," Traffic (Copenhagen, Denmark), 2004, vol. 5 (9), pp. 685-699.

Corbett T.H., et al., "Evaluation of Single Agents and Combinations of Chemotherapeutic Agents in Mouse Colon Carcinomas," Cancer, 1977, vol. 40 (5 suppl), pp. 2660-2680.

Cromwell M.E., et al., "Protein Aggregation and Bioprocessing," The Aaps Journal, 2006, vol. 8 (3), pp. E572-E579.

Database UniProt [Online] 11 RecName: Full=Lysosome-associated membrane glycoprotein 1; Short=LAMP-1; Short=Lysosome-associated membrane protein1 ; AltName: Full=CD107 antigen-like family member A; AltName: CD antigen=CD107a; Flags: Precursor, XP002714306, Jul. 1, 1989, Database accession No. P11279.

Database UniProt [Online], 11 SubName: Full=Lysosome-associated membrane glycoprotein 1, Flags: Fragment, XP002714307, Jan. 25, 2012, Database accession No. G7PVS1.

Denis N., et al., "Quantitative Proteomic Analysis of Pcsk9 Gain of Function in Human Hepatic Huh7 Cells," Journal of Proteome Research, 2011, vol. 10 (4), pp. 2011-2026.

Edge A.S., et al., "Deglycosylation of Glycoproteins by Trifluoromethanesulfonic Acid," Analytical Biochemistry, 1981, vol. 118 (1), pp. 131-137.

Enns C.A., et al., "The Transferrin Receptor," Biomembranes, 1996, vol. 4, pp. 255-287.

Foote J., et al., "Antibody Framework Residues Affecting the Conformation of the Hypervariable Loops," Journal of Molecular Biology, 1992, vol. 224 (2), pp. 487-499.

Fukuda M., et al., "Lysosomal Membrane Glycoproteins. Structure, Biosynthesis, and Intracellular Trafficking," The Journal of Biological Chemistry, 1991, vol. 266 (32), pp. 21327-21330.

Furuta K., et al., "Expression of Lysosome-Associated Membrane Proteins in Human Colorectal Neoplasms and Inflammatory Diseases," The American Journal of Pathology, 2001, vol. 159 (2), pp. 449-455.

Gazzano-Santoro H., et al., "A Non-Radioactive Complement-Dependent Cytotoxicity Assay for Anti-Cd20 Monoclonal Antibody," Journal of Immunological Methods, 1997, vol. 202 (2), pp. 163-171.

(56) References Cited

OTHER PUBLICATIONS

Gallies S.D., et al., "A Tissue-Specific Transcription Enhancer Element is Located in the Major Intron of a Rearranged Immunoglobulin Heavy Chain Gene," Cell, 1983, vol. 33 (3), pp. 717-28.
Gostring L, et al., "Quantification of Internalization of Egfr-Binding Affibody Molecules: Methodological Aspects," International Journal of Oncology, 2010, vol. 36 (4), pp. 757-763.
Gough N.R., et al., "Utilization of the Indirect Lysosome Targeting Pathway by Lysosome-associated Membrane Proteins (LAMPs) is Influenced Largely by the C-terminal Residue of their Gyxxphi Targeting Signals," Journal of cell science, 1999, vol. 112 (23), pp. 4257-4269.
Harmsen M.M., et al., "Properties, Production, and Applications of Camelid Single-Domain Antibody Fragments," Applied Microbiology and Biotechnology, 2007, vol. 77 (1), pp. 13-22.
Hasinoff B.B., "Biochemical and Proteomics Approaches to Characterize Topoisomerase II Cysteines and DNA as Targets Responsible for Cisplatin-Induced Inhibition of Topoisomerase II," Molecular Pharmacology, 2004, vol. 67 (3), pp. 937-947.
Hirao L.A., et al., "Immune Modulation Through 4-1Bb Enhances Siv Vaccine Protection in Non-Human Primates Against Sivmac251 Challenge," Plos One, 2011, vol. 6 (9), pp. e24250.
Holcombe R.F., et al., "Cell Surface Expression of Lysosome-Associated Membrane Proteins (LAMPs) in Scleroderma: Relationship of LAMP2 to Disease Duration, Anti-Sc170 Antibodies, Serum Interleukin-8, and Soluble Interleukin-2 Receptor Levels," Clinical Immunology and Immunopathology, 1993, vol. 67 (1), pp. 31-39.
International Preliminary Report on Patentability for Application No. PCT/EP2013/078017, dated Jun. 30, 2015, 24 pages.
International Search Report and Written Opinion for Application No. PCT/EP2013/078017, dated Aug. 7, 2014, 33 pages.
Jespers L.S., et al., "Guiding the Selection of Human Antibodies from Phage Display Repertoires to a Single Epitope of an Antigen," Bio/Technology (Nature Publishing Company), 1994, vol. 12 (9), pp. 899-903.
Joyce K., et al., "Antimicrobial Spectrum of the Antitumor Agent, Cisplatin," The Journal of Antibiotics, 2010, vol. 63 :8), pp. 530-532.
Julien S., et al., "Characterization of a Large Panel of Patient-Derived Tumor Xenografts Representing the Clinical Heterogeneity of Human Colorectal Cancer," Clinical Cancer Research, 2012, vol. 18 (19), pp. 5314-5328.
Jung Y., et al., "RNA Polymerase II Blockage by Cisplatin-Damaged DNA. Stability and Polyubiquitylation of Stalled Polymerase," The Journal of Biological Chemistry, 2005, vol. 281 (3), pp. 1361-1370.
Karolchik D., et al., "The Ucsc Genome Browser Database," Nucleic Acids Research, 2003, vol. 31 (1), pp. 51-54.
Kilpatrick K.E., et al., "Rapid Development of Affinity Matured Monoclonal Antibodies Using Rimms," Hybridoma, 1997, vol. 16 (4), pp. 381-389.
Kuwana Y., et al., "Expression of Chimeric Receptor Composed of Immunoglobulin-Derived V Regions and T-Cell Receptor-Derived C Regions," Biochemical and Biophysical Research Communications, 1987, vol. 149 (3), pp. 360-968.
LeFranc M.P., et al., "Imgt, the International Immunogenetics Information System," Nucleic Acids Research, 2009, vol. 37 (Databaseissue), pp. D1006-D1012.
LeFranc M.P., et al., "Imgt Unique Numbering for Immunoglobulin and T Cell Receptor Variable Domains and Ig Superfamily V-Like Domains," Developmental and Comparative Immunology, 2003, vol. 27 (1), pp. 55-77.
Litzen A., et al., "Separation and Quantitation of Monoclonal Antibody Aggregates by Asymmetrical Flow Field-Flow Fractionation and Comparison to Gel Permeation Chromatography," Analytical Biochemistry, 1993, vol. 212 (2), pp. 469-480.
Lund J., et al., "Multiple Interactions of IgG with its Core Oligosaccharide Can Modulate Recognition by Complement and Human Fc Gamma Receptor I and Influence the Synthesis of its Oligosaccharide Chains," The Journal of Immunology, 1996, vol. 157 (11), pp. 4963-4969.
Mason J.O., et al., "Transcription Cell Type Specificity is Conferred by an Immunoglobulin Vh Gene Promoter That Includes a Functional Consensus Sequence," Cell, 1985, vol. 41 (2), pp. 479-487.
Mattei M.G., et al., "Two Human Lysosomal Membrane Glycoproteins, H-Lamp-1 and H-Lamp-2, are Encoded by Genes Localized to Chromosome 13Q34 and Chromosome Xq24-25, Respectively," The Journal of Biological Chemistry, 1990, vol. 265 (13), pp. 7548-7551.
McCoy A.J., et al., "Phaser Crystallographic Software," Journal of Applied Crystallography, 2007, vol. 40 (Pt4), pp. 658-674.
McEarchern J.A., et al., "Engineered Anti-CD70 Antibody with Multiple Effector Functions Exhibits in Vitro and in Vivo Antitumor Activities," Blood, 2007, vol. 109 (3), pp. 1185-1192.
Miyaji H., et al., "Efficient Expression of Human Beta-Interferon in Namalwa Kjm-1 Cells Adapted to Serum-Free Medium by a Dhfr Gene Coamplification Method," Cytotechnology, 1990, vol. 4 (2), pp. 173-180.
Miyaji H., et al., "Expression of Human Beta-Interferon in Namalwa Kjm-1 Which was Adapted to Serum-Free Medium," Cytotechnology, 1990, vol. 3 (2), pp. 133-140.
Mizukami T., et al., "A New Sv40-Based Vector Developed for CDNA Expression in Animal Cells," Journal of Biochemistry, 1987, vol. 101 (5), pp. 1307-1310.
Monsellier E., et al., "Improving the Stability of an Antibody Variable Fragment by a Combination of Knowledge-Based Approaches: Validation and Mechanisms," Journal of Molecular Biology, 2006, vol. 362 (3), pp. 580-593.
Morrison S.L., et al., "Transfer and Expression of Immunoglobulin Genes," Annual Review of Immunology, 1984, vol. 2, pp. 239-256.
Needleman S.B., et al., "A General Method Applicable to the Search for Similarities in the Amino Acid Sequence of Two Proteins," Journal of Molecular Biology, 1970, vol. 48 (3), pp. 443-453.
Obermuller S., et al., "The Tyrosine Motifs of Lamp 1 and Lap Determine Their Direct and Indirect Targetting to Lysosomes," Journal of Cell Science, 2002, vol. 115 (Pt1), pp. 185-194.
Oerntoft T.F., et al., "Genome-Wide Study of Gene Copy Numbers, Transcripts, and Protein Levels in Pairs of Non-Invasive and Invasive Human Transitional Cell Carcinomas," Molecular & Cellular Proteomics, 2002, vol. 1 (1), pp. 37-45.
O'Hare K, et al. , "Transformation of Mouse Fibroblasts to Methotrexate Resistance by a Recombinant Plasmid Expressing a Prokaryotic Dihydrofolate Reductase," Proceedings of the National Academy of Sciences of the United States of America, 1981, vol. 78 (3), pp. 1527-1531.
Olshen A.B. et al. "Circular Binary Segmentation for the Analysis of Array-Based DNA Copy Number Data," . Biostatistics (Oxford, England), 2004, vol. 5 (4), pp. 557-572.
Padlan E.A., et al., "A Possible Procedure for Reducing the Immunogenicity of Antibody Variable Domains While Preserving Their Ligand-Binding Properties," Mol Immunol, 1991, vol. 28 (4-5), pp. 489-498.
Parkinson-Lawrence E.J., et al., "Immunochemical Analysis of Cd107A (Lamp-1)," Cellular Immunology, 2005, vol. 236 (1-2), pp. 161-166.
Peden A.A., et al., "Localization of the Ap-3 Adaptor Complex Defines a Novel Endosomal Exit Site for Lysosomal Membrane Proteins," The Journal of Cell Biology, 2004, vol. 164 (7), pp. 1065-1076.
Peters B., et al., "The Immune Epitope Database and Analysis Resource: from Vision to Blueprint," Plos Biology, 2005, vol. 3 (3), pp. e91.
Roguska M.A., et al., "Humanization of Murine Monoclonal Antibodies Through Variable Domain Resurfacing," Proceedings of the National Academy of Sciences of the United States of America, 1994, vol. 91 (3), pp. 969-973.
Rohrer J., et al., "The Targeting of Lamp1 to Lysosomes is Dependent on the Spacing of its Cytoplasmic Tail Tyrosine Sorting Motif Relative to the Membrane," The Journal of Cell Biology, 1996, vol. 132 (4), pp. 565-576.

(56) References Cited

OTHER PUBLICATIONS

Ruivo R. et al., "Molecular and Cellular Basis of Lysosomal Transmembrane Protein Dysfunction," Biochimica Et Biophysica Acta, 2009, vol. 1793 (4), pp. 636-649.
Saitoh O., et al., "Differential Glycosylation and Cell Surface Expression of Lysosomal Membrane Glycoproteins in Sublines of a Human Colon Cancer Exhibiting Distinct Metastatic Potential," The Journal of biological chemistry, 1992, vol. 267, pp. 5700-5711.
Sawada R., et al., "E-selectin-dependent adhesion efficiency of colonic carcinoma cells is increased by genetic manipulation of their cell surface lysosomal membrane glycoprotein-1 expression levels," Journal of Biological Chemistry, 1993, vol. 268 (17), pp. 12675-12681.
Shields R.L., et al., "High Resolution Mapping of the Binding Site on Human Igg1 for Fc Gamma Ri, Fc Gamma Rii, Fc Gamma Riii, and Fcm and Design of Igg1 Variants with Improved Binding to the Fc Gamma R," The Journal of Biological Chemistry, 2001, vol. 276 (9), pp. 6591-6604.
Shitara K., et al., "A New Vector for the High Level Expression of Chimeric Antibodies in Myeloma Cells," Journal of Immunological Methods, 1994, vol. 167 (1-2), pp. 271-278.
Shopes B.,"A Genetically Engineered Human IgG Mutant with Enhanced Cytolytic Activity," Journal of Immunology, 1992, vol. 148 (9), pp. 2918-2922.
Silverstein R.L., et al., "Identification of Lysosome-Associated Membrane Protein-2 as an Activation-Dependent Platelet Surface Glycoprotein," Blood, 1992, vol. 80 (6), pp. 1470-1475.
Sojar H.T., et al., "A Chemical Method for the Deglycosylation of Proteins," Archives of Biochemistry and Biophysics, 1987, vol. 259 (1), pp. 52-57.
Steipe B., et al., "Sequence Statistics Reliably Predict Stabilizing Mutations in a Protein Domain," Journal of Molecular Biology, 1994, vol. 240 (3), pp. 188-192.
Studnicka G.M., et al., "Human-engineered monoclonal antibodies retain full specific binding activity by preserving non-CDR complementarity-modulating residues," Protein Engineering, Design & Selection, 1994, vol. 7 (6), pp. 805-814.
Thotakura N.R., et al., "Enzymatic Deglycosylation of Glycoproteins," Methods in Enzymology, 1987, vol. 138, pp. 350-359.
Urlaub G., et al., "Isolation of Chinese Hamster Cell Mutants Deficient in Dihydrofolate Reductase Activity," Proceedings of the National Academy of Sciences of the United States of America, 1980, vol. 77 (7), pp. 4216-4220.
Vitetta E.S., et al., "Interaction and Activation of Antigen-Specific T and B Cells," Immunological Reviews, 1987, vol. 99 (1), pp. 193-239.
Vitetta E.S., et al., "Redesigning Nature's Poisons to Create Anti-Tumor Reagents," Science, 1987, vol. 238 (4830), pp. 1098-1104.
Wang L., et al., "Fractionation of monoclonal antibody aggregates using membrane chromatography," Journal of Membrane Science, 2008, vol. 318 (1-2), pp. 311-316.
Wennerberg A.E., et al., "Hepatocyte Paraffin 1: A Monoclonal Antibody That Reacts with Hepatocytes and Can Be Used for Differential Diagnosis of Hepatic Tumors," The American Journal of Pathology, 1993, vol. 143 (4), pp. 1050-4.
Winchester B.G., "Lysosomal membrane proteins," European Journal of Paediatric Neurology, 2001, vol. 5 (Suppl A), pp. 11-19.
Winn M.D., et al., "Overview of the Ccp4 Suite and Current Developments," Acta Crystallographica, Section D, Biological Crystallography, 2011, vol. 67 (Pt4), pp. 235-242.
Wolff A.C., et al., "American Society of Clinical Oncology/College of American Pathologists Guideline Recommendations for Human Epidermal Growth Factor Receptor 2 Testing in Breast Cancer," Archives of Pathology & Laboratory Medicine, 2007, vol. 131 (1), pp. 18-43.
Santacruz Biotechnology, Inc.: LAMP-1 (H-228): sc-5570, Santacruz Biotechnology online Catalogue, retrieved from http://datasheets.scbt.com/sc-5570.pdf on Oct. 8, 2013.
Tung et al., Distribution of Lysosome-Associated Membrane Proteins-1 and -2, and Cathepsin D in Eosinophilic Granular Bodies: Possible Relationship to Cyst Development in Pilocytic Astrocytomas, J. Int'l. Med. Res. 38(4) pp. 1354-1364 (2010).
Santacruz Biotechnology, Inc: LAMP-1 (H-228): sc-5570, Santacruz Biotechnology online Catalogue, retrieved from http://datasheets.scbt.com/sc-5570.pdf on Oct. 8, 2013.
Tung J.N., et al., "Distribution of Lysosome-Associated Membrane Proteins-1 and -2, and Cathepsin D in Eosinophilic Granular Bodies: Possible Relationship to Cyst Development in Pilocytic Astrocytomas," Journal of International Medical Research, 2010, vol. 38 (4), pp. 1354-1364.

* cited by examiner

Signal peptide

| | | |
|---|---|---|
| Human | 1 | MAAPGSARRPLLLLLLLLLLLGLMHCASAAMFMVKNGNGTACIMANFSAAFSVNYDTKSGP 60 |
| M. Fascicularis | 1 | MAAPGSARR--SLLLLLLLGLTHCASAAMFIVKNGNGTACIMANFSAAFSVNYDTKSGP 58 |
| Human | 61 | KNMTFDLPSDATVVLNRSSCGKENTSDPSLVIAFGRGHTLTLNFTRNATRYSVQLMSFVY 120 |
| M. Fascicularis | 59 | KNMTFDLPSDAKVVLNSSSCGKENTSDPSLVIAFGRGQTLTLNFTRNATRYSVQLMSFVY 118 |
| Human | 121 | NLSDTHLFPNASSKEIKTVESITDIRADIDKKYRCVSGTQVHMNNVTVTLHDATIQAYLS 180 |
| M. Fascicularis | 119 | NLSDTHLFPNASSKEIKTVESITDIRADIDKKYRCVSGTQVHMNNVTVTLHDATIQAYLS 178 |
| Human | 181 | NSSFSRGETRCEQDRPSPTTAPPAPPSPSPVPKSPSPSVDKYNVSGTNGTCLLASMGLQL 240 |
| M. Fascicularis | 179 | NSSFSREETRCEQDRPSPTTAPPAPPSPSPSPVPESPSVDKYNVSGTNGTCLLASMGLQL 238 |
| Human | 241 | NLTYERKDNTTVTRLLNINPNKTSASGSCGAHLVTLELHSEGTTVLLFQFGMNASSSRFF 300 |
| M. Fascicularis | 239 | NLTYERKDNTTVTRLLNINPNKTLASGSSLRALQATVGNSYKCNAEEHVRVTKAFSVNIFKVWVQ 298 |
| Human | 301 | LQGIQLNTILPDARDPAFKAANGSLRALQATVGNSYKCNAEEHVRVTKAFSVNIFKVWVQ 360 |
| M. Fascicularis | 299 | LQGIQLNTTLPDARDPAFKAANSSLRALQATVGNSYKCNAEEHVRVTKAFSVNIFKVWVQ 358 |
| Human | 361 | AFKVEGGQFGSVEECLLDENSM‎LIPIAVGGALAGLVLIVLIAYLVGRKRSHAGYQTI 417 |
| M. Fascicularis | 359 | AFKVEGGQFGSVEECLLDENNM‎LIPIAVGGALAGLVLIVLIAYLVGRKRSHAGYQTI 415 |

Transmembrane domain

FIG. 1

ANTI-LAMP1 ANTIBODIES AND ANTIBODY DRUG CONJUGATES, AND USES THEREOF

BACKGROUND

Antibodies are provided which specifically bind human and *Macaca fascicularis* lysosomal-associated membrane protein 1 (LAMP1) proteins and immunoconjugates comprising said antibodies conjugated or linked to a growth inhibitory agent. Pharmaceutical compositions comprising antibodies or immunoconjugates of the invention and use of the antibodies or immunoconjugates for the treatment of cancer are also provided, as well as LAMP1 antibodies, isolated nucleic acids, vectors and host cells comprising a sequence encoding said antibodies and the use of said antibody as a diagnostic tool. The application further provides for the detection of LAMP1 gene amplification or gain in cancer cells leading to the determination if patients with cancer are likely to respond to anti-LAMP1 therapy. Therefore, it is proposed an in vitro method of selecting patients with cancer which comprises determining, in a biological sample of a patient with cancer which includes cancer cells, if said patient harbors a LAMP1 gene copy number gain; and selecting the patient based on the presence of LAMP1 gene copy number gain. Anti-LAMP1 therapeutic agent for use for treating cancer in a patient harboring LAMP1 gene copy number gain in cancer cells is further provided.

Lysosome-associated membrane protein 1 (LAMP1), also known as CD107 antigen-like family member A (CD107a), is a single-pass type I membrane protein, which belongs to the LAMP family. LAMP2 is the closest member of the family and both proteins are the most abundant glycoproteins within the lysosomal membrane (Sawada, R. et al., 1993, J Biol Chem 268: 12675-12681).

Although encoded by separate genes, with LAMP1 located on chromosome 13q34 and LAMP2 on Xq24-25, the proteins are similar in their primary structure, with ~36% sequence homology (Mattei, M. G. et al., 1990, J Biol Chem 265:7548-7551). LAMP1 and LAMP2 consist of a polypeptide core of approximately 40 kDa; they are both anchored via their C-terminus to the lysosomal membrane and expose the largest part, extensively glycosylated, to the lumenal side of lysosomes. Both proteins are among the most heavily glycosylated of cellular proteins with ~50% of their mass as carbohydrates and these glycosylations seem to be the key for maintaining lysosome acidity and protecting the lysosomal membranes from autodigestion. However, the full biological function of these two highly glycosylated proteins in particular LAMP1 still needs to be elucidated (Fukuda, M., 1991, J Biol Chem, 266:21327-21330; Winchester, B., 2001, European Journal of Paediatry Neurology, 5:11-19; Gasnier, B., 2009 Biochimica et Biophysica Acta 1793:636-649).

LAMP1 is highly expressed in late endosomes and lysosomes designating LAMP1 as marker for these two organelles (Cook, N. R. et al., 2004, Traffic, 5 (9): 685-699). Thus, most of the literature on LAMP1 relates to endocytosis, pinoscyosis, or phagocytosis (Cook, N. R. et al., 2004, Traffic, 5 (9): 685-699).

Although the majority of LAMP1 and LAMP2 reside in the lysosome, some LAMP1 and LAMP2 immunoreactivity is also observed at low levels at the plasma membrane. The LAMP1 found in the plasma membrane represents only 1-2% of total LAMP1. This is for example true for peripheral blood lymphocytes (Holcombe, R. F. et al. 1993, Clin Immunol Immunopathol. 67(1): 31-39) and platelets (Silverstein, R. L. and Febbraio, M., 1992, Blood 80: 1470-1475).

Increased cell surface expression of LAMP1 and LAMP2 has been observed in tumor cell lines, for example in highly metastatic colonic carcinoma L4 cells (Saitoh, O. et al., 1992, J Biol Chem 267: 5700-5711), on human metastasizing melanoma A2058, HT1080 (human fibrosarcoma), CaCo-2 (human colon-adenocarcinoma) cells and in colorectal neoplasms (Furuta, K. et al., 2001, J Pathol 159 (2): 449-455).

The chromosomal region 13q34 in which LAMP1 is located has recently been linked to amplification events including a larger amplicon that involves CUL4A, LAMP1, TFDP1, and GAS6 in human breast cancer (Abba, Martin C. et al.; Cancer Res 2007; 4104). TFDP1 and perhaps CUL4A were identified in the above mentioned publication as the leading genes driving the amplification phenomenon. In particular, analysis of publicly available breast cancer gene expression (microarrays) data sets indicated that TFDP1 overexpression is associated with estrogen receptor (ER)-negative and high-grade breast carcinomas, as well as shorter overall survival, relapse-free survival, and metastasis-free interval. Conversely, LAMP1 expression did not significantly correlate with tumor grade. In the end, Abba et al. did not report that LAMP1 amplification translated into LAMP1 overexpression in human breast cancer cells.

The 11 amino-acid cytoplasmic tail of LAMP1 contains a 7 amino-acid linker sequence and a 4 amino acid long tyrosine motif (YQTI). It was shown that small changes in the spacing of this motif relative to the membrane dramatically impair sorting in the early/sorting endosomes. Mutations within said tyrosine motif were shown to have an impact on the binding of LAMP1 to adaptor proteins leading as well to impaired sorting (Obermuller, S. et al., 2002, Journal of Cell Science 115: 185-194; Rohrer, J. et al., 1996, Journal of Cell Biology 132(4): 565-576). Therefore, the abnormal cell surface expression of LAMP1 in different cancer cell lines might be related to mutations in the cytoplasmic tail even though the mechanism is still unclear. Furthermore, it has been shown that certain point mutations in the cytoplasmic tail lead to plasma membrane accumulation (Gough, N. R. et al., 1999, Journal of Cell Science 112 (23): 4257-4269).

Due to the fact that LAMP1 is a marker for endosomes and lysosomes, numerous commercially available anti-LAMP1 antibodies were developed for research purposes. These antibodies are either polyclonal or monoclonal and are restricted to some biochemical application such as immunohistochemistry (IHC), Western blots (WB), Fluorescence activated cell sorter (FACS) analysis, Immunoprecipitation (IP) and Enzyme-linked immunosorbent assay (ELISA).

LAMP1 protein also has been detected at the cell membrane of tumor cells.

E. Venetsanakos (WO 2005/012912) suggested that LAMP1 is expressed on the surface of colon cancer cells but not on the surface of normal colon cells and proposed that tumor growth might be reduced by targeting a cytotoxic agent to LAMP1 via an anti-LAMP1 antibody. Venetsanakos did not describe, however, preparation of anti-LAMP1 antibodies or conjugates thereof with cytotoxic or cytostatic agent or any data supporting his hypothesis. Indeed, though a decade has passed since Venetsanakos' initial filing and no anti-LAMP1 antibodies or their use as immunoconjugates in an anti-LAMP1 therapy has entered clinical development, so far. Accordingly, a great need exists for anti-LAMP1 antibodies or immunoconjugates for the treatment of cancer.

BRIEF DESCRIPTION OF THE DRAWINGS

FIG. 1: sequence alignment of human (SEQ ID NO: 24) and *Macaca fascicularis* LAMP1 (SEQ ID NO: 39) full-length proteins.

DETAILED DESCRIPTION

Definitions

Figure 2:
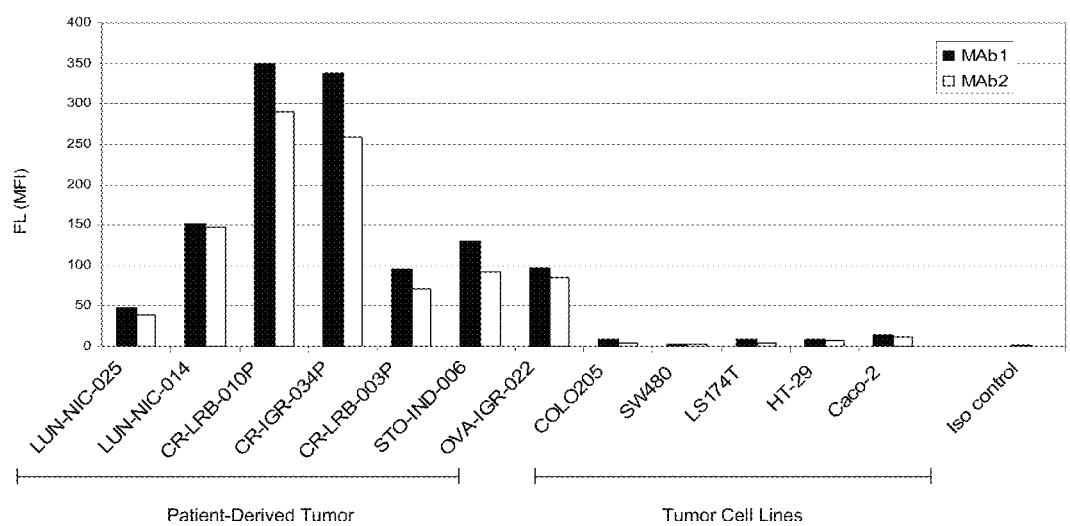
FIG. 2: Expression Profile of LAMP1 derived from FACS analysis with the monoclonal mouse antibodies Mab1 and MAb2.

As used herein "LAMP1" designates the "Lysosomal associated membrane protein 1", a member of a family of glycoproteins that is also known as LAMPA, CD107a or LGP120. LAMP1 is, according to protein expression data for human tumoral samples in comparison to non tumoral samples presented in the following Example 5, expressed at the cell surface of colon adenocarcinomas, gastrointestinal tumors (small intestine, rectum, parotid gland), vital organs tumors (lung, liver, stomach, pancreas and kidney), reproductive organ tumors (breast, ovary and prostate) as well as skin, larynx and soft tissue tumors.

The human gene LAMP1 is found on chromosome 13q34 (113,951,469-113,977,441) and has a total length of 26,273 kb.

A reference sequence of the cDNA coding for full-length human LAMP1, including the sequence encoding the signal peptide, is available from the GenBank database under accession number NM_005561.3 (SEQ ID NO: 23) and the representative protein sequence, including the signal peptide (positions 1-28) is available under NP_005552.3 (SEQ ID NO: 24). One potential isoform of LAMP1 has been reported which would miss the amino acids at positions 136-188 of SEQ ID NO: 24, corresponding to exon 4 of the gene coding for human LAMP1. No synonymous SNPs have been identified in Caucasian population of at least 60 individuals.

Concerning its orthologs, human LAMP1 shares 66% sequence identity with respectively mouse LAMP1 (NP_034814, SEQ ID NO: 25) and rat LAMP1 (NP_036989, SEQ ID NO: 26), and human and *Macaca mulatta* LAMP1 (XP_001087801, SEQ ID NO: 27) share 96% sequence identity.

The sequence of LAMP1 from *Macaca mulatta* (SEQ ID NO: 27) and the predicted sequence of *Macaca fascicularis* (SEQ ID NO: 39) are identical to 99%, said sequences differing by one additional leucine at position 11 of *Macaca mulatta* LAMP1 (SEQ ID NO: 27), i.e. in the signal peptide. Accordingly the sequences of mature LAMP1 from *Macaca mulatta* and *Macaca fascicularis* are identical.

The closest member of the LAMP family is LAMP 2 (P13473, human LAMP2, soluble LAMP2 protein SEQ ID NO: 40). Human LAMP1 and LAMP2 proteins share ~36% sequence identity, and comprise some conserved glycosylation sites.

A "domain" may be any region of a protein, generally defined on the basis of sequence homologies and often related to a specific structural or functional entity. The domain organization of LAMP1 has not been entirely published so far.

Human LAMP1 consists of 417 amino acid residues and 28 amino-terminal residues corresponding to a cleavable signal peptide. The major portion of LAMP1 resides on the lumenal side of the lysosome and is heavily glycosylated by N-glycans. LAMP1 contains 18 potential N-glycosylation sites of which 5 are occupied with poly-N-acetyllactosamine glycans (Carlsson, S. R. and Fukuda, M., 1990, J. Biol. Chem. 265(33): 20488-20495). They are clustered into two domains separated by a hinge-like structure enriched with prolines and serines many being linked to 0-glycans. LAMP1 has one transmembrane domain consisting of 24 hydrophobic amino acids near the COOH terminus, and contains a short cytoplasmic segment composed of 11 amino acid residues at the COOH-terminal end.

The nomenclature of the two domains of LAMP1, "the first lumenal domain" and the "second lumenal domain" are based on the orientation of LAMP1 within its original localization, the lysosome. Nevertheless, when LAMP1 is expressed at the cell surface, the two lumenal domains become extracellular domains, and therefore exposed at the cell surface. Therefore, in one embodiment "extracellular" in context of the invention refers to LAMP1 protein constructs comprising the first and/or second luminal domain(s) of LAMP1 as defined below and/or variants thereof. The domain organisation of human LAMP1 according to NP_005552.3 (SEQ ID NO: 24) has been mapped in example 6.1 and will be used in this document as follows:

TABLE 1

Description of human LAMP1 domains

| LAMP1 Domains | Positions in NP_005552 (SEQ ID NO: 24) |
| --- | --- |
| Peptide signal | Met1-Ala28 |
| First lumenal domain | Ala29-Arg195 |
| Loop 1, L1 | Ala29-Leu100 |
| Loop 2, L2 | Thr101-Arg195 |
| Hinge | Pro196-Thr 227 |
| Second lumenal domain | Asn228-Met382 |
| Loop 3, L3 | Asn228-Ile309 |
| Loop 4, L4 | Leu310-Met382 |
| Transmembrane domain | Leu383-Gly406 |
| Lysosome targeting motif | Arg407-Ile417 |

Accordingly, the domain consisting of the first to third loops of human LAMP1 consists of amino acids at positions 29-309 of SEQ ID NO: 24.

Domain organisation of *Macaca fascicularis* LAMP1 according to the predicted sequence (SEQ ID NO: 39) is as follows:

TABLE 2

Description of *Macaca fascicularis* LAMP1 domains

| LAMP1 Domains | Positions in SEQ ID NO: 39 |
| --- | --- |
| Peptide signal | Met1-Ala26 |
| First lumenal domain | Ala27-Arg193 |
| Loop 1, L1 | Ala27-L98 |
| Loop 2, L2 | Thr99-Arg193 |
| Hinge | Pro194-Thr 225 |
| Second lumenal domain | Asn226-Met380 |
| Loop 3, L3 | Asn226-Thr307 |
| Loop 4, L4 | Leu308-Met380 |
| Transmembrane domain | Leu381-Gly404 |
| Lysosome targeting motif | Arg405-Ile415 |

Accordingly, the domain consisting of first to third loops of *Macaca fascicularis* LAMP1 consists of amino acids at positions 27-307 of SEQ ID NO: 39.

A sequence alignment of human and *Macaca fascicularis* LAMP1 full-length proteins is shown on FIG. 1.

The loop region 4 of human and *Macaca fascicularis* LAMP1 do not contain any glycosylation site, which distinguishes Loop 4 from Loops 1-3 of LAMP1.

Loops 1-4 have been defined from the primary amino acid sequence, and has been mapped in example 6.1, but not from the 3D structure of LAMP1 since the structure was not solved prior to this work.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon. A region encoding an expression product present in the DNA is called "coding DNA sequence" or "CDS".

As used herein, references to specific proteins (e.g., antibodies) can include a polypeptide having a native amino acid sequence, as well as variants and modified forms regardless of their origin or mode of preparation. A protein which has a native amino acid sequence is a protein having the same amino acid sequence as obtained from nature. Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

As used herein, the term "marker" refers to any biological, chemical or physical mean allowing identifying the presence, and possibly quantifying the expression of a target gene and/or protein in a biological sample. Such markers are well known from one skilled in the art. Advantageously, the markers according to the invention are genetic markers and/or protein markers.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the terms "copy number variation", "copy number variant" and "CNV" are used indifferently and refer to a DNA segment of 1 kb or larger and present at variable copy number in comparison with a reference genome. The terms "structural variant", "duplicon", "indel", "intermediate-sized structural variant (ISV)", "low copy repeat (LCR)", "multisite variant (MSV)", "paralogous sequence variant (PSV)", "segmental duplication", "interchromosomal duplication", and "intrachromosomal duplication", found in the literature, are included herein in the term "CNV".

Furthermore, copy number variation can refer to a single gene, or include a contiguous set of genes.

As used herein "gene number" describes the numbers of genes present in the cell. In diploid organisms, in a normal state, two copies of each nucleic sequence are naturally present in the genome, therefore, the copy number (CN) is =2. In particular, the genome displays two alleles for each gene, one on each chromosome of a pair of homologous chromosomes (except for the genes localized on sexual chromosomes).

Herein the word "gene number" and "gene copy number" can be used interchangeably.

In the context of the invention, a "copy" of a sequence encompasses a sequence identical to said sequence but also allelic variations of said sequence.

One example to measure DNA copy number and therefore DNA copy number change is array-based CGH which is a high-throughput technique to measure DNA copy number change across the genome. The DNA fragments or "clones" of test and reference samples are hybridized to mapped array fragments. Log 2 intensity ratios of test to reference provide useful information about genome-wide profiles in copy number.

The "Log 2" or "Log 2 ratio" value is used to describe the copy number of a gene or a DNA fragment in a cell genome. In an ideal situation, the log 2 ratio of normal (copy-variation neutral) clones is log 2(2/2)=0, single copy losses is log 2(1/2)=−1, and single copy gains is log 2(3/2)=0.58. Multiple copy gains or amplifications would have values of log 2(4/2), log 2(5/2), . . . .

As used herein, the term "gain" of a sequence refers in general to the presence of a copy number ≥2.5 (alternatively a Log 2 ratio≥0.32) of said sequence in the diploid genome of a subject. These ≥2.5 copies may be adjacent or not on the genome; in particular they may be present in different regions of a pair of chromosomes or on chromosomes belonging to distinct pairs of chromosomes of the genome.

Accordingly, the term "gene copy number gain" refers to the presence of copy numbers (alternatively a Log 2 ratio≥0.32) of a specific gene in the diploid genome of a subject. When the copy number=2.5, 50% of the cells used for defining the copy number contain the usual 2 copies of the gene in a diploid organism and 50% of the cells used for defining the copy number contain the usual 2 copies and 1 additional copy more of said gene (in total 3 copies of said gene).

The term "low gain" of a sequence refers in general to the presence of a copy number ≥2.5 but <5 (alternatively 0.32≤log 2 ratio <1.32) of said sequence in the diploid genome of a subject. The terms "amplification", "Amp", or "high gain" refer herein to the presence of a copy number ≥5, or alternatively a Log 2≥1.32, of a specific sequence in the diploid genome of a subject. Accordingly, the term "gene number amplification" refers to the presence of ≥5 copy numbers of a specific gene in the diploid genome of a subject As used herein, a "fragment of a sequence" corresponds to a portion of said sequence, for instance of a nucleotide sequence. Said fragment is preferably at least 10 bp long. More preferably said fragment is at least 15 bp long, in particular at least 20 bp long. Most preferably, said fragment is at least 25 bp long, at least 30 bp long, in particular at least 33 bp long. A fragment of the above sequence may be in particular a primer or probe.

In the context of the invention, a "mutated sequence" of a reference sequence refers to a sequence including insertion(s), deletion(s) or substitution(s) of one or more nucleotide(s), wherein said mutated sequence is at least 75% identical to the reference sequence. The percentage of sequence identity is calculated by comparing the mutated sequence optimally aligned with the reference sequence, determining the number of positions at which the identical nucleic acid base (e.g., A, T, C, G, U, or I) occurs in both sequences to yield the number of matched positions, dividing the number of matched positions by the total number of positions of the reference sequence, and multiplying the result by 100 to yield the percentage of sequence identity. Preferably, the mutated sequence is at least 80%, 85%, 90%, 95% identical to the reference sequence.

Preferably said mutated sequence of a reference sequence is an allelic variant of said reference sequence. As used herein, an "allelic variant" denotes any of two or more alternative forms of a gene occupying the same chromosome locus.

A sequence "at least 85% identical to a reference sequence" is a sequence having, on its entire length, 85%, or more, in particular 90%, 91%, 92%, 93%, 94%, 95%, 96%, 97%, 98% or 99% sequence identity with the entire length of the reference sequence.

A percentage of "sequence identity" may be determined by comparing the two sequences, optimally aligned over a comparison window, wherein the portion of the polynucleotide or polypeptide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison is conducted by global pairwise alignment, e.g. using the algorithm of Needleman and Wunsch J. Mol. Biol. 48: 443 (1970). The percentage of sequence identity can be readily determined for instance using the program Needle, with the BLOSUM62 matrix, and the following parameters gap-open=10, gap-extend=0.5.

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine-tryptophane, lysine-arginine, alanine-valine, glutamate-aspartate, and asparagine-glutamine.

An "antibody" may be a natural or conventional antibody in which two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody. In the context of the invention, CDR/FR definition in an immunoglobulin light or heavy chain is to be determined based on IMGT definition (Lefranc, M. P. et al., 2003, Dev Comp Immunol. 27(1): 55-77; on the world wide web at imgt.org).

As used herein, the term "antibody" denotes conventional antibodies and fragments thereof, as well as single domain antibodies and fragments thereof, in particular variable heavy chain of single domain antibodies, and chimeric, humanised, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard H J (Appl. Microbiol. Biotechnol. 2007 November; 77(1): 13-22).

The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

The term "chimeric antibody" refers to an engineered antibody which in its broadest sense contains one or more regions from one antibody and one or more regions from on or more other antibody(ies). In particular a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin The term "humanised antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

"Fragments" of (conventional) antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab)2" refers to an antibody fragment having a molecular weight of about 100,000 and antigen binding activity, which is slightly larger than the Fab bound via a disulfide bond of the hinge region, among fragments obtained by treating IgG with a protease, pepsin.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)$_2$. "dsFv" is a VH::VL heterodimer stabilised by a disulphide bond. "(dsFv)2" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

By "purified" and "isolated" it is meant, when referring to a polypeptide (i.e. the antibody of the invention) or a nucleotide sequence, that the indicated molecule is present in the substantial absence of other biological macromolecules of the same type. The term "purified" as used herein in particular means at least 75%, 85%, 95%, or 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. In particular a subject according to the invention is a human.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Throughout the instant application, the term "and/or" is a grammatical conjunction that is to be interpreted as encompassing that one or more of the cases it connects may occur. For example, the sentence "quantifying the expression of a target gene and/or protein in a biological sample" indicates the expression of a target gene may be quantified (mRNA), or the expression of a protein or the expression of a target gene (mRNA) and the protein together may be quantified.

Accordingly, the wording "a variable domain of heavy chain of sequence SEQ ID NO: 1 or a sequence at least 85% identical thereto and/or a variable domain of light chain of sequence of sequence SEQ ID NO: 5, or a sequence at least 85% identical thereto" is to b interpreted as "a variable domain of heavy chain of sequence SEQ ID NO: 1 or a sequence at least 85% identical thereto" or "a variable domain of light chain of sequence of sequence SEQ ID NO: 5, or a sequence at least 85% identical thereto" or "a variable domain of heavy chain of sequence SEQ ID NO: 1 or a sequence at least 85% identical thereto and a variable domain of light chain of sequence of sequence SEQ ID NO: 5, or a sequence at least 85% identical thereto".

The term "cancer", "neoplasm", "tumor", and "carcinoma" are used interchangeably herein to refer to cells that exhibit relatively autonomous growth, so that they can exhibit an aberrant growth phenotype characterized by significant loss of control of cell proliferation. In general, cells of interest for detection or treatment in the present application include precancerous (e.g. benign), malignant, metastatic, and non-metastatic cells.

Immunoconjugates

For therapeutic purposes, it is advantageous to create an antibody with optimal characteristics for use as an antibody drug conjugate, i.e. an antibody which specifically recognizes a target present on the surface of cancer cells and which is capable of efficiently triggering internalization once bound to said target.

The inventors raised antibodies against colon tumor cells or lung tumor cells and screened resulting clones for the differential binding to tumor cells and non-tumor tissue.

The inventors identified in this way antibodies distinguishing tumoral from non-tumoral tissues. Three of those antibodies were selected (the so-called antibodies "MAb1", "MAb2" and "MAb3"), fulfilling the expected features necessary for therapeutical application, in particular in the form of ADC. Those three antibodies showed high binding affinity (within the nanomolar range) to cell surface expressed LAMP1 in cancer cells. Furthermore, those three anti-LAMP1 antibodies showed high capacity to trigger internalization of the LAMP1/anti-LAMP1 antibody complex, as shown in example 4.4 and 4.3.

The inventors demonstrated that the chimeric antibodies derived from MAb1, MAb2, MAb3 (chMAb1, chMAb2, chMAb3), combined with a cytotoxic maytansinoid (DM4) showed as well a high but slightly different binding affinity to human LAMP1 or cynomologus monkey LAMP1 then the naked antibody as shown in example 8.1.7 and 8.1.8.

Accordingly in one embodiment the immunoconjugate in context of the invention has an affinity ($EC_{50}$) for full length human LAMP1 and cynomologues monkey LAMP1 expressed at the cell surface of a recombinant cell line, wherein the cell line may be HCT116 and the apparent affinity measured via Flow Cytometry is ≤30 nM, for example ≤20 nM or ≤15 nM.

The Methods to measure the affinity ($EC_{50}$) for full length human LAMP1 and cynomologues monkey LAMP1 are further explained in the chapter "antibodies".

The inventors additionally demonstrated that a chimeric antibody derived from MAb1 (chMAb1), combined with a cytotoxic maytansinoid (DM4), induces cytotoxic activity in vitro on human HCT116 tumor cells containing a stable integration of the LAMP1 coding DNA sequence in the genomic DNA and expressing LAMP1 on their surface.

Furthermore, the inventors demonstrated that humanized antibodies derived from MAb1 (huMAb1_1, huMAb1_2, huMAb1_3), combined with a cytotoxic maytansinoid (DM4) induce cytotoxic activity in vitro on human HCT116 tumor cells containing a stable integration of the LAMP1 coding DNA sequence in the genomic DNA.

They have also shown that the immunoconjugate DM4-SPDB-chMAb1 induces a marked anti-tumor activity in vivo in mice bearing the primary human colon adenocarcinoma xenograft derived from patient CR-LRB-010P, when used at a dose of 10 mg/kg, 5 mg/kg and 2.5 mg/kg, with a single injection, as described in example 10.1.1.

Furthermore, the inventors showed that this immunoconjugate induces a marked anti-tumor activity in vivo in mice bearing the primary human lung tumor xenograft derived from patient LUN-NIC-0014, when used at a dose of 10 mg/kg, 5 mg/kg and 2.5 mg/kg, with a single injection, as described in example 10.1.2.

They have also shown that the immunoconjugates DM4-SPDB-huMAb1_1, DM4-SPDB-chMAb2, and DM4-SPDB-chMAb3 induce a marked anti-tumor activity in vivo in different patient-derived xenograft as shown in example 10.2-10.4.

For example, it was shown the immunoconjugate DM4-SPDB-huMAb1_1 induces a marked anti-tumor activity in vivo in a primary human invasive ductal carcinoma xenograft and primary human lung tumor xenograft derived from patient, when used at a dose of 10 mg/kg, 5 mg/kg, 2.5 mg/kg, or 1.25 mg/kg with a single injection, as described in example 10.2.2 and 10.2.3.

Also the immunoconjugates DM4-SPDB-chMAb2 and DM4-SPDB-chMAb3 induced a marked anti-tumor activity in vivo in a murine model of primary human invasive ductal carcinoma xenograft derived from patient, when used at a dose of 10 mg/kg, 5 mg/kg and 2.5 mg/kg or 5 mg/kg, 2.5 mg/kg and 1.25 mg/kg, respectively, with a single injection, as described in example 10.3.2 and 10.4.

Altogether, for the first time, these results validly identify LAMP1 as a therapeutic target for the treatment of cancer.

Accordingly, the invention relates to an immunoconjugate comprising an antibody which:

a) binds to human and *Macaca fascicularis* LAMP1 proteins; and b) is linked or conjugated to at least one growth inhibitory agent.

Any antibody which binds to human and *Macaca fascicularis* LAMP1 proteins, as described throughout the instant application (e.g. MAb4, fragments thereof, or chimeric or humanised version thereof), can be incorporated in the immunoconjugate according to the invention.

As used herein, "conjugate", "immunoconjugate", "antibody-drug conjugate" or "ADC" have the same meaning and are interchangeable.

A "growth inhibitory agent", or "anti-proliferative agent", which can be used indifferently, refers to a compound or composition which inhibits growth of a cell, especially tumour cell, either in vitro or in vivo. A growth inhibitory agent denotes in particular a cytotoxic agent or a radioactive isotope.

The term "radioactive isotope" is intended to include radioactive isotopes suitable for treating cancer, such as $At^{211}$, $Ac^{225}$, $Bi^{212}$, $Bi^{213}$, $Pb^{212}$, $Er^{169}$, $I^{131}$, $I^{124}$, $I^{125}$, $Y^{90}$, $In^{111}$, $P^{32}$, $Re^{186}$, $Re^{188}$, $Sm^{153}$, $Sr^{89}$, $Zr^{89}$, $Tc^{99m}$, $Ga^{68}$, $Cu^{64}$ and radioactive isotopes of Lu such as $Lu^{177}$. Such radioisotopes generally emit mainly beta-radiation. In an embodiment the radioactive isotope is alpha-emitter isotope, more precisely Thorium 227 ($Th^{227}$) which emits alpha-radiation. The immunoconjugates according to the present invention can be prepared as described in the application WO2004/091668.

In one embodiment, a radioactive isotope is selected from the group consisting of $At^{211}$, $Ac^{225}$, $Bi^{213}$, $Pb^{212}$, $Er^{169}$, $I^{124}$, $I^{125}$, $In^{111}$, $P^{32}$, $Re^{186}$, $Sm^{153}$, $Sr^{89}$, $Zr^{89}$, $Tc^{99m}$, $Ga^{68}$, Cu$^{64}$ and radioactive isotopes of Lu, for instance from At$^{211}$, Er$^{169}$, I$^{125}$, In$^{111}$, P$^{32}$, Re$^{186}$, Sm$^{153}$, Sr$^{89}$, radioactive isotopes of Lu, and Th$^{227}$.

The term "cytotoxic agent" as used herein refers to a substance that inhibits or prevents the function of cells and/or causes destruction of cells. The term "cytotoxic agent" is intended to include chemotherapeutic agents, enzymes, antibiotics, and toxins such as small molecule toxins or enzymatically active toxins of bacterial, fungal, plant or animal origin, including fragments and/or variants thereof, and the various antitumor or anticancer agents disclosed below. In some embodiments, the cytotoxic agent is a drug or a pro-drug of a compound consisting in an anti-tubulin agent such as taxoids or taxanes, a vinca-alkaloid, a maytansinoid or maytansinoid analog such as DM1 or DM4, a cryptophycin derivative, an auristatin or dolastatin analog; a DNA alkylating agent, such as a tomaymycin or pyrrolobenzodiazepine derivative, a CC-1065 or CC-1065 analog; a leptomycin derivative; a topoisomerase II inhibitor, an RNA polymerase II inhibitor such as alpha-amanitin.

According to a first embodiment, said at least one growth inhibitory agent is neither an undefined radioactive isotope, a chemotherapeutic drug, a protein or lectin, nor pokeweed antiviral protein, abrin, ricin and each of their A chains, doxorubicin, cisplastin, Iodine-131, Yttrium-90, Rhenium-188, Bismuth-212, Taxol, 5-Fluorouracil, VP-16 (etoposide), bleomycin, methotrexate, vindesine, adriamycin, vincristine, vinblastine, bis-chloroethylnitrosourea (BCNU), mitomycin, cyclophosphamide and a cytokine such as TNF and TNF-β.

According to this first embodiment, the invention relates in particular to an immunoconjugate comprising an antibody which:
a) binds to human and *Macaca fascicularis* LAMP1 proteins; and
b) is linked or conjugated to at least one growth inhibitory agents
   (i) a cytotoxic agent selected from the group consisting of enzymes other than from pokeweed antiviral protein; antibiotics other than from bleomycin and mitomycin; toxins of bacterial, fungal, or animal origin or of plant origin other than from abrin and ricin, including fragments and/or variants thereof; a drug or a pro-drug of a compound consisting in an anti-tubulin agent such as a maytansinoid or maytansinoid analog such as DM1 or DM4, a taxoid or taxane other than from paclitaxel (Taxol), a vinca-alkaloid other than from vindesine, vincristine and vinblastine, a cryptophycin derivative, an auristatin or dolastatin analog; a DNA alkylating agent other than from BCNU and cyclophosphamide, such as a tomaymycin or pyrrolobenzodiazepine derivative, a CC-1065 or CC-1065 analog; a leptomycin derivative; a topoisomerase II inhibitors other than doxorubicin (adriamycin) and etoposide, a RNA polymerase II inhibitor such as alpha-amanitin, or
   (ii) a radioactive isotope selected from the group consisting of At$^{211}$, Ac$^{225}$, Bi$^{213}$, Pb$^{212}$, Er$^{169}$, I$^{124}$, I$^{125}$, In$^{111}$, P$^{32}$, Re$^{186}$, Sm$^{153}$, Sr$^{89}$, Zr$^{89}$, Tc$^{99m}$, Ga$^{68}$, Cu$^{64}$ and radioactive isotopes of Lu such as Lu$^{177}$, and Th$^{227}$.

In one embodiment a radioactive isotope is selected from the group consisting of At$^{211}$, Er$^{169}$, I$^{125}$, In$^{111}$, P$^{32}$, Re$^{186}$, Sm$^{153}$, Sr$^{89}$, radioactive isotopes of Lu, and Th$^{227}$.

In said first embodiment, the antibody may bind in particular to a domain consisting of the first to third loops of human and *Macaca fascicularis* LAMP1 proteins; wherein the domain consisting of the first to third loops of human LAMP1 protein consists of amino acids Ala29 to Ile309 of SEQ ID NO: 24 and the domain consisting of the first to third loops of *Macaca fascicularis* LAMP1 protein consists of amino acids Ala27 to Thr307 of SEQ ID NO: 39

According to a second embodiment, the invention relates to an immunoconjugate wherein the antibody binds to a domain consisting of the first to third loops of human and *Macaca fascicularis* LAMP1 proteins; wherein the domain consisting of the first to third loops of human LAMP1 protein consists of amino acids Ala29 to Ile309 of SEQ ID NO: 24 and the domain consisting of the first to third loops of *Macaca fascicularis* LAMP1 protein consists of amino acids Ala27 to Thr307 of SEQ ID NO: 39.

Therefore, according to this second embodiment, the immunoconjugate comprises an antibody which a) binds to a domain consisting of the first to third loops of human and *Macaca fascicularis* LAMP1 proteins; wherein the domain consisting of the first to third loops of human LAMP1 protein consists of amino acids Ala29 to Ile309 of SEQ ID NO: 24 and the domain consisting of the first to third loops of *Macaca fascicularis* LAMP1 protein consists of amino acids Ala27 to Thr307 of SEQ ID NO: 39; and b) is linked or conjugated to said at least one growth inhibitory agent.

Although not compulsory, in said second embodiment, the at least one growth inhibitory agent may be different from an undefined radioactive isotope, a chemotherapeutic drug, a protein or lectin, in particular from pokeweed antiviral protein, abrin, ricin and each of their A chains, doxorubicin, cisplastin, Iodine-131, Yttrium-90, Rhenium-188, Bismuth-212, Taxol, 5-Fluorouracil, VP-16 (etoiposide), bleomycin, methotrexate, vindesine, adriamycin, vincristine, vinblastine, BCNU, mitomycin, cyclophosphamide and a cytokine such as TNF and TNF-β.

Accordingly, said at least one growth inhibitory agent may be a radioactive isotopes selected from the group consisting of At$^{211}$, Ac$^{225}$, Bi$^{213}$, Pb$^{212}$, Er$^{169}$, I$^{124}$, I$^{125}$, In$^{111}$, P$^{32}$, Re$^{186}$, Sm$^{153}$, Sr$^{89}$, Zr$^{89}$, Tc$^{99m}$, Ga$^{68}$, Cu$^{64}$ and radioactive isotopes of Lu such as Lu$^{177}$, and Th$^{227}$, for instance At$^{211}$, Er$^{169}$, I$^{125}$, In$^{111}$, P$^{32}$, Re$^{186}$, Sm$^{153}$, Sr$^{89}$, radioactive isotopes of Lu such as Lu$^{177}$, and Th$^{227}$, or a cytotoxic agent as defined in said first embodiment.

In said first and second embodiments, said at least one growth inhibitory agent may be in particular drug or a pro-drug of a compound consisting in a maytansinoid or maytansinoid analog such as DM1 or DM4, a tomaymycin or pyrrolobenzodiazepine derivative, a cryptophycin derivative, a leptomycin derivative, an auristatin or dolastatin analog, or a CC-1065 or CC-1065 analog, a RNA polymerase II inhibitor such as alpha-amanitin.

In one embodiment, a suitable tomamycin is a tomamycine dimer. Said tomamycin dimer is for instance (2E,2'E,11aS,11a'S)-8,8'-(((4-(2-(2-(2-((2-mercapto-2-methylpropyl)(methyl)amino)ethoxy)ethoxy)ethoxy)pyridine-2,6-diyl) bis(methylene))bis(oxy))bis(2-ethylidene-7-methoxy-2,3-dihydro-1Hbenzo[e]pyrrolo[1,2-a][1,4] diazepin-5 (11aH)-one).

The structural formula of (2E,2'E,11aS,11a'S)-8,8'-(((4-(2-(2-(2-((2-mercapto-2-methylpropyl)(methyl)amino) ethoxy)ethoxy)ethoxy)pyridine-2,6-diyl) bis(methylene))bis (oxy))bis(2-ethylidene-7-methoxy-2,3-dihydro-1Hbenzo[e] pyrrolo[1,2-a][1,4] diazepin-5(11aH)-one) is

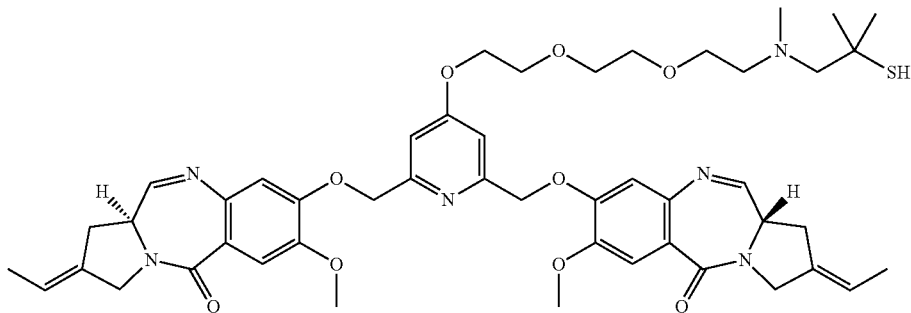 [SMILES: C/C=C1\C[C@H]2C=Nc3cc(OCc4cc(OCCOCCOCCN(C)CC(C)(C)S)cc(COc5cc6c(cc5OC)C(=O)N5C/C(=C/C)C[C@H]5C=N6)n4)c(OC)cc3C(=O)N2C1]

A "maytansinoid" as used herein denotes maytansinoids and maytansinoid analogs. Maytansinoids are drugs that inhibit microtubule formation and that are highly toxic to mammalian cells.

Examples of suitable maytansinoids include maytansinol and maytansinol analogs.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:

(1) C-19-dechloro (U.S. Pat. No. 4,256,746) (prepared by LAH reduction of ansamytocin P2);
(2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and
(3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);
(2) C-14-alkoxymethyl (demethoxy/$CH_2OR$) (U.S. Pat. No. 4,331,598);
(3) C-14-hydroxymethyl or acyloxymethyl ($CH_2OH$ or $CH_2OAc$) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from *Trewia nudiflora*);
(6) C-18-N-demethyl (U.S. Pat. Nos. 4,362,663 and 4,322,348) (prepared by the demethylation of maytansinol by *Streptomyces*); and
(7) 4,5-deoxy (U.S. Pat. No. 4,371,533) (prepared by the titanium trichloride/LAH reduction of maytansinol).

In a specific embodiment, the cytotoxic conjugates of the present invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

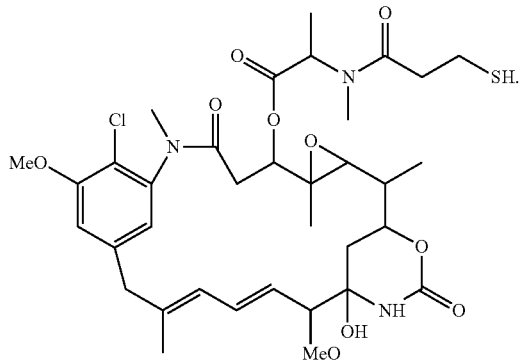

(I)

In another embodiment, the cytotoxic conjugates of the present invention utilize the thiol-containing maytansinoid DM4, formally termed $N^{2'}$-deacetyl-$N^{2'}$-(4-methyl-4-mercapto-1-oxopentyl)-maytansine, as the cytotoxic agent. DM4 is represented by the following structural formula (II):

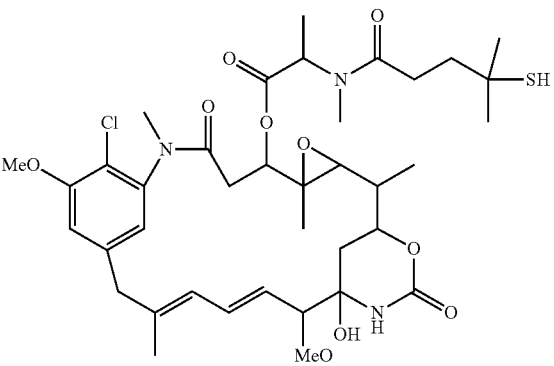

(II)

In further embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 reagents and any aggregate which may be present in the solution.

Examples of these cytotoxic agents and of methods of conjugation are further given in the application WO2008/010101 which is incorporated by reference.

In some embodiments of the present invention, the antibody is covalently attached, directly or via a cleavable or non-cleavable linker, to the at least one growth inhibitory agent.

"Linker", as used herein, means a chemical moiety comprising a covalent bond or a chain of atoms that covalently attaches a polypeptide to a drug moiety.

The conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Conjugation of an antibody of the invention with cytotoxic agents or growth inhibitory agents may be made using a variety of bifunctional protein coupling agents including but not limited to N-succinimidyl pyridyldithiobutyrate (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfo-butyric acid (sulfo-SPDB), N-succinimidyl (2-pyridyldithio) propionate (SPDP), SNPP (N-succinimidyl 4-(5-nitro-2-pyridyldithio) pentanoate), succinimidyl (N-maleimidomethyl) cyclohexane-1-carboxylate (SMCC), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026).

The linker may be a "cleavable linker" facilitating release of the cytotoxic agent or growth inhibitory agent in the cell. For example, an acid-labile linker, a peptidase-sensitive linker, an esterase labile linker, a photolabile linker or a disulfide-containing linker (See e.g. U.S. Pat. No. 5,208,020) may be used. The linker may be also a "non-cleavable linker" (for example SMCC linker) that might lead to better tolerance in some cases.

Alternatively, a fusion protein comprising the antibody of the invention and a cytotoxic or growth inhibitory polypeptide may be made, by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention may also be used in Dependent Enzyme Mediated Prodrug Therapy by conjugating the polypeptide to a prodrug-activating enzyme which converts a prodrug (e.g. a peptidyl chemotherapeutic agent, see WO81/01145) to an active anti-cancer drug (See, for example, WO 88/07378 and U.S. Pat. No. 4,975,278). The enzyme component of the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anticancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as 0-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. The enzymes can be covalently bound to the polypeptides of the invention by techniques well known in the art such as the use of the heterobifunctional crosslinking reagents discussed above.

According to said first and second embodiments, in the conjugate of the invention, the growth inhibitory agent may be a maytansinoid, in particular DM1 or DM4.

In such a conjugate, the antibody is conjugated to said at least one growth inhibitory agent by a linking group. In particular said linking group is a non-cleavable linker, such as SPDB, sulfo-SPDB, or SMCC.

In particular, the conjugate may be selected from the group consisting of:

i) an antibody-SPDB-DM4 conjugate of formula (III)

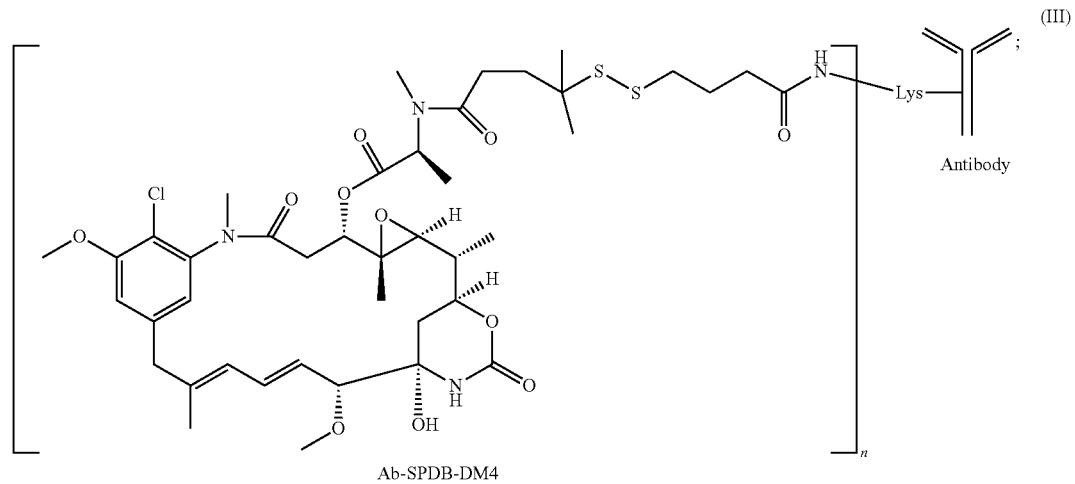

Ab-SPDB-DM4 ii) an antibody-sulfo-SPDB-DM4 conjugate of formula (IV)

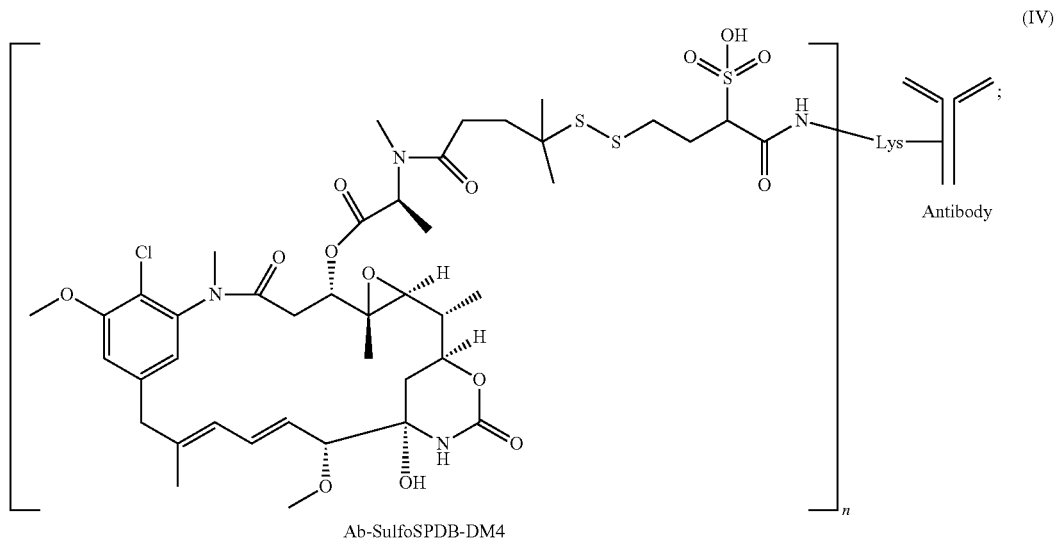

Ab-SulfoSPDB-DM4 iii) an antibody-SMCC-DM1 conjugate of formula (V)

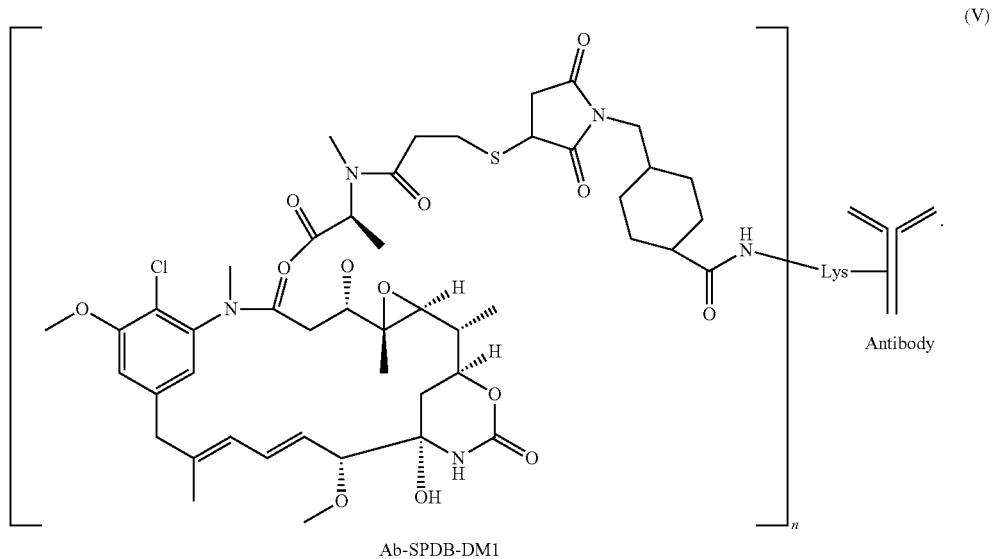

Ab-SPDB-DM1

In a further embodiment, in the conjugate of the invention, the growth inhibitory agent may be tomamycin, for instance a tomamycin dimer, for example (2E,2'E,11aS, 11a'S)-8,8'-(((4-(2-(2-(2-((2-mercapto-2-methylpropyl)(methyl)amino)ethoxy)ethoxy)ethoxy)pyridine-2,6-diyl) bis(methylene))bis(oxy))bis(2-ethylidene-7-methoxy-2,3-dihydro-1Hbenzo[e]pyrrolo[1,2-a][1,4] diazepin-5(11aH)-one).

In such a conjugate, the antibody is conjugated to said at least one growth inhibitory agent by a linking group, for instance by SNPP.

Accordingly, in one embodiment the conjugate may an antibody-SNPP-(2E,2'E,11aS,11a'S)-8,8'-(((4-(2-(2-(2-((2-mercapto-2-methylpropyl)(methyl)amino)ethoxy)ethoxy) ethoxy)pyridine-2,6-diyl).

In general, the conjugate can be obtained by a process comprising the steps of:
(i) bringing into contact an optionally-buffered aqueous solution of a cell-binding agent (e.g. an antibody according to the invention) with solutions of a linker and a cytotoxic compound;
(ii) then optionally separating the conjugate which was formed in (i) from the unreacted cell-binding agent.

The aqueous solution of cell-binding agent can be buffered with buffers such as, e.g. potassium phosphate, acetate, citrate or N-2-Hydroxyethylpiperazine-N'-2-ethanesulfonic acid (Hepes buffer). The buffer depends upon the nature of the cell-binding agent. The cytotoxic compound is in solution in an organic polar solvent, e.g. dimethyl sulfoxide (DMSO) or dimethylacetamide (DMA).

The reaction temperature is usually comprised between 20° C. and 40° C. The reaction time can vary from 1 to 24 hours. The reaction between the cell-binding agent and the cytotoxic agent can be monitored by size exclusion chromatography (SEC) with a refractometric and/or UV detector. If the conjugate yield is too low, the reaction time can be extended.

A number of different chromatography methods can be used by the person skilled in the art in order to perform the separation of step (ii): the conjugate can be purified e.g. by SEC, adsorption chromatography (such as ion exchange chromatography, IEC), hydrophobic interaction chromatography (HIC), affinity chromatography, mixed-support chromatography such as hydroxyapatite chromatography, or high performance liquid chromatography (HPLC). Purification by dialysis or diafiltration can also be used.

As used herein, the term "aggregates" means the associations which can be formed between two or more cell-binding agents, said agents being modified or not by conjugation. The aggregates can be formed under the influence of a great number of parameters, such as a high concentration of cell-binding agent in the solution, the pH of the solution, high shearing forces, the number of bonded dimers and their hydrophobic character, the temperature (see Wang, L. and Gosh, R., 2008, *J. Membr Sci.* 318: 311-316, and references cited therein); note that the relative influence of some of these parameters is not clearly established. In the case of proteins and antibodies, the person skilled in the art will refer to Cromwell, M. E. et al. (2006, *AAPS Journal* 8(3): E572-E579). The content in aggregates can be determined with techniques well known to the skilled person, such as SEC (see Walter et al., 1993, *Anal. Biochem.*, 212(2): 469-480).

After step (i) or (ii), the conjugate-containing solution can be submitted to an additional step (iii) of chromatography, ultrafiltration and/or diafiltration.

The conjugate is recovered at the end of these steps in an aqueous solution.

According to an embodiment, the conjugate according to the invention is characterised by a "drug-to-antibody ratio" (or "DAR") as measured by DAR UV ranging from 1 to 10, for instance from 2 to 5, in particular from 3 to 4. This is generally the case of conjugates including maytansinoid molecules.

This DAR number can vary with the nature of the antibody and of the drug (i.e. the growth-inhibitory agent) used along with the experimental conditions used for the conjugation (like the ratio growth-inhibitory agent/antibody, the reaction time, the nature of the solvent and of the cosolvent if any). Thus the contact between the antibody and the growth-inhibitory agent leads to a mixture comprising several conjugates differing from one another by different drug-to-antibody ratios; optionally the naked antibody; optionally aggregates. The DAR that is determined is thus a mean value.

A method which can be used to determine the DAR, herein called DAR UV, consists in measuring spectrophotometrically the ratio of the absorbance at of a solution of substantially purified conjugate at $\lambda_D$ and 280 nm. 280 nm is a wavelength generally used for measuring protein concentration, such as antibody concentration. The wavelength $\lambda_D$ is selected so as to allow discriminating the drug from the antibody, i.e. as readily known to the skilled person, $\lambda_D$ is a wavelength at which the drug has a high absorbance and $\lambda_D$ is sufficiently remote from 280 nm to avoid substantial overlap in the absorbance peaks of the drug and antibody. $\lambda_D$ may be selected as being 252 nm in the case of maytansinoid molecules. A method of DAR calculation may be derived from Antony S. Dimitrov (ed), LLC, 2009, Therapeutic Antibodies and Protocols, vol 525, 445, Springer Science:

The absorbances for the conjugate at $\lambda_D$ ($A_{\lambda_D}$) and at 280 nm ($A_{280}$) are measured using a classic spectrophotometer apparatus (allowing to calculate the "DAR parameter"). The absorbances can be expressed as follows:

$$A_{\lambda D}=(c_D \times \epsilon_{D\lambda D})+(c_A \times \epsilon_{A\lambda D})$$

$$A_{280}=(c_D \times \epsilon_{D280})+(c_A \times \epsilon_{A280})$$

wherein:

$c_D$ and $c_A$ are respectively the concentrations in the solution of the drug and of the antibody $\epsilon_{D\lambda D}$ and $\epsilon_{D280}$ are respectively the molar extinction coefficients of the drug at $\lambda_D$ and 280 nm $\epsilon_{A\lambda D}$ and $\epsilon_{A280}$ are respectively the molar extinction coefficients of the antibody at $A_D$ and 280 nm.

Resolution of these two equations with two unknowns leads to the following equations:

$$c_D=[(\epsilon_{A280} \times A_{\lambda D})-(\epsilon_{A\lambda D} \times A_{280})]/[(\epsilon_{D\lambda D} \times \epsilon_{A280})-(\epsilon_{A\lambda D} \times \epsilon_{D280})]$$

$$c_A=[A_{280}-(c_D \times \epsilon_{D280})]/\epsilon_{A280}$$

The average DAR is then calculated from the ratio of the drug concentration to that of the antibody: $DAR=c_D/c_A$.

In the immunoconjugate according to the invention, the antibody is in particular specific for human and *Macaca fascicularis* LAMP1 proteins.

The antibody is in particular a chimeric or humanised antibody. The antibody may also be an antibody fragment, or a bispecific or multispecific antibody.

Antibodies binding specifically to human and *Macaca fascicularis* LAMP1 proteins which are particularly contemplated to be included in the immunoconjugates of the invention are described in further details in the following "Antibodies" section.

Antibodies

The inventors identified four antibodies (the so-called antibodies "MAb1", "MAb2", "MAb3" and "MAb4") that bind specifically to human LAMP1 and distinguish tumoral from non-tumoral tissues. The antibodies MAb1, MAb2, MAb3 allowed for the first time to detect extracellularly expressed LAMP1 and thus to perform IHC analysis on Frozen-OCT (from Optimal Cutting Temperature) specimens and AFA (Alcohol Formalin Acetic acid Fixative) to distinguish cancerous from non-cancerous tissue.

However, IHC analysis of tumor tissues from biobanks or from hospitals before or during patient treatment is routinely done with formalin-fixed paraffin-embedded (FFPE) samples. Although MAb1, MAb2 and MAb3 allow LAMP1 membrane reinforcement in frozen-OCT and AFA (Alcohol Formalin Acetic acid Fixative) sample format, they can not lead to the detection of LAMP1 reinforcement in FFPE format. One of the reasons is probably the effect of the formalin fixative combined to the complexity of the protein. The inventors discovered peptides that allowed the production of a monoclonal antibody MAb4 that can be furthermore used for IHC experiments on the FFPE the format and thus allows the application of the herein presented methods on FFPE tumor biobanks and FFPE hospital samples.

Those four antibodies showed a high binding affinity (within the nanomolar range) to cell surface expressed LAMP1 in cancer cells. Furthermore, at least the anti-LAMP1 MAb1, MAb2 and MAb3 antibodies showed a high capacity to trigger internalization of the LAMP1/anti-LAMP1 antibody complex, as shown in example 4.4.

Additionally, the four antibodies are cross-reactive with *Macaca fascicularis* LAMP1 but do not display any cross-reactivity with human LAMP2 protein.

The binding sites of antibodies MAb1, MAb2 and MAb3 have been mapped to a domain consisting of the first to third loops of human and *Macaca fascicularis* LAMP1 proteins, in particular to the first lumenal domain of human LAMP1. More specifically the binding site of MAb1 was mapped in loops 1-2 and the binding site of MAb2 and MAb3 was mapped in loop1. The antibodies MAb1 and MAb2 do not compete with each other for binding to human LAMP1. Therefore at least two epitopes on LAMP1 have been found to interact with the antibodies of the invention.

The binding site of Antibody MAb4 has been mapped to a domain consisting of the third to fourth loop of human and *Macaca fascicularis* LAMP1 proteins, in particular to the fourth loop of human LAMP1. More specifically the antibody MAb4 binds to a region of Loop 4 comprising the amino acids 360 to 375 of human LAMP1 that consists of sequences SEQ ID NO: 82.

The inventors have determined the sequence of variable heavy and light chains of these monoclonal antibodies which are directed against the human and *Macaca fascicularis* LAMP1 proteins.

The so-called antibody "MAb1" comprises:

a variable domain of heavy chain consisting of sequence QVQLQQSGAELVKPGASVKMSCKASGYIFTNYNIH-WVKKSPGQGLEWIGAIYPGNGDAPY SQKFKDKATL-TADKSSSTTYMQLSRLTSEDSAVYYCVRANWDVA-FAYWGQGTLVSVSA (SEQ ID NO: 1, with CDRs shown in bold characters) in which FR1-H spans amino acid positions 1 to, 25, CDR1-H spans amino acid positions 26 to 33 (SEQ ID NO: 2), FR2-H spans amino acid positions 34 to 50, CDR2-H spans amino acid positions 51 to 58 (SEQ ID NO: 3), FR3-H spans amino acid positions 59 to 96, CDR3-H spans amino acid positions 97 to 107 (SEQ ID NO: 4), and FR4-H spans amino acid positions 108 to 118, and a variable domain of light chain consisting of sequence DIQMTQSPPSLSASLGGKVTITCKASQDIDRYMAWY-QDKPGKGPRLLIHDTSTLQPGIPSRF SGSGSGRDYSF-SISNLEPEDIATYYCLQYDNLWTFGGGTKLEIK (SEQ ID NO: 5, with CDRs shown in bold characters) in which FR1-L spans amino acid positions 1 to 26, CDR1-L spans amino acid positions 27 to 32 (SEQ ID NO: 6), FR2-L spans amino acid positions 33 to 49, CDR2-L spans amino acid positions 50 to 52, FR3-L spans amino acid positions 53 to 88, CDR3-L spans amino acid positions 89 to 96 (SEQ ID NO: 7), and FR4-H spans amino acid positions 97 to 106.

The so-called antibody "MAb2" comprises:

a variable domain of heavy chain consisting of sequence QVQLQQSAAELARPGASVKMSCKASGYTFTSYTMH-WVKQRPGQGLEWIGYFNPSSGYPE YNQKFKDKTTL-TADKSSNTAFIQLNSLTSEDSAVYYCSRGYYYGSRG-YALDFWGQGASVT VSS (SEQ ID NO: 8, with CDRs shown in bold characters) in which FR1-H spans amino acid positions 1 to 25, CDR1-H spans amino acid positions 26 to 33 (SEQ ID NO: 9), FR2-H spans amino acid positions 34 to 50, CDR2-H spans amino acid positions 51 to 58 (SEQ ID NO: 10), FR3-H spans amino acid positions 59 to 96, CDR3-H spans amino acid positions 97 to 111 (SEQ ID NO: 11), and FR4-H spans amino acid positions 112 to 122, and a variable domain of light chain consisting of sequence NIVLTQSPVSLAVSLGQRATISCRASESVDINGNTFM-HWYQQKPGQSPKLVIYAASNIESGV PARF-SGSGSSTDFTFTIDPVEADDVATYYCQQFNIEDPWTF-GGGTKVEIK (SEQ ID NO: 12, with CDRs shown in bold characters) in which FR1-L spans amino acid positions 1 to 26, CDR1-L spans amino acid positions 27 to 36 (SEQ ID NO: 13), FR2-L spans amino acid positions 37 to 53, CDR2-L spans amino acid positions 54 to 56, FR3-L spans amino acid positions 57 to 92, CDR3-L spans amino acid positions 93 to 101 (SEQ ID NO: 14), and FR4-H spans amino acid positions 102 to 111.

A variant of antibody MAb2, called herein "MAb2$_{Can}$" was also generated by introducing canonical residues by substitution of A116T in the variable domain of the heavy chain and by substitution of V9A, V51L, I58L, S72G and A108T in the variable domain of the light chain.

The so-called "antibody MAb2$_{Can}$" comprises:

a variable domain of heavy chain consisting of sequence QVQLQQSAAELARPGASVKMSCKASGYTFTSYT-MHWVKQRPGQGLEWIGYFNPS SGYPEYNQKFKDK-TTLTADKSSNTAFIQLNSLTSEDSAVYYCSRGYYYG-SRGYALDFWGQ GTSVTVSS (SEQ ID NO: 15).

a variable domain of light chain consisting of sequence NIVLTQSPASLAVSLGQRATISCRASESVDINGNTF-MHWYQQKPGQSPKLLIYAASN LESGVPARFSGSGS-GTDFTFTIDPVEADDVATYYCQQNIEDPWTFGGGT-KLEIK (SEQ ID NO: 16).

Both "MAb2$_{Can}$" and "MAb2", under chimeric form, have the same affinity for human LAMP1 (see Table 13).

The so-called antibody "MAb3" comprises:

a variable domain of heavy chain consisting of sequence QIQLVQSGPELKKPGETVKISCKASGYIFTNYGMN-WVKQAPGKGLKWMGWINTYTGESRY ADDFKGR-FALSLETSASTAYLQINNLENEDMATYFCAREDYYG-NSPWFFDVWGAGTTVTV SS (SEQ ID NO: 42, with CDRs shown in bold characters) in which FR1-H spans amino acid positions 1 to 25, CDR1-H spans amino acid positions 26 to 33 (SEQ ID NO: 43), FR2-H spans amino acid positions 34 to 50, CDR2-H spans amino acid positions 51 to 58 (SEQ ID NO: 44), FR3-H spans amino acid positions 59 to 96, CDR3-H spans amino acid positions 97 to 111 (SEQ ID NO: 45), and FR4-H spans amino acid positions 112 to 122, and a variable domain of light chain consisting of sequence DIQMTQTTSSLSASLGDRVTISCNASQGINKYLNWY-QQKPDGTVKLLIYYTSTLHSGVPSRF SGSGSGTDYS-LTINNLEPEDIATYYCQQYTKLPFTFGSGTKLEIK (SEQ ID NO: 46, with CDRs shown in bold characters) in which FR1-L spans amino acid positions 1 to 26, CDR1-L spans amino acid positions 27 to 32 (SEQ ID NO: 47), FR2-L spans amino acid positions 33 to 49, CDR2-L spans amino acid positions 50 to 52, FR3-L spans amino acid positions 53 to 88, CDR3-L spans amino acid positions 89 to 97 (SEQ ID NO: 48), and FR4-H spans amino acid positions 98 to 107.

A variant of MAb3 ("MAb3 VL_R24_R93") was generated by introducing into VL sequence of MAb3 the following amino acid substitutions: N24R and K93R. Accordingly, the variable domain of light chain of MAb3 VL_R24_R93 consist of DIQMTQTTSSLSASLGDRVTISCRASQGINKYLN-WYQQKPDGTVKLLIYYTSTLHSG VPSRFSGSGSGT-DYSLTINNLEPEDIATYYCQQYTRLPFTFGSGTKLEIK (SEQ ID NO: 51) (the mutated residues as compared with VL of MAb3 being shown in enlarged characters).

CDR3-L of MAb3 VL_R24_R93 thus consists of QQYTRLPFT (SEQ ID NO: 52).

The so called "MAb4" comprises:

a variable domain of heavy chain consisting of sequence QVQLQQSGAELVRPGTSVKVSCKASGYAFT-NYLIEVWVKQRPGQGLEWIGVINPGS GGTNYNEK-FKGKATLTADKSSSTAYMQLSSLTSDDSAVYF-CARYRSYDWYFDVWGAGTT VTVSS (SEQ ID NO: 88, with CDRs shown in bold characters) in which FR1-H spans amino acid positions 1 to 25, CDR1-H spans amino acid positions 26 to 33 (SEQ ID NO: 83), FR2-H spans amino acid positions 34 to 50, CDR2-H spans amino acid positions 51 to 58 (SEQ ID NO: 84), FR3-H spans amino acid positions 59 to 96, CDR3-H spans amino acid positions 97 to 108 (SEQ ID NO: 85), and FR4-H spans amino acid positions 109 to 119, and a variable domain of light chain consisting of sequence DIQMTQSPASLSASVGETVTITCRVSGNIH-NYLAWYQQKQGKSPQLLVYNAKTLAD GVPSRF-SGSGSGTQYSLKINSLQPEDFGSYYCQHFWSNPYTF-GGGTKLEIK (SEQ ID NO: 89, with CDRs shown in bold characters) in which FR1-L spans amino acid positions 1 to 26, CDR1-L spans amino acid positions 27 to 32 (SEQ ID NO: 86), FR2-L spans amino acid positions 33 to 49, CDR2-L spans amino acid positions 50 to 52, FR3-L spans amino acid positions 53 to 88, CDR3-L spans amino acid positions 89 to 97 (SEQ ID NO: 87), and FR4-H spans amino acid positions 98 to 107.

The antibody may also be a humanised antibody or a fragment of a humanised antibody. For example, the antibody of the invention may result from humanisation of any of the antibodies defined above.

Numerous methods for humanisation of an antibody sequence are known in the art; see e.g. the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus the biological activity of the parent antibody, back mutations may be introduced at selected positions of the CDR grafted antibody in order to retain the binding specificity and affinity of the parent antibody. Identification of positions for possible back mutations can be performed using information available in the literature and in antibody databases. An alternative humanization technique to CDR grafting and back mutation is resurfacing, in which non-surface exposed residues of non-human origin are retained, while surface residues are altered to human residues. Another alternative technique is known as "guided selection" (Jespers, L. S. et al., 1994, Biotechnology 12(9): 899-993) and can be used to derive from a murine antibody a fully human antibody conserving the epitope and binding characteristics of the parental antibody. The technique of humanization based on molecular dynamic calculations as disclosed in the application WO2009/032661 may be used. Thus in one embodiment humanized antibodies may also be called "resurfaced" antibodies.

For chimeric antibodies, humanisation typically involves modification of the framework regions of the variable region sequences.

Amino acid residues that are part of a CDR will typically not be altered in connection with humanisation, although in certain cases it may be desirable to alter individual CDR amino acid residues, for example to remove a glycosylation site, a deamidation site, an undesired cysteine residue, a lysine residue in the case of ADC. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, in particular by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues. In the case of ADC, attachment of a cytotoxic to mAb could be prepared via covalent linkage to lysine side chain residue. This steric hindrance may interfere with mAb binding to antigen. It may therefore be desirable to remove the lysine residue, typically by an arginine conservative substitution. Substitution in a CDR sequence to remove one of the implicated residues is also intended to be encompassed by the present invention. The inventors further generated humanized antibodies "huMAb1_1", "huMAb1_2", "huMAb1_3" based on CDR grafting and/or on Molecular Dynamic Trajectories (4D humanization protocol) as described in example 7.2.1 and herein below.

Accordingly, in one embodiment, the anti-LAMP1 antibodies in context of the invention are humanized anti-LAMP1 antibodies obtained through CDR grafting and/or based on Molecular Dynamic Trajectories (4D humanization protocol).

Accordingly, in an embodiment, the humanized anti-LAMP1 antibody "huMAb1_1" comprises:

the variable domain (VH1) of heavy chain chain consisting of sequence
QVQLVQSGAEVKKPGSSVKVSCKASGYIFTNYNI-HWVKKSPGQGLEWIGAIYPGNG DAPYSQKFQG-KATLTADTSTSTTYMELSSLRSEDTAVYYCVRANWD-VAFAYWGQGTLVTV SS (SEQ ID NO: 53) and the variable domain (VL1) of light chain of huMAb1_1 consisting of sequence
DIQMTQSPSSLSASVGDRVTITCKASQDIDRY-MAWYQDKPGKAPRLLIHDTSTLQS GVPSRFSGSGS-GRDYTLTISNLEPEDFATYYCLQYDNLWTFGGGTK-VEIK (SEQ ID NO: 56).

The humanized antibody "huMAb1_2" comprises:

a variable domain (VH2) of heavy chain consisting of sequence
QVQLVQSGAELVKPGASVKMSCKASGYIFTNYNI-HWVKKSPGQGLEWIGAIYPGNG DAPYSQK-FQDRATLTADTSSSTTYMELSSLTSEDSAVYYCVRAN-WDVAFAYWGQGTLVS VSS (SEQ ID NO: 54), and a variable domain of light chain (VL2) consisting of sequence
DIQMTQSPPSLSASVGGKVTITCKASQDIDRY-MAWYQDKPGKGPKLLIHDTSTLQP GIPSRFSGSGS-GRDYSFSISNLEPEDIATYYCLQYDNLWTFGGGT-KLEIK (SEQ ID NO: 57)

The humanized antibody "huMAb1_3" comprises:

a variable domain (VH3) of heavy chain consisting of sequence
QVQLVQSGAELVKPGASVKMSCKASGYIFTNYNI-HWVRQAPGQGLEWIGAIYPGN GDAPYAQK-FQGRATLTADTSSSTTYMELSSLTSEDTAVYYCVRAN-WDVAFAYWGQGTLV TVSS (SEQ ID NO: 55), and a variable domain of light chain (VL3) consisting of sequence
DIQMTQSPSSLSASVGGKVTITCKASQDIDRY-MAWYQQKPGKGPKLLIHDTSTLQP GVPSRFSGSGS-GRDYSLTISSLEPEDIATYYCLQYDNLWTFGGGT-KLEIK (SEQ ID NO: 58)

The invention relates to an antibody which binds specifically to human and *Macaca fascicularis* LAMP1 proteins.

"Affinity" is defined, in theory, by the equilibrium association between the whole antibody and the antigen. It can be experimentally assessed by a variety of known methods, such as measuring association and dissociation rates with surface plasmon resonance or measuring the $EC_{50}$ in an immunochemical assay (ELISA, FACS). Enzyme-linked immunosorbent assay (ELISA) is a biochemistry assay that uses a solid-phase enzyme immunoassay to detect the presence of a substance, usually an antigen, in a liquid sample or wet sample. Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate. Fluorescence-activated cell sorting (FACS) provides a method for sorting a heterogeneous mixture of biological cells into two or more containers, one cell at a time, based upon the specific light scattering and fluorescent characteristics of each cell. In these assays, the $EC_{50}$ is the concentration of the antibody which induces a response halfway between the baseline and maximum after some specified exposure time on a defined concentration of antigen by ELISA (enzyme-linked immuno-sorbent assay) or cell expressing the antigen by FACS (Fluorescence Activated Cell Sorting).

A monoclonal antibody binding to antigen 1(Ag1) is "cross-reactive" to antigen 2 (Ag2) when the $EC_{50}$s are in a similar range for both antigens. In the present application, a monoclonal antibody binding to Ag1 is cross-reactive to Ag2 when the ratio of affinity of Ag2 to affinity of Ag1 is equal or less than 10 (in particular 5, 2, 1 or 0.5), affinities being measured with the same method for both antigens.

A monoclonal antibody binding to Ag1 is "not significantly cross-reactive" to Ag2 when the affinities are very different for the two antigens. Affinity for Ag2 may not be measurable if the binding response is too low. In the present application, a monoclonal antibody binding to Ag1 is not significantly cross-reactive to Ag2, when the binding response of the monoclonal antibody to Ag2 is less than 5% of the binding response of the same monoclonal antibody to Ag1 in the same experimental setting and at the same antibody concentration. In practice, the antibody concentration used can be the $EC_{50}$ or the concentration required to reach the saturation plateau obtained with Ag1.

A monoclonal antibody "binds specifically" to Ag1 when it is not significantly cross-reactive to Ag2.

The antibody according to the invention binds specifically to human and *Macaca fascicularis* LAMP1 proteins. It does not significantly cross-react with human LAMP2 (SEQ ID NO: 40).

In one embodiment, the antibody according to the invention has an affinity ($EC_{50}$) for human and/or cynomolgus monkey LAMP1 expressed at the cell surface of a recombinant cell line, wherein the cell line may be HEK293 and/or HCT116 and the apparent affinity measured via Flow Cytometry is ≤70 nM, for example ≤60 nM, ≤50 nM, ≤45 nM, ≤40 nM, ≤35 nM, ≤30 nM, ≤25 nM, ≤20 nM, ≤15 nM or ≤10 nM.

In one embodiment, the antibody according to the invention has an affinity ($EC_{50}$) for full length human and cynomolgus monkey LAMP1 expressed at the cell surface of a recombinant cell line, wherein the cell line may be HCT116 and the apparent affinity measured via Flow Cytometry is ≤20 nM, in particular ≤10 nM, ≤8 nM or ≤7 nM.

In one example, the antibody according to the invention has an affinity ($EC_{50}$) for cynomolgus monkey LAMP1 expressed at the cell surface of a recombinant cell line, wherein the cell line may be HEK293 and the apparent affinity measured via Flow Cytometry is ≤50 nM, for example ≤40 nM or ≤35 nM.

In another example, the antibody according to the invention has a KD for full purified human LAMP1 (SEQ ID NO 28) expressed in HEK293 cells measured via surface plasmon resonance (SPR) is ≤70 nM, for example ≤60 nM, ≤50 nM, ≤40 nM, ≤30 nM, ≤20 nM or ≤10 nM.

The use of surface plasmon resonance to determine is known to the skilled in the art. In one example the binding kinetics of for example the murine, chimer or humanized anti-LAMP1 mAbs were determined by surface plasmon resonance assay using typically a BIAcore 2000 (BIAcore Inc., Uppsala, N.J.). Therefore, for example a CM5 BIAcore biosensor chip was docked into the instrument and activated with for example 70 μL of 1:1 NHS/EDC at room temperature. Typically, a mouse anti-αhuman Fc IgG1 (BIAcore #BR-1008-39) and rabbit anti-αmurine Fc IgG1 (BIAcore #BR-1008-38) (50 μg/mL in 1 M acetate buffer, pH5) were immobilized on the activated chips in all flow cells. The immobilization was carried out at a flow rate of for example 10 μL/min up to saturation. The chip was then blocked by for example injection of 70 μL of ethanolamine-HCl, pH 8.5, followed by one wash with 3 M $MgCl_2$ for anti-αhuman Fc IgG1 and one wash with 10 mM Glycine-HCl pH 1.7 for anti-αmurine Fc IgG1. To measure the binding of for example anti-LAMP1 mAbs to LAMP1, antibodies were used at 1-5 μg/mL in BIAcore running buffer (HBS-EP). The antigen for example (Sequence ID No 28 protein produced as described in example 6.2) was injected from for example 1 to 256 nM. Following completion of the injection phase, dissociation was monitored in a BIAcore running buffer at the same flow rate for typically 600 sec. The surface was typically regenerated between injections using for example 2×5 μL 3 M $MgCl_2$ (2×30 s) or anti-αhuman Fc IgG1 and 1×30 μL 10 mM Glycine-HCl pH 1.7 for anti-αmurine Fc IgG1 (180 s). Individual sensorgrams were typically analyzed using BIAevaluation software.

Thus, the polypeptide according to the invention may be used in toxicological studies performed in monkeys, wherein the toxicity profile obtained from those studies is relevant to anticipate potential adverse effects in humans.

Alternatively, or furthermore, the antibody according to the invention has an affinity ($EC_{50}$) for LAMP1 expressed on the surface of advanced human primary colon tumor CR-IGR-034P and measured via Flow Cytometry is ≤50 nM, ≤40 nM, in particular ≤30 nM, ≤20 nM or ≤5 nM.

Antibody binding capacity or ABC is the quantification of cell surface antigen. ABC can be measured using QIFIKIT® (Registered trademark of BIOCYTEX). The antibodies according to the invention have a high ABC on many Patient derived Xenografts of different origin (≥20.000, in particular ≥50.000, ≥100.000, ≥150.000 ABC) and tumor cell lines, in particular colon tumor cells such as Colo205, SW480 or LS174T (≥1.500, ≥2.500, ≥4.000 ABC).

Alternatively, or furthermore, the antibody according to the invention has the ability to internalize and recycle LAMP1 to the cell membrane. In particular, when bound by an antibody according to the invention, a molecule of LAMP1 at the membrane of cancer cell has the capacity undergo at least 1, 4, 7 or 9 recyclings at the cell membrane. In other words, one molecule of LAMP1 expressed at the surface of a cancer cell can be bound by, and therefore internalize, at least 2, 5, 8 or 10 molecules of antibody according to the invention. Still in other words, according to an embodiment, at least 2, 5, 8 or 10 molecules of antibody according to the invention are internalized by one molecule of LAMP1 expressed at the surface of a cancer cell.

Internalization may be assayed for instance by determining an internalization score or by a fluorescence-based quenching method.

The internalization score (IS) is defined as a ratio of the fluorescence intensity inside the cell to the intensity of the entire cell. It may be measured as described by using the imaging flow cytemeter ImageStream$^x$ (from the supplier Amnis® Corporation, 2505 Third Avenue, Suite 210, Seattle, Wash. 98121-1480, on the world wide web at amnis.com). The higher the score, the greater the fluorescence intensity is inside the cell. As described by Amnis (see the world wide web at amnis.com), the inside of the cell is defined by an erosion of a mask that fits the membrane of the cell. The score is invariant to cell size and can accommodate concentrated bright regions and small dim spots. The ratio is mapped to a logarithmic scale to increase the dynamic range to values between {-inf, inf}. The thickness of the membrane (in pixels) determines which pixels are used to define the boundary and the membrane portions of the cell. The user supplies an 'internal' mask based on the brightfield image that covers the inside of the cell, the thickness of the membrane in pixels and the fluorescent channel of interest. The cell is divided into 2 regions: External (B) and internal (I). The user supplies the internal region as the mask. The external region is determined by: 1. Dilating the internal mask by the membrane thickness. 2. Combining 1 with the object mask of the channel of interest. 3. External region equals mask 2 and not the internal mask. Next, the mean intensity of the upper quartile of the pixels in each region is determined. The Internalization Score (IS) is then computed as follows:

$$IS = \log\left(\frac{\alpha}{1-\alpha}\right), \text{ where } \alpha = \frac{m_I}{m_I + m_B}\frac{p_I}{p_B}$$

mI=Mean intensity of upper quartile pixels in I, mB=Mean intensity of upper quartile pixels in B, pI=Peak intensity of upper quartile pixels in I, pB=Peak intensity of upper quartile pixels in B.

In the case of transferrin, (Williams A. et al., 1996, Biomembranes, 4:255-287) the authors have obtained an IS of 0 when the cells were left on ice and an IS of 0.9 when the cells were incubated at 37° C. for one hour.

For the antibodies of the invention, the inventors have shown that the internalization scores (IS) at 37° C. were 10-fold higher than at 4° C. Since internalization of antibodies does not take place at 4° C., the internalization scores obtained at 4° C. reflect the density of LAMP1 molecules at the cell surface. A 10-fold higher value of the IS parameter at 37° C. than at 4° C. therefore means that the LAMP1 protein is quickly and repeatedly recycling at the cell membrane. In other words the antibodies according to the invention have a very high internalization capacity, much higher than the capacity calculated from the density of the LAMP1 protein at the cell surface.

Quantification of internalization can also be performed by fluorescence-based quenching methods. In particular, a fluorescence-based Alexa488-quenching method has been described to analyze internalisation of targeting agents (Frejd et al. 2010, International Journal of Oncology, 36: 757-763). According to said description, internalization is calculated as the Mean fluorescence intensity (MFI) value of quenched cells (intracellular compartments only) divided by the MFI value of unquenched cells (both cell surface and intracellular compartments) at 37° C., according to the following formula:

$$\text{Percentage of iternalized fraction} = \frac{FL \text{ of quenched cells at } 37° \text{ C.}}{FL \text{ of unquenched cells at } 37° \text{ C.}} \times 100$$

Cells incubated with Alexa488-labelled compounds at 4° C. are used as a control since internalization of antibodies does not take place at 4° C.

The inventors showed that after quenching, the total fluorescence of Alexa488-MAb1 measured from cells labelled at 37° C. (both cell surface and intracellular compartments) was 10-fold higher than the fluorescence of cells labelled at 4° C. (cell surface) after 4 h (example 4.4). Accordingly, these results also indicate that the LAMP1 protein is quickly and repeatedly recycling at cell membrane.

Thus, the inventors showed for the first time that LAMP1 can function as a receptor mediating the internalization of antibodies and suggest that availability of specific internalizing antibodies should aid in developing novel therapeutic methods to target toxins, drugs or short-range isotopes to be delivered specifically to the interior of the cancer cells.

Furthermore the inventors could show that the results from example 4.4 taken together indicate that each LAMP1 molecule is involved in several (at least up to 10 on average) internalization cycles via recycling at cell membrane during the course of the experiment.

The antibody of the invention binds specifically to a domain consisting in particular of the first to third loops of human and *Macaca fascicularis* LAMP1 proteins. The domain consisting of the first to third loops of human LAMP1 protein is defined by the amino acids Ala29 to Ile309 of SEQ ID NO: 24, and the domain consisting of the first to third loops of *Macaca fascicularis* LAMP1 protein is defined by the amino acids Ala27 to Thr307 of SEQ ID NO: 39. According to an embodiment, the antibody of the invention binds specifically to the first lumenal domain of human and *Macaca fascicularis* LAMP1 proteins.

The first lumenal domain of human LAMP1 is defined by the amino acids at positions Ala29 to Arg195 of SEQ ID NO: 24, and the first lumenal domain of *Macaca fascicularis* LAMP1 protein is defined by the amino acids at positions Ala27 to Arg193 of SEQ ID NO: 39. More specifically, the antibody can bind to the human and *Macaca fascicularis* first lumenal domain indifferently whether expressed as a soluble extracellular domain (e.g. amino acids Ala29-Met382 for human LAMP1 (SEQ ID NO: 24) or Ala27-Met380 for *Macaca fascicularis* LAMP1 (SEQ ID NO: 39)), or as a membrane-anchored full-length LAMP1 protein recombinantly expressed at the surface of a cell line, for instance HT29, Colo205 and HCT116, HEK293 cell line. The inventors demonstrated that MAb1 binds to the amino acids 101 to 195 of SEQ ID NO: 24 corresponding to Loop 2 of human LAMP1, for example to the amino acids 101 to 110 (SEQ ID NO: 72), 144 to 157 (SEQ ID NO:73) and 174 to 188 (SEQ ID NO: 74) of SEQ ID NO: 24 as herein described in example 4.8. It has been further identified by crystallography, that the binding site of MAb1 further encompasses the amino acids Asn35, Cys80, Gly 81, Glu83, Asn84 located in loop 1 of SEQ ID NO: 24.

Accordingly, MAb1 also binds to the amino acids at positions 29 to 100 of SEQ ID NO: 24 corresponding to Loop 1 of human LAMP1, for example to a region that consists of the amino acids at positions 35 to 84 of SEQ ID NO: 24 (SEQ ID NO:97), or to two regions that consists of Asn35 of SEQ ID NO: 24 and amino acids at positions 80-84 of SEQ ID NO: 24.

Furthermore both MAb2 and MAb3 bind to the amino acids 29 to 100 (SEQ ID NO: 77) of SEQ ID NO: 24 corresponding to Loop 1 of human LAMP1, for instance MAb2 and MAb3 both bind to the the amino acids 29 to 41 (SEQ ID NO: 75) and 68 to 80 (SEQ ID NO: 76) of SEQ ID NO: 24.

In a further antibody, the antibody of the invention binds specifically to the second luminal domain of human and *Macaca fascicularis* LAMP1 proteins, for instance to the fourth loop.

The fourth loop of human LAMP1 protein consists of amino acids at positions Leu310 to Met382 of SEQ ID NO: 24 and the fourth loop of *Macaca fascicularis* LAMP1 protein consists of amino acids at positions Leu 308 to Met380 of SEQ ID NO: 39.

More specifically, the antibody binds to a region of Loop 4 comprising the amino acids 360 to 375 of human LAMP1 that consists of sequences SEQ ID NO: 82.

In another embodiment, the antibody of the invention binds specifically to human and *Macaca fascicularis* LAMP1 proteins indifferently whether in non-glycosylated or glycosylated form.

Accordingly, in an embodiment, the invention relates to an antibody which binds to:

three regions of Loop 2 of human LAMP1 that consist of sequences SEQ ID NO: 72, SEQ ID NO: 73 and SEQ ID NO: 74, respectively, and optionally further to a region of Loop1 of human LAMP1 that consists of sequence (SEQ ID NO:97); or two regions of Loop 1 of human LAMP1 that consist of sequences SEQ ID NO: 75 and SEQ ID NO: 76, respectively; or a region of Loop4 of human LAMP1 that consist of sequence SEQ ID NO: 82.

Furthermore, the inventors identified the residues R146, D150, K152, R106, A108, N181, S182, S183, R186 and G187 of SEQ ID NO: 24 as likely to interact with MAb1 as described in example 6.5. They further identified the residues A29, M30, M32, G36, A40, S69, D70, T72, V74, L75, and R77 of SEQ ID NO: 24 as likely to interact with MAb2 and/or MAb3. Those residues have been individually replaced by an alanine residue in the LAMP1 sequence derived from hLAMP1_ΔGYQTI and encoded in plasmid pXL5626 as described in example 6.6. The inventors observed loss of binding to MAb1 for alanine mutations at positions I149, D150 and R186 of SEQ ID NO: 24 in the LAMP1 protein, indicating that these positions are important for MAb1 binding to LAMP1. Furthermore, loss of binding was demonstrated for LAMP1 to MAb3 for alanine mutations at positions G38 and D70 of SEQ ID NO: 24 due to Ala substitution in LAMP1 protein indicating that these positions are important for MAb3 binding to LAMP1.

Accordingly, in an embodiment, the invention relates to an antibody which binds to:

the amino acids I149, D150 and R186 of SEQ ID NO: 24, or the amino acids G38 and D70 of SEQ ID NO: 24, or The invention also provides for an antibody which competes for binding to a domain consisting of the first to third loops of human and *Macaca fascicularis* LAMP1 proteins with an antibody selected from the group consisting of the so-called antibodies Mab1, Mab2, MAb2$_{Can}$, MAb3, MAb3 VL_R24_R93, huMAb1_1 and huMAb1_2, huMAb1_3 i.e.:

(i) an antibody comprising a variable domain of heavy chain of sequence SEQ ID NO: 1 and/or a variable domain of light chain of sequence of sequence SEQ ID NO: 5; or (ii) an antibody comprising a variable domain of heavy chain of sequence SEQ ID NO: 8 and/or a variable domain of light chain of sequence of sequence SEQ ID NO: 12; or (iii) an antibody comprising a variable domain of heavy chain of sequence SEQ ID NO: 15 and/or a variable domain of light chain of sequence of sequence SEQ ID NO: 16; or (iv) an antibody comprising a variable domain of heavy chain of sequence SEQ ID NO: 42 and/or a variable domain of light chain of sequence of sequence SEQ ID NO: 46; or (v) an antibody comprising a variable domain of heavy chain of sequence SEQ ID NO: 42 and/or a variable domain of light chain of sequence of sequence SEQ ID NO: 51; or (vi) an antibody comprising a variable domain of heavy chain of sequence SEQ ID NO: 53 and/or a variable domain of light chain of sequence of sequence SEQ ID NO: 56; or (vii) an antibody comprising a variable domain of heavy chain of sequence SEQ ID NO: 54 and/or a variable domain of light chain of sequence of sequence SEQ ID NO: 57; or (viii) an antibody comprising a variable domain of heavy chain of sequence SEQ ID NO: 55 and/or a variable domain of light chain of sequence of sequence SEQ ID NO: 58.

In an embodiment, said antibody competes for binding to the first lumenal domain of human and *Macaca fascicularis* LAMP1 proteins. For instance the invention provides for an antibody which competes for binding to:

three regions of Loop 2 of human LAMP1 that consist of sequences SEQ ID NO: 72, SEQ ID NO: 73 and SEQ ID NO: 74, respectively; or two regions of Loop 1 of human LAMP1 that consist of sequences SEQ ID NO:75 and SEQ ID NO: 76, respectively, with an antibody comprising a variable domain of heavy chain and a variable domain of light chain as defined according to i-viii) above, as appropriate (i.e. with said three regions of Loop 2 for an antibody as defined according to i and vi-viii) above, or with said two regions of Loop 1 for an antibody as defined according to ii-v)).

In one embodiment the competition is determined by use of an ELISA as described in Example 4.8 of the specification, wherein competition is defined by a signal of less than 80% of signal compared to mAb control alone as assessed by absorption, when the two competing antibodies are in solution at similar molarity, and wherein competition is defined by a signal of less than 80%, for instance less than 70%, 60%, 50%, 40%, 30%, 20%, 10%.

The ability of an antibody to compete for binding to a domain consisting of the first to third loops, in particular to the first lumenal domain, of human and *Macaca fascicularis*

LAMP1 proteins with an antibody comprising the variable heavy and light chains of an antibody selected from the group consisting of the so-called antibodies MAb1, MAb2, MAb2$_{Can}$, MAb3, MAb3_VLR24-R93, huMAb1_1, huMAb1_2 and huMAb1_3 (hereafter a "reference" antibody) may be readily assayed, for instance, by competitive ELISA wherein the antigen (i.e. a polypeptide comprising or consisting of a fragment of human or *Macaca fascicularis* LAMP1 including the first to third loops of LAMP1, or the first lumenal domain, in particular a protein containing the first lumenal domain of LAMP1 from human and cynomolgus origin such as presented in example 6.3) is bound to a solid support and two solutions containing the candidate antibody and the reference antibody, respectively, are added and the antibodies are allowed to compete for binding to the antigen. The amount of reference antibody bound to the antigen may then be measured, and compared to the amount of reference antibody bound to the antigen when measured against a negative control. An amount of bound reference antibody in presence of the candidate antibody decreased as compared to the amount of bound reference antibody in presence of the negative control indicates that the candidate antibody has competed with the reference antibody. Conveniently, the reference antibody may be labeled (e.g. fluorescently) to facilitate detection of bound reference antibody. Repeated measurements may be performed with serial dilutions of the candidate and/or reference antibody.

In another example binding competition between MAb1 and MAb2 or MAb3 can be typically measured between two anti-LAMP1 mAbs by ELISA with recombinant human LAMP1 coated on plate (as described in example 6.2). Briefly, typically two mAbs were added simultaneously at concentrations of for example 0.06 and 15 mg/L, the concentration of typically 0.06 mg/L being close to the EC$_{50}$. MAb format was chosen so that the two mAbs had different Fc domains (either human or murine). Individual measurements of mAb binding could be performed typically by their unique specific binding to Fc (for example with Peroxidase-AffiniPure Goat Anti-Human IgG Ab, Fcγ Fragment Specific (Jackson 109-035-098) or with Peroxidase-AffiniPure Goat Anti-Mouse IgG Ab, Fcγ Fragment Specific (Jackson 115-035-164)). The results were reported as a percentage of the value obtained from the mAb alone at the same concentration.

In particular, the antibody according to the invention comprises the CDR sequences of the heavy and/or light chains of one of so-called anti-LAMP1 antibodies MAb1, MAb2 and MAb3. More specifically, the antibody can comprise the CDR sequences of the heavy light chain, or the the CDR sequences of the heavy and light chains, of one of so-called anti-LAMP1 antibodies MAb1, MAb2, MAb3 and MAb3 VL_R24_R93.

Accordingly, the antibody of the invention may comprise:
a CDR1-H of sequence SEQ ID NO: 2 or a sequence differing from SEQ ID NO: 2 by one amino acid substitution, a CDR2-H of sequence SEQ ID NO: 3 or a sequence differing from SEQ ID NO: 3 by one amino acid substitution, and a CDR3-H of sequence SEQ ID NO: 4 or a sequence differing from SEQ ID NO: 4 by one amino acid substitution;
and/or
a CDR1-L of sequence SEQ ID NO: 6 or a sequence differing from SEQ ID NO: 6 by one amino acid substitution, a CDR2-L of sequence DTS or a sequence differing from DTS by one amino acid substitution and a CDR3-L of sequence SEQ ID NO: 7 or a sequence differing from SEQ ID NO: 7 by one amino acid substitution; or (ii) a CDR1-H of sequence SEQ ID NO: 9 or a sequence differing from SEQ ID NO: 9 by one amino acid substitution, a CDR2-H of sequence SEQ ID NO: 10 or a sequence differing from SEQ ID NO: 10 by one amino acid substitution, a CDR3-H of sequence SEQ ID NO: 11 or a sequence differing from SEQ ID NO: 11 by one amino acid substitution;
and/or
a CDR1-L of sequence SEQ ID NO: 13 or a sequence differing from SEQ ID NO: 13 by one amino acid substitution, a CDR2-L of sequence AAS or a sequence differing from AAS by one amino acid substitution, and a CDR3-L of sequence SEQ ID NO: 14 or a sequence differing from SEQ ID NO: 14 by one amino acid substitution; or (iii) a CDR1-H of sequence SEQ ID NO: 43 or a sequence differing from SEQ ID NO: 43 by one amino acid substitution, a CDR2-H of sequence SEQ ID NO: 44 or a sequence differing from SEQ ID NO: 44 by one amino acid substitution, and a CDR3-H of sequence SEQ ID NO: 45 or a sequence differing from SEQ ID NO: 45 by one amino acid substitution; and/or
a CDR1-L of sequence SEQ ID NO: 49 or a sequence differing from SEQ ID NO: 47 by one amino acid substitution, a CDR2-L of sequence YTS or a sequence differing from YTS by one amino acid substitution, and a CDR3-L of sequence SEQ ID NO: 48 or SEQ ID NO: 52 or a sequence differing from SEQ ID NO: 48 or SEQ ID NO: 52 by one amino acid substitution.

In a further embodiment, the antibody according to the invention comprises the CDR sequences of the heavy and/or light chains of so-called anti-LAMP1 antibody MAb4. More specifically, the antibody can comprise the CDR sequences of the heavy light chain, or the the CDR sequences of the heavy and light chains, of the so-called anti-LAMP1 antibody MAb4.

Accordingly, the antibody of the invention may comprise a CDR1-H of sequence SEQ ID NO: 83, a CDR2-H of sequence SEQ ID NO: 84, a CDR3-H of sequence SEQ ID NO: 85, a CDR1-L of sequence SEQ ID NO: 86, a CDR2-L of sequence NAK, and a CDR3-L of sequence SEQ ID NO: 87.

Furthermore, the antibody of the invention may comprise, or consist of, a heavy chain of sequence SEQ ID NO: 98 and/or a light chain of sequence of sequence SEQ ID NO: 99 (i.e. heavy and/or light chain of MAb4 as described in example 17.2.3).

In one embodiment this antibody may be chimeric, humanized, or an antibody fragment.

In the antibody of the invention, one individual amino acid may be altered by substitution, in particular by conservative substitution, in one or more (in particular in only one) of the above CDR sequences. Such an alteration may be intended for example to remove a glycosylation site or a deamidation site, in connection with humanisation of the antibody. Another alteration could also be intended to remove a lysine in a CDR, since covalent attachment to cytotoxic via lysine side chain residue may interfere with binding to antigen in the case of ADC. For instance, SEQ ID NO: 48 and SEQ ID NO: 52 are CDR3-L sequences that differ by one amino acid substitution at their position 5.

According to an embodiment, the antibody comprises
(i) a CDR1-H of sequence SEQ ID NO: 2, a CDR2-H of sequence SEQ ID NO: 3, and a CDR3-H of sequence SEQ ID NO: 4; and/or
a CDR1-L of sequence SEQ ID NO: 6, a CDR2-L of sequence DTS, and a CDR3-L of sequence SEQ ID NO: 7; or (ii) a CDR1-H of sequence SEQ ID NO: 9, a CDR2-H of sequence SEQ ID NO: 10, a CDR3-H of sequence SEQ ID NO: 11; and/or
a CDR1-L of sequence SEQ ID NO: 13, a CDR2-L of sequence AAS, and a CDR3-L of sequence SEQ ID NO: 14; or (iii) a CDR1-H of sequence SEQ ID NO: 43, a CDR2-H of sequence SEQ ID NO: 44, and a CDR3-H of sequence SEQ ID NO: 45, and/or
a CDR1-L of sequence SEQ ID NO: 47, a CDR2-L of sequence YTS, and a CDR3-L of sequence SEQ ID NO: 48 or SEQ ID NO: 52.

In particular, the antibody can comprise:
(i) a CDR1-H of sequence SEQ ID NO: 2, a CDR2-H of sequence SEQ ID NO: 3, a CDR3-H of sequence SEQ ID NO: 4, and/or
a CDR1-L of sequence SEQ ID NO: 6, a CDR2-L of sequence DTS, and a CDR3-L of sequence SEQ ID NO: 7; or (ii) a CDR1-H of sequence SEQ ID NO: 9, a CDR2-H of sequence SEQ ID NO: 10, a CDR3-H of sequence SEQ ID NO: 11; and/or
a CDR1-L of sequence SEQ ID NO: 13, a CDR2-L of sequence AAS, and a CDR3-L of sequence SEQ ID NO: 14; or (iii) a CDR1-H of sequence SEQ ID NO: 43, a CDR2-H of sequence SEQ ID NO: 44, a CDR3-H of sequence SEQ ID NO: 45, and/or
CDR1-L of sequence SEQ ID NO: 47, a CDR2-L of sequence YTS, and a CDR3-L of sequence SEQ ID NO: 48 or SEQ ID NO: 52, or (iv) a fragment of an antibody as defined in (i), (ii), or (iii).

The inventors crystallized recombinant Fab from huMAb1_1 that was identified to bind to loop 1 and loop 2 in a complex with non-glycosylated LAMP1 protein according to the protocol described in example 7.3.1. Based on the determination of the tridimensional structure of huMab1_1 in complex with LAMP1, most of its CDRs can be associated to specific canonical structure as referenced in Al-Lazikini, Lesk and Chothia (1997) J. Mol. Biol. 273:927-948 mentioned above. The crystal structure allowed determining mutations that can be introduced into the CDRS without disturbing said canonical structure. It is known to the skilled in the art that disturbation of said canonical structure would result in a modified binding behavior. They thus identified by analyzing the crystallographic structure, that Q27 and D28 of SEQ ID NO: 68 located in CDR1-L can be replaced by any amino acid as long as the loop retains the canonical structure κ2B and 129 of SEQ ID NO: 68 can be replaced by an equivalent hydrophobic residues, for instance Leu or Val. T51 of SEQ ID NO: 68 and S52 of SEQ ID NO: 68, both located in CDR2-L can be replaced by a Ser, in case of T51 and by any amino acid, in the case of S52, as long as this loop retains the classic γ-turn conformation. Residues D92, N93, L94 of SEQ ID NO: 68, located in CDR3-L can be replaced by any amino acids as long as the loop retains canonical structure λ1B. Furthermore, G26 of SEQ ID NO: 69, located in CDR-1H can be replaced by any amino acid, Y27 of SEQ ID NO: 69, located in CDR-1H by a phenylalanine, T30 of SEQ ID NO: 69, located in CDR-1H by any amino acid, as long as the loop retains the canonical structure 1. Residues D102, V103 and A104 of SEQ ID NO: 69, located in CDR-3H can be replaced by any amino acid of similar sizes and properties.

Accordingly, the invention provides for an antibody which binds to three regions of Loop 2 of human LAMP1 that consist of sequences SEQ ID NO: 72, SEQ ID NO: 73 and SEQ ID NO: 74, respectively; and comprises a) a CDR1-L consisting of sequence $X_1X_2X_3$DRY (SEQ ID NO:93) wherein each of $X_1$ and $X_2$ is any amino acid and $X_3$ is selected from Ile, Leu and Val; and
a CDR2-L consisting of sequence $DX_1X_2$ wherein $X_1$ a is selected from T or S and $X_2$ is any amino acid; and
a CDR3-L consisting of the sequence LQYX$_1$X$_2$X$_3$WT, in which $X_1$, $X_2$ and $X_3$ is any amino acid; and/or b) a CDR1-H consisting of sequence $X_1X_2$IFX$_3$NYN (SEQ ID NO: 82) wherein each of $X_1$ and $X_3$ are any amino acid and $X_2$ is selected from Tyr or Phe; and a CDR2-H consisting of SEQ ID NO: 3; and
CDR3-H consisting of sequence VRANWX$_1$X$_2$X$_3$FAY (SEQ ID NO: 84) wherein each of $X_1$, $X_2$, $X_3$, is any amino acid.

In one embodiment said antibody retains the ability to bind to loop 2.

The skilled in the art knows methods to verify if the antibody according to the definition retains its ability to bind to three regions of loop 2 of human LAMP1 that consist of sequences SEQ ID NO: 72, SEQ ID NO: 73 and SEQ ID NO: 74, respectively, and thus does not suffer from a disturbed canonical structure.

The invention also provides antibodies as defined above further comprising at least the variable domain of heavy chain and/or the variable domain of light chain of one of the so-called anti-LAMP1 antibodies MAb1, MAb2, $MAb2_{Can}$, MAb3, MAb3 VL_R24_R93, huMAb1_1 and huMAb1_2, huMAb1_3, for instance MAb1, MAb2, $MAb2_{Can}$, MAb3, MAb3 VL_R24_R93.

Thus the invention relates in particular to an antibody which comprises:

(i) a variable domain of heavy chain of sequence SEQ ID NO: 1 or a sequence at least 85% identical thereto and/or a variable domain of light chain of sequence of sequence SEQ ID NO: 5, or a sequence at least 85% identical thereto; or (ii) a variable domain of heavy chain of sequence SEQ ID NO: 8, or a sequence at least 85% identical thereto, and/or a variable domain of light chain of sequence of sequence SEQ ID NO: 12, or a sequence at least 85% identical thereto; or (iii) a variable domain of heavy chain of sequence SEQ ID NO: 15, or a sequence at least 85% identical thereto, and/or a variable domain of light chain of sequence of sequence SEQ ID NO: 16, or a sequence at least 85% identical thereto; or (iv) a variable domain of heavy chain of sequence SEQ ID NO: 42, or a sequence at least 85% identical thereto, and/or a variable domain of light chain of sequence of sequence SEQ ID NO: 46 or SEQ ID NO: 51, or a sequence at least 85% identical thereto; or (v) a variable domain of heavy chain of sequence SEQ ID NO: 53 or a sequence at least 85% identical thereto and/or a variable domain of light chain of sequence of sequence SEQ ID NO: 56, or a sequence at least 85% identical thereto; or (vi) a variable domain of heavy chain of sequence SEQ ID NO: 54 or a sequence at least 85% identical thereto and/or a variable domain of light chain of sequence of sequence SEQ ID NO: 57, or a sequence at least 85% identical thereto; or (vii) a variable domain of heavy chain of sequence SEQ ID NO: 55 or a sequence at least 85% identical thereto and/or a variable domain of light chain of sequence of sequence SEQ ID NO: 58, or a sequence at least 85% identical thereto.

In one embodiment, the invention relates to an isolated anti-LAMP-1 antibody which comprises:

(i) a CDR1-H of sequence SEQ ID NO: 2, a CDR2-H of sequence SEQ ID NO: 3, and a CDR3-H of sequence SEQ ID NO: 4; and/or
a CDR1-L of sequence SEQ ID NO: 6, a CDR2-L of sequence DTS, and a CDR3-L of sequence SEQ ID NO: 7; or (ii) a CDR1-H of sequence SEQ ID NO: 9, a CDR2-H of sequence SEQ ID NO: 10, a CDR3-H of sequence SEQ ID NO: 11; and/or
a CDR1-L of sequence SEQ ID NO: 13, a CDR2-L of sequence AAS, and a CDR3-L of sequence SEQ ID NO: 14; or (iii) a CDR1-H of sequence SEQ ID NO: 43, a CDR2-H of sequence SEQ ID NO: 44, and a CDR3-H of sequence SEQ ID NO: 45, and/or
a CDR1-L of sequence SEQ ID NO: 47, a CDR2-L of sequence YTS, and a CDR3-L of sequence SEQ ID NO: 48 or SEQ ID NO: 52; or (iv) CDR1-H of sequence SEQ ID NO: 83, a CDR2-H of sequence SEQ ID NO: 84, a CDR3-H of sequence SEQ ID NO: 85, and/or
a CDR1-L of sequence SEQ ID NO: 86, a CDR2-L of sequence NAK, and a CDR3-L of sequence SEQ ID NO: 87; or a heavy chain of sequence SEQ ID NO: 60 or a light chain of sequence SEQ ID NO: 59; or (v) a heavy chain of sequence SEQ ID NO: 62 or a light chain of sequence SEQ ID NO: 61; or (vi) a heavy chain of sequence SEQ ID NO: 64 or a light chain of sequence SEQ ID NO: 63.

For instance, the sequence of the variable domain of heavy or light chain may differ from the reference sequence SEQ ID NO: 1, 5, 8, 12, 15, 16, 42, 46 or 51, 53, 56, 54, 57, 55, 58, for instance from SEQ ID NO: 1, 5, 8, 12, 15, 16, 42, 46 or 51 as appropriate, by one or more amino acid substitution(s), in particular by one or more conservative amino acid substitution(s) and/or substitution(s) with canonical residues.

In particular, the sequence of the variable domain of heavy or light chain may differ from the reference sequence SEQ ID NO: 1, 5, 8, 12, 15, 16, 42, 46 or 51, 53, 56, 54, 57, 55, 58, for example from SEQ ID NO: 1, 5, 8, 12, 15, 16, 42, 46 or 51 by conservative amino acid substitution(s), only.

The sequence alterations as compared with sequence SEQ ID NO: 1, 5, 8, 12, 15, 16, 42, 46 or 51, 53, 56, 54, 57, 55, 58, for example from SEQ ID NO: 1, 5, 8, 12, 15, 16, 42, 46 or 51 will in particular be present essentially in one or more of the framework regions, FR1-L, FR2-L, FR3-L, FR4-L and/or FR1-H, FR2-H, FR3-H, FR4-H.

However, amino acid substitutions in one or more CDRs are also possible.

The invention also provides antibodies as defined above further comprising at least the variable domain of heavy chain and/or the variable domain of light chain of one of the so-called anti-LAMP1 antibodies MAb4.

Thus the invention relates in particular to an antibody which comprises a variable domain of heavy chain of sequence SEQ ID NO: 88 or a sequence at least 85% identical thereto and/or a variable domain of light chain of sequence of sequence SEQ ID NO: 89, or a sequence at least 85% identical thereto.

The antibody according to the invention is in particular a conventional antibody, in particular a conventional monoclonal antibody, or an antibody fragment, a bispecific or multispecific antibody.

According to an embodiment, the antibody according to the invention comprises or consists of an IgG, or a fragment thereof.

The antibody of the invention and a fragment thereof may be, respectively, a murine antibody and a fragment of a murine antibody.

The antibody may also be a chimeric antibody, and in particular a murine/human antibody, e.g. an antibody comprising murine variable domains of heavy and light chains and a CH domain and a CL domain from a human antibody. The antibody may be a fragment of such an antibody.

According to an embodiment, the antibody of the invention is:

a) a chimeric antibody comprising, or consisting of, a heavy chain of sequence SEQ ID NO: 17 and/or a light chain of sequence of sequence SEQ ID NO: 18 (i.e. heavy and/or light chain of chMAb1 as described in example 7); or b) a chimeric antibody comprising, or consisting of, a heavy chain of sequence SEQ ID NO: 19 and/or a light chain of sequence of sequence SEQ ID NO: 20; (i.e. heavy and/or light chain of chMAb2 as described in example 7); or c) a chimeric antibody comprising, or consisting of, a heavy chain of sequence SEQ ID NO: 21 and/or a light chain of sequence of sequence SEQ ID NO: 22; (i.e. heavy and/or light chain of chMAb2$_{Can}$ as described in example 7); or d) a chimeric antibody comprising, or consisting of, a heavy chain of sequence SEQ ID NO: 49 and/or a light chain of sequence of sequence SEQ ID NO: 50; (i.e. heavy and/or light chain of chMAb3); or e) a chimeric antibody comprising, or consisting of, a heavy chain of sequence SEQ ID NO: 49 and/or a light chain of sequence of sequence SEQ ID NO:81; (i.e. heavy and/or light chain of chMAb3_VLR24-R93; or f) a fragment of the chimeric antibody defined in a), b), c), d) and e).

The antibody of the invention may also be a humanized antibody. Thus, according to an embodiment, the antibody of the invention comprises, or consists of:

i) a heavy chain of sequence SEQ ID NO: 60 or a sequence at least 85% identical thereto and/or a light chain of sequence of sequence SEQ ID NO: 59 or a sequence at least 85% identical thereto (i.e. heavy and/or light chain of huMAb1_1 as described in example 7.2); or ii) a heavy chain of sequence SEQ ID NO: 62 or a sequence at least 85% identical thereto and/or a light chain of sequence of sequence SEQ ID NO: 61 or a sequence at least 85% identical thereto (i.e. heavy and/or light chain of huMAb1_2 as described in example 7.2); or iii) a heavy chain of sequence SEQ ID NO: 64 a or a sequence at least 85% identical thereto nd/or a light chain of sequence of sequence SEQ ID NO: 63 or a sequence at least 85% identical thereto (i.e. heavy and/or light chain of huMAb1_3 as described in example 7.2).

In one embodiment the antibody of the invention is a humanized antibody. In a further embodiment said humanized antibody is obtained through the resurfacing technology. Such antibodies may also be called "resurfaced" antibodies.

The antibody according to the invention may also be a single domain antibody or a fragment thereof. In particular, a single domain antibody fragment may consist of a variable heavy chain (VHH) which comprises the CDR1-H, CDR2-H and CDR3-H of the antibodies as described above. The antibody may also be a heavy chain antibody, i.e. an antibody devoid of light chain, which may or may not contain a CH1 domain.

The single domain antibody or a fragment thereof may also comprise the framework regions of a camelid single domain antibody, and optionally the constant domain of a camelid single domain antibody.

The antibody according to the invention may also be an antibody fragment, in particular a humanised antibody fragment, selected from the group consisting of Fv, Fab, F(ab')2, Fab', dsFv, (dsFv)2, scFv, sc(Fv)2, and diabodies.

The antibody may also be a bispecific or multispecific antibody formed from antibody fragments, at least one antibody fragment being an antibody fragment according to the invention. Multispecific antibodies are polyvalent protein complexes as described for instance in EP 2 050 764 A1 or US 2005/0003403 A1.

The bispecific or multispecific antibodies according to the invention can have specificity for (a) the first to third loops, in particular to the first lumenal domain on human/*Macaca fascicularis* LAMP1 targeted by one of the so-called MAb1, MAb2, MAb2$_{Can}$, MAb3, MAb3_VLR24-R93 antibodies and (b) at least one other antigen. According to an embodiment the at least one other antigen is not a human or *Macaca fascicularis* LAMP1 family member, and in particular not at least one or all of human and *Macaca fascicularis* LAMP2. According to another embodiment, the at least one other antigen may be an epitope on human *Macaca fascicularis* LAMP1 other than said first to third loops, in particular first lumenal domain targeted by one of the so-called MAb1, MAb2, MAb2 C$_{an}$ and MAb3 antibodies.

Said antibodies can be produced by any technique well known in the art. In particular said antibodies are produced by techniques as hereinafter described.

Antibodies and fragments thereof according to the invention can be used in an isolated (e.g., purified) from or contained in a vector, such as a membrane or lipid vesicle (e.g. a liposome).

The antibodies of the invention may represent any combination of the above mentioned features.

Nucleic Acids, Vectors and Recombinant Host Cells

A further object of the invention relates to a nucleic acid sequence comprising or consisting of a sequence encoding an antibody of the invention as defined above.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for animal cell include enhancer and promoter of human cytomegalovirus (Nelson, J., 1996 J. Virology 70: 3207-3986), early promoter and enhancer of SV40 (Mizukami, T. and Itoh, S. et al., 1987, J Biochem. 101(5): 1307-1310), LTR promoter and enhancer of Moloney mouse leukemia virus (Kuwana Y. et al., 1987, Biochem Biophys Res Commun. 149: 960-968), promoter (Mason, J. O. et al., 1985, Cell 41: 479-487) and enhancer (Gillies, S. D. et al., 1983, Cell 33: 717-728) of immunoglobulin H chain and the like.

Any expression vector for animal cell can be used, so long as a gene encoding the human antibody C region can be inserted and expressed. Examples of suitable vectors include pAGE107 (Miyaji, H. et al., 1990, Cytotechnology 3(2): 133-140), pAGE103 (Mizukami, T. and Itoh, S. et al., 1987, J Biochem. 101(5): 1307-1310), pHSG274 (Brady, G. et al., 1984, Gene 27(2): 223-232), pKCR (O'Hare, K. et al., 1981, Proc Natl Acad Sci USA. 78(3): 1527-1531), pSG1 beta d2-4-(Miyaji, H. et al., 1990, Cytotechnology 4: 173-180) and the like.

Other examples of plasmids include replicating plasmids comprising an origin of replication pCEP5, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce a recombinant antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, HEK293 cells etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub, G. et al.; 1980, Proc Natl Acad Sci USA. 77(7): 4216-4220), rat YB2/3HL.P2.G11.16Ag.20 cell (ATCC CRL1662, hereinafter referred to as "YB2/0 cell"), and the like. The YB2/0 cell is of interest, since ADCC activity of chimeric or humanised antibodies is enhanced when expressed in this cell.

In particular, for expression of humanised antibody, the expression vector may be either of a type in which a gene encoding an antibody heavy chain and a gene encoding an antibody light chain exists on separate vectors or of a type in which both genes exist on the same vector (tandem type). In respect of easiness of construction of a humanised antibody expression vector, easiness of introduction into animal cells, and balance between the expression levels of antibody H and L chains in animal cells, humanised antibody expression vector of the tandem type is preferred (Shitara, K. et al., 1994, J Immunol Methods. January 3: 167(1-2): 271-8). Examples of tandem type humanised antibody expression vector include pKANTEX93 (WO 97/10354), pEE18 and the like.

The present invention also relates to a method of producing a recombinant host cell expressing an antibody according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody.

Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or immunoglobulin chains, by standard techniques for production of polypeptides. For instance, they can be synthesized using well-known solid phase method, in particular using a commercially available peptide synthesis apparatus (such as that made by Applied Biosystems, Foster City, Calif.) and following the manufacturer's instructions. Alternatively, antibodies and immunoglobulin chains of the invention can be synthesized by recombinant DNA techniques as is well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In particular, the invention further relates to a method of producing an antibody of the invention, which method comprises the steps consisting of: (i) culturing a transformed host cell according to the invention; (ii) expressing said antibody or polypeptide; and (iii) recovering the expressed antibody or polypeptide.

Methods for producing humanised or chimeric antibodies involve conventional recombinant DNA and gene transfection techniques are well known in the art (See Morrison, S. L. and Oi, V. T., 1984, Annu Rev Immunol 2: 239-256 and patent documents U.S. Pat. No. 5,202,238; and U.S. Pat. No. 5,204,244).

In a particular embodiment, a chimeric antibody of the present invention can be produced by obtaining nucleic sequences encoding the murine VL and VH domains as previously described, constructing a chimeric antibody expression vector by inserting them into an expression vector for animal cell having genes encoding human antibody CH and human antibody CL, and expressing the coding sequence by introducing the expression vector into an animal cell.

In another particular embodiment, a humanised antibody of the present invention can be produced by obtaining nucleic sequences encoding humanised VL and VH domains as previously described, constructing a humanised antibody expression vector by inserting them into an expression vector for animal cell having genes encoding human antibody CH and human antibody CL, and expressing the coding sequence by introducing the expression vector into an animal cell.

As the CH domain of a humanized or chimeric antibody, it may be any region which belongs to human immunoglobulin heavy chains, but those of IgG class are suitable and any one of subclasses belonging to IgG class, such as IgG1, IgG2, IgG3 and IgG4, can also be used. Also, as the CL of a human chimeric antibody, it may be any region which belongs to human immunoglobulin light chains, and those of kappa class or lambda class can be used.

Antibodies can be humanised using a variety of techniques known in the art including, for example, the technique disclosed in the application WO2009/032661, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka, G. M. et al., 1994, Protein Eng. 7(6): 805-814; Roguska, M. A. et al., 1994, Proc Natl Acad Sci USA 91(3): 969-973), and chain shuffling (U.S. Pat. No. 5,565,332) The general recombinant DNA technology for preparation of such antibodies is also known (see European Patent Application EP 125023 and International Patent Application WO 96/02576).

Antibodies of the invention are suitably separated from the culture medium by conventional immunoglobulin purification procedures such as, for example protein A affinity chromatography, ceramic hydroxyapatite chromatography, mixed-mode chromatography, size-exclusion chromatography etc.

The Fab of the present invention can be obtained by treating an antibody which specifically reacts with LAMP1 with a protease, such as papaine. Also, the Fab can be produced by inserting DNA sequences encoding both chains of the Fab of the antibody into a vector for prokaryotic expression, or for eukaryotic expression, and introducing the vector into procaryotic or eukaryotic cells (as appropriate) to express the Fab.

The F(ab')2 of the present invention can be obtained treating an antibody which specifically reacts with LAMP1 with a protease, pepsin. Also, the F(ab')2 can be produced by binding Fab' described below via a thioether bond or a disulfide bond.

The Fab' of the present invention can be obtained treating F(ab')2 which specifically reacts with LAMP1 with a reducing agent, such as dithiothreitol. Also, the Fab' can be produced by inserting DNA sequences encoding Fab' chains of the antibody into a vector for prokaryotic expression, or a vector for eukaryotic expression, and introducing the vector into prokaryotic or eukaryotic cells (as appropriate) to perform its expression.

The scFv of the present invention can be produced by taking sequences of the CDRs or VH and VL domains as previously described, constructing a DNA encoding an scFv fragment, inserting the DNA into a prokaryotic or eukaryotic expression vector, and then introducing the expression vector into prokaryotic or eukaryotic cells (as appropriate) to express the scFv. To generate a humanised scFv fragment, a well known technology called CDR grafting may be used, which involves selecting the complementary determining regions (CDRs) according to the invention, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

The single chain antibody or VHH directed against LAMP1 may be obtained for instance by a method comprising the steps of (a) immunizing a mammal belonging to the *Camelidae* with LAMP1 or a fragment thereof, so as to elicit antibodies (and in particular heavy chain antibodies) against LAMP1; (b) obtaining a biological sample from the *Camelidae* thus immunized, said sample comprising heavy chain antibody sequences and/or $V_{HH}$ sequences that are directed against LAMP1; and (c) recovering (e.g. isolating) heavy chain antibody sequences and/or $VH_H$ sequences that are directed against LAMP1 from said biological sample. Suitable single chain antibody or VHH may also be obtained by screening a library comprising heavy chain antibody sequences and/or VHH sequences for heavy chain antibody sequences and/or VHH sequences that compete for binding to the first to third loops, in particular to the first lumenal domain of human and *Macaca fascicularis* LAMP1 proteins with an antibody comprising the variable heavy and light chains of an antibody selected from the group consisting of the so-called antibodies MAb1, MAb2, MAb2$_{Can}$, MAb3, huMAb1_1 and huMAb1_2, huMAb1_3, for instance MAb1, MAb2, MAb2$_{Can}$, MAb3.

Modification of the Antibodies of the Invention

Amino acid sequence modification(s) of the antibodies described herein are contemplated. For example, it may be desirable to improve the binding affinity and/or other biological properties of the antibody.

Modifications and changes may be made in the structure of the antibodies of the present invention, and in the DNA sequences encoding them, and still result in a functional antibody or polypeptide with desirable characteristics.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate −3.5); asparagine (−3.5); lysine (−3.9); and arginine (−4.5).

A further object of the present invention also encompasses function-conservative variants of the polypeptides of the present invention.

For example, certain amino acids may be substituted by other amino acids in a protein structure without appreciable loss of activity. Since the interactive capacity and nature of a protein define its biological functional activity, certain amino acid substitutions can be made in a protein sequence, and of course in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein. It is also possible to use well-established technologies, such as alanine-scanning approaches, to identify, in an antibody or polypeptide of the invention, all the amino acids that can be substituted without significant loss of binding to the antigen. Such residues can be qualified as neutral, since they are not involved in antigen binding or in maintaining the structure of the antibody. One or more of these neutral positions can be substituted by alanine or by another amino acid can without changing the main characteristics of the antibody or polypeptide of the invention.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron, P. C. et al., 1992, J Exp Med. 176(4): 1191-1195 and Shopes B., 1992, J Immunol. 148(9): 2918-2922)

Another type of amino acid modification of the antibody of the invention may be useful for altering the original glycosylation pattern of the antibody, i.e. by deleting one or more carbohydrate moieties found in the antibody, and/or adding one or more glycosylation sites that are not present in the antibody. The presence of either of the tripeptide sequences asparagine-X-serine, and asparagine-X-threonine, where X is any amino acid except proline, creates a potential glycosylation site. Addition or deletion of glycosylation sites to the antibody is conveniently accomplished by altering the amino acid sequence such that it contains one or more of the above-described tripeptide sequences (for N-linked glycosylation sites).

Another type of modification of the antibody of the invention may be to remove a lysine in a CDR or spacially close to a CDR since covalent attachment to cytotoxic via lysine side chain residue may interfere with binding to antigen in the case of ADC.

Another type of modification involves the removal of sequences identified, either in silico or experimentally, as potentially resulting in degradation products or heterogeneity of antibody preparations. As examples, deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in an antibody or polypeptide of the invention, it may therefore be desirable to remove the site, typically by conservative substitution to remove one of the implicated residues. Such substitutions in a sequence to remove one or more of the implicated residues are also intended to be encompassed by the present invention.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, or tyrosine, (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr, H. et al. (1987, Arch Biochem Biophys. 259(1): 52-57) and by Edge, A. S. et al. (1981, Anal Biochem. 118(1): 131-137). Enzymatic cleavage of carbohydrate moieties on antibodies can be achieved by the use of a variety of endo- and exo-glycosidases as described by Thotakura, N R. et al. (1987, Methods Enzymol 138: 350-359).

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. Nos. 4,640,835; 4,496, 689; 4,301, 144; 4,670, 417; 4,791, 192 or 4,179,337.

Pharmaceutical Compositions

The antibodies or immunoconjugates of the invention may be combined with pharmaceutically acceptable excipients, and optionally sustained-release matrices, such as biodegradable polymers, to form therapeutic compositions.

Thus, another object of the invention relates to a pharmaceutical composition comprising an antibody or an immunoconjugate of the invention and a pharmaceutically acceptable carrier.

The invention also relates to a polypeptide or an immunoconjugate according to the invention, for use as a medicament.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and gender of the patient, etc.

The pharmaceutical compositions of the invention can be formulated for a topical, oral, parenteral, intranasal, intravenous, intramuscular, subcutaneous or intraocular administration and the like.

In particular, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody or immunoconjugate of the invention may be dissolved or dispersed in a pharmaceutically acceptable carrier or aqueous medium.

The pharmaceutical forms suitable for injectable use include sterile aqueous solutions or dispersions; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (for example, glycerol, propylene glycol, and liquid polyethylene glycol, and the like), suitable mixtures thereof. The proper fluidity can be maintained, for example, by the use of a coating, such as lecithin, by the maintenance of the required particle size in the case of dispersion and by the use of surfactants, stabilizing agents, cryoprotectants or antioxidants. The prevention of the action of microorganisms can be brought about by antibacterial and antifungal agents. In many cases, it will be preferable to include isotonic agents, for example, sugars or sodium chloride.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibody or immunoconjugate of the invention of the invention may be formulated within a therapeutic mixture to comprise about 0.01 to 100 milligrams, per dose or so.

Therapeutic Methods and Uses

The inventors have shown that an antibody directed against the first to third loops of LAMP1, in particular against the first lumenal domain of LAMP1, in particular MAb1 and MAb2 and Mab3, is able to actively internalize the LAMP1 receptor-antibody complex after binding and accumulate probably via coated pits. Internalized antibodies MAb1, MAb2 and Mab3 localized to early endosomes and subsequently trafficked to and accumulation in lysosomal compartments.

ImageStream multispectral imaging flow cytometer (Amnis corp.) reveals that the internalized antibodies accumulate in lysosomal compartments. Immunofluorescence analysis of viable Colo205 cells incubated with MAb1, MAb2 and MAb3 at 4° C. showed distinct plasma membrane staining. Incubation of cells at 37° C. with MAb1, MAb2 and MAb3 revealed labeling of both plasma membrane and intracellular vesicles after 4 hours incubation. Since the internalization score (IS) revealing the fluorescence inside cells (as measured at 37° C.) is 10-fold higher than the fluorescence at the cell surface (as measured at 4° C.), this means that the LAMP1 protein is quickly recycling at cell membrane. All together, our results show for the first time that LAMP1 might function as a receptor mediating the internalization of antibodies and suggest that availability of specific internalizing antibodies should aid in developing novel therapeutic methods to target toxins, drugs or short-range isotopes to be delivered specifically to the interior of the cancer cells.

Furthermore, they have shown that an antibody according to the invention, combined with a cytotoxic maytansinoid (DM4), induces cytotoxic activity in vitro on human HCT116 tumor or HEK293 cells containing a stable integration of the LAMP1 coding DNA sequence in the genomic DNA wherein individual clones present different intensities of LAMP1 on the cell surface.

In another example 9.4, the inventors showed that an antibody according to the invention, combined with a cytotoxic tomamycin dimer, induces cytotoxic activity in vitro.

They have also shown that an antibody combined with a cytotoxic maytansinoid (DM4) induces a marked anti-tumor activity in vivo in a murine model of primary human colon adenocarcinoma xenografts derived from patient, when used at a dose of 10 mg/kg, 5 mg/kg and 2.5 mg/kg, with a single injection at day 17 post tumor implantation as described in example 10.1.1.

Furthermore, they have also shown that this immunoconjugate induces a marked anti-tumor activity in vivo in a murine model of primary human lung tumor xenografts derived from patient, when used at a dose of 10 mg/kg, 5 mg/kg and 2.5 mg/kg, with a single injection at day 26 post tumor implantation as described in example 10.1.2.

The inventors have also shown that the immunoconjugates of DM4-SPDB-huMAb1_1, DM4-SPDB-chMAb2, DM4-SPDB-chMAb3 induce a marked anti-tumor activity in vivo in different murine model of different cancer xenograft models as shown in example 10.2-10.4.

For example, it was shown the immunoconjugate DM4-SPDB-huMAb1_1 induces a marked anti-tumor activity in vivo primary human invasive ductal carcinoma xenograft and primary human lung tumor xenograft derived from patient, when used at a dose of 10 mg/kg, 5 mg/kg and 2.5 mg/kg, with a single injection, as described in example 10.2.2 and 10.2.3.

Also the immunoconjugates DM4-SPDB-chMAb2 and DM4-SPDB-chMAb3 induce a marked anti-tumor activity in primary human invasive ductal carcinoma xenograft derived from patient, when used at a dose of 10 mg/kg, 5 mg/kg and 2.5 mg/kg or 5 mg/kg, 2.5 mg/kg and 1.25 mg/kg, respectively, with a single injection, as described in example 10.3.2 and 10.4.

Thus, polypeptides, antibodies, immunoconjugates, or pharmaceutical compositions of the invention may be useful for treating cancer.

The invention further relates to an anti-LAMP1 therapeutic agent for use for treating cancer in a patient harboring LAMP1 gene copy number gain in cancer cells.

In an embodiment, said patient harboring LAMP1 gene copy number gain in cancer cells has been selected by the in vitro method of selecting patients with cancer according to the invention. In particular, the use comprises selecting said patient harboring LAMP1 gene copy number gain in cancer cells by a method of selecting patients with cancer according to the invention.

The invention also relates to a method of treating a patient with cancer which comprises
a) selecting a patient with cancer who is likely to respond to anti-LAMP1 therapy by a in vitro method of selecting patients with cancer according to the invention; and
b) administering anti-LAMP1 therapy to said selected patient.

The invention further relates to a method of selecting a patient with cancer for anti-LAMP1 therapy, comprising:
(a) determining, in a biological sample of a patient with cancer which includes cancer cells, if said patient harbors a LAMP1 gene copy number gain; and
(b) administering to said patient anti-LAMP1 therapy, if said patient harbors a LAMP1 gene copy number gain.

The invention also relates to a method of treating cancer in a patient, comprising:
(a) determining, in a biological sample of a patient with cancer which includes cancer cells, if said patient harbors a LAMP1 gene copy number gain; and
(b) administering to said patient anti-LAMP1 therapy, if said patient harbors a LAMP1 gene copy number gain.

The cancer to be treated with antibodies, immunoconjugates, or pharmaceutical compositions of the invention is a cancer expressing LAMP1 on the cell surface, in particular overexpressing LAMP1 on the cell surface as compared to normal (i.e. non tumoral) cells of the same tissular origin.

Expression of LAMP1 by cancer cells may be readily assayed for instance by using an antibody according to the invention, as described in the following section "Diagnostic uses", and in particular by an immunohistochemical method fo instance as described in Example 5.

In particular the cancer may be colon adenocarcinomas but also gastrointestinal tumors (small intestine, rectum, parotid gland), vital organs tumors (lung, liver, pancreas, stomach and kidney), reproductive organ tumors (breast, ovary and prostate) as well as skin, larynx and soft tissue tumors, for instance the cancer is selected from the group consisting of colon adenocarcinoma, gastrointestinal tumors (small intestine, rectum, parotid gland), vital organs tumors (lung, liver, pancreas and kidney), reproductive organ tumors (breast, ovary and prostate) as well as skin, larynx or soft tissue tumors.

In one embodiment gastrointestinal tumors are small intestine tumor, rectum tumor and/or parotid gland tumor.

In one embodiment reproductive organ tumors gastrointestinal tumors are lung tumor, liver tumor, pancreas tumor, stomach tumor and kidney tumor.

In one embodiment reproductive organ tumors are breast tumor, ovary tumor or prostate tumor.

Screening of a panel of human tumors by immunohistochemistry using a mouse anti-human LAMP1 antibody according to the invention indeed showed antibody staining in these types of cancers, as described in further details in Example 5.

In particular, LAMP1 expressing human tumoral cells may be selected from the group consisting of colon, stomach, rectum, lung squamous cell carcinoma, breast invasive ductal and lobular carcinoma and prostate adenocarcinoma cells. These tumors were indeed found to display more than 50% of cells positive for LAMP1 expression at the cell membrane (see example 5).

The antibodies or immunoconjugates of the invention may be used alone or in combination with any suitable growth-inhibitory agent.

The antibodies of the invention may be conjugated or linked to a growth inhibitory agent, cytotoxic agent, or a prodrug-activating enzyme as previously described. Antibodies of the invention may be indeed useful for targeting said growth inhibitory agent, cytotoxic agent, or a prodrug to the cancerous cells expressing or over-expressing LAMP1 on their surface.

It is also well known that therapeutic monoclonal antibodies can lead to the depletion of cells bearing the antigen specifically recognized by the antibody. This depletion can be mediated through at least three mechanisms: antibody mediated cellular cytotoxicity, complement dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 was also contemplated. It is known to the skilled in the art that specific mutations such as the D265A mutation according to the nomenclature described by Kabat et al. (Sequences of Proteins of Immunological Interest, 5th edition, National Institute of Health, Bethesda, Md., 1991) significantly decrease binding to Fc☐Rs and ADCC (Lund et al., J. Immunol., 157:4963-4969, 1996; Shields et al., J. Biol. Chem., 276(1): 6591-6604, 2001).

In one example the mutation of 266A of for example SEQ ID NO: 56 in the huIgG1 corresponds to the D265A mutation mentioned above and thus significantly decrease binding to Fc☐Rs and ADCC.

Thus, an object of the invention relates to a method for treating a cancer comprising administering a subject in need thereof with a therapeutically effective amount of a polypeptide, an antibody, an immunoconjugate or a pharmaceutical composition of the invention.

"Antibody-dependent cellular phagocytosis" or "ADCP" refers to a form of cytotoxicity in which antibodies bound onto Fc receptors (FcRs) present on certain cytotoxic cells (e.g. macrophages) enable these cytotoxic effector cells to bind specifically to an antigen-bearing target cell and subsequently kill the target cell by phagocytosis. To assess ADCP activity of a molecule of interest, an in vitro ADCP assay, such as that described in McEarchem et al., 2007, Blood 109:1185.

In the context of the invention, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth of malignant cells of a tumour and/or the progression of metastases from said tumor. Such treatment can also lead to the regression of tumor growth, i.e., the decrease in size of a measurable tumor. In particular, such treatment leads to the complete regression of the tumor or metastase.

According to the invention, the term "patient" or "patient in need thereof" is intended for a human or non-human mammal affected or likely to be affected with a malignant tumor. In particular, said patient may be a patient who has been determined to be susceptible to a therapeutic agent targeting LAMP1, in particular to an antibody or immunoconjugate according to the invention, for instance according to a method as described herebelow.

As disclosed above, "anti-LAMP1 therapy" is a therapy which involves a therapeutic agent targeting LAMP1. According to the invention, the term "therapeutic agent targeting LAMP1" or "anti-LAMP1 therapeutic agent" describe an agent binding to LAMP1 and having cytotoxic and/or cytostatic activity.

As used herein, the term "binding agent" refers to a molecule that exhibits specific binding activity towards LAMP1. Such a binding molecule can include a variety of different types of molecules including, for example, macromolecules and small organic molecules. Small molecule binding agents can include, for example, receptor ligands, antagonists and agonists. Macromolecules can include, for example, peptide, polypeptide and protein, nucleic acids encoding polypeptide binding agents, lectins, carbohydrate and lipids. It is understood that the term includes fragments and domains of the agent so long as binding function is retained. Similarly, the boundaries of the domains are not critical so long as binding activity is maintained. In the specific example where the binding agent is a peptide, polypeptide or protein, such binding proteins can include monomeric or multimeric species. Heteromeric binding proteins are a specific example of multimeric binding proteins. It is understood that when referring to multimeric binding proteins that the term includes fragments of the subunits so long as assembly of the polypeptides and binding function of the assembled complex is retained. Heteromeric binding proteins include, for example, antibodies and fragments thereof such as Fab and F(ab')2 portions.

According to an embodiment, the anti-LAMP1 therapeutic agent is an anti-LAMP1 antibody or an immunoconjugate comprising an anti-LAMP1 antibody and at least one growth inhibitory agent.

By a "therapeutically effective amount" of the polypeptide of the invention is meant a sufficient amount of the polypeptide to treat said cancer disease, at a reasonable benefit/risk ratio applicable to any medical treatment. It will be understood, however, that the total daily usage of the polypeptides and compositions of the present invention will be decided by the attending physician within the scope of sound medical judgment. The specific therapeutically effective dose level for any particular patient will depend upon a variety of factors including the disorder being treated and the severity of the disorder; activity of the specific polypeptide employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. Another object of the invention relates to a polypeptide, an antibody, an immunoconjugate or a pharmaceutical composition of the invention for use in the treatment of a malignant tumour.

In particular, the polypeptide, antibody, immunoconjugate or pharmaceutical composition may be used for inhibiting the progression of metastases of a malignant tumour.

Polypeptides of the invention may be used in combination with any other therapeutical strategy for treating malignant tumour (e.g. adjuvant therapy), and/or for reducing the growth of the metastatic tumour.

Efficacy of the treatment with an antibody or immunoconjugate according to the invention may be readily assayed in vivo, for instance on a mouse model of cancer and by measuring e.g. changes in tumor volume between treated and control groups, % tumor regression, partial regression and/or complete regression as defined in Example 10.

In one embodiment, the antibody is one of the anti-LAMP1 antibodies developed by the applicant (the so-called antibodies "MAb1", "MAb2", "MAb3", huMAb1_1 and huMAb1_2, huMAb1_3) that bind specifically to human LAMP1 and distinguish tumoral from non-tumoral tissues as further described in the section "Antibodies" above.

Diagnostic Uses

The antibody according to the invention revealed that some LAMP1 expression occurred at the membrane of non-tumoral cells but was restricted to stomach epithelial cells, oesophageal epithelial cells, breast epithelial cells, prostate epithelial cells, testicular epithelial cells and limited to a few cells. Nevertheless, prevalence and mean intensities for LAMP1 expression at the membrane of non-tumoral samples were lower than those found in tumours.

Instead, LAMP1 is highly expressed at the surface of a variety other carcinomas than colon adenocarcinomas, including gastrointestinal tumors (small intestine, rectum, parotid gland), vital organs tumors (lung, liver, stomach, pancreas and kidney), reproductive organ tumors (breast, ovary and prostate) as well as skin, larynx and soft tissue tumors, for example gastrointestinal tumors (small intestine, rectum, parotid gland), vital organs tumors (lung, liver, pancreas and kidney), reproductive organ tumors (breast, ovary and prostate) as well as skin, larynx and soft tissue tumors. Therefore, LAMP1 constitutes a marker of certain cancers and, therefore, has the potential to be used to indicate the effectiveness of an anti-cancer therapy or detecting recurrence of the disease.

In particular, LAMP1 is highly expressed at the surface of carcinomas selected from the group consisting of colon, rectum, lung squamous cell carcinoma, stomach, breast invasive ductal and lobular carcinoma and prostate adenocarcinoma cells, more particularly colon, rectum, lung squamous cell carcinoma, breast invasive ductal and lobular carcinoma and prostate adenocarcinoma cells.

As described above in the chapter 'antibodies', the inventors developped antibodies MAb1, MAb2, MAb3 allowing for the first time to detect extracellularly expressed LAMP1 and thus to perform IHC analysis on Frozen-OCT (from Optimal Cutting Temperature) specimens and AFA (Alcohol Formalin Acetic acid Fixative) and MAb4 allowing LAMP1 reinforcement in FFPE format and thus allows to distinguish cancerous from non-cancerous tissue.

In a preferred embodiment, the antibody of the invention is used as component of an assay in the context of a therapy targeting LAMP1 expressing tumours, in order to determine susceptibility of the patient to the therapeutic agent, monitor the effectiveness of the anti-cancer therapy or detect recurrence of the disease after treatment. In particular, the same antibody of the invention is used both as component of the therapeutic agent and as component of the diagnostic assay.

Thus, a further object of the invention relates to an antibody according to the invention for use for in vivo detecting LAMP1 expression in a subject, or for use for ex vivo detecting LAMP1 expression in biological sample of a subject. Said detection may be intended in particular for a) diagnosing the presence of a cancer in a subject, or b) determining susceptibility of a patient having cancer to a therapeutic agent targeting LAMP1, in particular an immunoconjugate according to the invention, or c) monitoring effectiveness of anti-LAMP1 cancer therapy or detecting cancer relapse after anti-LAMP1 cancer therapy, in particular for therapy with an immunoconjugate according to the invention by detecting expression of the surface protein LAMP1 on tumor cells.

In an embodiment, the antibody is intended for an in vitro or ex vivo use. For example, LAMP1 may be detected in vitro or ex vivo in a biological sample obtained from a subject, using an antibody of the invention. The use according to the invention may also be an in vivo use. For example, an antibody according to the invention is administered to the subject and antibody-cell complexes are detected and/or quantified, whereby the detection of said complexes is indicative of a cancer.

The invention further relates to an in vitro or ex vivo method of detecting the presence of a cancer in a subject, comprising the steps consisting of:

a) contacting a biological sample of a subject with an antibody according to the invention, in particular in conditions sufficient for the antibody to form complexes with said biological sample, b) measuring the level of antibody bound to said biological sample, c) detecting the presence of a cancer by comparing the measured level of bound antibody with a control, an increased level of bound antibody compared to control being indicative of a cancer.

The invention also relates to an in vitro or ex vivo method of determining susceptibility of a patient having cancer to a therapeutic agent targeting LAMP1, in particular to an immunoconjugate according to the invention, which method comprises the steps consisting of:

a) contacting a biological sample sample of a patient having cancer with an antibody according to the invention, in particular in conditions sufficient for the antibody to form complexes with said biological sample, b) measuring the level of antibody bound to said biological sample sample, c) comparing the measured level of bound antibody to said biological sample sample with the level of antibody bound to a control, wherein an increased level of bound antibody to said biological sample sample compared to control is indicative of a patient susceptible to a therapeutic agent targeting LAMP1.

In the above methods, said control can be a normal, non cancerous, biological sample of the same type, or a reference value determined a representative of the antibody binding level in normal biological sample of the same type. In an embodiment, the antibodies of the invention are useful for diagnosing a LAMP1 expressing cancer, such as a colon adenocarcinoma, gastrointestinal tumors (small intestine, rectum, parotid gland), vital organs tumors (lung, liver, pancreas and kidney), reproductive organ tumors (breast, ovary and prostate) as well as skin, larynx and soft tissue tumors.

The invention further relates to an in vitro or ex vivo method of monitoring effectiveness of anti-LAMP1 cancer therapy, comprising the steps consisting of:

a) contacting a biological sample of a subject undergoing anti-LAMP1 cancer therapy, with an antibody according to the invention, in particular in conditions sufficient for the antibody to form complexes with said biological sample, b) measuring the level of antibody bound to said biological sample, c) comparing the measured level of bound antibody with the level of antibody bound to a control;

wherein a decreased level of bound antibody to said biological sample compared to control is indicative of effectiveness of said anti-LAMP1 cancer therapy.

In said method, an increased level of bound antibody to said biological sample compared to control is indicative of ineffectiveness of said anti-LAMP1 cancer therapy.

Said control is in particular a biological sample of the same type as the biological sample submitted to analysis, but which was obtained from the subject previously in time, during the course of the anti-LAMP1 cancer therapy.

The invention further relates to an in vitro or ex vivo method of detecting cancer relapse after anti-LAMP1 cancer therapy, comprising the steps consisting of:

(a) contacting a biological sample of a subject having completed anti-LAMP1 cancer therapy, with an antibody according to the invention, in particular in conditions sufficient for the antibody to form complexes with said biological sample, (b) measuring the level of antibody bound to said biological sample, (c) comparing the measured level of bound antibody with the level of antibody bound to a control, wherein a increased level of bound antibody to said biological sample compared to control is indicative of cancer relapse after anti-LAMP1 cancer therapy.

Said control is in particular a biological sample of the same type as the biological sample submitted to analysis, but which was obtained from the subject previously in time, upon or after completion of the anti-LAMP1 cancer therapy.

Said anti-LAMP1 cancer therapy is in particular a therapy using an antibody or immunoconjugate according to the invention. Said anti-LAMP1 cancer therapy targets a LAMP1 expressing cancer, in particular a colon adenocarcinoma, gastrointestinal tumors (small intestine, rectum, parotid gland), vital organs tumors (lung, liver, pancreas, stomach and kidney), reproductive organ tumors (breast, ovary and prostate) as well as skin, larynx and soft tissue tumors.

In an embodiment, antibodies of the invention may be labelled with a detectable molecule or substance, such as a fluorescent molecule, a radioactive molecule or any other labels known in the art that provide (either directly or indirectly) a signal.

As used herein, the term "labeled", with regard to the antibody according to the invention, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the polypeptide, as well as indirect labeling of the polypeptide by reactivity with a detectable substance.

An antibody of the invention may be labelled with a radioactive molecule by any method known to the art. For example radioactive molecules include but are not limited radioactive atom for scintigraphic studies such as $I^{123}$, $I^{124}$, $I^{125}$, $In^{111}$, $Re^{186}$, $Re^{188}$, $Tc^{99}$, and isotopes for Positron Emission Tomography such as $Zr^{89}$, $I^{124}$, $Ga^{68}$ or $Cu^{64}$.

A "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. Therefore, biological samples encompass clinical samples, cells in culture, cell supernatants, cell lysates, serum, plasma, biological fluid, and tissue samples, in particular tumor sample.

In particular, the biological tissues may be prepared as frozen-OCT (Optimal Cutting Temperature) or AFA (acetic formalin alcohol) samples. Indeed, antibodies according to the invention can advantageously be used on AFA sample which is a format used by hospitals to collect and archive tissue samples.

Measuring or determining the level of antibody bound the said biological sample may be performed by any suitable method known in the art such as FACS or IHC, for instance.

The invention also relates to an in vivo method of detecting the presence of a cancer in a subject, comprising the steps consisting of:

a) administering an antibody according to the invention detectably labelled to a patient, b) detecting localisation of said detectably labelled antibody in the patient by imaging.

Antibodies of the invention may be useful for staging of cancer (e.g., in radioimaging). They may be used alone or in combination with other cancer markers.

The terms "detection" or "detected" as used herein includes qualitative and/or quantitative detection (measuring levels) with or without reference to a control.

In the content of the invention, the term "diagnosing", as used herein, means the determination of the nature of a medical condition intended to identify a pathology which affects the subject from a number of collected data.

In said method, the cancer is a LAMP1 expressing cancer, in particular a colon adenocarcinoma, gastrointestinal tumors (small intestine, rectum, parotid gland), vital organs tumors (lung, liver, pancreas and kidney), reproductive organ tumors (breast, ovary and prostate) as well as skin, larynx and soft tissue tumors.

Method of Selecting Patients with Cancer

The invention relates to an in vitro method of selecting patients with cancer which comprises:
a) determining, in a biological sample of a patient with cancer which includes cancer cells, if said patient harbors a LAMP1 gene copy number gain; and
b) selecting the patient based on the presence of LAMP1 gene copy number gain.

In an embodiment, said method is for selecting a patient with cancer who is likely to respond to anti-LAMP1 therapy, and said patient is selected as likely to respond to anti-LAMP1 therapy if said patient harbors a LAMP1 gene copy number gain. If said patient does not harbor a LAMP1 gene copy number gain, the patients may nevertheless be selected as likely to respond to anti-LAMP1 therapy based, for instance, on the detection of cell surface expression of LAMP1 as expression or overexpression of LAMP1 at the surface of tumor cells may have other causes than LAMP1 gene copy number gain.

The LAMP1 gene gain can be related to a focal somatic gain or amplification, a somatic large region gain or amplification on 13q, a somatic chromosome duplication, a somatic chromosome triplication or polyploidy. LAMP1 gene copy number gain or amplification is included in a larger amplicon. The term "amplicon" as used herein refers to a segment of the genome that forms multiple linear copies. According to the invention, the amplicon which might undergo copy number variation leading to a LAMP1 gene copy number gain will be called herein LAMP1 amplicon.

Said "LAMP1 amplification" comprises a DNA region which can measure between 378 kb and 34.2 MB. Said "LAMP1 gain" comprises a DNA region wich can mesaure between 523 kb and 95.8 MB In one embodiment, the LAMP1 gene copy number gain can be signified by the CNV of a LAMP1 amplicon in colon PDX which comprises at least 454 kb from base 113785387 to base 114240314 on human chromosome 13 (NC_000013). Said minimal LAMP1 amplicon contains others genes than LAMP1, for example the genes ADPRHL1, CUL4A, DCUNID2, GRTP1, LAMP1, LOC100130463, PCID2, PRO7, TFDP1, TMCO3 and F10.

In another embodiment said LAMP1 amplicon comprises at least the genes ADPRHL1, ATP11A, ATP4B, CUL4A, DCUNID2, F10, F7, FAM70B, FLJ41484, FLJ44054, GAS6, GRK1, GRTP1, LAMP1, LINC00552, LOC100128430, LOC100130463, LOC100506063, LOC100506394, MCF2L, MCF2L-AS1, PCID2, PROZ, RASA3, TFDP1 and TMCO3C13orf35.

In a further embodiment the LAMP1 amplicon comprises 95.8 Mb from base 19,296,544 to base 115,107,245 on human chromosome 13 (NC_000013).

In the context of the present invention, the positions of the nucleotides are indicated accordingly to the NCBI human genome sequence (Build 37, February 2009). It is known to the one skilled in the art, that a genome sequence is variable from an individual to another. Therefore, the positions defined herein for the LAMP1 amplicon may slightly change according to the human genome sequence used. However, methods to compare genomic sequences and nucleotide positions are well known to the one skilled in the art.

There are numerous methods allowing determining the presence of a LAMP1 gene copy number change in biological samples which are well known from the one skilled in the art. These methods include, without being limited, hybridization methods with DNA probes specific of marker sequences, such as comparative genomic hybridization (CGH), matrix-CGH, array-CGH, oligonucleotide arrays, representational oligonucleotide microarray (ROMA), high-throughput technologies for SNP genotyping, for example Affymetrix SNP chips, and amplification methods such as quantitative PCR.

In particular, the presence of said marker LAMP1 gene copy number change is determined by amplification, or by hybridization with DNA probes specific for LAMP1 gene or genes included in the LAMP1 amplicon. In an embodiment, the method of the invention is implemented by Fluorescence In Situ Hybridization (FISH), Comparative Genomic Hybridization (CGH), New Generation Sequencing (NGS) and/or Polymerase Chain Reaction (PCR).

Accordingly, the invention relates to a method, wherein LAMP1 gene copy number gain is determined with a method selected from the group consisting of FISH, CGH, NGS and/or PCR.

Methods of quantitative PCR are well-known in the art and include real-time PCR, competitive PCR and radioactive PCR. For instance, a quantitative PCT method to enumerate DNA copy number has been described in the U.S. Pat. No. 6,180,349.

As used herein, the term "primer" refers to an oligonucleotide which is capable of annealing to a target sequence and serving as a point of initiation of DNA synthesis under conditions suitable for amplification of the primer extension product which is complementary to said target sequence. The primer is typically single stranded for maximum efficiency in amplification. In particular, the primer is an oligodeoxyribonucleotide. The length of the primer depends on several factors, including temperature and sequence of the primer, but must be long enough to initiate the synthesis of amplification products. In an embodiment the primer is from 15 to 35 nucleotides in length. A primer can further contain additional features which allow for detection, immobilization, or manipulation of the amplified product. The primer may furthermore comprise covalently-bound fluorescent dyes, which confer specific fluorescence properties to the hybrid consisting of the primer and the target-sequence or non covalently-bound fluorescent dyes which can interact with the double-stranded DNA/RNA to change the fluorescence properties. Fluorescent dyes which can be used are for example SYBR-green or ethidium bromide.

A "pair of primers" or "primer pair" as used herein refers to one forward and one reverse primer as commonly used in the art of DNA amplification such as in PCR amplification.

As used herein, a "probe" refers to an oligonucleotide capable of binding in a base-specific manner to a complementary strand of nucleic acid. A probe may be labeled with a detectable moiety. Various labeling moieties are known in the art. Said moiety may, for example, either be a radioactive compound, a detectable enzyme (e.g., horse radish peroxidase (HRP)) or any other moiety capable of generating a detectable signal such as calorimetric, fluorescent, chemiluminescent or electrochemiluminescent signal. The detectable moiety may be detected using known methods. A probe may vary in length from about 5 to 100 nucleotides, for instance from about 10 to 50 nucleotides, or from about 20 to 40 nucleotides. In an embodiment, a probe comprises 33 nucleotides.

The terms "hybridize" or "hybridization," as is known to those skilled in the art, refer to the binding of a nucleic acid molecule to a particular nucleotide sequence under suitable conditions, namely under stringent conditions.

The term "stringent condition" or "high stringency condition" as used herein corresponds to conditions that are suitable to produce binding pairs between nucleic acids having a determined level of complementarity, while being unsuitable to the formation of binding pairs between nucleic acids displaying a complementarity inferior to said determined level. Stringent conditions are the combination of both hybridization and wash conditions and are sequence dependent. These conditions may be modified according to methods known from those skilled in the art (Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, high stringency conditions are selected to be about 5° C. lower than the thermal melting point (Tm), for instance at a temperature close to the Tm of perfectly base-paired duplexes (Andersen, Nucleic acid Hybridization, Springer, 1999, p. 54). Hybridization procedures are well known in the art and are described for example in Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

High stringency conditions typically involve hybridizing at about 50° C. to about 68° C. in 5×SSC/5×Denhardt's solution/1.0% SDS, and washing in 0.2×SSC/0.1% SDS at about 60° C. to about 68° C.

In one embodiment, the invention relates to a method wherein the mean LAMP1 gene copy number in cancer cells is ≥2.5. In particular the mean LAMP1 gene copy number in cancer cells may be ≥2.5 and <5.

In one embodiment, the invention relates to a method wherein the mean LAMP1 gene copy number in cancer cells is ≥5.

The method of the invention can further comprise determining if LAMP1 is expressed at the surface of cancer cells of the patient, and i) said patient is selected as likely to respond to anti-LAMP1 therapy if said patient harbors a LAMP1 gene copy number gain and if said cancer cells of the patient express LAMP1 at their surface or ii) said patient is selected as unlikely to respond to anti-LAMP1 therapy if said cancer cells of the patient do not express LAMP1 at their surface.

There are numerous methods allowing determining if LAMP1 is expressed at the surface of cancer cells, or overexpressed as compared with normal cells (i.e. non tumoral) of the same tissular origin, as which are well known from the one skilled in the art. These methods include for example, without being limited, IHC, Western Blot (WB), Fluorescence activated cell sorting (FACS) analysis, immunofluorescence (IF), immunoprecipitation (IP) and Enzyme-linked immunosorbent assay (ELISA).

In an embodiment, immunohistochemistry (IHC) is used for determining if LAMP1 is expressed or over-expressed at the surface of cancer cells.

Expression of LAMP1 by cancer cells may be readily assayed for instance by using an anti-LAMP1 antibody as described in example 3.

The inventors showed that, LAMP1 gain is detected in 28 tumor types, including Colorectal adenocarcionoma, Stomach, Liver, Lung (Adenocarcinoma and Squamous), Breast (Basal, BRCA, LUMA, LUMB and HER2), Ovary, Head & neck, Kidney (Kidney Chromophobe, Kidney Renal Clear Cell Carcinoma, Kidney Renal Papilliary), Cell Carcinoma, Cervical squamous Cell, Pancreatic, Prostate, Bladder urothelial, Glioma (Low grade glyoma and Glioblastoma multiform), Uterus, Thyroid, Leukemia, Lymphoma, Esophageal, Melanoma and Soft tissue sarcoma. High gain or amplification is detected in, breast, cervical, colorectal, glioblastoma, head and neck, liver, lung, glioma, ovarian, stomach and uterine cancer.

Accordingly, in an embodiment of the method of the invention, the patient is having a cancer selected from the group consisting of colorectal, stomach, liver, lung, breast, ovarian, head and neck, kidney, pancreatic, prostate, uterine, glioma, bladder, thyroid cancer and leukemia, lymphoma, esophageal, melanoma and soft tissue sarcoma, for instance colorectal, stomach, liver, lung, ovarian, head and neck, kidney, pancreatic, prostate, uterine, glioma, bladder, thyroid cancer and leukemia, lymphoma, esophageal, melanoma and soft tissue sarcoma.

In a further embodiment the patient is having a cancer selected from the group consisting of, breast, cervical, colorectal, glioblastoma, head and neck, liver, lung, glioma, ovarian, stomach, and uterine cancer; or in particular from the group consisting of cervical, colorectal, glioblastoma, head and neck, liver, lung, glioma, ovarian, stomach, thyroid, and uterine cancer; or still more particularly from the group consisting of colon and lung cancer.

LAMP1 gene copy number gain and high expression of LAMP1 could be detected at the surface of cancers selected from the group consisting of colon, lung, liver, pancreatic, kidney breast, ovarian, prostate, stomach cancer.

Thus in one embodiment the cancer may be selected from colon, lung, liver, pancreatic, kidney, ovarian, prostate, stomach cancer, for example from colon, lung, liver, pancreatic, kidney, ovarian, prostate, stomach cancer.

Furthermore, LAMP1 gene copy gain is correlated with the LAMP1 mRNA expression in bladder, breast, colon, lung, stomach and ovarian cancer. A significant association is shown between LAMP1 gene copy number gain/amplification and the expression of LAMP1 at the plasma membrane of tumor cells for colon, stomach and lung tumor PDX.

Accordingly, in a further embodiment of the method of the invention, the patient is having a cancer selected from the group consisting of breast, colon, lung, stomach, and ovarian. In another embodiment, the patient is having a cancer selected from the group consisting of colon, lung, stomach and ovarian.

An "anti-LAMP1 therapy" is a therapy which involves a therapeutic agent targeting LAMP1. In one embodiment, such an anti-LAMP1 therapy is an anti-LAMP1 antibody or immunoconjugate. Anti-LAMP1 therapy is described in further details hereafter.

The cancer may be in particular bladder, cervical, colorectal, glioblastoma, head and neck, kidney, liver, lung, glioma, ovarian, pancreatic, prostate, stomach, thyroid, and uterine cancer. In another example the cancer is particularly colorectal or lung cancer.

Kits

Finally, the invention also provides kits comprising at least one antibody or immunoconjugate of the invention.

Kits containing antibodies of the invention find use in detecting the surface protein LAMP1, or in therapeutic or diagnostic assays. Kits of the invention can contain a polypeptide or antibody coupled to a solid support, e.g. a tissue culture plate or beads (e.g. sepharose beads). Kits can be provided which contain antibodies for detection and quantification of the surface protein LAMP1 in vitro, e.g. in an ELISA or a Western blot. Such an antibody useful for detection may be provided with a label such as a fluorescent or radiolabel.

The invention will be further illustrated in light of the following Figures and Examples.

BRIEF DESCRIPTION OF THE SEQUENCES

SEQ ID NO: 1 shows the VH sequence of the "MAb1" antibody.

SEQ ID NO: 2-4 show the sequences of the CDR1-H, CDR2-H, CDR3-H of the "MAb1" antibody.

SEQ ID NO: 5 shows the VL sequence of the "MAb1" antibody.

SEQ ID NO: 6-7 show the sequences of the CDR1-L, CDR3-L of the "MAb1" antibody.

SEQ ID NO: 8 shows the VH sequence of the "MAb2" antibody.

SEQ ID NO: 9-11 show the sequences of the CDR1-H, CDR2-H, CDR3-H of the "MAb2" antibody.

SEQ ID NO: 12 shows the VL sequence of the "MAb2" antibody.

SEQ ID NO: 13-14 show the sequences of the CDR1-L, CDR3-L of the "MAb2" antibody.

SEQ ID NO: 15 shows the VH sequence of the so-called "Mab2$_{Can}$" antibody.

SEQ ID NO: 16 shows the VL sequence of the so-called "Mab2$_{Can}$" antibody.

SEQ ID NO: 17 shows the sequence of the heavy chain of the chimeric antibody "chMAb1" antibody.

SEQ ID NO: 18 shows the sequence of the light chain of the chimeric antibody "chMAb1" antibody.

SEQ ID NO: 19 shows the sequence of the heavy chain of the chimeric antibody "chMAb2" antibody.

SEQ ID NO: 20 shows the sequence of the light chain of the chimeric antibody "chMAb2" antibody.

SEQ ID NO: 21 shows the sequence of the heavy chain of the chimeric antibody "chMab2$_{Can}$" antibody.

SEQ ID NO: 22 shows the sequence of the light chain of the chimeric antibody "chMab2$_{Can}$" antibody.

SEQ ID NO: 23 shows the DNA sequence of full-length human LAMP1 as available from GenBank database under accession number NM_005561.3.

SEQ ID NO: 24 shows the Protein sequence of full-length human LAMP1 as available from GenBank database under NP_005552.3.

SEQ ID NO: 25 shows the Protein sequence of full-length mouse LAMP1 as available from GenBank database under NP_034814

SEQ ID NO: 26 shows the Protein sequence of full-length rat LAMP1 as available from GenBank database under NP_036989.

SEQ ID NO: 27 shows the Protein sequence of full-length *Macaca mulatta* LAMP1 as available from GenBank database under XP_002723509.

SEQ ID NO: 28 shows the sequence of human LAMP1 extracellular domain without Peptide Signal, followed by C-terminal 6 amino acid His-Tag.

SEQ ID NO: 29 shows the sequence of cynomologous monkey LAMP1 extracellular domain without Peptide Signal, followed by C-terminal tag including 6 amino acid His-sequence.

SEQ ID NO: 30 shows the sequence of a human and mouse LAMP1 chimer containing mouse Loop1 region of LAMP1 and human Loop2-4 of LAMP1 without Peptide Signal, followed by C-terminal 6 amino acid His-Tag.

SEQ ID NO: 31 shows the sequence of a human and mouse LAMP1 chimer containing mouse Loop1-2 region of LAMP1 and human Loop3-4 of LAMP1 without Peptide Signal, followed by C-terminal 6 amino acid His-Tag.

SEQ ID NO: 32 shows the sequence of a human and mouse LAMP1 chimer containing human Loop1-2 region of LAMP1 and mouse Loop3-4 of LAMP1 without Peptide Signal, followed by C-terminal tag including 6 amino acid His sequence.

SEQ ID NO: 33 shows the sequence of a human and mouse LAMP1 chimer containing human Loop1-3 region of LAMP1 and mouse Loop4 of LAMP1 without Peptide Signal, followed by C-terminal tag including 6 amino acid His sequence.

SEQ ID NO: 34 shows the sequence of mouse LAMP1 extracellular domain without Peptide Signal, followed by C-terminal tag including 6 amino acid His sequence.

SEQ ID NO: 35 shows the light chain sequence of the "MAb1" antibody.

SEQ ID NO: 36 shows the heavy chain sequence of the "MAb1" antibody.

SEQ ID NO: 37 shows the light chain sequence of the "MAb2" antibody.

SEQ ID NO: 38 shows the heavy chain sequence of the "MAb2" antibody.

SEQ ID NO: 39 shows the predicted full-length LAMP1 protein sequence of *Macaca fascicularis*.

SEQ ID NO: 40 shows the sequence of human LAMP2 extracellular domain without Peptide Signal, followed by C-terminal 10 amino acid His-Tag.

SEQ ID NO: 41 shows the full-length protein sequence of human LAMP2.

SEQ ID NO: 42 shows the VH sequence of the "MAb3" antibody.

SEQ ID NO: 43-45 show the sequences of the CDR1-H, CDR2-H, CDR3-H of the "MAb3" antibody.

SEQ ID NO: 46 shows the VL sequence of the "MAb3" antibody.

SEQ ID NO: 47 and 48 show the sequences of the CDR1-L and CDR3-L of the "MAb3" antibody.

SEQ ID NO: 49 shows the sequence of the heavy chain of the chimeric antibody "chMAb3" antibody.

SEQ ID NO: 50 shows the sequence of the light chain of the chimeric antibody "chMAb3" antibody.

SEQ ID NO: 51 shows the sequence of the variable domain of light chain of antibody "MAb3 VL_R24_R93".

SEQ ID NO: 52 shows the sequence of CDR3-L of antibody "MAb3 VL_R24_R93".

SEQ ID NO: 53 shows the VH1 sequence of the humanized antibody "huMAb1_1" antibody.

SEQ ID NO: 54 shows the VH2 sequence of the humanized antibody "huMAb1_2" antibody.

SEQ ID NO: 55 shows the VH3 sequence of the humanized antibody "huMAb1_3" antibody.

SEQ ID NO: 56 shows the VL1 sequence of the humanized antibody "huMAb1_1" antibody.

SEQ ID NO: 57 shows the VL2 sequence of the humanized antibody "huMAb1_2" antibody.

SEQ ID NO: 58 shows the VL3 sequence of the humanized antibody "huMAb1_3" antibody.

SEQ ID NO: 59 shows the light chain variant 1 sequence of the "huMAb1_1" antibody.

SEQ ID NO: 60 shows the heavy chain variant 1 sequence of the "huMAb1_1" antibody.

SEQ ID NO: 61 shows the light chain variant 2 sequence of the "huMAb1_2" antibody.

SEQ ID NO: 62 shows the heavy chain variant 2 sequence of the "huMAb1_2" antibody.

SEQ ID NO: 63 shows the light chain variant 3 sequence of the "huMAb1_3" antibody.

SEQ ID NO: 64 shows the heavy chain variant 3 sequence of the "huMAb1_3" antibody.

SEQ ID NO: 65 shows the light chain sequence of the negative control "huMAb1_negA" antibody with the mutations 36A and 95A.

SEQ ID NO: 66 shows the heavy chain sequence of the negative control "huMAb1_negA" antibody with the mutation 101A.

SEQ ID NO: 67 shows the heavy chain sequence of the negative control "huMAb1_negB" antibody with the mutation 266A.

SEQ ID NO: 68 shows the light chain sequence of the recombinant huMAb1_1 for crystallization.

SEQ ID NO: 69 shows the heavy chain sequence of the recombinant huMAb1_1 for crystallization comprising a C-terminal His-tag.

SEQ ID NO: 70 shows the sequence of a human Loop1-2 region of LAMP1 with a cleavable thioredoxin (trx A) tag, a His-Tag and a thrombin cleavage site.

SEQ ID NO: 71 shows the sequence of the untagged hLAMP1-29-195.

SEQ ID NO: 72 shows the amino acid sequence corresponding to the amino acids 101 to 110 of SEQ ID NO: 24.

SEQ ID NO: 73 shows the amino acid sequence corresponding to the amino acids 144 to 157 of SEQ ID NO: 24.

SEQ ID NO: 74 shows the amino acid sequence corresponding to the amino acids 174 to 188 of SEQ ID NO: 24.

SEQ ID NO: 75 shows the amino acid sequence corresponding to the amino acids 29 to 41 of SEQ ID NO: 24.

SEQ ID NO: 76 shows the amino acid sequence corresponding to the amino acids 68 to 80 of SEQ ID NO: 24.

SEQ ID NO: 77 shows the amino acid sequence corresponding to the amino acids 29 to 100 of SEQ ID NO: 24.

SEQ ID NO: 78 shows the amino acid sequence corresponding to the amino acids 97 to 110 of SEQ ID NO: 24.

SEQ ID NO: 79 shows the amino acid sequence corresponding to the amino acids 173 to 189 of SEQ ID NO: 24.

SEQ ID NO: 80 shows the amino acid sequence corresponding to the amino acids 132 to 302 of SEQ ID NO: 70.

SEQ ID NO: 81 shows the sequence of the light chain of the chimeric antibody "chMAb3 VL_R24_R93". SEQ ID NO: 82 shows the amino acid sequence corresponding to the amino acids 360 to 375 of SEQ ID NO: 24.

SEQ ID NO: 83-85 show the sequences of the CDR1-H, CDR2-H, CDR3-H of the "MAb4" antibody.

SEQ ID NO: 86 and 87 show the sequences of the CDR1-L and CDR3-L of the "MAb4" antibody.

SEQ ID NO: 88 shows the VH1 sequence of the antibody "MAb4".

SEQ ID NO: 89 shows the VL1 sequence of the antibody "MAb4".

SEQ ID NO: 90 shows the amino acid sequence corresponding to the amino acids 47 to 61 of SEQ ID NO: 24.

SEQ ID NO: 91 shows the amino acid sequence corresponding to the amino acids 140 to 155 of SEQ ID NO: 24.

SEQ ID NO: 92 shows the amino acid sequence corresponding to the amino acids 307 to 321 of SEQ ID NO: 24.

SEQ ID NO: 93 shows a consensus sequence for CDR1-L of MAb1/huMAb1_1/huMAb1_2/huMAb1_3 antibody family based on residues identified as important for the canonical structure and thus the binding of human LAMP1 using crystallography.

SEQ ID NO: 94 shows a consensus sequence for CDR3-L of MAb1/huMAb1_1/huMAb1_2/huMAb1_3 antibody family based on residues identified as important for the canonical structure and thus the binding of human LAMP1 using crystallography.

SEQ ID NO: 95 shows a consensus sequence for CDR1-H of MAb1/huMAb1_1/huMAb1_2/huMAb1_3 antibody family based on residues identified as important for the canonical structure and thus the binding of human LAMP1 using crystallography.

SEQ ID NO: 96 shows a consensus sequence for CDR3-H of MAb1/huMAb1_1/huMAb1_2/huMAb1_3 antibody family based on residues identified as important for the canonical structure and thus the binding of human LAMP1 using crystallography.

SEQ ID NO: 97 shows the amino acid sequence corresponding to the amino acids 35 to 84 of SEQ ID NO: 24.

SEQ ID NO: 98 shows the light chain sequence of the "MAb4" antibody.

SEQ ID NO: 99 shows the heavy chain sequence of the "MAb4" antibody.

EXAMPLES

Example 1: Preparation of Patient-Derived Tumor Xenografts (PDX)

Example 1.1: Preparation of CR-LRB-010P, CR-LRB-003P, and CR-IGR-034P PDXs

A large collection of colorectal cancer models directly derived from tumor samples collected during patient surgery was develop. Patient-derived colorectal cancer tumor were collected, after patient's informed consent, in 3 medical centers: Curie Institute (Paris, France), Gustave Roussy Institute (Villejuif, France), and Lariboisiere Hospital (Paris, France). Immediately after surgery (1 hour after resection in average), 2 fragments were transferred in culture medium including DMEM with 10 mmol/L HEPES, 4.5 g/L glucose, 1 mmol/L pyruvate sodium, 200 U/mL penicillin, 200 mg/mL streptomycin, 200 mg/mL gentamicin, 5 mg/mL ciprofloxacin, 20 mg/mL metronidazole, 25 mg/mL vancomycin, and 2.5 mg/mL fungizone orDMEM with Nanomycopulitine (Abcys) for engraftment. After 2 to 24 hours following the patient surgery, the tumor samples were engrafted on 2 Swiss nude mice. Small fragments (50 mm$^3$) were subcutaneously engrafted into the scapular area or on the flank of anesthetized mice. (xylazine/ketamine or isoflurane protocol). Tumor growth was measured at least once a week and serial fragment grafts of each given tumor were conducted on 3 to 5 Swiss nude or CB17-SCID (after 3 passages) mice when the tumors reached a volume of 800 to 1500 mm$^3$. (Julien, S. 2012, Clin. Cancer Res. 18(19):5314-5328.

Example 1.2: Preparation of LUN-NIC-0014 PDX and LUN-NIC-0070 PDXs

Non-small-cell lung carcinoma samples were collected, after patient's informed consent, in CHU Pasteur (Nice, France). Immediately after surgery, a piece of the patient tumor was transferred in AQIX medium and sent to Sanofi (Vitry sur Seine, France). After 24 to 48 hours following the patient surgery, the tumors samples were engrafted on 2-5 CB17-SCID mice. Small fragments (50 mm$^3$) were subcutaneously engrafted on the mice flank. Tumor growth was followed at least once a week and serial fragment grafts of each given tumor were conducted on 5 to 10 CB17-SCID (after 3 passages) mice when the tumor reached a volume of 800 to 1500 mm$^3$.

Example 1.3: Preparation of BRE-IGR-0159 PDX

Breast carcinoma samples were collected, after patient's informed consent, in Gustave Roussy Institute (Villejuif, France). Immediately after surgery (1 hour after resection in average), 4 fragments were transferred in culture medium including DMEM, penicillin, streptomycin and fungizone for engraftment. After a maximum of 12 hours following the patient surgery, the tumor samples (fragments about 50 mm$^3$) were engrafted on fat pad on 4 BALB nude mice. Tumor growth was followed at least once a week and sent to Sanofi (Vitry sur Seine). Serial fragment grafts of each given tumor were conducted on 3 to 5 BALB nude or CB17-SCID mice (after 3 passages) when the tumors reach a volume of 800 to 1500 mm$^3$.

Example 2: Generation of Monoclonal Mouse Anti LAMP1 Antibodies and First Screening Immunizations, fusion and screening were performed essentially as described previously using primary disaggregated tumor CR-LRB-010P or CR-LRB-003P or LUN-NIC-0014 mentioned in example 1 for immunization and P3X63-Ag8.653 myeloma cells for fusion. Using the classical method described by Wennerberg A. E et al. (1993, Am. J. Pathol. 143(4): 1050-1054), 6-8 weeks old female BALB/c mice (S082342; Charles River Labs, Bar Harbor, Me.) each received three rounds of immunization over a course of 41 days. Antigens were administered intraperitonealy to ventral site of mice. Three days after the last injection, mice were sacrificed and spleens were isolated aseptically and washed with fresh RPMI medium. Lymphocytes were released from the spleens and single-cell suspension was washed twice with RPMI medium before being fused with P3X63-AG8.653 myeloma cells using polyethylene glycol. After fusion, the cell mixture was incubated in an incubator at 37° C. for 16-24 hours. The resulting cells preparation was transferred into selective semi-solid medium and aseptically plated out into 100 mm Petri plates and incubated at 37° C. Ten days after initiation of selection, the plates were examined for hybridoma growth, and visible colonies were picked-up and placed into 96-well plates containing 200 μL of growth medium. The 96-well plates were kept in an incubator at 37° C. for 2 to 4 days.

Primary screening for IgG production was performed by Enzyme-linked immunosorbent assay (ELISA) using a anti-mouse kappa light chain antibody (Bethyl #A90-119A) as capturing antigen. Plates were coated with mouse kappa light chain antibody at 0.5 μg/well in PBS and 100 μL/well of primary antibody was added to the plate. The plate was incubated at 37° C. for 1 h and washed five times with PBS containing 0.05% Tween-20 (PBS-T). Then, 100 μL of a 1:50 000 dilution of goat anti-mouse IgG (Fc) conjugated with horseradish peroxidase (Pierce #31349) was added to each well. Following incubation at 37° C. for 1 h in darkness, plates were washed with PBS-T five times. Antibody binding was visualized by adding TMB-H$_2$O$_2$ buffer and read at a wavelength of 450. Antibodies with the murine IgG, C kappa isotype were selected for further screening.

Example 3: Hybridoma Screening by Immunohistochemistry (IHC)

Individual hybridoma supernatants raised against tumor tissue CR-LRB-010P were screened by IHC on a macroarray slide containing frozen sections of immunizing tumor (CR-LRB-010P), human non-tumoral colon and human non-tumoral skin. Frozen-OCT (from Optimal Cutting Temperature) specimens of non-tumoral colon and skin were obtained from surgical cases (commercial sources such as Asterand, US Biomax, Strasbourg Hospital). The automated immunostaining was performed unsing Ventana Discovery and Discovery XT automated systems (Ventana Medical Systems, Inc, USA).

Frozen 10 μm cryostat sections were incubated with IgG culture supernatants as primary antibody (unknown concentration, dilution ⅓ in Phosphate Buffer Saline, PBS) for 40 min at 37° C. Culture medium was used as negative control. A postfixation step with glutaraldehyde (0.05% in NaCl 0.9% w/v) for 4 min was done. The secondary antibody Affinipure rabbit anti-mouse IgG (315-005_008, Jackson Immunosearch Laboratories, Inc. USA) was used at 4.8 μg/mL and incubated for 12 min at 37° C. Immunostaining was done with UltraMap Red chromogenic detection kit according to manufacturers recommendations for 8 min. Cryostat sections were subsequently couterstaining with hematoxylin II (790-2208, Ventana Medical Systems, Inc USA) and bluing for 4 min (760-2037). Stained slides were dehydrated and coverslipped with Coverquick 2000 mounting medium (Labonord, Ref 05547530).

Sections immunostained with mAbs were analyzed by microscope (Nikon Eclipse E400). After the immunohistochemical screening clones of interest were identified as those with reactivity with areas of tumoral colon cells but not normal epithelial cells of colon mucosa. MAb1 antibody showed evidence of tumor-associated reactivity and were negative on epidermal human non-tumoral cells.

Similar results were obtained with MAb2 and MAb3. Based on these IHC results, MAb1 MAb2 and MAb3 were purified for further evaluation, including extensive IHC characterization on non-tumoral and tumoral tissues for MAb1.

Example 4: mAb Characterization

Antibodies MAb1 MAb2 and MAb3 were analysed for cell surface binding on human primary disaggregated colon tumor by FACS using Guava®easyCyte™8HT Flow Cytometry System.

The apparent affinity expressed as EC50 values was estimated using BIOST@T-SPEED software.

Mouse hybridomas expressing antibody were produced into T500 flask and conditioned media collected after 7 days of growth. Antibody was purified by passing the conditioned media through a Protein-G column, washed and eluted with Glycine/HCl 100 mM pH 2.7 buffer. The eluate was dialyzed against PBS before sterile filtration and stored at 4° C.

Example 4.1: Apparent Affinity of Antibodies MAb1 and MAb2 to Human Primary Colon Tumor PDX by Flow Cytometry Advanced human primary colon tumor CR-IGR-034P was obtained from Patient-derived xenograft in mice. Tumor CR-IGR-034P was enzymatically dissociated using collagenase Type IV (Invitrogen; #17104-019) and deoxyribonuclease I (Invitrogen; #18047-019) for 1 h at 4° C. Cell viability was estimated by Viacount application using Guava® easyCyte™ 8HT Flow Cytometry System. For apparent affinity estimation, CR-IGR-034P tumoral cells were coated at 40,000 cells/well on 96-well High Bind plate (MSD L15XB-3) and 100 μL/well of antibody was added in 2-fold serial dilutions starting at 20 μg/ml up to 12 dilutions in assay diluent for 45 min at 4° C. and washed three times with PBS 1% BSA. 100 μL/well of goat anti-mouse IgG conjugated with Alexa647 (Invitrogen; #A2135) or goat anti-human IgG conjugated with Alexa488 (Invitrogen; #A11013) was added for 45 min at 4° C. and washed three times with PBS 1% BSA. The antibody binding was evaluated after centrifugation and resuspension of cells by adding 200 μl/well PBS 1% BSA and read using Guava® easyCyte™ 8HT Flow Cytometry System. EC50 values were estimated using BIOST@T-SPEED software. EC50 values obtained with the advanced human primary colon tumor CR-IGR-034P are listet in Table 3.

TABLE 3

| $EC_{50}$ obtained with CR-IGR-034P | | | |
|---|---|---|---|
| | MAb1 | MAb2 | MAb3 |
| CR-IGR-034P | 5 nM | 14 nM | 6 nM |

Antibody binding capacity of antibody was determined using Mouse IgG Calibrator kit (Biocytex #7208) or Human IgG Calibrator Kit (Biocytex #CP010) according to the manufacturer's instructions. Antibody binding capacity of 230 000 and 180 000 were measured for antibody MAb1 and MAb2 respectively on CR-IGR-034P.

Example 4.2: The Antibodies Bind to Multiple Cancer Cells

MAb1 and MAb2 Antibodies Bind to Multiple Cancer Cells and Determination of Antibody Binding Capacity Antibodies were found to be able of binding to multiple tumor cells by Flow Cytometry using the conditions described in example 4.1. The panel of tumor cells comprises Patient-derived tumor xenografts from different origins and tumor cell lines. FIG. 2 illustrates the expression profile and Table 4 summarizes the antibody binding capacity results.

TABLE 4

| Antibody Binding Capacity by FACS on Patient-derived xenografts | | |
|---|---|---|
| | Antibody Binding Capacity (ABC) | |
| | MAb2 | MAb1 |
| PDX/origin | | |
| CR-LRB-003P/colorectal | 22 000 | 25 000 |
| CR-LRB-010P/colorectal | 95,000 | 140,000 |
| CR-IGR-034P/colorectal | 180,000 | 230,000 |
| OVA-IGR-0022/ovary | 60,000 | 67,000 |
| STO-IND-006/stomach | 64,000 | 90,000 |
| LUN-NIC-025/lung | 27,000 | 33,000 |
| LUN-NIC-014/lung | 102,000 | 104,000 |

TABLE 4-continued

| Antibody Binding Capacity by FACS on Patient-derived xenografts | | |
|---|---|---|
| | Antibody Binding Capacity (ABC) | |
| | MAb2 | MAb1 |
| Cell lines/origin | | |
| Colo205/colon | 4,000 | 6,000 |
| SW480/colon | 1,700 | 2,500 |
| LS174T/colon | 3,600 | 6,000 |

The monoclonal antibodies MAb1 and MAb2 led to high ABC in several PDXs of colorectal, ovary, stomach and lung origin and lower ABC in cell lines than in PDXs of colon origin.

MAb3 Antibodies Bind to Multiple Cancer Cells

Figure 12:
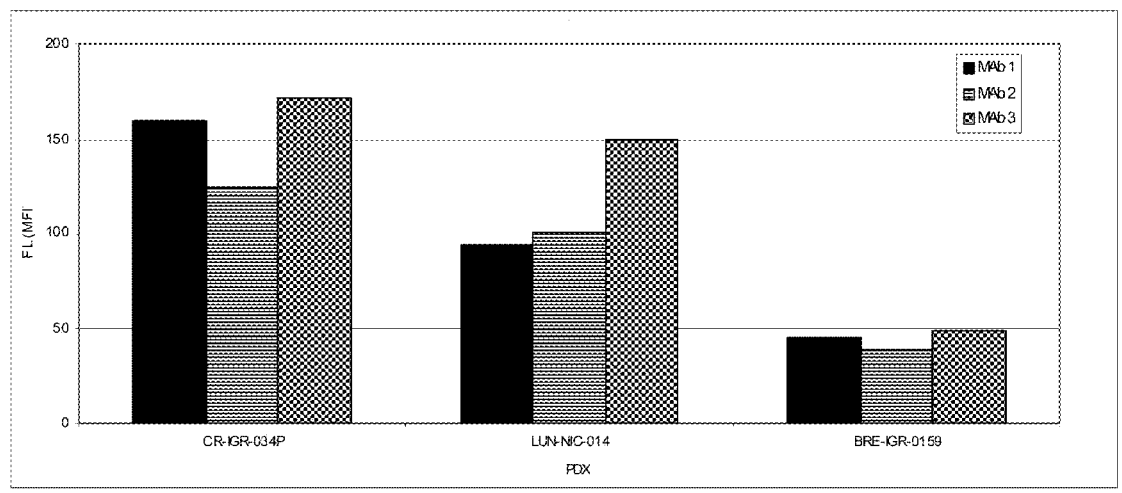
FIG. 12: Expression profile oMAb1, 2 and 3 onto three PDXs (CR-IGR-034P, LUN-Nlc-014 and BRE-IGR-0159).

Advanced human primary tumors from colon (CR-IGR-034P), lung (LUN-NIC-014P and breast (BRE-IGR-0159) indications were obtained from patient-derived xenograft (PDX) in mice as described in example 1. PDXs were enzymatically dissociated using collagenase Type IV (Invitrogen; #17104-019) and deoxyribonuclease I (Invitrogen, #18047-019) for 1 h at 4° C. Cell viability was estimated by Viacount application using Guava® easyCyte™ 8HT Flow Cytometry System. Tumoral cells were coated at 40,000 cells/well on 96-well High Bind plate (MSD L15XB-3) and 100 μL of antibody was added at 20 μg/mL for 45 min at 4° C. and washed three times with PBS 1% BSA. 100 μL of goat anti-human IgG conjugated with Alexa488 (Invitrogen; #A11013) was added for 45 min at 4° C. and washed three times with PBS 1% BSA. The antibody binding was evaluated after centrifugation and resuspension of cells by adding 200 μL/well PBS 1% BSA and read using Guava® easyCyte™ 8HT Flow Cytometry System. The mean fluorescence was recorded and plotted in the graph shown in FIG. 12 to illustrate the expression profile of the three mAbs onto the three PDXs. Results presented in FIG. 12 show that MAb3 binds to the different patient-derived xenografts from colon, lung and breast origin as Mab1 and Mab2 do.

Example 4.3: Internalization Score of MAb1, MAb2 and MAb3 Following Binding to Colon Colo205 Tumoral Cells Expressing LAMP1 by ImageStream Multispectral Imaging Flow Cytometer (Amnis Corp.)

Viable Colo205 cells ($5 \times 10^5$ cells) were seeded into wells of 6-well plates and incubated for 4 hours at 37° C./5% $CO_2$ (or 4° C. on ice for negative control) with 10 μg/ml of AlexaFluor488-labeled antibody MAb1 or AlexaFluor488-labeled antibody MAb2 or AlexaFluor488-labeled antibody MAb3. Cells were washed by centrifugation with PBS 1% BSA at 400 g for 5 minutes. Cells were fixed and permeabilized using 100 μL of Perm/Fix buffer on ice for 20 minutes. Cells were washed by centrifugation with 1 mL of Perm/Wash Cell buffer at 400 g for 5 minutes.

To test whether internalized antibodies accumulate in lysosomes, simultaneous uptake of mAbs and AlexaFluor647-labeled CD107a (a lysosomal marker) were carried out. Labelled AlexaFluor647 anti-CD107a antibody at 10 μg/mL was incubated on ice for 20 minutes. After incubation, 1 mL Perm/Wash Cell buffer was added to wash, before centrifuging (400 g, 5 min). The supernatant was flicked from the plate before the cells were fixed with 200 μL 1% formaldehyde on ice for 20 minutes. The fluorescence of cells was analyzed with the ImageStream multispectral imaging flow cytometer (Amnis corp.) using the Internalization feature. Five thousand events were acquired for each experimental condition and the corresponding images were analyzed using the IDEAS image-analysis software.

TABLE 5

Internalization score by Fluorescence-Based ImageStream Imaging Flow Cytometer

| mAb | Internalization score (IS) 4° C., 4 hr | Internalization score (IS) 37° C., 4 hr |
|---|---|---|
| MAb1 | 0.22 | 2.22 |
| MAb2 | 0.19 | 2.24 |
| MAb3 | 0.11 | 1.56 |

The monoclonal antibodies MAb1 MAb2 and MAb3 led to high internalization scores in Colo205 cell line as shown in Table 5.

Example 4.4: Quenching of Alexa488 by Use of the Anti-Alexa488 Antibody, Flow Cytometry and Calculation of Internalized Fraction of MAb1

Alexa488-labelled MAb1 (66 nM) was incubated with 6×10$^5$ Colo205 cells in complete medium for 4 h at 37° C. or 4° C. The cells were washed twice in ice cold PBS in a cold centrifuge, and resuspended in 500 nM quenching anti-Alexa488 antibody diluted in ice cold PBS. All tubes were incubated for 1 h on ice. Without washing, all cells were fixed in two volumes of 2% paraformaldehyde for 10 min at room temperature. The paraformaldehyde was removed by one wash in PBS, and the cells were resuspended in PBS and analyzed in a flow cytometer (Guava® easyCyte 8HT Flow Cytometry System).

An internalization positive control experiment was done in parallel with Alexa488-labelled Transferrin (600 nM).

Mean fluorescence intensity (MFI) values obtained from the flow cytometry reading of 5×10$^4$ cells per tube were used for all calculations. Internalization was calculated as the MFI value of quenched cells (intracellular compartments only) divided by the MFI value of unquenched cells (both cell surface and intracellular compartments) at 37° C. as described in the formula:

$$\text{Percentage of iternalized fraction:} \frac{FL \text{ of quenched cells at } 37° \text{ C.}}{FL \text{ of unquenched cells at } 37° \text{ C.}} \times 100$$

The cells incubated with Alexa488-labelled compounds at 4° C. were used as a control since internalization of antibodies does not take place significantly at 4° C.

After 4 h at 37° C., about 97.0% of the total cell fluorescence from Alexa488-MAb1 was intracellular. By comparison, about 98.5% of the total cell fluorescence from Alexa488-Transferrin was intracellular. Transferrin is known to be internalized very efficiently by Colo205 cells.

After quenching, the fluorescence of Alexa488-MAb1 measured from cells labelled at 37° C. (both cell surface and intracellular compartments) was 10-fold higher than that of cells labelled at 4° C. (cell surface). Because the fluorescence of Alexa488-MAb1 measured at cell surface at 4° C. is proportional to the antigen density, all the above results taken together indicate that each LAMP1 molecule is involved in several (10 on average) internalization cycles via recycling at cell membrane during the course of the experiment.

Our results show for the first time that LAMP1 can function as a receptor mediating the internalization of antibodies very efficiently via receptor recycling to the cell surface and suggest that the availability of specific internalizing antibodies should aid in developing novel therapeutic methods to target toxins, drugs or short-range isotopes to be delivered specifically to the interior of the cancer cells, as shown in Table 6.

TABLE 6

Internalization measurements by Flow Cytometry

| mAb | 4° C. | 4° C. Quencher | 37° C. | 37° C. Quencher |
|---|---|---|---|---|
| MFI, Alexa488-MAb1 | 16.89 | 4.46 | 172.14 | 167.08 |
| MFI, Alexa488-Transferrin | 35.78 | 8.98 | 1228 | 1210 |

Example 4.5: Purification and Identification of the MAb1, MAb2 and MAb3 Antibody Antigen Target The antigen target of MAb1, MAb2 and MAb3 are purified from a membrane fraction enriched by human primary colon tumor CR-LRB-010P or CR-IGR-034P using Pierce Classic IP Kit (#26146) according to the manufacturer's instructions.

Pulled-down proteins were separated by SDS-PAGE and proteins stained with silver nitrate. Stained bands were submitted to an in-gel tryptic digestion, and eluted peptides were analyzed by tandem MS (LC-MS/MS) on an Orbitrap bentchtop mass spectrometer (Thermo). Raw MS/MS data analysis with Mascot (Matrix Science) database search engine, revealed LAMP1.

This target was confirmed by ELISA with the recombinant human LAMP1 as described in example 6.2 (SEQ ID NO: 28). The obtained EC$_{50}$ are listed in Table 7 and Table 11.

TABLE 7

EC$_{50}$ determined by ELISA values on recombinant human LAMP1 (29-382 of SEQ ID NO: 28)

| Antibody | EC$_{50}$ |
|---|---|
| MAb1 | 0.18 nM |
| MAb2 | 0.25 nM |

Example 4.6: Specificity to LAMP1

LAMP2 is the closest member of the LAMP family with 35% sequence identity to LAMP1. For evaluating specificity to LAMP1 of MAb1, MAb2 and MAb3 antibodies, 96-well plates were coated with recombinant human LAMP2 with a C-terminal 10 His-tag (SEQ ID NO: 40) (R&D Systems 6228-LM) using the same coating conditions described previously. Anti-LAMP1 antibodies were added to the plates and detected by using rabbit anti-mouse IgG conjugated with horseradish peroxidase (Sigma; #A9044). Antibody binding was visualized by adding TMB-H$_2$O$_2$ buffer and read at a wavelength of 450 nm. No binding to LAMP2 was detected with MAb1, MAb2 and MAb3 antibodies.

Example 4.7: Cross-Reactivity with Cynomolgus Monkey LAMP1

Figure 3:
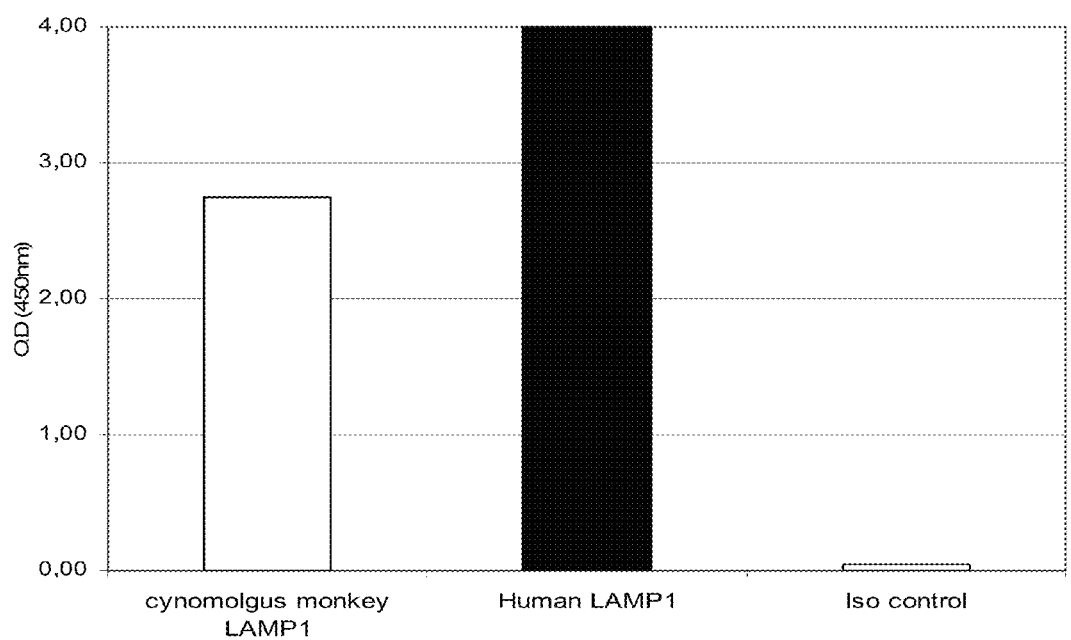
FIG. 3: Reactivity of MAb1 with human LAMP1 and cynomolgus monkey LAMP1.

Antibody MAb1 was assessed for its ability to bind primate LAMP1 protein by ELISA. Extracellular domain of LAMP1 of human (Ala29-Met382 of SEQ ID NO: 24) and cynomolgus monkey LAMP1 (Ala27-Met380 of SEQ ID NO: 39) were prepared as described in example 6.2. Plate was coated with cynomolgus monkey LAMP1 protein (SEQ ID NO: 29), antibody MAb1 was added to the plate and detected with rabbit anti-mouse IgG conjugated with horseradish peroxidase (Sigma; #A9044). The antibody binding was visualized by adding TMB-$H_2O_2$ buffer and read at a wavelength of 450 nm. Binding affinity was in the same range with both proteins as shown on FIG. 3 for MAb1.

Antibody MAb1 was also assessed for its ability to bind human LAMP1 and primate LAMP1 proteins expressed at the surface of recombinant HEK293 cells by FACS. LAMP1 Coding DNA Sequence, RefSeq NM_005561.3 (SEQ ID NO: 23) was cloned internally. The CDS of Macaca mulatta LAMP1, RefSeq XP_001087801 (SEQ ID NO: 27) was also cloned internally. The predicted sequences of mature LAMP1 from Macaca mulatta and Macaca fascicularis are identical to 99%, said sequence differing by one additional Leucin at position 11 of Macaca mulatta (SEQ ID NO: 27), i.e. in the signal peptide. The mature LAMP1 proteins of Macaca mulatta and Macaca fascicularis are identical. Therefore the secreted LAMP1 used in the following example is referred to cynomolgus monkey. Both CDS were cloned into mammalian expression plasmids under CMV enhancer/promoter and SV40 polyA signals. HEK293 cells (Invitrogen; #K9000-10.) were transiently transfected with human LAMP1 or cynomolgus LAMP1 plasmids using FreeStyle™ MAX 293 Expression System according to the manufacturer's instructions. Human LAMP1 transfected HEK293 cells and cynomolgus LAMP1 transfected HEK293 cells were coated at 40,000 cells/well on 96-well High Bind plate (MSD L15XB-3) and 100 μL/well of antibody MAb1 was added in 2-fold serial dilutions starting at 20 μg/ml up to 12 dilutions in assay diluent for 45 min at 4° C. and washed three times with PBS 1% BSA. 100 μL/well of goat anti-mouse IgG conjugated with Alexa647 (Invitrogen; #A2135) was added for 45 min at 4° C. and washed three times with PBS 1% BSA. The antibody binding was evaluated after centrifugation and resuspension of cells by adding 200 μl/well PBS 1% BSA and read using Guava® easyCyte™ 8HT Flow Cytometry System. EC50 values were estimated using BIOST@T-SPEED software. Binding affinity was in the same range with $EC_{50}$ of 14 and 44 nM to respectively human and cynomlogus monkey LAMP1 expressed transiently at the cell surface of HEK293 for MAb1.

Antibody MAb1 was assessed for its ability to bind human LAMP1 and primate LAMP1 proteins expressed at the surface of recombinant HCT116 stable clones by FACS. HCT116 cells were infected by a lentiviral vector allowing stable integration of the human or the cynomolgus LAMP1 CDS in genomic DNA of cells. Individual clones with different densities of human or cynomolgus LAMP1 cell surface localization were derived from a pool of HCT116 infected cells. HCT116 cells expressing human or cynomolgus LAMP1 were plated in 96-well plates at 200 000 per well and MAb1 was added in 2-fold serial dilutions starting at 40 μg/ml up to 12 dilutions in assay diluant for 1 h at 4° C. and washed two times with PBS 1% BSA. 100 μL/well of goat anti-human IgG conjugated with Alexa488 (Invitrogen; #A11013) was added for 1 h at 4° C. and washed two times with PBS 1% BSA. The antibody binding was evaluated after centrifugation and resuspension of cells in 100 μl fixing solution (paraformaldehyde at 4% in PBS). Samples were read using Galaxy® Flow Cytometry System (Partec). EC50 values were estimated using BIOST@T-SPEED software. Antibody MAb1 binds to human and cynomolgus LAMP1 expressed at the cell surface of recombinant HCT116 with similar affinity and $EC_{50}$ of 4.9 and 5.5 nM respectively.

Antibody MAb2 was assessed for its ability to bind human LAMP1 and primate LAMP1 proteins expressed at the surface of recombinant HCT116 stable clones by FACS. Recombinant HCT116 cells were coated at 40,000 cells/well on 96-well High Bind plate (MSD L15XB-3) and 100 μL/well of antibody MAb2 was added in 2-fold serial dilutions starting at 20 μg/ml up to 12 dilutions in assay diluent for 45 min at 4° C. and washed three times with PBS 1% BSA. 100 μL/well of goat anti-mouse IgG conjugated with Alexa647 (Invitrogen; #A2135) was added for 45 min at 4° C. and washed three times with PBS 1% BSA. The antibody binding was evaluated after centrifugation and re-suspension of cells by adding 200 μl/well PBS 1% BSA and read using Guava® easyCyte™ 8HT Flow Cytometry System. EC50 values were estimated using BIOST@T-SPEED software. Antibody MAb2 binds to human and cynomolgus LAMP1 expressed at the cell surface of recombinant HCT116 with similar affinity and $EC_{50}$ of 6.3 and 6.6 nM respectively for MAb2.

Therefore MAb1 and MAb2 bind to LAMP1 of human and cynomolgus origin with similar affinity.

Antibody MAb3 was assessed by flow cytometry for its ability to bind to human LAMP1 and primate LAMP1 proteins expressed respectively at the surface of HCT116 or HEK293 stable clones. HCT116 stable clone was obtained as described above. HEK293 cells were infected by a lentiviral vector allowing stable integration of the human or the cynomolgus LAMP1 CDS in genomic DNA of cells. Individual clones with different densities of cynomolgus LAMP1 cell surface localization were derived from a pool of HEK293 infected cells. Protocol as described in example above. $EC_{50}$ values were estimated using BIOST@T-SPEED software. Antibody MAb3 binds to human and cynomolgus LAMP1 expressed at the surface of HCT116 or HEK293 with similar affinity and $EC_{50}$ of 7.6 and 4.0 nM respectively.

Therefore MAb1, MAb2 and MAb3 bind to LAMP1 of human and cynomolgus origin with similar affinity.

Example 4.8: Binding Competition Between MAb According to the Invention and/or Commercially Available Anti-LAMP1 H4A3

The following examples present information on the competition of the mAbs towards the epitope onto LAMP1 by ELISA. It confirmed data obtained on the epitope binding site as described in example 6 and allowed the comparison with a commercially available anti-LAMP1 mAb.

Binding Competition Between MAb1 and MAb2

Figure 4:
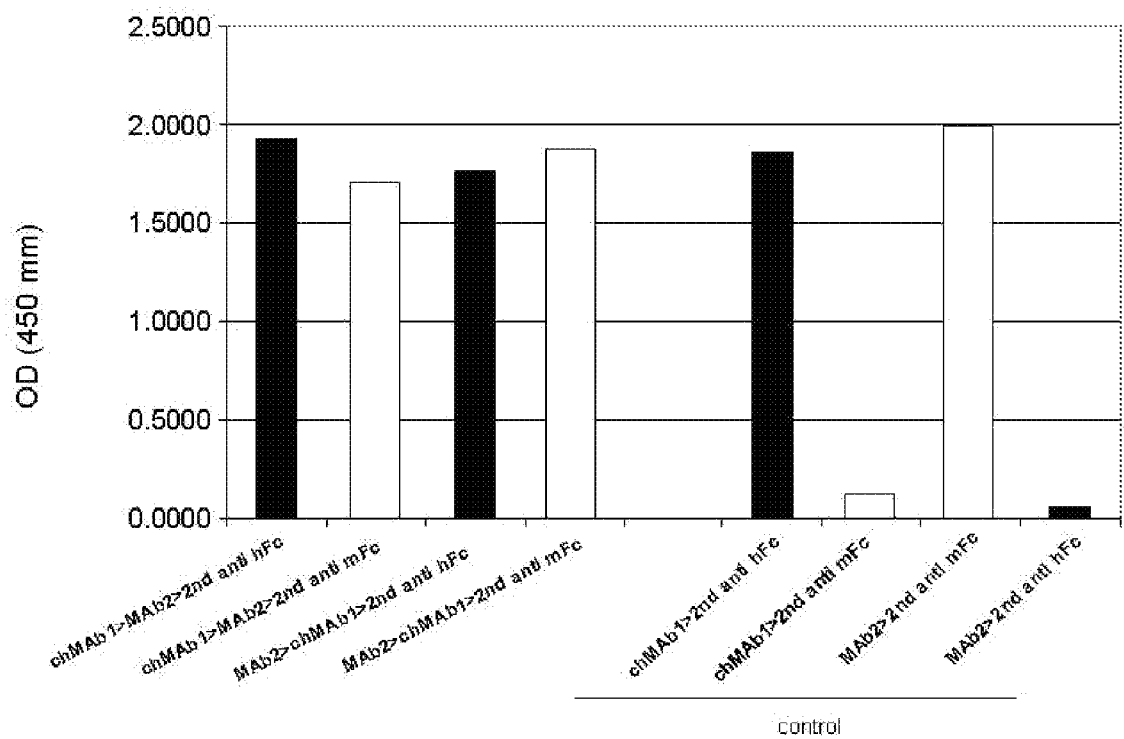
FIG. 4: Evaluation of the competition of MAb2 (murine) with MAb1 (chimeric) for binding to LAMP1. With 2nd anti hFc being a secondary antibody anti-human Fc and 2nd anti mFc being secondary antibody anti-mouse Fc.

Competition between MAb2 (murine) and MAb1 (chimeric) for binding to LAMP1 was assayed by ELISA and is illustrated on FIG. 4. No competition was observed.

Binding Competition Between MAb1 and MAb2 or MAb3

Competition experiments between two anti-LAMP1 mAbs were performed by ELISA with recombinant human LAMP1 coated on plate (as described in example 6.2). Briefly, two mAbs were added simultaneously at concentrations of 0.06 and 15 mg/L, the concentration of 0.06 mg/L being close to the $EC_{50}$. MAb format was chosen so that the two mAbs had different Fc domains (either human or murine). Individual measurements of mAb binding could be performed specifically by their unique specific binding to Fc (with Peroxidase-AffiniPure Goat Anti-Human IgG Ab, Fcγ Fragment Specific (Jackson 109-035-098) or with Peroxidase-AffiniPure Goat Anti-Mouse IgG Ab, Fcγ Fragment Specific (Jackson 115-035-164)). Results were reported as a percentage of the value obtained from the mAb alone at the same concentration, see Table 8.

TABLE 8

Competition between chMAb1 and MAb2 or MAb3

| Sample ID | Added mAbs | mAb concentration | Secondary Ab | Percentage of signal compared to mAb control alone |
|---|---|---|---|---|
| 1 | chMAb1 + MAb2 | 0.06 mg/L 15 mg/L | Anti-Human IgG_HRP | 80% |
| 2 | chMAb1 + MAb2 | 0.06 mg/L 15 mg/L | Anti-Mouse IgG_HRP | 100% |
|  | chMAb1 | 0.06 mg/L | Anti-Human IgG_HRP | 100% |
|  | chMAb1 | 0.06 mg/L | Anti-Mouse IgG_HRP | 0% |
|  | MAb2 | 15 mg/L | Anti-Human IgG_HRP | 0% |
|  | MAb2 | 15 mg/L | Anti-Mouse IgG_HRP | 100% |
| 3 | chMAb1 + MAb3 | 0.06 mg/L 15 mg/L | Anti-Human IgG_HRP | 80% |
| 4 | chMAb1 + MAb3 | 0.06 mg/L 15 mg/L | Anti-Mouse IgG_HRP | 90% |
|  | MAb3 | 15 mg/L | Anti-Human IgG_HRP | 0% |
|  | MAb3 | 15 mg/L | Anti-Mouse IgG_HRP | 100% |
| 5 | chMAb1 + MAb1 | 0.06 mg/L 15 mg/L | Anti-Human IgG_HRP | 10% |
| 6 | chMAb1 + MAb1 | 0.06 mg/L 15 mg/L | Anti-Mouse IgG_HRP | 90% |
|  | MAb1 | 15 mg/L | Anti-Human IgG_HRP | 0% |
|  | MAb1 | 15 mg/L | Anti-Mouse IgG_HRP | 100% |

It was found that MAb1 does not compete with MAb2 or MAb3. Therefore the LAMP1 epitope binding site for MAb1 does not overlap with the epitope binding sites for MAb2 or MAb3.

Binding Competition Between H4A3 and MAb1 or MAb2 or MAb3 and Between MAb2 and MAb3

Competition experiments between anti-LAMP1 H4A3 (BioLegend 328602) and MAb1, Mab2, or MAb3 and between MAb2 and MAb3 were performed as described in above Example B4.81 Results were reported as a percentage of the value obtained from the mAb alone at the same concentration, see Table 9.

TABLE 9

Competition between H4A3 and chMAb1 or chMAb2 or chMAb3

| Sample ID | Added mAbs | mAb concentration | Secondary Ab | Percentage of signal compared to mAb control alone |
|---|---|---|---|---|
| 1 | H4A3 + chMAb1 | 0.06 mg/L 15 mg/L | Anti-Human IgG_HRP | 96% |
|  | H4A3 + chMAb1 | 0.06 mg/L 15 mg/L | Anti-Mouse IgG_HRP | 98% |
|  | chMAb1 | 15 mg/L | Anti-Human IgG_HRP | 100% |
|  | chMAb1 | 15 mg/L | Anti-Mouse IgG_HRP | 0% |
|  | H4A3 | 0.06 mg/L | Anti-Human IgG_HRP | 0% |
|  | H4A3 | 0.06 mg/L | Anti-Mouse IgG_HRP | 100% |
|  | MAb1 + chMAb1 | 0.06 mg/L 15 mg/L | Anti-Human IgG_HRP | 96% |
|  | MAb1 + chMAb1 | 0.06 mg/L 15 mg/L | Anti-Mouse IgG_HRP | 28% |
|  | MAb1 | 0.06 mg/L | Anti-Human IgG_HRP | 0% |
|  | MAb1 | 0.06 mg/L | Anti-Mouse IgG_HRP | 100% |
| 2 | H4A3 + chMAb2 | 0.06 mg/L 15 mg/L | Anti-Human IgG_HRP | 100% |
|  | H4A3 + chMAb2 | 0.06 mg/L 15 mg/L | Anti-Mouse IgG_HRP | 57% |
|  | chMAb2 | 15 mg/L | Anti-Human IgG_HRP | 100% |
|  | chMAb2 | 15 mg/L | Anti-Mouse IgG_HRP | 0% |
|  | MAb2 + chMAb2 | 0.06 mg/L 15 mg/L | Anti-Human IgG_HRP | 100% |

TABLE 9-continued

Competition between H4A3 and chMAb1 or chMAb2 or chMAb3

| Sample ID | Added mAbs | mAb concentration | Secondary Ab | Percentage of signal compared to mAb control alone |
|---|---|---|---|---|
| | MAb2 + chMAb2 | 0.06 mg/L 15 mg/L | Anti-Mouse IgG_HRP | 9% |
| | MAb2 | 0.06 mg/L | Anti-Human IgG_HRP | 0% |
| | MAb2 | 0.06 mg/L | Anti-Mouse IgG_HRP | 100% |
| 3 | H4A3 + chMAb3 | 0.06 mg/L 15 mg/L | Anti-Human IgG_HRP | 100% |
| | H4A3 + chMAb3 | 0.06 mg/L 15 mg/L | Anti-Mouse IgG_HRP | 11% |
| | chMAb3 | 15 mg/L | Anti-Human IgG_HRP | 100% |
| | chMAb3 | 15 mg/L | Anti-Mouse IgG_HRP | 0% |
| | MAb3 + chMAb3 | 0.06 mg/L 15 mg/L | Anti-Human IgG_HRP | 100% |
| | MAb3 + chMAb3 | 0.06 mg/L 15 mg/L | Anti-Mouse IgG_HRP | 15% |
| | MAb3 | 0.06 mg/L | Anti-Human IgG_HRP | 0% |
| | MAb3 | 0.06 mg/L | Anti-Mouse IgG_HRP | 100% |
| 4 | MAb3 + chMAb2 | 0.06 mg/L 15 mg/L | Anti-Human IgG_HRP | 99% |
| | MAb3 + chMAb2 | 0.06 mg/L 15 mg/L | Anti-Mouse IgG_HRP | 58% |
| | MAb3 | 0.06 mg/L | Anti-Human IgG_HRP | 0% |
| | MAb3 | 0.06 mg/L | Anti-Mouse IgG_HRP | 100% |

It was found that H4A3 competes with MAb3, partially competes with Mab2 and does not compete with MAb1 for binding to LAMP1.

It was found that MAb2 and MAb3 partially compete for binding to LAMP1.

Example 5: Immunohistochemistry (IHC) Characterization of Purified MAb1 on Human Non-Tumoral and Tumoral Tissues The monoclonal antibody MAb1 was purified for further evaluation and antibody validation by extensive IHC characterization on non-tumoral and tumoral tissues. Therefore a large panel of human non-tumoral and tumoral tissues from commercial Tissue-Micro-Arrays or whole cryostat sections was tested for LAMP1 immunoreactivity either as Frozen-OCTs (Optimal Cutting Temperature) or Acetic Formalin Alcohol (AFA) or formalin patient-derived human xenografts. The PDXs samples used were described in example 1.

Immunostaining on AFA Format

Classical IHC was performed using Ventana automatic instrument (Discovery XT, Ventana Medical Systems, Inc, USA). Sections were dewaxed and incubated with avidin and biotin blocking reagent (Endogenous Block, Ventana, 760-050) followed by Serum Block incubation (Ventana 760-4212). The murine monoclonal antibody MAb1 was then incubated at final concentration of 4 µg/mL during 1 hour at 37° C. A post-fixation step with glutaraldehyde (0.05% in NaCl 0.9% w/v) during 4 min was done. The secondary goat anti-mouse IgG2a-biotinilated was incubated for 12 min at 37° C. (Southern Biotech, Ref 1080-08, and dilution ¹⁄₂₀₀ in Ventana's diluent). Immunostaining was done with DAB Map chromogenic detection kit according to manufacturer's recommendations. A counterstaining step was applied to the cryostat sections with hematoxylin II (790-2208, Ventana Medical Systems, Inc USA) and bluing reagent was applied for 4 min (760-2037). Stained slides were dehydrated and coverslipped with Coverquick 2000 mounting medium (Labonord, ref 05547530). The negative controls used in this study consisted in omission of primary antibody and the use of IgG2a isotype (final concentration 1 µg/mL in PBS).

Immunostaining on PFA Format

Classical IHC was performed using Ventana automatic instrument (Discovery XT, Ventana Medical Systems, Inc, USA). Sections were dewaxed and antigen retrieval Cell Conditioning 1 (CC1) buffer (ref 950-123 Ventana) was applied during 52 min. The sections were incubated with avidin and biotin blocking reagent (Endogenous Block, Ventana, 760-050) and Serum Block reagent (Ventana, 760-4212). The murine monoclonal antibody MAb1 was then incubated at final concentration of 4 µg/mL during 1 hour at 37° C. A post-fixation step with glutaraldehyde (0.05% in NaCl 0.9% w/v) during 4 min was done. The secondary goat anti-mouse IgG2a-biotinilated was incubated for 12 min at 37° C. (Southern Biotech, Ref 1080-08, and dilution ¹⁄₂₀₀ in Ventana's diluent). Immunostaining was done with DAB Map chromogenic detection kit according to manufacturer's recommendations. A counterstaining step was applied to the cryostat sections with hematoxylin II (790-2208, Ventana Medical Systems, Inc USA) and bluing reagent was applied for 4 min (760-2037). Stained slides were dehydrated and coverslipped with Coverquick 2000 mounting medium (Labonord, ref 05547530). The negative controls used in this study consisted in omission of primary antibody and the use of IgG2a isotype (final concentration 1 µg/mL in PBS).

Immunostaining on Frozen-OCT Format

After avidin and biotin blocking (Endogenous Block, Ventana, 760-050), frozen sections were incubated with murine monoclonal antibody MAb1 (final concentration 1 µg/mL (for human samples) and 1 and 5 µg/mL (for monkey samples) in Phosphate Buffer Saline, PBS) for 32 min at 37° C. A postfixation step with glutaraldehyde (0.05% in NaCl 0.9% w/v) for 4 min was done. The secondary goat anti-mouse IgG2a-biotinylated was incubated for 12 min at 37°

C. (Southern Biotech, Ref 1080-08, dilution 1/200 in Ventana's diluent). Immunostaining was done with DAB Map chromogenic detection kit according to manufacturers recommendations. A couterstaining step was applied to the cryostat sections with hematoxylin II (790-2208, Ventana Medical Systems, Inc USA) and bluing reagent was applied for 4 min (760-2037). Stained slides were dehydrated and coverslipped with Coverquick 2000 mounting medium (Labonord, Ref 05547530).

The negative controls used in this study consisted in omission of primary antibody and the use of IgG2a isotype (final concentration 1 µg/mL in PBS).

Data Analysis

Sections immunostained with purified murine antibody MAb1 were scanned and digitized at a magnification of ×20 using Scan Scope XT system (Aperio Technologies, Vista Calif.). Digitized images were then captured using Image Scope software (v10.2.2.2319 Aperio, Technologies).

Staining evaluation included several parameters: histologic site of reactivity (cytoplasm, nuclei or membrane), main type of reactive cell, staining intensity and cell staining frequency. The positive samples were scored with a scale of intensity from 1 to 3. Ranges of intensities were described as negative (0), weak (1), moderate (2) and strong (3). Cell frequency was the percentage of immunostained cells and was estimated by the histologist observation as a median by sample. The cell frequency was ordered in 5 categories: 1 (0-5%), 2 (6-25%), 3 (26-50%), 4 (51-75%) and 5 (76-100%).

A global expression was calculated according the Allred Score (AS) description. AS was obtained by adding the intensity and the proportion scores to obtain a total score that ranged from 0-8. The AS was reported as a percent of the maximum global score and ranged in 5 categories: very low (0-25%), weak (26-50%), moderate (51-75%) and high (75-100%). The prevalence was defined as the percent of positive cases for the indication.

Basic descriptive statistics were calculated with Microsoft Excel 2003. For each indication, number of cases, positive cases number, prevalence, intensity score mean, frequency mean and Allred score were described.

Non-Tumoral Tissue Distribution

Globally, the experimental data show that the IHC pattern of LAMP1 on cells of non-tumoral adult tissues is predominantly cytoplasmic.

LAMP1 was expressed in the cytoplasm of a large panel of tissues, including vital organs, gastrointestinal, reproductive, urinary, endocrine, lymphoid and others as skin, muscle, eye, spinal cord) and no membrane staining was observed in main organs as heart, liver, pancreas, lung and kidney.

However, some LAMP1 expression at the membrane occurred but was restricted to stomach epithelial cells, oesophageal epithelial cells, breast epithelial cells, prostate epithelial cells, testicular epithelial cells (Table 10).

Nevertheless, prevalence and mean intensities for LAMP1 expression at the membrane of non-tumoral samples were lower than those found in tumours.

TABLE 10

LAMP1 immunostaining in human non-tumoral samples- Membrane pattern
Non tumoral tissues

| Tissue Type | N | Prev Cyto | % Prv Cyto | Prev Memb | % Prev Memb (Mean) | Intensity Memb (Mean) | % +cells Memb (Mean) | Cell type |
|---|---|---|---|---|---|---|---|---|
| Stomach | 28 | 28/28 | 100% | 3/28 | 11% | 2 | 16 | Epithelial C. |
| Esophagus | 17 | 16/17 | 94% | 2/17 | 12% | 2.5 | 5 | Epithelial Basal C. |
| Breast | 17 | 17/17 | 100% | 6/17 | 35% | 1.5 | 15 | Epithelial C. |
| Prostate | 26 | 26/26 | 100% | 1/26 | 4% | 2 | 5 | Epithelial C. |
| Testis | 14 | 14/14 | 100% | 5/14 | 36% | 2.2 | 12 | Germinal + Leyding |

Tumoral Tissue Distribution

The immunohistochemical pattern using MAb1 or MAb2 in human tumoral tissues demonstrates that the antigen is located in the cytoplasm and/or membrane of tumoral tissues. Protein expression data for human tumoral samples displaying the membrane pattern show that LAMP1 antigen is not restricted to colon adenocarcinomas. A variety of other carcinomas, including gastrointestinal tumors (small intestine, rectum, parotid gland), vital organs tumors (lung, liver, stomach, pancreas and kidney), reproductive organ tumors (breast, ovary and prostate) as well as skin, larynx and soft tissue tumors (Table 11).

TABLE 11

LAMP1 immunostaining in human tumoral samples: Membrane pattern
TUMORAL TISSUES

| Organ | Tumor Type | N | Prev Memb | % Prev Memb | Intensity Memb (Mean) | % +Cells Memb (Mean) | Alred Score | Neg | 1-5% | 6-25% | 26-50% | 51-75% | 76-100% | >50% |
|---|---|---|---|---|---|---|---|---|---|---|---|---|---|---|
| Colon | Adenocarcinoma | 86 | 38/86 | 44 | 2.5 | 30 | 69 | 56% | | 17% | 16% | 2% | 7% | 9% |
| Small Intestine | Adenocarcinoma | 1 | 1/1 | 100 | 3.0 | 30 | 75 | | | | 100% | | | |
| Rectum | Adenocarcinoma | 14 | 9/14 | 64 | 3.0 | 21 | 63 | 36% | 21% | 14% | 21% | 7% | | |
| Parotid Gland | Adenocarcinoma | 3 | 2/3 | 67 | 2.0 | 18 | 50 | 33% | | 33% | 33% | | | |

TABLE 11-continued

LAMP1 immunostaining in human tumoral samples: Membrane pattern
TUMORAL TISSUES

| Organ | Tumor Type | N | Prev Memb | % Prev Memb | Intensity Memb (Mean) | % +Cells Memb (Mean) | Alred Score | Neg | 1-5% | 6-25% | 26-50% | 51-75% | 76-100% | >50% |
|---|---|---|---|---|---|---|---|---|---|---|---|---|---|---|
| Lung | Squamous Cell Carc | 29 | 6/29 | 21 | 2.5 | 31 | 69 | 79% | 3% | 10% | | 3% | 3% | 6% |
|  | Adenocarcinoma | 12 | 4/12 | 33 | 2.5 | 26 | 69 | 67% | 8% | 8% | 17% | | | |
| Liver | Hepatocellular Carc | 2 | 1/2 | 50 | 2 | 5 | 38 | 50% | 50% | | | | | |
| Pancreas | Adenocarcinoma | 18 | 1/18 | 6 | 2 | 10 | 50 | 94% | | 6% | | | | |
| Kidney | Clear Cell Carc | 9 | 1/9 | 11 | 3 | 5 | 50 | 89% | 11% | | | | | |
| Breast | InvDucCar | 70 | 27/70 | 39 | 2.4 | 41 | 68 | 61% | 3% | 13% | 9% | 7% | 7% | 14% |
|  | InvLobCar | 3 | 2/3 | 67 | 2.5 | 60 | 81 | 33% | | | 33% | | 33% | 33% |
| Ovary | Adenocarcinoma | 21 | 5/21 | 24 | 3.0 | 15 | 63 | 76% | 5% | 5% | 14% | | | |
|  | Serous Carcinoma | 6 | 1/6 | 17 | 2 | 10 | 50 | 83% | | 17% | | | | |
| Prostate | Adenocarcinoma | 16 | 4/16 | 25 | 3.0 | 43 | 75 | 75% | | | 19% | 6% | | 6% |
| Stomach | Adenocarcinoma | 32 | 8/32 | 25 | 2.3 | 45 | NA | 75% | | 3% | 9% | 9% | 3% | 13% |
| Skin | Squamous Cell Carc | 6 | 1/6 | 17 | 3.0 | 10 | 63 | 83% | | 17% | | | | |
|  | Malignant Melanoma | 4 | 1/4 | 25 | 2.0 | 40 | 63 | 75% | | | 25% | | | |
| Larynx | Squamous Cell Carc | 5 | 1/5 | 20 | 2.0 | 5 | 38 | 80% | | 20% | | | | |
| Soft Tissue | Giant cell tumor of thigh | 2 | 1/2 | 50 | 3.0 | 5 | 50 | 50% | 50% | | | | | |

Tumor indications were ranked in terms of LAMP1 expression level based on the percentage of samples displaying more than 50% of membrane frequency (positive cells).

Based on this parameter the first tumor indications were colon, rectum, lung squamous cell carcinoma, breast invasive ductal and lobular carcinoma, stomach adenocarcinoma and prostate adenocarcinoma.

Additionally, indications displaying 25-50% of positive cells at the membrane, could be also considered as relevant indications, including small intestine adenocarcinoma, parotid gland adenocarcinoma, lung adenocarcinoma, ovary adenocarcinoma, skin malignant melanoma and larynx squamous cell carcinoma (Table 11).

Moreover, LAMP1 immunostaining was not detected at the membrane in the following tumor indications: Lung small cell carcinoma (0/3), esophagus squamous cell carcinoma (0/11), cervix squamous cell carcinoma 0/3), endometrium adenocarcinoma (0/3), vulva squamous cell carcinoma (0/6), testis seminoma (0/4), testis embryonal carcinoma (0/1), bladder transitional cell carcinoma (0/1), thyroid papillary adenocarcinoma (0/3) and mullerian mixed tumor of the oral cavity (0/5).

Example 6—Binding Site Identification

In this example LAMP1 domains were defined and human-murine hybrid LAMP1 proteins were designed to generate secreted as well as membrane-anchored LAMP1 proteins allowing the characterization of the binding site of the anti-LAMP1 mAbs towards LAMP1.

Example 6.1: Definition of LAMP1 Domains

LAMP1 also named CD107a is the Lysosomal Associated Membrane Protein 1. It is is a transmembrane type I protein of around 120 kDa. The protein is a highly glycosylated monomer with eighteen N-glycosylation and six O-glycosylation sites. It is composed of two lumenal domains separated by a hinge. Each lumenal domain has two disulphide bridges that define two loops. According to RefSeq NP_005552.3 (SEQ ID NO: 24) the different domains of LAMP1 have been mapped as shown in Table 1. Based on structural information and in particular beta-strands and amino acids differences between human and mouse LAMP1 several hybrid LAMP1 molecules were designed.

Example 6.2: Preparation of Recombinant Extracellular Domains of LAMP1 Proteins

The high level of glycosylation of the antigen required a specific approach to determine the binding site of the anti-LAMP1 mAbs on LAMP1. The LAMP1 monoclonal antibodies MAb1 and MAb2 do not show any binding to the mouse LAMP1 protein. This absence of binding was used to design several chimeric LAMP1 proteins in which one or several of the LAMP1 domains (Loop1-Loop4) in the human construct were replaced by the murine counterpart. The absence of binding once the binding site of the antibody was replaced by the murine counterpart allowed for identification of the antibody binding side.

Hence, the extracellular protein domains of LAMP1 from human, cynomolgus monkey (c) and murine (m) origin or hybrid between murine and human LAMP1 domains have been prepared by transient expression in human embryonic kidney HEK293 cells with plasmids allowing expression of the respective cDNA as outlined on Table 12.

Each expression plasmid was complexed with 293Fectin™ (Life Technologies) and eight days post-transfection in suspension-cultivated 293-F cells (derived from HEK293 cells), the corresponding soluble protein was purified by IMAC (GE Healthcare) to generate a protein batch.

TABLE 12

Description of the recombinant extracellular domains of LAMP1 proteins

| Protein name | Description of protein domains | Sequence ID. |
|---|---|---|
| LAMP1::histag | human LAMP1 (29-382) | SEQ ID NO: 28 |
| cLAMP1::histag | cynomolgus LAMP1 (27-380) | SEQ ID NO: 29 |
| mLAMP1_L1_LAMP1_L234::histag | Loop1: mouse LAMP1 (25-94) Loop2-4: human LAMP1 (101-382) | SEQ ID NO: 30 |
| mLAMP1_L12_LAMP1_L34::histag | Loop1-2: mouse LAMP1 (25-189) Loop3-4: human LAMP1 (196-382) | SEQ ID NO: 31 |
| LAMP1_L12_mLAMP1_L34::histag | Loop1-2: human LAMP1 (29-195) Loop3-4: mouse LAMP1 (190-369) | SEQ ID NO: 32 |
| LAMP1_L123_mLAMP1_L4::histag | Loop1-3: human LAMP1 (29-309) Loop4: mouseLAMP1 (299-369) | SEQ ID NO: 33 |
| mLAMP1::histag | mouse LAMP1 (25-369) | SEQ ID NO: 34 |

Example 6.3: Determination of Binding Affinity and Epitope by ELISA

Secreted LAMP1 proteins described in example 6.2 were used to identify the binding domain to anti-LAMP1 mAbs by ELISA. MAb1 recognizes loop 2 of LAMP1 and MAb2 recognizes loop 1 of LAMP1 with $EC_{50}$ to LAMP1 of around 0.2 and 0.3 nM respectively.

TABLE 13

$EC_{50}$ (nM) obtained for murine or chimeric hybridoma mAbs

| | Protein | | | | | |
|---|---|---|---|---|---|---|
| Antibody | human LAMP1 | Mouse LAMP1 | Loop1: mLAMP1 Loop2-4: hLAMP1 | Loop1-2: mLAMP1 Loop3-4: hLAMP1 | Loop1-2: hLAMP1 Loop3-4: mLAMP1 | Loop1-3: hLAMP1 Loop4: mLAMP1 |
| MAb1 | 0.18 | No binding | 0.15 | No binding | 0.18 | 0.16 |
| MAb2 | 0.25 | No binding | No binding | No binding | 0.25 | 0.25 |
| chMAb1 | 0.12 | No binding | 0.11 | No binding | 0.11 | 0.11 |
| chMAb3 | 0.11 | No binding | No binding | No binding | 0.12 | 0.11 |

Example 6.4: Expression of LAMP1 Transmembrane Proteins

Different LAMP1 proteins were expressed at the cell membrane of HEK293 cells after transient expression from mammalian plasmids encoding the entire coding sequence of LAMP1 deleted of the intracellular lysosome-targeting motif GYQTI and substituted by a 5-Ala repeat sequence. Mammalian plasmids had similar expression signals as plasmids used to produce recombinant LAMP1 described in example 6.2. Table 14 below lists all the plasmids that were designed in order to confirm the results obtained with soluble LAMP1 protein by ELISA in example 6.3 and further characterize the binding domains of the anti-LAMP1 mAbs.

TABLE 14

Description of LAMP1 transmembrane proteins

| Plasmid | Encoded Protein | Short description of LAMP1 transmembrane protein/ with amino acid positions according to SEQ ID NO: 24 |
|---|---|---|
| pXL5626 | hLAMP1_ΔGYQTI | human LAMP1 |
| pXL5668 | LAMP1_mL1_hL234_ΔGYQTI | Hybrid LAMP1 murine in L1 and human in L2 to L4 |
| pXL5669 | LAMP1_hL12_mL34_ΔGYQTI | Hybrid LAMP1 human in L1 and L2 murine in L3 and L4 |
| pXL5719 | hLAMP1_ΔglycaninL1_ΔGYQTI | human LAMP1 with substitution of N >Q at positions 37, 45, 62, 76 and 84 in L1 |
| pXL5720 | hLAMP1_ΔglycaninL2_ΔGYQTI | human LAMP1 with substitution of N >Q at positions 103, 107, 121, 130, 165 and 181 in L2 |
| pXL5988 | LAMP1_mL1_hL2_mL34_ΔGYQTI | Hybrid LAMP1 murine in L1, L3 and L4 human in L2 |

TABLE 14-continued

Description of LAMP1 transmembrane proteins

| Plasmid | Encoded Protein | Short description of LAMP1 transmembrane protein/ with amino acid positions according to SEQ ID NO: 24 |
|---|---|---|
| pXL5997 | LAMP1_hL1_mL2_hL34_ΔGYQTI | Hybrid LAMP1 human in L1, L3 and L4 murine in L2 |
| pXL5990 | LAMP1_mseq6_ΔGYQTI | Hybrid LAMP1; human sequence except murine sequence at position 97 to 110 in L2 |
| pXL5991 | LAMP1_mseq7_ΔGYQTI | Hybrid LAMP1 human sequence except murine sequence at position 110 to 128 in L2 |
| pXL5992 | LAMP1_mseq8_ΔGYQTI | Hybrid LAMP1 human sequence except murine sequence at position 128 to 144 in L2 |
| pXL5993 | LAMP1_mseq9_ΔGYQTI | Hybrid LAMP1 human sequence except murine sequence at position 144 to 157 in L2 |
| pXL5994 | LAMP1_mseq10_ΔGYQTI | Hybrid LAMP1 human sequence except murine sequence at position 157 to 173 in L2 |
| pXL5995 | LAMP1_mseq11_ΔGYQTI | Hybrid LAMP1 human sequence except murine sequence at position 173 to 189 in L2 |
| pXL5996 | LAMP1_mseq12_ΔGYQTI | Hybrid LAMP1 human sequence except murine sequence at position 189 to 196 in L2 |
| pXL6009 | mLAMP1_ΔGYQTI | murine LAMP1 |
| pXL6012 | LAMP1_mseq1_ΔGYQTI | Hybrid LAMP1 human sequence except murine sequence at position 29 to 41 in L1 |
| pXL6013 | LAMP1_mseq2_ΔGYQTI | Hybrid LAMP1 human sequence except murine sequence at position 41 to 56 in L1 |
| pXL6014 | LAMP1_mseq3_ΔGYQTI | Hybrid LAMP1 human sequence except murine sequence at position 56 to 68 in L1 |
| pXL6015 | LAMP1_mseq4_ΔGYQTI | Hybrid LAMP1 human sequence except murine sequence at position 68 to 80 in L1 |
| pXL6017 | LAMP1_mseq5_ΔGYQTI | Hybrid LAMP1 human sequence except murine sequence at position 80 to 97 in L1/L2 |
| pXL6041 | mLAMP1_hseq6-11_ΔGYQTI | Hybrid LAMP1 murine sequence except human sequence at position 91 to 104 and 167 to 183 in L2 |
| pXL6047 | mLAMP1_hseq6_ΔGYQTI | Hybrid LAMP1 murine sequence except human sequence at position 91 to 104 in L2 |
| pXL6048 | mLAMP1_hseq11_ΔGYQTI | Hybrid LAMP1 murine sequence except human sequence at position 167 to 183 in L2 |
| pXL6092 | mLAMP1_hseq6-9-11_ΔGYQTI | hybrid LAMP1 murine sequence except human sequence at position 91 to 104 and 138 to 151 and 167 to 183 in L2 |

Example 6.5: Determination of Binding Affinity and Epitope by Flow Cytometry Each expression plasmid described in example 6.4 was complexed with 293Fectin™ in suspension-cultivated 293-F cells as using the protocol outlined in example 6.2. Two days post transfection cells were processed, analyzed by flow cytometry (Guava® easyCyte™ 8HT) as mentioned in example 4.7, and the mean fluorescence was recorded. This fluorescence represents a semi-quantitative assessment of binding.

The results obtained with plasmids pXL5626, pXL5668, pXL5669, pXL5719 and pXL5720 are summarized in Table 15.

TABLE 15

Binding of huMAb1_1, chMAb1, chMAb2 and chMAb3 onto LAMP1 proteins by flow cytometry (Mean fluorescence)

| Plasmid | pXL5626 | pXL5668 | pXL5669 |
|---|---|---|---|
| Protein | hLAMP1_ΔGYQTI | LAMP1_mL1_hL234_ΔGYQTI | LAMP1_hL12_mL34_ΔGYQTI |
| huMAb1_1 | 864 | 1112 | 934 |
|  | Binding | Binding | Binding |

TABLE 15-continued

Binding of huMAb1_1, chMAb1, chMAb2 and chMAb3 onto LAMP1 proteins by flow cytometry (Mean fluorescence)

| chMAb1 | 1047 | 1059 | 1484 |
|---|---|---|---|
|  | Binding | Binding | Binding |
| chMAb2 | 1025 | 6 | 814 |
|  | Binding | No binding | Binding |
| chMAb3 | 640 | 21 | 764 |
|  | Binding | No binding | Binding |

| Plasmid |  | pXL5719 | pXL5720 |
|---|---|---|---|
| Protein |  | hLAMP1_ΔglycaninL1_ΔGYQTI | hLAMP1_ΔglycaninL2_ΔGYQTI |
| huMAb1_1 |  | 1103 | 528 |
|  |  | Binding | Binding |
| chMAb1 |  | 1113 | 1006 |
|  |  | Binding | Binding |
| chMAb2 |  | 458 | 958 |
|  |  | Binding | Binding |
| chMAb3 |  | 706 | 765 |
|  |  | Binding | Binding |

This first set of affinity data (Table 15) with membrane-anchored LAMP1 proteins are in agreement with the ELISA data reported on Example 6.3 with the secreted LAMP1 proteins. MAb1 binds to hLAMP1 in L2 positions 101 to 195 of hLAMP1 (SEQ ID No: 24), MAb2 and MAb3 bind to hLAMP1 in L1 positions 29 to 100 of hLAMP1. These data also showed that none of the three anti-LAMP1 bind to a glycotope since MAb1 binds to LAMP1 for which L2 was engineered to have no N-glycosylation site and MAb2 and MAb3 bind to LAMP1 for which L1 was engineered to have no N-glycosylation site. The results obtained with plasmids pXL5626, pXL5988, pXL5669, pXL5990 to pXL5997 are summarized in Table 16.

TABLE 16

Binding of huMAb1_1 and chMAb2 onto LAMP1 proteins by flow cytometry (mean fluorescence)

| Plasmid | Protein | huMAb1_1 | chMAb2 |
|---|---|---|---|
| pXL5626 | hLAMP1_ΔGYQTI | 1412 | 1498 |
|  |  | Binding | Binding |
| pXL5988 | LAMP1_mL1_hL2_mL34_ΔGYQTI | 1180 | 10 |
|  |  | Binding | No binding |
| pXL5997 | LAMP1_hL1_mL2_hL34_ΔGYQTI | 25 | 1167 |
|  |  | No Binding | Binding |
| pXL5990 | LAMP1_mseq6_ΔGYQTI | 11 | 1721 |
|  |  | No Binding | Binding |
| pXL5991 | LAMP1_mseq7_ΔGYQTI | 1400 | 1412 |
|  |  | Binding | Binding |
| pXL5992 | LAMP1_mseq8_ΔGYQTI | 1440 | 1688 |
|  |  | Binding | Binding |
| pXL5993 | LAMP1_mseq9_ΔGYQTI | 545 | 1461 |
|  |  | Binding | Binding |
| pXL5994 | LAMP1_mseq10_ΔGYQTI | 1414 | 1555 |
|  |  | Binding | Binding |
| pXL5995 | LAMP1_mseq11_ΔGYQTI | 16 | 1378 |
|  |  | No Binding | Binding |
| pXL5996 | LAMP1_mseq12_ΔGYQTI | 1303 | 1365 |
|  |  | Binding | Binding |
| ballast | no LAMP1 | 1 | 1 |
|  |  | No binding | No binding |

The results obtained with plasmids pXL5626, pXL6041, pXL6047, pXL6048, and pXL6009 are summarized in Table 17.

TABLE 17

Binding of MAb1 and MAb2 onto LAMP1 proteins by flow cytometry (mean fluorescence

| Plasmid | Protein | Experiment n°1 | | Experiment n°2 |
|---|---|---|---|---|
| | | MAb1 | MAb2 | MAb1 |
| pXL5626 | hLAMP1_ΔGYQTI | 1748 Binding | 1183 binding | 551 Full binding |
| pXL6041 | mLAMP1_hseq6-11_ΔGYQTI | 680 Binding | 28 No binding | 211 binding |
| pXL6047 | mLAMP1_hseq6_ΔGYQTI | 7 No binding | 25 No binding | 3 No binding |
| pXL6048 | mLAMP1_hseq11_ΔGYQTI | 6 No binding | 28 No binding | 2 No binding |
| pXL6092 | mLAMP1_hseq6-9-11_ΔGYQTI | Not done | Not done | 499 Full binding |
| pXL6009 | mLAMP1_ΔGYQTI | 4 No binding | 21 No binding | 2 No binding |

The results obtained with plasmids pXL5626, pXL6012 to pXL6015, pXL6017 and pXL6009 are summarized in Table 18.

TABLE 18

Binding of MAb1, MAb2 and MAb3 onto LAMP1 proteins by flow cytometry (mean fluorescence

| Plasmid | Protein | MAb1 | MAb2 | MAb3 |
|---|---|---|---|---|
| pXL5626 | hLAMP1_ΔGYQTI | 914 Binding | 757 Binding | 749 Binding |
| pXL6012 | LAMP1_mseq1_ΔGYQTI | 1027 Binding | 105 Low binding | 2.8 No binding |
| pXL6013 | LAMP1_mseq2_ΔGYQTI | 990 Binding | 694 Binding | 803 Binding |
| pXL6014 | LAMP1_mseq3_ΔGYQTI | 888 Binding | 694 Binding | 674 Binding |
| pXL6015 | LAMP1_mseq4_ΔGYQTI | 891 Binding | 27 No binding | 3 No binding |
| pXL6017 | LAMP1_mseq5_ΔGYQTI | 846 Binding | 629 Binding | 721 Binding |
| pXL6009 | mLAMP1_ΔGYQTI | 13 No binding | 27 No binding | 3 No binding |

The affinity data described in Table 16 with membrane-anchored LAMP1 proteins demonstrated that MAb1 binds to LAMP1 in L2 positions 101 to 195 of hLAMP1 (SEQ ID NO: 24) (pXL5626, pXL5988 and pXL5997). More specifically MAb1 does not bind to hybrid LAMP1 protein where human LAMP1 residues from positions 97 to 110 or from positions 173 to 189 have been substituted by murine LAMP1 residues, but it binds to hybrid LAMP1 protein where human LAMP1 residues from positions 110 to 173 or from positions 189 to 196 in L2 have been substituted by murine LAMP1 residues. Of note some binding is also lost when human LAMP1 residues from position 144 to 157 are replaced by the murine LAMP1 residues. In addition data reported in Table 17 Experiment No 1 showed that residues from positions 97 to 110 and from positions 173 to 189 are simultaneously needed to restore some of the binding. Data reported in Table 17 experiment No 2 showed that residues from positions 91 to 104 and 138 to 151 and 167 to 183 in Loop2 are simultaneously needed to restore full binding of MAb1.

From these sets of affinity data (Tables 15, 16, 17 and 18) obtained by flow cytometry with membrane-anchored LAMP1 proteins and the ELISA results with the secreted LAMP1 proteins described in Example 6.3, the following conclusions could be derived:

MAb1 binds to L2 positions 101 to 195 of LAMP1, MAb2 and MAb3 bind to L1 positions 29 to 100 of LAMP1.

None of the three anti-LAMP1 bind to a glycotope since MAb1 binds to LAMP1 for which L2 was engineered to have no N-glycosylation site and MAb2 and MAb3 bind to LAMP1 for which L1 was engineered to have no N-glycosylation site.

MAb1 does not bind to hybrid LAMP1 protein where human LAMP1 residues from positions 97 to 110 (SEQ ID NO: 78) or from positions 173 to 189 (SEQ ID NO: 79) have been substituted by murine LAMP1 residues. But it binds to hybrid LAMP1 protein where human LAMP1 residues from positions 110 to 173 or from positions 189 to 196 in L2 have been substituted by murine LAMP1 residues.

MAb1 interacts with amino acids located within L2 and more specifically MAb1 interacts with amino acids located within sequences from positions 101 to 110 (SEQ ID NO: 72) and/or from positions 174 to 188 (SEQ ID NO: 74) and to some extent to sequence from positions 144 to 157 (SEQ ID NO: 73). Therefore, we can infer from these results and from amino acid differences between murine and human sequences that human LAMP1 residues among R146, D150, K152, R106, A108, N181, S182, S183, R186 and G187 are likely to interact with MAb1.

MAb2 interacts with amino acids located within L1 and more specifically MAb2 interacts with amino acids located within sequences from positions 68 to 80 (SEQ ID NO: 76) and to some extent within sequences from positions 29 to 41 (SEQ ID NO: 75). Therefore, we can infer from these results and from amino acid differences between murine and human sequences that human LAMP1 residues among A29, M30, M32, G36, A40, S69, D70, T72, V74, L75, and R77 are likely to interact with MAb2.

MAb3 interacts with amino acids located within L1 and more specifically MAb3 interacts with amino acids located within sequences from positions 29 to 41 (SEQ ID NO: 75) and/or from positions 68 to 80 (SEQ ID NO: 76). Therefore, we can infer from these results and from amino acid differences between murine and human sequences that human LAMP1 residues among A29, M30, M32, G36, A40, S69, D70, T72, V74, L75, and R77 are likely to interact with MAb3.

Example 6.6: Determination of Individual Amino Acid Involved in Epitope Binding by Ala Scan Individual residues identified in example 6.5 and not involved in β-strand structure have been individually replaced by an alanine residue in the LAMP1 sequence derived from hLAMP1_ΔGYQTI and encoded in plasmid pXL5626 (example 6.4). A total of 21 plasmids were engineered from pXL5626 (see Table 19) and used to assay LAMP1 expression at the cell membrane of HEK293 cells after transient transfection. Two days post transfection cells were processed, analyzed by flow cytometry (Guava® easy-Cyte™ 8HT) as mentioned in example 4.7, and the mean fluorescence was recorded. This fluorescence represents a semi-quantitative assessment of binding. Loss of binding is reported on Table 19 when there is a decrease of more than 50% of the mean fluorescence compared to the control protein encoded from pXL5626.

TABLE 19

Loss of binding to anti-LAMP1 mAb with Alascan LAMP1 transmembrane proteins

| Plasmid | Position of mutation in hLAMP1_ΔGYQTI | Binding to MAb1 | Binding to MAb3 |
|---|---|---|---|
| pXL5626 | none | | |
| pXL6058 | G36A | | |
| pXL6065 | N37A | | |
| pXL6059 | G38A | | Binding loss |
| pXL6060 | L67A | | |
| pXL6066 | P68A | | |
| pXL6067 | S69A | | |
| pXL6069 | D70A | | Binding loss |
| pXL6072 | N107A | | |
| pXL6073 | A108T | | |
| pXL6080 | T109A | | |
| pXL6070 | I149A | Binding loss | |
| pXL6085 | D150A | Binding loss | |
| pXL6071 | K151A | | |
| pXL6079 | Y178A | | |
| pXL6074 | L179A | | |
| pXL6075 | S180A | | |
| pXL6076 | N181A | | |
| pXL6077 | F184A | | |
| pXL6081 | R186A | Binding loss | |
| pXL6082 | G187A | | |

Loss of binding to MAb1 at positions I149, D150 and R186 due to Ala substitution in LAMP1 protein indicates that these positions are important for MAb1 binding to LAMP1.

Loss of binding to MAb3 at positions G38 and D70 due to Ala substitution in LAMP1 protein indicate that these positions are important for MAb2 binding to LAMP1.

Example 7: Determination of mAb Sequences

Example 7.1: Determination of mAb Sequences and Generation of Chimeric mAbs

The sequences of the variable domains of the mAb were retrieved from the hybridoma and cloned into an expression vector to ensure that the cloned mAbs had the same characteristics as the initial murine mAbs.

The cDNA encoding the variable domains of the monoclonal antibodies were obtained as follows. cDNA has been retrieved and sequenced by RT-PCR (transcriptase SuperScript III from Invitrogen and polymerase Phusion from Finnzymes) from 100 hybridoma cells and oligonucleotides located at the 5'-end of the cDNA encoding the variable regions and the constant domains.

High Resolution Mass Spectrometry of Hybridoma (HRMS):

Mass spectra were obtained on a Waters Synapt G2 TOF system in electrospray positive mode (ES+). Chromatographic conditions are the following: column: UPLC MassPrep 20 μm 2.1X5 mm; solvents: A: $H_2O$+0.1% formic acid: B; $CH_3CN$+0.1% formic acid; column temperature: 80° C.; flow rate 0.2 mL/min; gradient elution (10 min): 10% B for 30 sec; from 10 to 50% of B in 7 min 10 sec; 8 min:90% B; 8 min 30 sec:10% B; 10 min: 10% B. Samples were reduced 30 min at 37° C. in Gdn.HCL 6M/DTT 1M before LC/MS analysis.

The derived amino acid sequences provided information in agreement with the data obtained on purified mAbs derived from the hybridoma by N-terminal sequencing and mass spectrometry (LC/MS) of the heavy and light chains (LC, HC) Table 20. No identical sequences were found in the patented sequences from GenomeQuest.

TABLE 20

Mass spectrometry analysis of anti-LAMP1 mAbs from hybridoma

| Clone ID | Chain | Mass (Da) by LC/MS from batch | Mass (Da) in silico value retrieved from sequence |
|---|---|---|---|
| MAb1 | LC | 23587 | 23587 |
| | HC (G0F) | 50700 | 50700 |
| MAb2 | LC | 23911 | 23911 |
| | HC (G0F) | 50702 | 50704 |
| MAb3 | LC | 23725 + higher masses due to N-glycans | 23723 |
| | HC (G0F) | 50852 | 50848 |

The nucleic acid sequences of the variable domains VH and VL were cloned into expression vectors in fusion with the human IgG1 or the human Ckappa constant domain coding sequences, respectively, to then generate batches of chimeric mAbs by transient expression in 293-F cells as described in Example 6.2. Batches were purified by protein A affinity chromatography (MabSelect, GE Heathcare). The eluate was dialyzed against PBS before sterile filtration and storage at 4° C.

Affinity to LAMP1 remained similar for murine and chimeric mAbs illustrated by the $EC_{50}$ obtained by ELISA with LAMP1 in Table 21.

TABLE 21

$EC_{50}$ (nM) obtained with LAMP1 for murine hybridoma and corresponding chimeric mAbs

| $EC_{50}$ obtained for murine hybridoma mAbs: clone ID | hLAMP1 | $EC_{50}$ obtained for chimeric mAbs: clone ID | hLAMP1 |
|---|---|---|---|
| MAb1 | 0.18 nM | chMAb1 | 0.12 nM (assay A) |
| | | | 0.12 nM (assay B) |
| MAb2 | 0.25 nM | chMAb2 | 0.12 nM (assay A) |
| | | $chMAb2_{can}$ | 0.12 nM (assay A) |
| | | chMAb3 | 0.12 nM (assay B) |
| | | chMAb3VL_R24_R93 | 0.11 nM (assay B) |

Based on the data described above, the amino acid sequences of the HC and the LC were validated.

The LC and HC sequences of MAb1 are shown in SEQ ID NO: 35 and SEQ ID NO: 36, respectively.

The LC and HC sequences of MAb2 are shown in SEQ ID NO: 37 and SEQ ID NO: 38, respectively.

The sequences for the CDR regions were deduced from the protein sequence using the IMGT nomenclature.

The LC and HC sequences of chMAb1 are shown in SEQ ID NO: 18 and SEQ ID NO: 17, respectively, and the LC and HC sequences of chMAb2 are shown in SEQ ID NO: 20 and SEQ ID NO: 19, respectively. The LC and HC sequences of chMAb3 are shown in SEQ ID NO: 49 and SEQ ID NO: 50, respectively.

Of note, canonical residues have been introduced into clone MAb2 at positions A9, L51, L58, G72 and L108 on VL and at position T116 on VH sequence, to generate MAb2$_{can}$. The corresponding amino acid sequences of the VH and the VL of MAb2$_{can}$ are SEQ ID NO: 15 and SEQ ID NO: 16, respectively. The HC and LC sequences of chMAb2$_{can}$ are shown in SEQ ID NO: 21 and 22, respectively.

A batch of clone chMAb2$_{can}$ was generated in the same conditions as the batch corresponding to clone chMAb2. This highlights that point mutations in the FR can be made without any impact on binding but more importantly provide an alternative to the production process.

A batch of clone chMAb3_VLR24-R93 was generated in the same conditions as the batch corresponding to clone chMAb3. This highlights that point mutations in the CDR can be made without any impact on binding.

Affinity to LAMP1 by SPR:

The binding kinetics of the murine, chimer or humanized anti-LAMP1 mAbs were determined by surface plasmon resonance assay using a BIAcore 2000 (BIAcore Inc., Uppsala, N.J.). Briefly, a CM5 BIAcore biosensor chip was docked into the instrument and activated with 70 µL of 1:1 NHS/EDC at room temperature. A mouse anti-αhuman Fc IgG1 (BIAcore #BR-1008-39) and rabbit anti-αmurine Fc IgG1 (BIAcore #BR-1008-38) (50 µg/mL in 1 M acetate buffer, pH5) were immobilized on the activated chips in all flow cells. The immobilization was carried out at a flow rate of 10 µL/min up to saturation. The chip was then blocked by injection of 70 µL of ethanolamine-HCl, pH 8.5, followed by one wash with 3 M MgCl$_2$ for anti-αhuman Fc IgG1 and one wash with 10 mM Glycine-HCl pH 1.7 for anti-αmurine Fc IgG1. To measure the binding of anti-LAMP1 mAbs to LAMP1, antibodies were used at 1-5 µg/mL in BIAcore running buffer (HBS-EP). The antigen (SEQ ID NO: 28 protein produced as described in example 6.2) was injected from 1 to 256 nM. Following completion of the injection phase, dissociation was monitored in a BIAcore running buffer at the same flow rate for 600 sec. The surface was regenerated between injections using 2×5 µL 3 M MgCl$_2$ (2×30 s) or anti-αhuman Fc IgG1 and 1×30 µL 10 mM Glycine-HCl pH 1.7 for anti-αmurine Fc IgG1 (180 s). Individual sensorgrams were analyzed using BIAevaluation software.

Affinity to LAMP1 for the murine, chimer or humanized mAbs is reported on Table 22. It was found to be independent of the MAb format.

MAb1 binds to LAMP1 with K$_D$ ranging from 4.8 to 8.2 nM

MAb2 binds to LAMP1 with K$_D$ ranging from 63.5 to 68.8 nM

MAb3 binds to LAMP1 with K$_D$ ranging from 4.7 to 7.2 nM

The commercially available anti-LAMP1 mAb (H4A3 (BioLegend 328602)) has a significantly kigher K$_D$ and thus a lower binding efficiency than Mab1, Mab 2 and MAb 3 with a Kd of around 100 nM.

TABLE 22

Binding kinetics to LAMP1 for the murine, chimer or humanized mAbs

| Mab | k$_a$ (M$^{-1}$·s$^{-1}$) | k$_d$ (s$^{-1}$) | K$_D$ (nM) |
|---|---|---|---|
| Mab1 | 14.8E+04 | 0.71E−03 | 4.8 |
| huMAb1_1 | 19.1E+04 | 1.57E−03 | 8.2 |
| chMAb2can | 7.21E+04 | 4.96E−03 | 68.8 |
| Mab2 | 6.33E+04 | 4.02E−03 | 63.5 |
| chMAb3VL_R24_R93 | 17.3E+04 | 1.25E−03 | 7.2 |
| MAb3 | 24.2E+04 | 1.13E−03 | 4.7 |
| Murine H4A3 (BioLegend 328602) | 5.80E+04 | 6.09E−03 | 105 |

Example 7.2: Obtention and Characterisation of Humanized Variants Derived from MAb1

In this example, humanized variants of parental murine IgG MAb1 have been designed in silico. The resulting huMAb1 variants were produced and provided similar characteristics as the chimer chMAb1.

Example 7.2.1 Design of the Humanized Anti-LAMP1 huMAb1

Humanization Based on CDR Grafting

This approach consists in the transplantation of CDRs of the parental murine MAb1 into relevant human FRs. The variable light and heavy regions of murine MAb1 were compared to human germline sequences from IMGT Information system (Lefranc et al. Nucl. Acids. Res. 2009, 37:D1006-D1012) to select the human light and heavy variable sequences that would serve as the basis of the humanized MAb1 regions (huMAb1).

The mouse light chain variable region displayed 68.8% identity over the V region and 74.7% identity within the FRs alone to the human germline kappa light chain IGKV1-27. For the joining region, mouse J region displayed 90% identity to human germline IGKJ4. Consequently human V region IGKV1-27 combined to human J region IGKJ4 given a global germinality index (identity calculated on FRs only) of 76.4% have been selected as human acceptor sequences for humanization of the mouse MAb1 light chain. This then became the basis of the humanized variant of the anti-LAMP1 MAb1 light chain, which comprised the CDRs of the murine MAb1 Vk region and the FRs of the human IGKV1-27_IGKJ4 regions.

The mouse heavy chain variable region displayed 65.3% identity over the V region and 70.0% identity within the FRs alone to the human heavy variable germline IGHV1-69. For the joining region, mouse J region displayed 78% identity to human heavy joining germline IGHJ4. Consequently human germline V region IGHV1-69 combined to human germline J region IGHJ4 given a global germinality index (identity calculated on FRs only) of 71.4% have been selected as human acceptor sequences for humanization of the murine MAb1 heavy region. This then became the basis of the humanized variant of the anti-LAMP1 MAb1 heavy chain, which comprised the CDRs of the murine MAb1 Vh region and the FRs of the human IGHV1-69_IGHJ4 regions.

However, some FRs residues are also important for the biological activity of the antibody since they can impact CDRs conformation and thus antigen binding. Back mutations to murine amino acid may be introduced at selected positions of FRs grafted antibody in order to retain the binding specificity and affinity of the parent antibody. Thus, the next step in the design process was to study the protein sequences of the humanized variant to determine if any of these amino acid residues were likely to alter the conformation or orientation of the CDRs loops. A 3D homology model of the variable regions of both the murine and the humanized antibodies were built using model antibody framework protocol of Discovery studio 3.1 from Accelrys Software Inc.

The VL and VH sequences of the murine MAb1 were compared to the protein database (PDB) (Berman et al. Nucleic Acids Research, 2000, 28:235-242).

The structure model of the antithrombotic monoclonal antibody 82D6A3 with the PDB identity number 2ADF was used as template for the light chain (96.6% identity on light chain framework) and the structure model of of IL-23 in complex with neutralizing FAB with the PDB identity number 3D85 was used as template for the heavychain (83.5% identity on heavy chain framework).

In the same way, the VL and VH sequences of the humanized variant (human FRs and murine CDR) were compared to the protein database (PDB) (Berman et al. Nucleic Acids Research, 2000, 28:235-242). The model with the PDB identity number 3AAZ was used as template for the light chain (86.6% identity on light chain framework) and the model with the PDB identity number 3KDM was used as template for the heavy chain (84.3% identity on heavy chain framework) (All PDB references refer to the PDB identity number as available on Nov. 26, 2013).

Both 3D homology models, the murine MAb1 and the humanized version were compared and each amino acid substitution from mouse to human version were carefully looked. When the substitution of a mouse to a human residue was done at a position that could influence the conformation of the CDRs, a back mutation to the murine residue was done.

Humanization Based on Molecular Dynamic Trajectories (4D Humanization Protocol)

A molecular dynamics (MD) simulation of the 3D homology model of the murine MAb1 (as described in section above on grafting protocol) was subsequently performed, with constraints on the protein backbone at 500 K temperature for 1.1 nanoseconds (ns) in Generalized Born implicit solvent. 10 diverse conformations were extracted from this first MD run every 100 picoseconds (ps) for the last 1 ns. These diverse conformations were then each submitted to a MD simulation, with no constraints on the protein backbone and at 300 K temperature, for 2.3 ns. For each of the 10 MD runs, the last 2,000 snapshots, one every ps, from the MD trajectory were then used to calculate, for each murine MAb1 amino acid, its root mean square deviations (rmsd) compared to a reference medoid position. By comparing the average rmsd on the 10 separate MD runs of a given amino acid to the overall average rmsd of all MAb1 murine amino acids, one decides if the amino acid is flexible enough, as seen during the MD to be considered as likely to interact with B-cell receptors and responsible for activation of the immune response. 28 amino acids were identified as flexible in the murine MAb1 antibody, excluding the CDRs and its immediate 5 Å vicinity.

The motion of the 60 most flexible murine MAb1 amino acids, during the 20 ns (10×2 ns) of molecular dynamic simulation, were then compared to the motion of the corresponding flexible amino acids of 49 human 3D homology models, for each of which were run the same simulations. These 49 human models have been built by systematically combining a representative panel of 7 human light chains (namely vk1, vk2, vk3, vk4, vlambda1, vlambda2, vlambda3) with a representative panel of 7 human heavy chains (namely vh1a, vh1b, vh2, vh3, vh4, vh5, vh6).

The vk1-vh1b combination showed the highest 4D similarity of its flexible amino acids compared to the flexible amino acids of the murine MAb1 antibody; this model was therefore used to humanize the MAb1 antibody, focusing on the flexible amino acids. For the pairwise amino acid association between the murine MAb1 and vk1-vh1b amino acids, the 2 sequences were aligned based on the optimal 3D superposition of the alpha carbons of the 2 corresponding homology models.

In addition, to improve the stability of the resulting humanized MAb1 antibody, the amino acids of the light and heavy chains with low frequency of occurrence vs their respective canonical sequences, excluding the CDRs, are originally proposed to be mutated into the most frequently found amino acids (ΔΔGth>0.5 kcal/mol; (Monsellier et al. J. Mol. Biol. 2006, 362, 580-593). A first list of consensus mutations for the LC and for the HC has been restricted to the amino acids found in the closest human model (i.e. vk1-vh1b). None of these mutations are located in the "Vernier" zone (Foote et al., J. Mol. Biol. 1992, 224, 487-499). Other criteria are taken into account to consider these consensus mutations for potentially stabilizing the anti-LAMP1 MAb1 antibody. These criteria are a favourable change of hydropathy at the surface or a molecular mechanics based predicted stabilization of the mutant. Stabilizing mutations reported to be successful in the literature (Bedouelle, H. J. Mol. Biol. 2006, 362, 580-593; Steipe B. J. Mol. Biol. 1994, 240, 188-192) were considered.

Resulting Humanized VL and VH Regions

Based on both approached, the CDRs grafting and the 4D protocols, three versions for the variable light chain (VL1, VL2 and VL3) and three versions for the variable heavy chain (VH1, VH2 and VH3) are proposed. The particular combination of amino acid residues mutated in each humanized MAb1 VL and VH variants are set forth in Table 23 and Table 24 respectively. The complete amino acid sequences of the humanized VH and VL domains are set forth in Table 25.

For the Variable Light Region:

The humanized VL1 variant with SEQ ID NO: 56 displays a total of 12 mutations compared to mouse sequence with SEQ ID NO: 5. This variant derives from frameworks of human germline IGKV1-27_IGKJ4 sequences with 6 back mutations done because they were suspected to have negative impact on mAb structure, CDRs conformation and therefore, on binding to its target. In addition, for amino acids at position 43 and 83, mutation in a more frequent amino acid present in IGKV1 germlines (A43 and F83) was preferred.

The humanized VL2 variant with SEQ ID NO: 57 displays 2 mutations which derive from the direct comparison between the non-CDR most flexible amino acids of the murine MAb1 light chain and the vk1 human light chain sequence.

The humanized VL3 variant with SEQ ID NO: 58 derives from VL2 and includes 6 new mutations that are consensus (vk1 sequence) and potentially stabilizing.

The particular combination of amino acid residues mutated in the individual humanized light chains of huMAb1 thus VL of huMab1_1, huMab1_2 and huMab1_3 are set forth in Table 23.

TABLE 23

Mutations of the VL variants of the anti-LAMP1 MAb1 antibody

| Mouse MAb1 VL | HuMab1_1 (VL1) | HuMab1_2 (VL2) | HuMab1_3 (VL3) |
|---|---|---|---|
| P9 | S9 | | S9 |
| L15 | V15 | V15 | V15 |
| G17 | D17 | | |
| K18 | R18 | | |
| D38 | | | Q38 |
| G43 | A43 | | |
| R45 | | K45 | K45 |
| P56 | S56 | | |
| I58 | V58 | | V58 |
| S72 | T72 | | |
| F73 | L73 | | L73 |
| S74 | T74 | | T74 |
| N77 | | | S77 |
| I83 | F83 | | |
| L103 | V103 | | |

For the Variable Heavy Region:

The VH1 variant (SEQ ID NO: 53) displays a total of a total of 15 residues substitution compared to the mouse sequence (SEQ ID NO: 1). This variant derives from frameworks of human germline IGHV1-69_IGHJ4 sequences with 9 back mutations done because they were expected to have negative impact on mAb structure, CDRs conformation and therefore, on binding to its target. In addition, K74 of SEQ ID NO: 1 in vicinity of CDRs was mutated into T to anticipate a potential problem if targeted by the conjugation process.

The VH2 variant displays 7 mutations: 6 mutations deriving from the direct comparison between the non-CDR most flexible amino acids of the murine MAb1 heavy chain and the vh1b human heavy chain sequence, plus mutation of K74 of SEQ ID NO: 1 into T to anticipate a potential problem if targeted by the conjugation process.

The VH3 variant derives from VH2 and includes 7 new mutations that are consensus (vh1b sequence) and potentially stabilizing.

The particular combination of amino acid residues mutated in the individual humanized light chains of huMAb1 thus VH of huMab1_1, huMab1_2 and huMab1_3 are set forth in Table 24.

TABLE 24

Mutations of the VH variants of the anti-LAMP1 MAb1 antibody

| Mouse MAb1 VH | HuMab1_1 (VH1) | HuMab1_2 (VH2) | HuMab1_3 (VH3) |
|---|---|---|---|
| Q5 | V5 | V5 | V5 |
| L11 | V11 | | |
| V12 | K12 | | |
| A16 | S16 | | |
| M20 | V20 | | |
| K38 | | | R38 |
| K39 | | | Q39 |
| S40 | | | A40 |
| S61 | | | A61 |
| K65 | Q65 | Q65 | Q65 |
| D66 | G66 | | G66 |
| K67 | | R67 | R67 |
| K74 | T74 | T74 | T74 |
| S76 | T76 | | |
| Q82 | E82 | E82 | E82 |
| R85 | S85 | S85 | S85 |
| T87 | R87 | | |
| S91 | T91 | | T91 |
| S115 | T115 | | T115 |
| A118 | S118 | S118 | S118 |

The resulting humanized sequences were blasted for sequence similarity against the Immune Epitope Data Base (IEDB) database ((PLos Biol (2005) 3(3)e91) on the world wide web at immuneepitope.org;) to ensure that none of the sequences contain any known B- or T-cell epitope listed in.

The complete amino acid sequences of the humanized VH and VL domains are set forth in Table 25.

TABLE 25

VH and VL amino acid sequences of humanized anti-LAMP1 antibodies.

| VH or VL variant | Sequence | SEQ ID NO. |
|---|---|---|
| huMAb1_1 VH1 | QVQLVQSGAEVKKPGSSVKVSCKASGYIFTN YNIHWVKKSPGQGLEWIGAIYPGNGDAPYSQ KFQGKATLTADTSTSTTYMELSSLRSEDTAVY YCVRANWDVAFAYWGQGTLVTVSS | SEQ ID NO: 53 |
| huMAb1_2 VH2 | QVQLVQSGAELVKPGASVKMSCKASGYIFTN YNIHWVKKSPGQGLEWIGAIYPGNGDAPYSQ KFQDRATLTADTSSSTTYMELSSLTSEDSAVY YCVRANWDVAFAYWGQGTLVSVSS | SEQ ID NO: 54 |
| huMAb1_3 VH3 | QVQLVQSGAELVKPGASVKMSCKASGYIFTN YNIHWVRQAPGQGLEWIGAIYPGNGDAPYAQ KFQGRATLTADTSSSTTYMELSSLTSEDTAVY YCVRANWDVAFAYWGQGTLVTVSS | SEQ ID NO: 55 |
| huMAb1_1 VL1 | DIQMTQSPSSLSASVGDRVTITCKASQDIDRY MAWYQDKPGKAPRLLIHDTSTLQSGVPSRFS GSGSGRDYTLTISNLEPEDFATYYCLQYDNLW TFGGGTKVEIK | SEQ ID NO: 56 |
| huMAb1_2 VL2 | DIQMTQSPPSLSASVGGKVTITCKASQDIDRY MAWYQDKPGKGPKLLIHDTSTLQPGIPSRFS GSGSGRDYSFSISNLEPEDIATYYCLQYDNLW TFGGGTKLEIK | SEQ ID NO: 57 |

TABLE 25-continued

VH and VL amino acid sequences of humanized anti-LAMP1 antibodies.

| VH or VL variant | Sequence | SEQ ID NO. |
|---|---|---|
| huMAb1_3 VL3 | DIQMTQSPSSLSASVGGKVTITCKASQDIDRY MAWYQQKPGKGPKLLIHDTSTLQPGVPSRFS GSGSGRDYSLTISSLEPEDIATYYCLQYDNLW TFGGGTKLEIK | SEQ ID NO: 58 |

Example 7.2.2: Production and Characterization of Three Humanized Anti-LAMP1 huMAb1 Variants The corresponding nucleic acid sequences encoding the humanized variable VH and VL domains described in example 7.2.1 were synthesized at Geneart and cloned into expression vectors in fusion with the human IgG1 or the human Ckappa constant domain coding sequences, respectively, to then generate batches of humanized mAbs by transient expression in 293-F cells as described in Example 6.2. The three mAbs were referred to—huMAb1_1 that contains LC1 (VL1-huCk) (SEQ ID NO: 59) and HC1 (VH1-huIgG1) (SEQ ID NO: 60),
  huMAb1_2 that contains LC2 (VL2-huCk) (SEQ ID NO: 61) and HC2 (VH2-huIgG1) (SEQ ID NO: 62),
  huMAb1_3 that contains LC3 (VL3-huCk) (SEQ ID NO: 63) and HC3 (VH3-huIgG1) (SEQ ID NO: 64).

A negative control was generated and referred to as huMAb1_negA. It contains LCnegA (VL1_36A-95A-huCk) (SEQ ID NO: 65) and HCnegA (VH1_101A-huIgG1) (SEQ ID NO: 67).

Another control was generated and referred to as huMAb1_negB. It contains LC1 (VL1-huCk) (SEQ ID NO: 59) and HCnegB (VH1-huIgG1_266A) (SEQ ID NO: 68). The mutation 266A in the huIgG1 corresponds to the D265A mutation according to the nomenclature described by Kabat et al., Sequences of Proteins of Immunological Interest, 5th edition, National Institute of Health, Bethesda, Md., 1991. It was reported to significantly decrease binding to FcγRs and ADCC (Lund et al., J. Immunol., 157:4963-4969, 1996; Shields et al., J. Biol. Chem., 276(1): 6591-6604, 2001).

Significant decrease in binding to FcγRI, II and III was also verified by ELISA with recombinant proteins (recombinant human FcγRI/CD64 reference 1257-FC-050, recombinant human FcγRIIA/CD32a reference 1330-CD-050/CF, recombinant human FcγRIIIa/CD16a, reference 4325-FC-050, all obtained from R&D System).

Batches were purified by protein A affinity chromatography (MabSelect, GE Heathcare). The eluate was dialyzed against PBS before sterile filtration and storage at 4° C. Batches were analysed by High Resolution Mass Spectrometry as described in Example 7. Data were in agreement with the in silico value retrieved from amino acid sequences, Table 26.

TABLE 26

Mass spectrometry analysis of humanized anti-LAMP1 mAbs

| mAb ID | Chain | by LC/MS from batch (Mass Da) | in silico value retrieved from sequence (Mass Da) |
|---|---|---|---|
| huMAb1_1 | LC1 | 23483 Da | 23484 Da |
|  | HC1 (G0F) | 50219 Da | 50219 Da |

TABLE 26-continued

Mass spectrometry analysis of humanized anti-LAMP1 mAbs

| mAb ID | Chain | by LC/MS from batch (Mass Da) | in silico value retrieved from sequence (Mass Da) |
|---|---|---|---|
| huMab1_2 | LC2 | 23375 Da | 23376 Da |
|  | HC2 (G0F) | 50209 Da | 50209 Da |
| huMAb1_3 | LC3 | 23318 Da | 23318 Da |
|  | HC3 (G0F) | 50176 Da | 50175 Da |
| huMAb1_negA | LCnegA | 23277 Da | 23277 Da |
|  | HCnegA (G0F) | 50103 Da | 50104 Da |
| huMAb1_negB | LC1 | 23484 Da | 23484 Da |
|  | HCnegB (G0F) | 50175 Da | 50175 Da |

Secreted human LAMP1 protein described in example 6.2 was used to determine the binding domain to the humanized anti-LAMP1 mAbs by ELISA. Affinity to LAMP1 remained similar for chimer and humanized mAbs as illustrated by the $EC_{50}$ obtained by ELISA with LAMP1 in Table 27. No binding is detected with huMAb1_negA.

TABLE 27

$EC_{50}$ (nM) obtained with LAMP1 for chimer and humanized mAbs

| mAb ID | hLAMP1 |
|---|---|
| chMAb1 | 0.09 nM |
| huMAb1_1 | 0.11 nM |
| huMAb1_2 | 0.11 nM |
| huMAb1_3 | 0.12 nM |
| huMAb1_negA | No binding detected |
| huMAb1_negB | 0.07 nM |

Example 7.2.3: Cross Reactivity of huMAb1_1; huMAb1_2 and huMAb1_3 with Cynomolgus Monkey LAMP1

HuMAb1_1, huMAb1_2 and huMAb1_3 antibodies were assessed by flow cytometry for their ability to bind to human LAMP1 or cynomolgus LAMP1 proteins expressed respectively at the surface of HCT116 or HEK293 stable clones. HCT116 stable clone was obtained as described in example 4.7. HEK293 stable clone was obtained according to the protocol described in example 4.7. $EC_{50}$s, estimated using BIOST@T-SPEED software, are listed in Table 28.

TABLE 28

Apparent affinity of huMAb1_1; huMAb1_2 and huMAb1_3 to human LAMP1 or cynomolgus monkey LAMP1

| | $EC_{50}$ (nM) | | |
|---|---|---|---|
| | HCT116 huLAMP1 clone 8 | HEK293 cynoLAMP1 clone 44 | Ratio of $EC_{50}$s |
| huMAb1_1 | 15.0 | 30.1 | 2.0 |
| huMAb1_2 | 6.6 | 13.3 | 2.0 |
| huMAb1_3 | 10.3 | 17.7 | 1.7 |

The result show, that huMAb1_1 binds to LAMP1 of human and cynomolgus origin with similar affinity with a ratio of $EC_{50s}$ of 2. HuMAb1_1 cross-reacts with cynomolgus LAMP1. HuMAb1_2 binds to LAMP1 of human and cynomolgus origin with similar affinity with a ratio of $EC_{50s}$ of 2.01. HuMAb1_2 cross-reacts with cynomolgus LAMP1. HuMAb1_3 binds to LAMP1 of human and cynomolgus origin with similar affinity with a ratio of $EC_{50s}$ of 1.71. HuMAb1_3 cross-reacts with cynomolgus LAMP1.

Example 7.3: Identification of the Epitope Binding Site of huMAb1_1 by Crystallography

Example 7.3.1: Obtention of Fab1/LAMP1 Complex

Expression and Purification of Fab from huMAb1_1

Recombinant Fab from huMAb1_1 (Fab1) was obtained from transiently transfected HEK293 cells, using two plasmids encoding the light chain LC1 or the C-terminal His-tagged heavy chain derived from HC1 with SEQ ID NO: 68 and 69, respectively. After cell clarification, growth supernatant was applied on an immobilized-metal affinity resin (IMAC). After elution from the resin, the fractions containing highly pure Fab1 were pooled & extensively dialysed against PBS. Fab1 solution was stored at 4° C.

Expression and Purification of Human Non-Glycosylated LAMP1-29-195

In order to obtain a non-glycosylated LAMP1 domain, bacterial expression system was used. A thioredoxin fusion protein was designed for expressing the domain L1-L2 of human LAMP1 protein with SEQ ID NO: 70(TrxA-His-Thr-LAMP1-29-195 where Thr means thrombin cleavage site). The fusion protein was expressed using a T7 promoter, in a trxB-gor deficient *E. coli* strain. High cell density culture of the recombinant strain was performed in a proprietary chemically defined medium, in bioreactor. From cell paste, the fusion protein was extracted by French press lysis, the cell lysate was clarified by ultracentrifugation and the clarified supernatant was applied on an IMAC column. After elution from the resin, the fractions containing the recombinant protein were pooled and the thrombin protease (Sigma-Aldrich) was used for cleaving off the TrxA-His, one hour at room temperature. The solution was then applied on a Benzamidine Sepharose column (GE Healthcare) and on an IMAC column, for removing the thrombin and the free TrxA-His fusion partner, respectively. Purified untagged LAMP1-29-195 domain was stored at 4° C. till complex preparation. The sequence of untagged LAMP1-29-195 domain is referenced under SEQ ID NO: 71.

Preparation and Purification of the Complexes

Recombinant Fab (Fab1) and antigen (untagged LAMP1-29-195 domain) were mixed at a 1.5:1 molar ratio, incubated 30 min at room temperature & the complexes were further purified by preparative size exclusion on a Superdex 200 PG column (GE Healthcare), equilibrated with PBS. The fractions containing highly pure complex were pooled & stored at 4° C. till crystallography assays.

Example 7.3.2: Structure Determination of Fab1/LAMP1

Crystallization and Data Collection

The complex was concentrated to 12 mg/mL in PBS10 mM pH7. Crystallization was done using the sitting drop method. It crystallized in 20% PEG3350, 200 mM NaF (cond1) and 20% PEG3350, 200 mM DL-Malic acid pH7 (cond2). 25% ethylene glycol was included as cryoprotectant prior freezing.

Datasets were collected from both crystals at beamline ID29 ESRF.

Crystals diffracted in the same spacegroup C2 at 2.37 Å (cond1) or 2.51 Å (cond2).

Structure Solution

A model of the constant domain of the Fab1 was obtained using the PDB structure referenced under 4JGO. A model of the variable domain was constructed in Maestro (Schroedinger).

Molecular replacement was carried out using Phaser (Coy et al, J. Appl. Cryst. (2007) 40, 658-674) of the CCP4 suite (Winn et al, Acta Cryst D67 (2011), 235-242) in both datasets but was successful only in cond2: an initial refinement run confirmed the presence of two Fabs in the asymmetric unit. Additional density was visible above the variable domains but too partial to place the antigen.

A second molecular replacement was carried out in cond1, using the results from the previous run in cond2. This time, clear density could be visible above one of the variable domain, allowing the manual construction of a Lamp1 molecule. The second Lamp1 molecule was then constructed using the non-crystallographic symmetry between the two complexes.

The structure was refined using Buster (Buster-TNT 2.11.5, Global Phasing Ltd) at 2.37 Å to a Rfree of 26.1% and Rfactor 22.6%

Results

There are two Fab1/LAMP1 complexes in the asymmetric unit, with significantly different overall temperature factors. Interactions between the two proteins are identical in both complexes; in consequence, the most stable complex was taken as reference for analysis.

Figure 13:
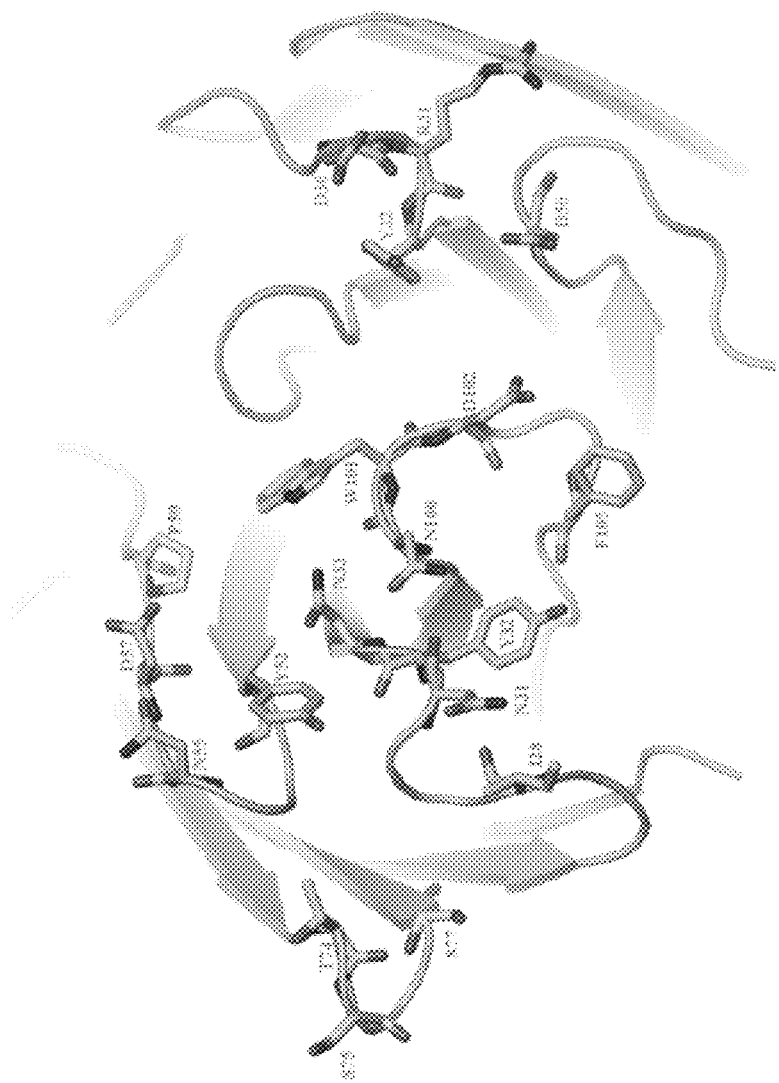
FIG. 13: Graphical representation showing the residues of Fab1 that are part of the paratope (ie residues with atoms within 4A of the antigen atoms).

The first luminal domain of LAMP1 corresponding to amino acids Ala29 to Arg195 of SEQ ID NO: 24 interacts mostly with the heavy chain of Fab1. In FIG. 13 are indicated the residues of Fab1 which are part of the paratope (ie residues with atoms within 4A of the antigen atoms). The amino acids that are part of the paratope are localized in the light chain, more exactly in the CDR1-L with Asp30, Arg31 and Tyr32 of SEQ ID NO: 68 and CDR2-L with Asp50 of SEQ ID NO: 68. They are further localized in the heavy chain, more precisely in CDR1-H (Ile28, Asn31, Tyr32, Asn33), CDR2-H (Tyr52, Asn55, Asp57, Pro59), in FR3 loop (Thr74, Ser75, Ser77) and CDR3-H (Asn100, Trp101, Asp102, Phe105) SEQ ID NO: 69.

Figure 14:
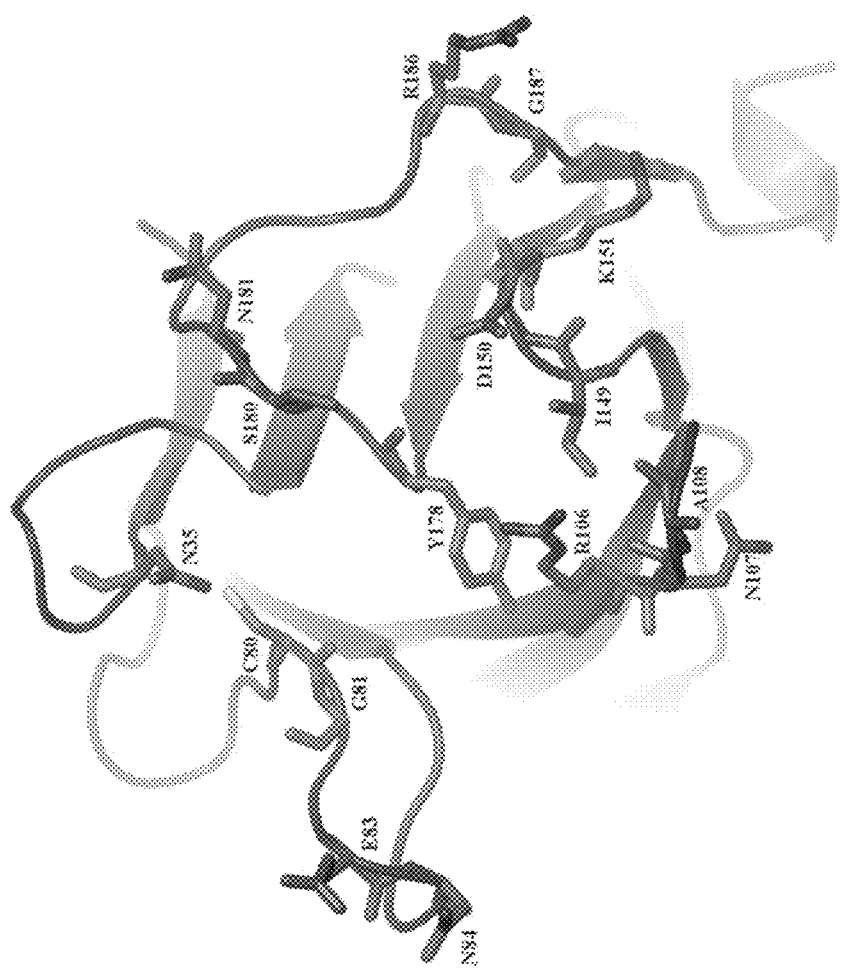
FIG. 14: Graphical representation showing the residues of hLAMP1 forming the epitope for Fab1 (ie residues with atoms within 4A of the antigen atoms).
Figure 15:
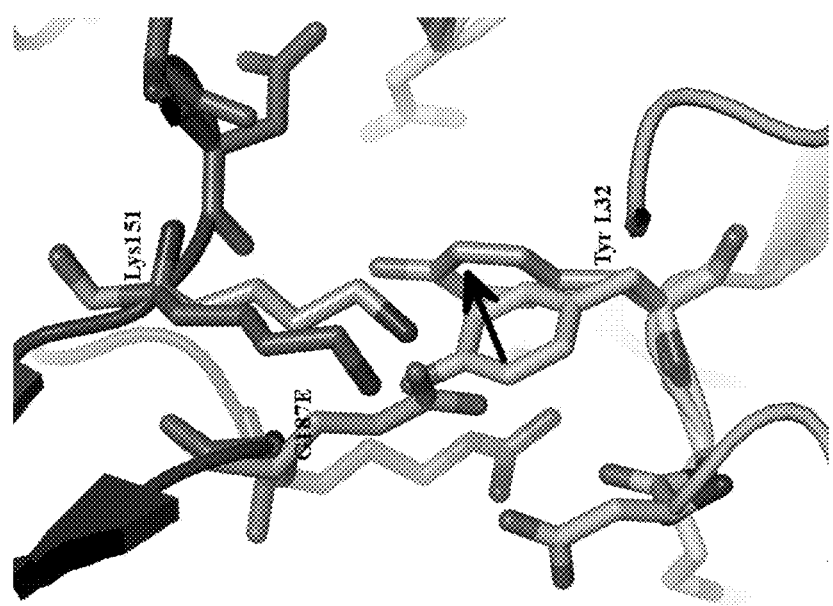
FIG. 15: Graphical representation showing the overlay of the residues of hLAMP1 and a model of G187E corresponding to cLAMP1. Differences in orientation of Lys151 of hLAMP1 and of Tyr32 of Fab1-LC are indicated, necessary to accommodate the mutation from Glycine to Glutamine at position 187.
Figure 16:
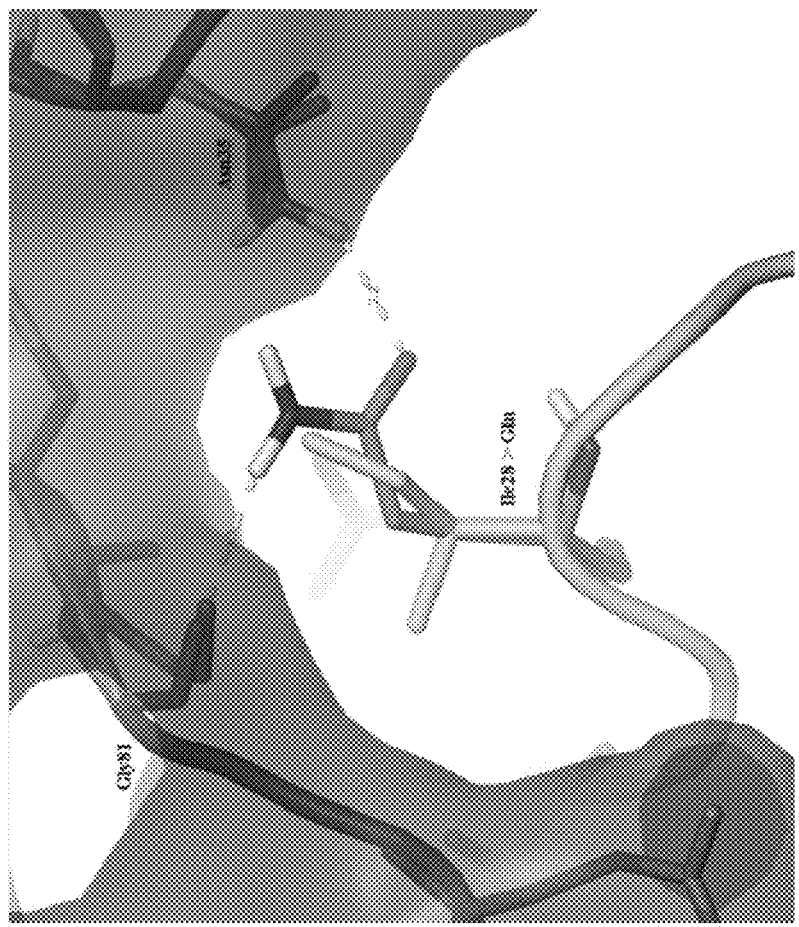
FIG. 16: Graphical representation showing an overlay of the heavy chain residues of Fab1 and a model of Fab1 with the mutation I28Q in its heavy chain sequence of SEQ ID NO: 53 and the interaction with LAMP1.
Figure 17:
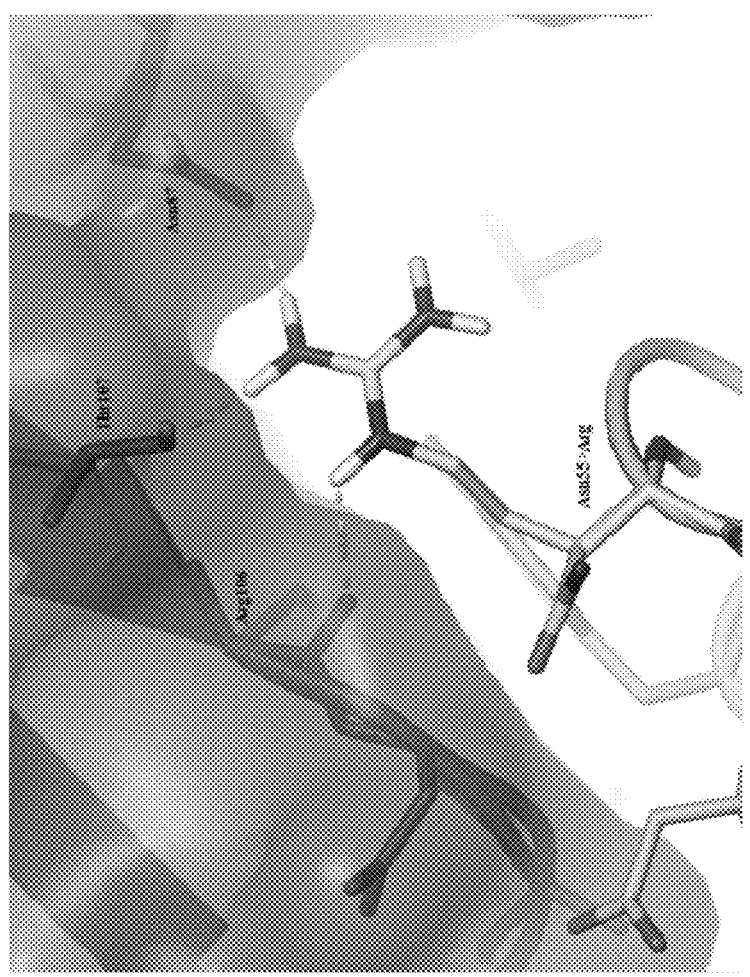
FIG. 17: Graphical representation showing an overlay of the heavy chain residues of Fab1 and a model of Fab1 with the mutation N55R in its heavy chain sequence of SEQ ID NO: 53 and the interaction with LAMP1.

The epitope of LAMP1 for Fab1, determined as residues with atoms within 4A of the Fab1 atoms, is indicated in bold in the sequence below and displayed in FIG. 14:

GSHMAMFMVKNGNGTACIMANFSAAFSVNYDTKS-GPKNMTFDLPSDATVVLNRSSCGK ENTSDPSLVI-AFGRGHTLTLNFTRNATRYSVQLMSFVYNLSDTH-LFPNASSKEIKT VESITDIRADIDKKYRCVSGTQVHMNNVTVTLH-DATIQAYLSNSSFSRGETRCEQ DR (SEQ ID NO 80)

Said epitope identified by crystallography consist of the amino adis Asn35, Cys80, Gly 81, Glu83, Asn84, Arg106, Asn107, Ala108, Ile149, Asp150, Lys151, Tyr 178, Ser180, Asn181, Arg186 and Gly187 of SEQ ID NO: 24.

As visible in the alignment displayed in FIG. 1, there is only one residue difference in the epitope region between *Macacus fascicularis* and *Homo sapiens*: at Position 187 of SEQ ID NO: 24 with Gly187Glu. A model of this mutation was built and minimized: the results show that binding to Fab1 remains possible provided side-chain movement of light chain Tyr32 and slight movement of LAMP1 Lys151 as indicated in FIG. 15.

Based on the crystallographic structure that was herein obtained, it is possible to suggest regions for affinity maturation. Two hot spots may be the amino acid Ile28 in the heavy chain sequence of SEQ ID NO: 53 and the amino acid Asn55 in the heavy chain sequence of SEQ ID NO: 53. Replacing the hydrophobic residue Ile 28 by a Glutamine might lead to interaction with nearby Gly81 and Asn35 of LAMP1 (SEQ ID: 24) and should improve binding between the two proteins as shown in FIG. 16. Mutating Asn55 to an Arginine would add interactions to Asn87, Arg106 and Thr107 of LAMP1 (SEQ ID: 24) as shown in FIG. 17.

Example 8: Production and Characterization of ADC

Example 8.1: Production and Characterization of ADC with a Maytansinoid

DAR Calculation:

A conjugate comprises generally from 1 to 10 molecule(s) of the maytansinoid attached covalently to the antibody (so called, "drug-to-antibody ratio" or "DAR"). This number can vary with the nature of the antibody and of the maytansinoid used along with the experimental conditions used for the conjugation (like the ratio maytansinoid/antibody, the reaction time, the nature of the solvent and of the cosolvent if any). Thus the contact between the antibody and the maytansinoid leads to a mixture comprising: several conjugates differing from one another by different drug-to-antibody ratios; optionally the naked antibody; optionally aggregates. The DAR that is determined is thus a mean value.

The method used herein to determine the DAR consists in measuring spectrophotometrically the ratio of the absorbance at 252 nm and 280 nm of a solution of the substantially purified conjugate. In particular, said DAR can be determined spectrophotometrically using the measured extinction coefficients at respectively 280 and 252 nm for the antibody ($\epsilon_{A280}$ and $\epsilon_{A252}$) and for the maytansinoid ($\epsilon_{D280}$=5,180 $M^{-1}$ $cm^{-1}$ and $\epsilon_{D252}$=26,159 $M^{-1}$ $cm^{-1}$). The method of calculation is derived from Antony S. Dimitrov (ed), LLC, 2009, Therapeutic Antibodies and Protocols, vol 525, 445, Springer Science and is described in more details below:

The absorbances for the conjugate at 252 nm (A252) and at 280 nm (A280) are measured on a spectrophotometer apparatus to calculate the DAR. The absorbances can be expressed as follows:

$$A_{252}=(c_D\times\epsilon_{D252})+(c_A\times\epsilon_{A252})$$

$$A_{280}=(c_D\times\epsilon_{D280})+(c_A\times\epsilon_{A280})$$

wherein:

$c_D$ and $c_A$ are respectively the concentrations in the solution of the maytansinoid and of the antibody $\epsilon_{D252}$ and $\epsilon_{D280}$ are respectively the molar extinction coefficients of the maytansinoid at 252 nm and 280 nm $\epsilon_{A252}$ and $\epsilon_{A280}$ are respectively the molar extinction coefficients of the antibody at 252 nm and 280 nm.

Resolution of these two equations with two unknowns leads to the following equations:

$$c_D=[(\epsilon_{A280}\times A_{252})-(\epsilon_{A252}\times A_{280})]/[(\epsilon_{D252}\times\epsilon_{A280})-(\epsilon_{A252}\times\epsilon_{D280})]$$

$$c_A=[A_{280}-(c_D\times\epsilon_{D280})]/\epsilon_{A280}$$

The average DAR is then calculated from the ratio of the drug concentration to that of the antibody:

$$DAR=c_D/c_A$$

Deglycosylation and High Resolution Mass Spectrometry of Conjugates (HRMS)

Deglycosylation is a technique of enzymatic digestion by means of glycosidase. The deglycosylation is made from 50 µl of conjugated+10 µl of N-glycosidase-F (PN Gase F) enzyme (100 units of freeze-dried enzyme/100 µl of water). The medium is vortexed and maintained one night at 37° C. The deglycosylated sample is then ready to be analyzed in HRMS. Mass spectra were obtained on a Waters XEVO QTof system in electrospray positive mode (ES+). Chromatographic conditions are the following: column:UPLC BEH300 C4 1.7 µm 2.1X150 mm; solvents: A: $H_2O$+0.1% formic acid: B; $CH_3CN$+0.1% formic acid; column temperature: 70° C.; flow rate 0.5 mL/min; gradient elution (10 min): 20% B for 2 min 50 sec; from 20 to 80% of B in 2 min 5 sec; 8 min 50 sec: 80% B; 8 min 55 sec: 20% B; 10 min: 20% B.

Buffers Content

Buffer A (pH 6.5): NaCl (50 mM), Potassium Phosphate buffer (50 mM), EDTA (2 mM)

Buffer HGS (pH 5.5): histidine (10 mM), glycine (130 mM), sucrose 5% (w/v), HCl (8 mM)

PBS (pH 7.4): $KH_2PO_4$ (1.03 mM), NaCl (155.17 mM), $Na_2HPO_4$-$7H_2O$ (2.97 mM)

Abbreviations Used

DAR: Drug Antibody Ratio; DMA: dimethylacetamide; HEPES: 4-(2-hydroxyethyl)-1-piperazine-ethanesulfonic acid; HRMS: High Resolution Mass Spectroscopy; Nitro-SPDB: butanoic acid, 4-[(5-nitro-2-pyridinyl)dithio]-, 2,5-dioxo-1-pyrrolidinyl ester (could be prepared as described in WO2004016801 patent); RT: room temperature.

Example 8.1.1: Antibody Drug Conjugate (ADC) (Chimer chMAb1)

The naked chimer of MAb1 was prepared. It is a chimeric mAb (chMAb1) derived from the murine clone MAb1 with a human IgG1, Ck isotype having a heavy chain of sequence SEQ ID NO: 17 and a light chain of sequence SEQ ID NO: 18.

In this example, a cleavable conjugate (indifferently called DM4-SPDB-chMAb1 or chMAb1-SPDB-DM4) was obtained from the naked chMAb1, as described in example 7, and from DM4 with LC and HC sequences of the chimeric mAb corresponding to SEQ ID NO: 17 and 18.

DM4 has the following chemical name $N^{2'}$-deacetyl-$N^{2'}$-(4-mercapto-4-methyl-1-oxopentyl) maytansine.

For chMAb1, $\epsilon_{A280}$=223,400 $M^{-1}$ $cm^{-1}$ and $\epsilon_{A252}$=80,240 $M^{-1}$ $cm^{-1}$ Preparation and Analytical Data of the Cleavable Chimer chMAb1-SPDB-DM4 Conjugate To 12.1 mL of a solution of of chMAb1 antibody at a concentration of 8.23 mg/mL in buffer A is added under magnetic stirring 465 μL of HEPES 1N, 1 mL DMA and a 5.9-fold molar excess of a 15 mM solution of nitro-SPDB in DMA. After 1 h30 at RT, the reaction mixture is diluted with 17.3 mL of PBS buffer and 1.64 mL DMA, prior to addition of a 15 mM solution of DM4 in DMA.

The reaction mixture is stirred at RT for 2 h40 and then purified by TFF on Sius-LSn Prostream 30 kD cassette. The sample is diafiltrated against 600 mL of HGS buffer, concentrated, collected and filtered over Millex® 0.22 μM PVDF filter to yield product (11 mL).

Figure 7:
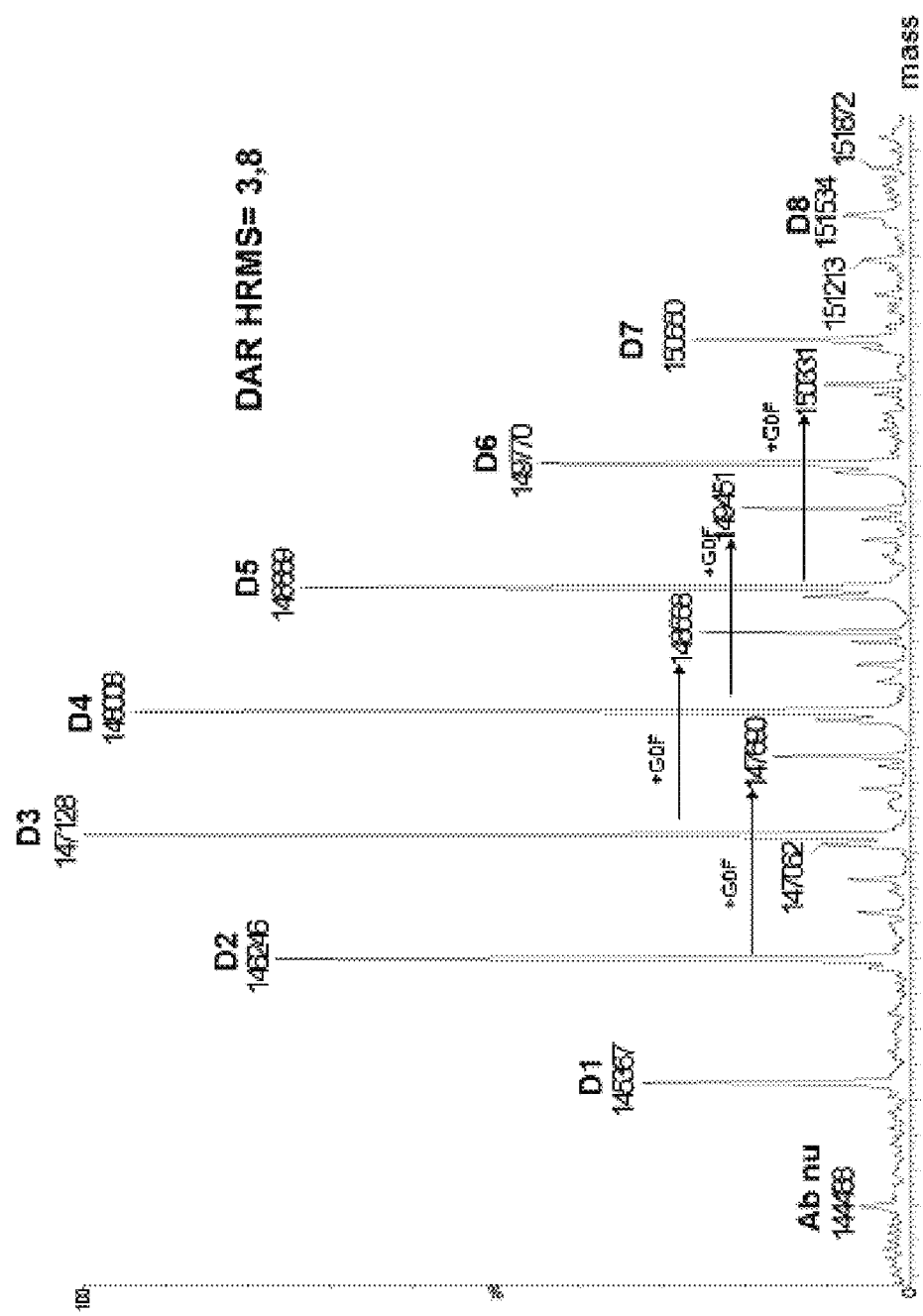
FIG. 7: HRMS data of DM4-SPDB-chMAb1 conjugate.

The final conjugate is assayed spectrophotometrically; an average DAR of 4.5 DM4 per molecule of antibody (5.7 mg/mL) was determined. HRMS data: see FIG. 7.

Example 8.1.2: Antibody Drug Conjugate (Humanized huMAb1_3)

The naked humanized huMAb1_3 was prepared as described in example 7.2.2. It is a humanized mAb derived from the murine clone MAb1 with a human IgG1 and Ck isotype, Ck isotype having a heavy chain (VH3-huIgG1) sequence of SEQ ID NO: 64 and a light chain (VL3-huCk) sequence SEQ ID NO: 63.

Extinction coefficients mentioned herein were measured at respectively 280 and 252 nm for the antibody $\epsilon_{A280}$=223,400 $M^{-1}$ $cm^{-1}$ and $\epsilon_{A252}$=79,413 $M^{-1}$ $cm^{-1}$ Preparation of DM4-SPDB-huMAb1_3 Conjugate To 3.6 mL of a solution of huMAb1_3 antibody at a concentration of 5.18 mg/mL in DPBS is added under magnetic stirring, 0.316 mL DMA and a 5.2-fold molar excess of a 15 mM solution of nitro-SPDB in DMA. After 2 h15 at RT 0.3 equivalent of a 15 mM solution of nitro-SPDB in DMA is added. After 1 h45 the reaction mixture is diluted with 1.99 mL of PBS buffer and 0.187 mL DMA, prior to addition of a 15 mM solution of DM4 in DMA.

The reaction mixture is stirred at RT for 2 h and then purified by gel filtration (HiPrep 26/10 desalting, Sephadex G25, GE Healthcare) previously equilibrated with buffer HGS pH=5.5. The collected sample is filtered over Millex® 0.22 μM PVDF filter to yield product (9.4 mL). This solution is injected on a Chromasorb® Millipore 0.08 mL device (CHRFA1PD09), The collected sample is concentrated over Amicon Ultra-15 10KD, Millipore and filtered over Millex® 0.22 μM PVDF filter to yield product (4.3 mL).

Figure 18:
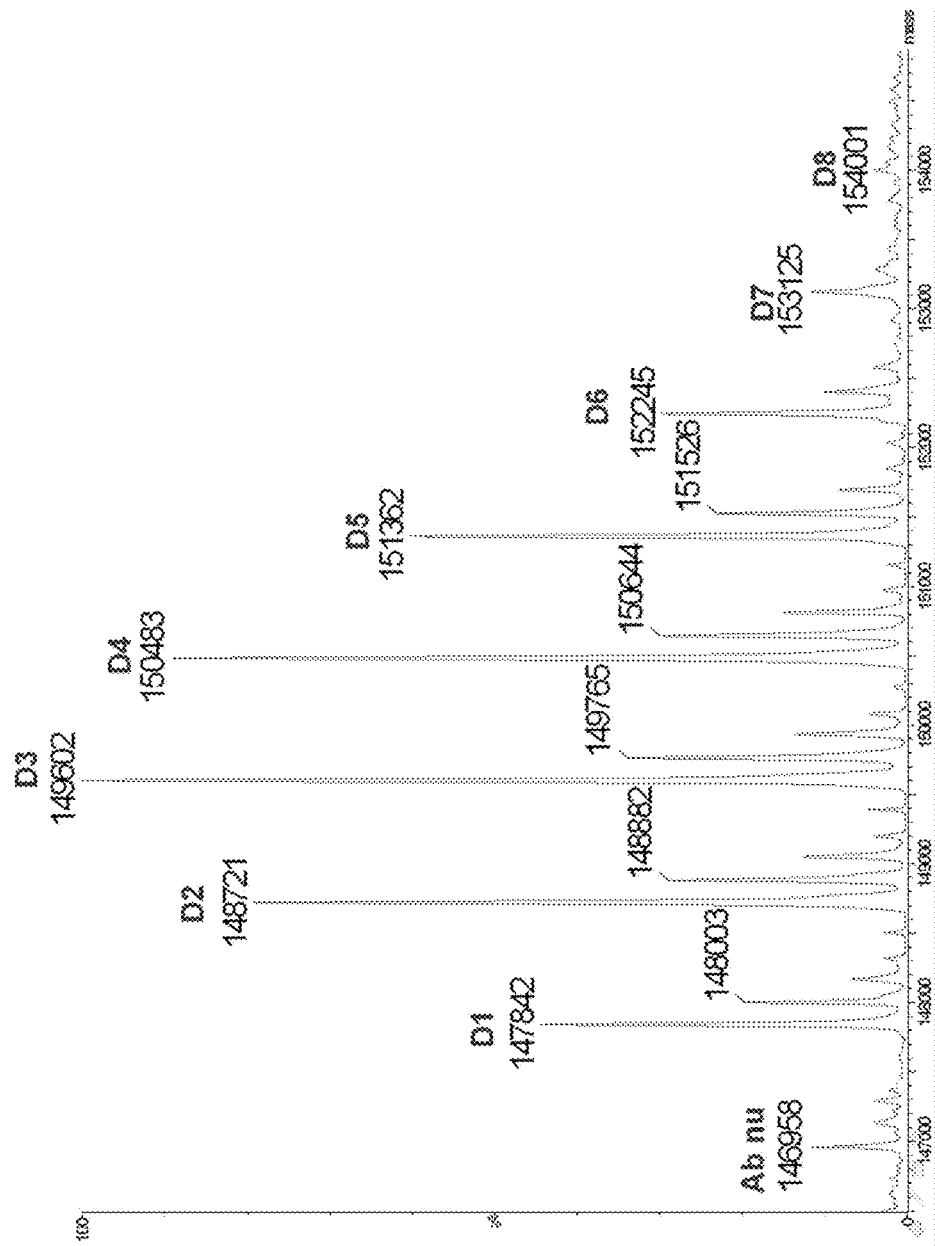
FIG. 18: HRMS data of DM4-SPDB-huMAb1_3 conjugate.

The final conjugate is assayed spectrophotometrically; an average DAR of 3.5 DM4 per molecule of antibody (1.9 mg/mL) was determined. HRMS data: see FIG. 18.

Example 8.1.3: Antibody Drug Conjugate (Humanized huMAb1_1)

The naked humanized huMAb1_1 was prepared as described in example 7.2.2. It is a humanized mAb derived from the murine clone MAb1 with a human IgG1 and Ck isotype, Ck isotype having a heavy chain (VH1-huIgG1) sequence of SEQ ID NO: 60 and a light chain sequence (VL1-huCk) of SEQ ID NO: 59

Extinction coefficients are measured at respectively 280 and 252 nm for the antibody $\epsilon_{A280}$=223,400 $M^{-1}$ $cm^{1}$ and $\epsilon_{A252}$=80,041 $M^{-1}$ $cm^{-1}$ Preparation of DM4-SPDB-huMAb1_1 Conjugate To 3.6 mL of a solution of huMAb1_1 antibody at a concentration of 4.81 mg/mL in DPBS is added under magnetic stirring, 0.321 mL DMA and a 5.0-fold molar excess of a 15 mM solution of nitro-SPDB in DMA. After 2 h at RT 0.3 equivalent of a 15 mM solution of nitro-SPDB in DMA is added. After 1 h30 the reaction mixture is diluted with 1.59 mL of PBS buffer and 0.147 mL DMA, prior to addition of a 15 mM solution of DM4 in DMA.

The reaction mixture is stirred at RT for 1 h30 and then purified by gel filtration (HiPrep 26/10 desalting, Sephadex G25, GE Healthcare) previously equilibrated with buffer HGS pH=5.5. The collected sample is filtered over Millex® 0.22 μM PVDF filter to yield 9.4 mL of solution. This solution is injected on a Chromasorb® Millipore 0.08 mL device (CHRFA1PD09), The collected sample is concentrated over Amicon Ultra-15 10KD, Millipore and filtered over Millex® 0.22 μM PVDF filter to yield product (4.9 mL).

Figure 19:
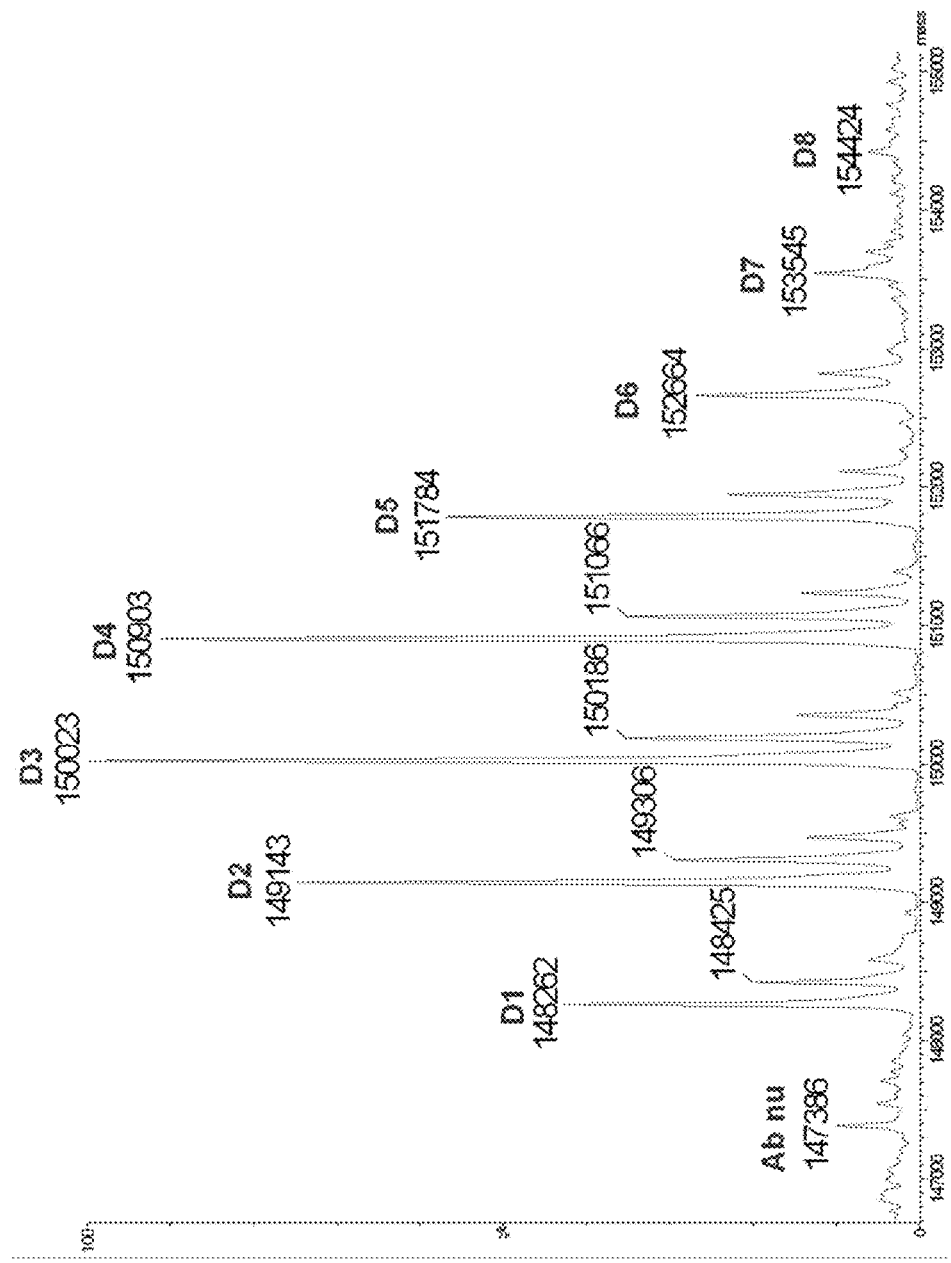
FIG. 19: HRMS data of DM4-SPDB-huMAb1_1 conjugate.

The final conjugate is assayed spectrophotometrically; an average DAR of 3.4 DM4 per molecule of antibody (1.45 mg/mL) was determined. HRMS data: see FIG. 19.

Example 8.1.4: Antibody Drug Conjugate (Humanized huMAb1_2)

The naked humanized huMAb1_2 was prepared as described in example B7. It is a humanized mAb derived from the murine clone MAb1 with a human IgG1 and Ck isotype, Ck isotype having a heavy chain sequence (VH2-huIgG1) of SEQ ID NO: 62 and a light chain sequence (VL2-huCk) SEQ ID NO: 61.

Extinction coefficients are measured at respectively 280 and 252 nm for the antibody $\epsilon_{A280}$=223,400 $M^{-1}$ $cm^{-1}$ and $\epsilon_{A252}$=79,474 $M^{-1}$ $cm^{-1}$.

Preparation of DM4-SPDB-huMAb1_2 Conjugate

To 3.6 mL of a solution of huMAb1_2 antibody at a concentration of 5.06 mg/mL in b DPBS is added under magnetic stirring, 0.317 mL DMA and a 5.2-fold molar excess of a 15 mM solution of nitro-SPDB in DMA. After 2 h the reaction mixture is diluted with 1.89 mL of PBS buffer and 0.179 mL DMA, prior to addition of a 15 mM solution of DM4 in DMA.

The reaction mixture is stirred at RT for 1 h30 and then purified by gel filtration (HiPrep 26/10 desalting, Sephadex G25, GE Healthcare) previously equilibrated with buffer HGS pH=5.5. The collected sample is filtered over Millex® 0.22 μM PVDF filter to yield product (9.7 mL).

Figure 20:
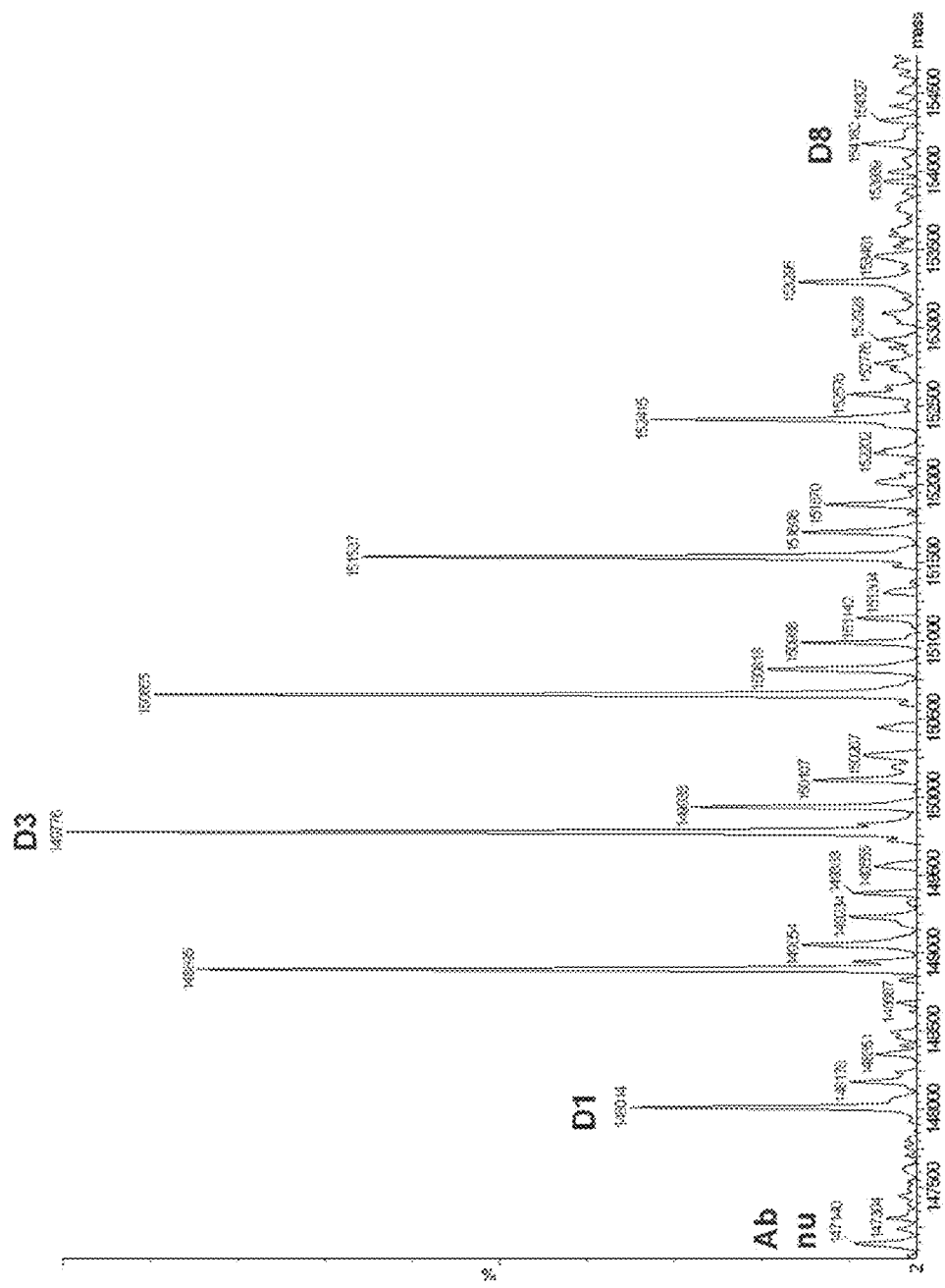
FIG. 20: HRMS data of DM4-SPDB-huMAb1_2 conjugate.

The final conjugate is assayed spectrophotometrically; an average DAR of 4.05 DM4 per molecule of antibody (1.36 mg/mL) was determined. HRMS data: see FIG. 20.

Example 8.1.5: Antibody Drug Conjugate (Chimer chMAb2can)

The naked chimer chMAb2can was prepared as described in example 7. It is a chimer mAb derived from the murine clone MAb2 with a human IgG1 and Ck isotype. Ck isotype having a heavy chain sequence of SEQ ID NO: 21 and a light chain of sequence SEQ ID NO: 22.

Extinction coefficients at respectively 280 and 252 nm for the antibody $\epsilon_{A280}$=223,400 $M^{-1}$ $cm^{-1}$ and $\epsilon_{A252}$=74,417 $M^{-1}$ $cm^{-1}$ Preparation of DM4-SPDB-chMAb2can Conjugate To 9.2 mL of a solution of chMAb2can antibody at a concentration of 5.21 mg/mL in DPBS is added under magnetic stirring, 0.813 mL DMA and a 5.0-fold molar excess of a 15 mM solution of nitro-SPDB in DMA. After 2 h at RT 0.2 equivalent of a 15 mM solution of nitro-SPDB in DMA is added. After 1 h30 the reaction mixture is diluted with 5.17 mL of PBS buffer and 0.497 mL DMA, prior to addition of a 15 mM solution of DM4 in DMA.

The reaction mixture is stirred at RT for 1 h30 and then purified by gel filtration (HiPrep 26/10 desalting, Sephadex G25, GE Healthcare) previously equilibrated with buffer HGS pH=5.5. The collected sample is filtered over Millex® 0.22 μM PVDF filter to yield product (23 mL).

Figure 21:
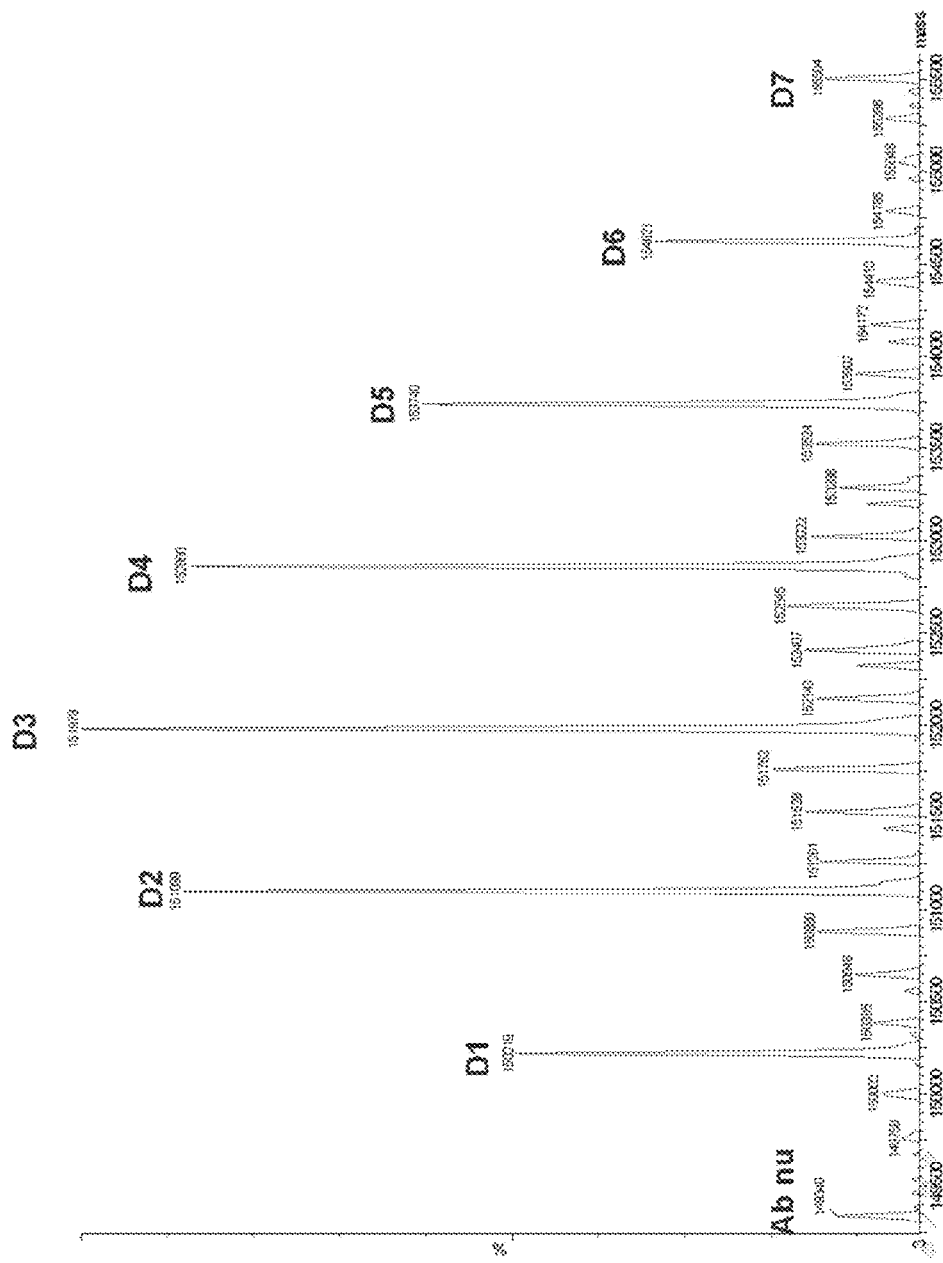
FIG. 21: HRMS data of DM4-SPDB-chMAb2 conjugate.

The final conjugate is assayed spectrophotometrically; an average DAR of 3.7 DM4 per molecule of antibody (1.58 mg/mL) was determined. HRMS data: see FIG. 21.

Example 8.1.6: Antibody Drug Conjugate (Chimer chMAb3_VLR24-R93)

The naked chimer chMAb3_VLR24-R93 was prepared as described in example 7. It is a chimer mAb derived from the murine clone MAb3 with a human IgG1 and Ck isotype, Ck isotype having a heavy chain sequence of SEQ ID NO: 49 and a light chain of sequence SEQ ID NO: 81.

Extinction coefficients are measured at respectively 280 and 252 nm for the antibody $\epsilon_{A280}=234539$ M$^{-1}$ cm$^{-1}$ and $\epsilon_{A252}=85303$ M$^{-1}$ cm$^{-1}$.

Preparation of DM4-SPDB-chMAb3 VLR24-R93 Conjugate

Figure 22:
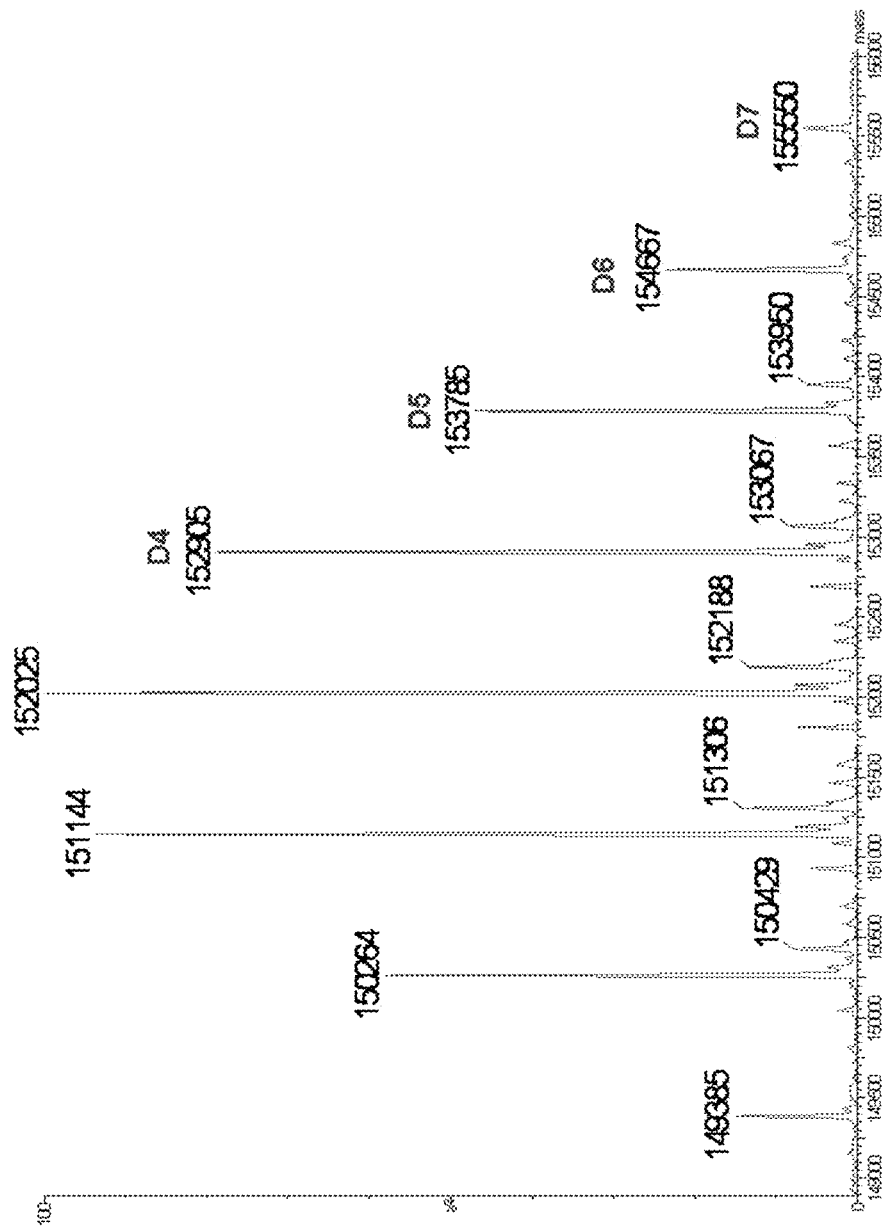
FIG. 22: HRMS data of DM4-SPDB-chMAb3 VLR24-R93 conjugate.

To 7.3 mL of a solution of chMAb3_VLR24-R93 antibody at a concentration of 6.85 mg/mL in DPBS were added under magnetic stirring, 7.7 mL of PBS, 1.5 mL DMA and a 5.0-fold molar excess of a 10 mM solution of nitro-SPDB in DMA. After 3 h30, 155 μL of a solution of L-DM4 (15.1 mM in DMA) were added to the reaction mixture. The reaction mixture was stirred at RT for 1 h30 and then purified by gel filtration (HiPrep 26/10 desalting, Sephadex G25, GE Healthcare) previously equilibrated with buffer HGS pH=5.5. The collected sample was filtered over Millex® 0.22 μM PVDF filter to yield product (23 mL). The final conjugate was assayed spectrophotometrically; an average DAR of 3.7 DM4 per molecule of antibody (2.0 mg/mL) was determined. HRMS data: see FIG. 22.

Example 8.1.7: Cross Reactivity of DM4-SPDB-chMAb1, DM4-SPDB-chMAb2, and DM4-SPDB-chMAb3, to Human LAMP1/Cyno LAMP1

DM4-SPDB-chMAb1, DM4-SPDB-chMAb2 and DM4-SPDB-chMAb3 were assessed by flow cytometry for their ability to bind to human LAMP1 or cynomolgus LAMP1 proteins expressed respectively at the surface of HCT116 or HEK293 stable clones. HCT116 stable clone and HEK293 stable clone were obtained as described in the protocol in example 4.7 $EC_{50}s$, estimated using BIOST@T-SPEED software, are listed in Table 29.

TABLE 29

Apparent affinity of DM4-SPDB-chMAb1, DM4-SPDB-chMAb2, DM4-SPDB-chMAb3 to human LAMP1 or cynomolgus monkey LAMP1

| | $EC_{50}$ (nM) | | |
|---|---|---|---|
| | HCT116 huLAMP1 clone 8 | HEK293 cynoLAMP1 clone 44 | Ratio of $EC_{50}s$ |
| DM4-SPDB-chMAb1 | 6.6 | 6.6 | 1.0 |
| DM4-SPDB-chMAb2 | 5.5 | 12.8 | 2.3 |
| DM4-SPDB-chMAb3 | 9.1 | 6.1 | 0.7 |

DM4-SPDB-chMAb1 binds to LAMP1 of human and cynomolgus origin with similar affinity. $EC_{50s}$ ratio was 1 and therefore DM4-SPDB-chMAb1 cross-reacted with cynomolgus LAMP1. DM4-SPDB-chMAb2 binds to LAMP1 of human and cynomolgus origin with similar affinity. $EC_{50s}$ ratio was 2.3 and therefore DM4-SPDB-chMAb2 cross-reacted with cynomolgus LAMP1. DM4-SPDB-chMAb3 binds to LAMP1 of human and cynomolgus origin with similar affinity. $EC_{50s}$ ratio was 0.7 and therefore DM4-SPDB-chMAb2 cross-reacted with cynomolgus LAMP1.

Example 8.1.8: Cross Reactivity of DM4-SPDB-huMAb1_1 to Human LAMP1/Cyno LAMP1

DM4-SPDB-huMAb1_1 was assessed by flow cytometry for its ability to bind to human LAMP1 or cynomolgus LAMP1 proteins expressed respectively at the surface of HCT116 or HEK293 stable clones, both obtained as described in the protocol of example 4.7. $EC_{50}s$, estimated using BIOST@T-SPEED software, are listed in Table 30.

TABLE 30

Apparent affinity of DM4-SPDB-huMAb1_1 to human LAMP1 or cynomolgus monkey LAMP1

| | $EC_{50}$ (nM) | | |
|---|---|---|---|
| | HCT116 huLAMP1 clone 8 | HEK293 cynoLAMP1 clone 44 | Ratio of $EC_{50}s$ |
| DM4-SPDBhuMAb1_1 | 12.65 | 33.50 | 2.65 |

DM4-SPDB-huMAb1_1 binds to LAMP1 of human and cynomolgus origin with similar affinity with a ratio of $EC_{50s}$ of 2.65. Therefore, DM4-SPDBhuMAb1_1 cross-reacts with cynomolgus LAMP1.

Example 8.2: Production and Characterization of ADC with a Tomaymycine Dimer DAR Calculation:

DAR calculation is determined similarly than for maytansinoid ADC, using the measured extinction coefficients at respectively 280 and 322 nm for the antibody ($\epsilon_{A280}=223,400$ M$^{-1}$ cm$^{-1}$ and $\epsilon_{A322}=0$ M$^{-1}$ cm$^{-1}$) and for the tomaymycine dimer ($\epsilon_{D280}=4,436$ M$^{-1}$ cm$^{-1}$ and $\epsilon_{D322}=7,843$ M$^{-1}$ cm$^{-1}$).

Preparation of a huMAb1_1 conjugate modified with SNPP (N-succinimidyl 4-(5-nitro-2-pyridyldithio)pentanoate) with (2E,2'E,11aS,11a'S)-8,8'-(((4-(2-(2-(2-((2-mercapto-2-methylpropyl)(methyl) amino)ethoxy)ethoxy)ethoxy)pyridine-2,6-diyl) bis (methylene))bis(oxy))bis(2-ethylidene-7-methoxy-2,3-dihydro-1Hbenzo[e]pyrrolo[1,2-a][1,4] diazepin-5 (11aH)-one)

To 56 mg of huMAb1_1 in 2.8 ml of buffer A are added 0.48 mg of SNPP (N-succinimidyl 4-(5-nitro-2-pyridyldithio)pentanoate) dissolved in 67 µL of DMA under stirring. After 3 hours at room temperature, the solution of modified antibody is fractionated into two and purified by gel filtration on two Sephadex G25 columns (PD-10 GE column) pre-equilibrated in an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8. After mixing and homogenizing the two filtrates thus obtained, the modified antibody is assayed by spectrophotometry using the extinction coefficients of nitropyridinethiol ($\epsilon_{280\ nm}$=3344 $M^{-1}$ $cm^{-1}$ and $\epsilon_{325\ nm}$=10964 $M^{-1}$ $cm^{-1}$): an average of 3.32 dithio-nitropyridine groups per antibody molecule was determined at a concentration of 6.28 mg/mL.

To 9.4 mg of modified antibody above in 1.5 ml of an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8 are added 0.56 mL of DMA and 1.12 mg of (2E,2'E,11aS,11a'S)-8,8'-(((4-(2-(2-(2-((2-mercapto-2-methylpropyl)(methyl)amino)ethoxy)ethoxy) ethoxy)pyridine-2,6-diyl)bis(methylene))bis(oxy))bis(2-ethylidene-7-methoxy-2,3-dihydro-1Hbenzo[e] pyrrolo[1,2-a][1,4] diazepin-5(11aH)-one) dissolved in 0.06 mL of dimethylacetamide (DMA) under stirring. After 17 at 30° C., 0.01N HCl is added until pH=6.6 and the resulting mixture is purified on a CHT 80 (type II) column (20 mm×8 mm I.D.) initially equilibrated with 2 mL of a 200 mM potassium phosphate buffer of pH 6.5 followed by 4 mL of a 10 mM potassium phosphate buffer of pH 6.5. After injection and washing with 5 mL of the last 10 mM phosphate buffer, elution is realized with 6 mL of the previous 200 mM phosphate buffer. 2.5 mL of the resulting batch is then filtered on a Sephadex G25 column (PD-10 GE column) pre-equilibrated in an aqueous buffer of pH=6.5 with a concentration of 10 mM histidine, containing 10% sucrose.

Figure 37:
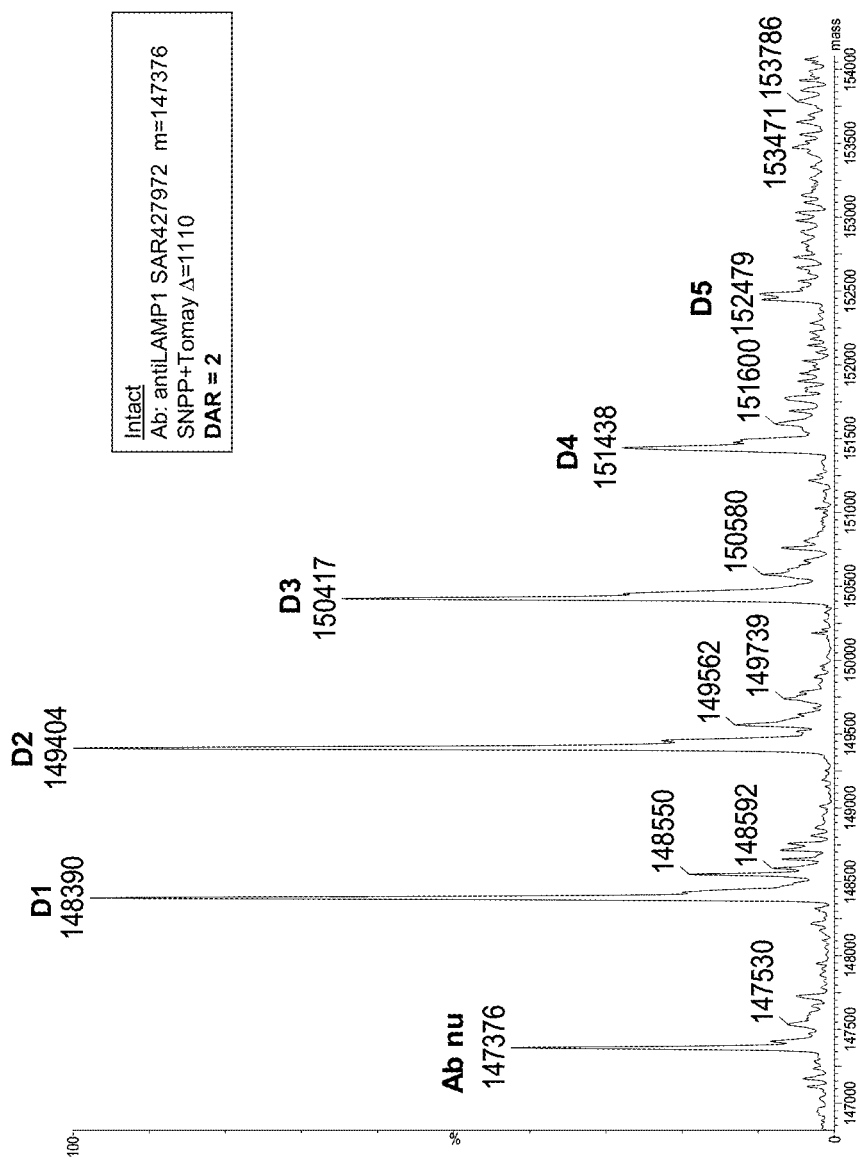
FIG. 37: HRMS data of huMAb1_1 conjugate modified with SNPP with (2E,2'E,11aS,11a'S)-8,8'-(((4-(2-(2-(2-((2-mercapto-2-methylpropyl)(methyl)amino)ethoxy)ethoxy)ethoxy)pyridine-2,6-diyl) bis(methylene))bis(oxy))bis(2-ethylidene-7-methoxy-2,3-dihydro-1Hbenzo[e]pyrrolo[1,2-a][1,4] diazepin-5(11aH)-one)DM4-SPDB-chMAb2 conjugate.

The chemical structure for (2E,2'E,11aS,11a'S)-8,8'-(((4-(2-(2-(2-((2-mercapto-2-methylpropyl) (methyl)amino)ethoxy)ethoxy)ethoxy)pyridine-2,6-diyl)bis(methylene))bis (oxy))bis(2-ethylidene-7-methoxy-2,3-dihydro-1Hbenzo[e] pyrrolo[1,2-a][1,4] diazepin-5(11aH)-one) is as follows:

The conjugate obtained (3.5 mL) is assayed by spectrophotometry: an average of 2.85 (2E,2'E,11aS,11a'S)-8,8'-(((4-(2-(2-(2-((2-mercapto-2-methylpropyl)(methyl)amino) ethoxy)ethoxy) ethoxy)pyridine-2,6-diyl)bis(methylene))bis (oxy))bis(2-ethylidene-7-methoxy-2,3-dihydro-1Hbenzo[e] pyrrolo[1,2-a][1,4]diazepin-5(11aH)-one) per antibody molecule was determined at a concentration of 1.84 mg/mL. HRMS data: see FIG. 37.

Example 9: In Vitro Cytotoxicity

Example 9.1: In Vitro Cytotoxicity of DM4-SPDB-chMAb1

HCT116 cells were infected by a lentiviral vector allowing stable integration of the LAMP1 CDS in genomic DNA of cells, as reported in example 4.7 Individual clones with different densities of LAMP1 cell surface localization were derived from pool of HCT116 infected cells. HCT116 clone 8 was used to compare EC50 of chMAb1 and DM4-SPDB-chMAb1. Cells were plated in 96-well plates at 200 000 per well and MAb1 or DM4-SPDB-chMAb1 was added in 2-fold serial dilution up to 12 dilutions in assay diluent for 1 h at 4° C. and washed two times with PBS 1% BSA. 100 µL/well of goat anti-human IgG conjugated with Alexa488 (Invitrogen; #A11013) was added for 1 h at 4° C. and washed two times with PBS 1% BSA. The antibody binding was evaluated after centrifugation and resuspension of cells in 100 ul fixing solution (paraformaldehyde at 4% in PBS). Samples were read using Galaxy® Flow Cytometry System (Partec). EC50 values were estimated using BIOST@T-SPEED software. chMAb1 and DM4-SPDB-chMAb1 bind with similar affinity and $EC_{50}$ of 6.0 and 6.6 nM respectively.

Several HCT116 clones with different antigen densities were used to evaluate cytotoxicity of DM4-SPDB-chMAb1 by assessment of cell viability using the Cell Titer-Glo kit (Promega).

HCT116-LAMP1 cells were plated in 96-well plates and allowed to adhere during 4 hours in 37° C./5% $CO_2$ atmosphere. Different concentrations of DM4-SPDB-chMAb1 were added to the seeded cells, in triplicate for each concentration. The cells were then incubated for 96 hours in the same atmosphere. Cell Titer-Glo reagent was then added to the wells for 10 min at room temperature and the luminescent signal was measured using a Victor plate reader (Perkin-Elmer). The half maximal inhibitory concentration ($IC_{50}$) is a measure of the effectiveness of a compound in inhibiting biological function. It is defined as the concentration of the antibody which led to cell killing with a response halfway between the baseline and maximum after some specified exposure time. The $IC_{50}$ values were esti-

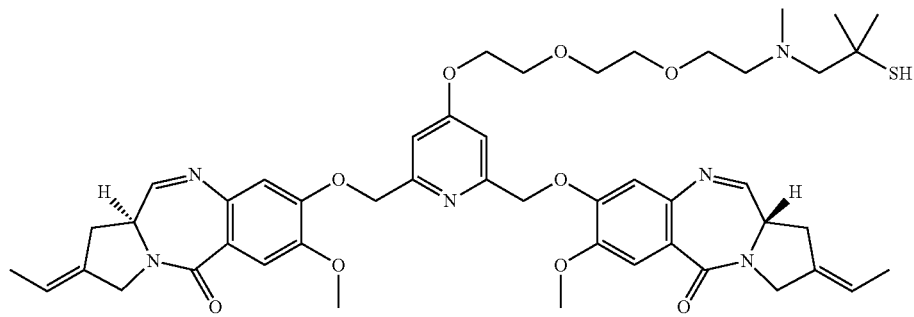 [SMILES: C/C=C1\C[C@H]2C=Nc3cc(OCc4cc(OCCOCCOCCN(C)CC(C)(C)S)cc(COc5cc6c(cc5OC)C(=O)N5C/C(=C/C)C[C@H]5C=N6)n4)c(OC)cc3C(=O)N2C1]

mated using BIOST@T-SPEED software. DM4-SPDB-chMAb1 killed cells with an $IC_{50}$ of around 0.2 nM.

TABLE 31

Cytotoxicity of DM4-SPDB-chMAb1 on HCT116 cell lines expressing LAMP1

| HCT116-LAMP1 | Antigen density | Cytotoxic activity $IC_{50}$ (nM) (mean ± SD; n = 3) |
|---|---|---|
| Clone 5 | 451 000 | 0.2 ± 0.1 |
| Clone 8 | 160 000 | 0.1 ± 0.1 |

Cytotoxic IC50 of DM4-SPDB-chMAb1 is sub-nM for clones of HCT116 with high expression of LAMP1.

Example 9.2: In Vitro Cytotoxicity of DM4-SPDB-huMAb1_1 DM4-SPDB-huMAb1_2, DM4-SPDB-huMAb1_3

HCT116 clone 8, as described in example 9, was used to evaluate cytotoxicity of DM4-SPDB-huMAb1_1, DM4-SPDB-huMAb1_2 and DM4-SPDB-huMAb1_3. The same protocol as described in example 9 was applied.

The three constructs killed cells with an equivalent efficacy. $IC_{50}$ are 0.10 nM, 0.07 nM and 0.12 nM for DM4-SPDB-huMAb1_1, DM4-SPDB-huMAb1_2 and DM4-SPDB-huMAb1_3 respectively.

Example 9.3: In Vitro Cytotoxicity of DM4-SPDB-chMAb2 and DM4-SPDB-chMAb3

HCT116 clone 8, as described in example 9, was used to compare cytotoxicity of DM4-SPDB-chMAb2 and DM4-SPDB-chMAb3. Same protocol as described in example 9 was applied. The two constructs killed cells with an equivalent efficacy. $IC_{50}$ are 0.07 nM and 0.06 nM for DM4-SPDB-chMAb2 and DM4-SPDB-chMAb3 respectively.

Example 9.4: Evaluation of the Inhibition of Proliferation of the Cell Lines HCT116 and HT29 with ADC with Tomaymycine Dimer HCT116 (respectively HT29) cells in their exponential growth phase are trypsinized and resuspended in their culture medium (DMEM Gibco#11960+10% SVF+2 mM glutamine). The cell suspension is seeded in Cytostar 96-well plates (GE Healthcare Europe, #RPNQ0163) in whole culture medium containing serum to a density of 3000 (respectively 5000) cells/well. After incubation for 4 hours, successive dilutions of the antibody-cytotoxic agent immunoconjugate are added to the wells at decreasing concentrations from $10^{-7}$ to $10^{-12}$ M (in duplicate (respectively in quadruplate) for each concentration). The cells are cultured at 37° C. under an atmosphere containing 5% $CO_2$ in the presence of the antibody-cytotoxic agent immunoconjugate for 3 days. On the fourth day, 10 µl of a solution 14C-thymidine (0.1 µCi/well, Perkin Elmer #NEC56825000) are added to each well. The incorporation of 14C-thymidine is measured 96 hours after the start of the experiment with a Microbeta radioactivity counter (Perkin Elmer). The data are expressed in the form of a percentage of survival by determining the ratio between accounts obtained with the cells treated with the immunoconjugate and that obtained with the cells of the control wells (treated with the culture medium alone).

The construct killed the HCT116 and HT29 cells with an equivalent efficacy. $IC_{50}$ are 56 µM for the HCT116 cells and 72 nM for the HT29 cells.

Example 10: In Vivo Efficacy

Example 10.1: In Vivo Efficacy of DM4-SPDB-chMAb1

In this example, the cleavable DM4-SPDB-chMAb1 conjugate was shown to lead to in vivo efficacy.

Example 10.1.1: Evaluation of the Antitumor Activity of DM4-SPDB-chMAb1 Against Primary Human Colon Adenocarcinoma CR-LRB-010P Materials and Methods The conjugate DM4-SPDB-chMAb1 was evaluated at 3 doses against measurable primary colon CR-LRB-010P tumors implanted subcutaneously in female SCID mice. Control groups were left untreated. DM4-SPDB-chMAb1 was administered at 10, 5 and 2.5 mg/kg by an intravenous (IV) bolus injection, on day 17 post tumor implantation. Animals were weighed daily and tumors were measured 2 times weekly by caliper. A dosage producing a 20% weight loss or 15% weight loss for 3 consecutive days or 10% or more drug deaths, was considered an excessively toxic dosage. Animal body weights included the tumor weights. Tumor volumes were estimated from 2 dimensional tumor measurements and calculated according to the following formula (Corbett, T. H. et al., 1977, Cancer 40: 2660-2680): Tumor volume $(mm^3)$=[Length (mm)×Width$^2$ (mm$^2$)]/2. The primary efficacy end points are ratio of change in tumor volume changes from baseline between treated and control groups (ΔT/ΔC), percent median regression, partial regression (PR) and complete regression (CR).

Changes in tumor volume for each treated (T) and control (C) are calculated for each tumor by subtracting the tumor volume on the day of first treatment from the tumor volume on the specified observation day. The median ΔC is calculated for the untreated control group and the median ΔT is calculated for the treated group. Then the ratio ΔT/ΔC is calculated and expressed as a percentage: ΔT/ΔC=(delta T/delta C)×100 as described before The dose is considered as therapeutically active when ΔT/ΔC is lower than 40% and very active when ΔT/ΔC is lower than 10%. If ΔT/ΔC is lower than 0, the dose is considered as highly active and the percentage of regression is dated (Plowman J, Dykes D J, Hollingshead M, Simpson-Herren L and Alley M C. Human tumor xenograft models in NCI drug development. In: Feibig H H B A, editor. Basel: Karger.; 1999 p 101-125):

% tumor regression: is defined as the % of tumor volume decrease in the treated group at a specified observation day compared to its volume on the first day of first treatment.

At a specific time point and for each animal, % regression is calculated. The median % regression is then calculated for the group.

$$\% \text{ regression (at } t) = \frac{volume_{t0} - volume_t}{volume_{t0}} \times 100$$

Partial regression (PR): Regressions are defined as partial if the tumor volume decreases to 50% of the tumor volume at the start of treatment.

Complete regression (CR): Complete regression is achieved when tumor volume=0 mm$^3$ (CR is considered when tumor volume cannot be recorded).

Figure 5:
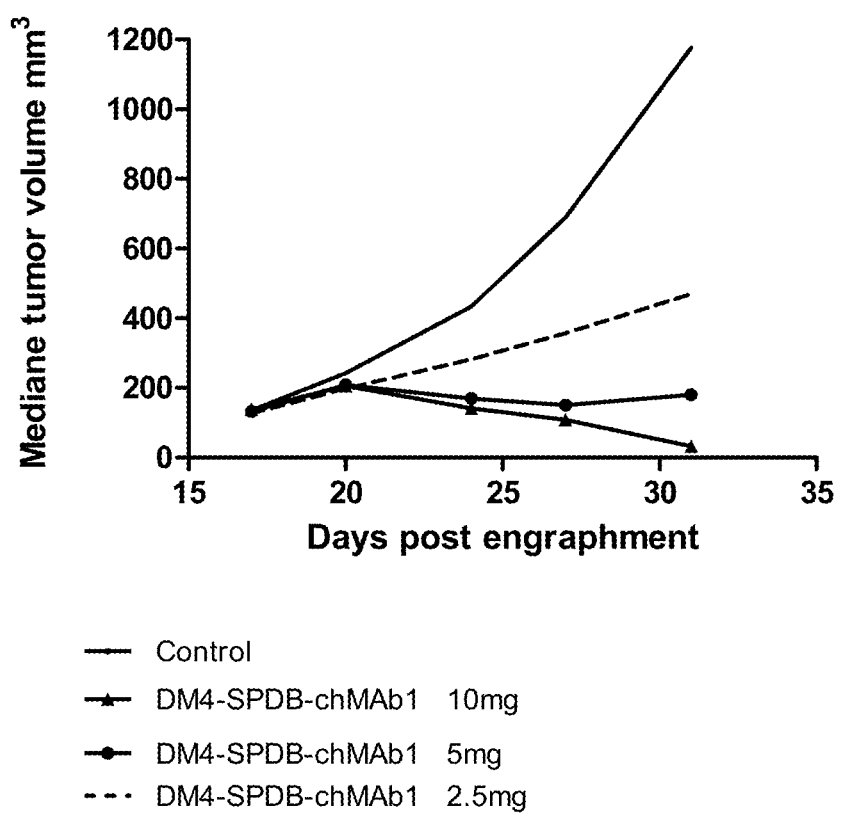
FIG. 5: Evaluation of the anti-tumor activity of DM4-SPDB-chMAb1 conjugate against primary human colon adenocarcinoma CR-LRB-010P in SCID female mice.

Results:

The results are presented on FIG. 5 and Table 32 (below). DM4-SPDB-chMAb1 given at 10.0, 5.0 and 2.5 mg/kg was well tolerated with a maximal body weight loss of 3.7% at 10 mg/kg. After a single administration at 10.0 and 5.0 mg/kg DM4-SPDB-chMAb1 was highly active and statistically significant (p<0.0001 for each dose), as compared to control, producing a ΔT/ΔC<0 and regressions of the initial tumor volume of 75 and 7%, respectively with 5/6 PR and 2/6 CR at 10 mg/kg and 1/6 PR at 5 mg/kg. The dosage below 2.5 mg/kg was active with ΔT/ΔC=31% and no regressions.

TABLE 32

Evaluation of the anti-tumor activity of DM4-SPDB-chMAb1 against primary human colon adenocarcinoma CR-LRB-010P in SCID female mice

| Agent[1] | Route/Dosage in mL/kg per injection | Dosage in mg/kg (total dose) | Schedule in days | Drug death (Day of deatch) | Average body weight change in % per mouse at nadir (day of nadir) | Median $\Delta T/\Delta c$ in % (day) | Median % of regression (day) | Regressions Partial | Regressions Complete | Tumor free survivors at day 55 | Biostatistic p value (day)[2] |
|---|---|---|---|---|---|---|---|---|---|---|---|
| DM4-SPDB-chMAb1 | IV (10 mL/Kg) | 10.0 (10.0) | 17 | 0/6 | −3.7 (18) | −11 (31) | 75 (31) | 5/6 | 2/6 | 0/6 | P < 0.0001 (31) |
| DM4-SPDB-chMAb1 | IV (5 mL/Kg) | 5.0 (5.0) | | 0/6 | −3.2 (18) | −2 (27) | 7 (27) | 1/6 | 0/6 | 0/6 | P < 0.0001 (27) |
| DM4-SPDB-chMAb1 | IV (2.5 mL/Kg) | 2.5 (2.5) | | 0/6 | +0.1 (18) | 31 (31) | | 0/6 | 0/6 | 0/6 | P = 0.0001 (31) |
| Controls | | | | 0/10 | −2.7 (18) | | | 0/10 | 0/10 | 0/10 | |

[1]Drug formulation: buffer HGS pH 5.5 (10 mM histidine, 130 mM glycine, 5% (w/v) sucrose, 0.01% Tween 80)
[2] p-value: Dunnett's test versus control following a two-way Anova with repeated measures performed separately for each compounds on ranks of changes from baseline. A probability less than 5% (p < 0.05) was considered as significant.
NS = non significant.
Tumor doubling time = 4.3 days. Tumor size at start of therapy was 96-216 mm$^3$, with a median tumor burden per group of 126-138 mm$^3$.

Example 10.1.2: Evaluation of the Antitumor Activity of DM4-SPDB-chMAb1 Against Primary Human Lung Tumor LUN-NIC-0014

Materials and Methods

DM4-SPDB-chMAb1 was evaluated at 3 doses against measurable primary lung tumor LUN-NIC-0014 implanted s.c in female SCID mice. Control groups were left untreated. DM4-SPDB-chMAb1 was administered at 10.0, 5.0 and 2.5 mg/kg by an intravenous (IV) bolus injection, on day 26 post tumor implantation. Animals were weighed daily and tumors were measured 2 times weekly by caliper. A dosage producing a 20% weight loss or 15% weight loss for 3 consecutive days or 10% or more drug deaths, was considered an excessively toxic dosage. Animal body weights included the tumor weights.

Toxicity and efficacy evaluation were performed as reported in example 10-1.

Results

Figure 6:
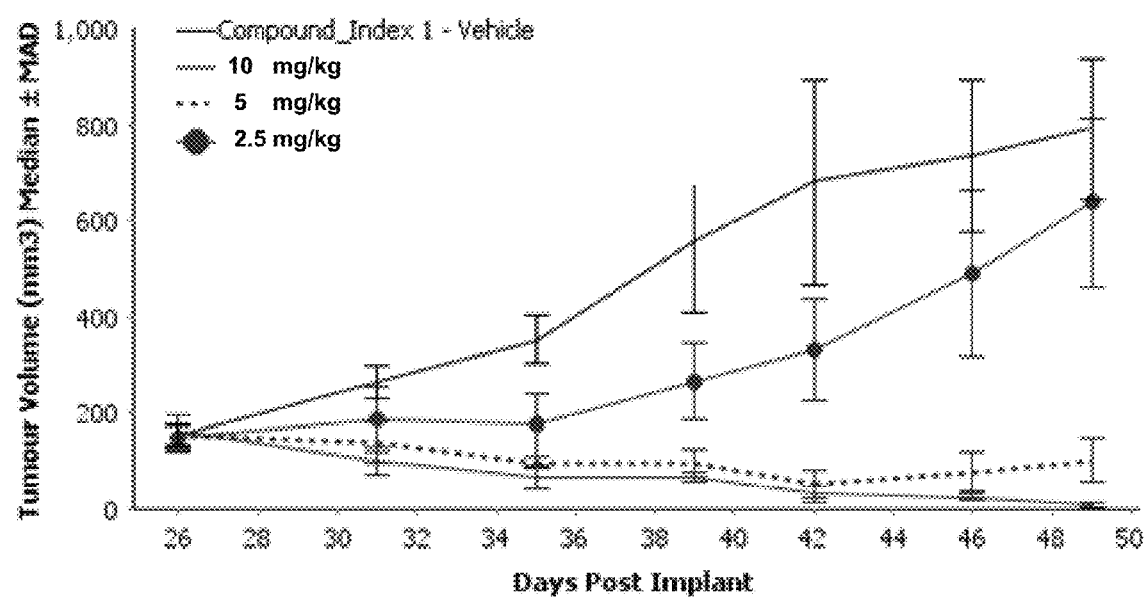
FIG. 6: Evaluation of the anti-tumor activity of DM4-SPDB-chMAb1 conjugate against primary lung tumor LUN-NIC-0014 in SCID female mice.

DM4-SPDB-chMAb1 given at 10.0, 5.0 and 2.5 mg/kg was well tolerated with a maximal body weight loss of 3.3% at 2.5 mg/kg. After a single administration at 10.0 and 5.0 mg/kg DM4-SPDB-chMAb1 was highly active as compared to control, producing a $\Delta T/\Delta C<0$ and regressions of the initial tumor volume of 81% and 65%, respectively, and with 6/6 CR at 10 mg/kg and 5/6 PR at 5 mg/kg. The dosage below 2.5 mg/kg was active with $\Delta T/\Delta C=33\%$ and no regressions. (Table 33, FIG. 6).

Example 10.2: In Vivo Efficacy of DM4-SPDB-huMAb1_1

Example 10.2.1: Evaluation of the Anti-Tumor Activity of DM4-SPDB-huMAb1_1 Against Primary Human Colon Adenocarcinoma CR-LRB-010P Material and Method DM4-SPDB-huMAb1_1 was evaluated at 2 doses against measurable primary colon CR-LRB-010P tumors implanted s.c in female SCID mice. Control groups were left untreated. DM4-SPDB-huMAb1_1 was administered at 5 and 2.5 mg/kg by an intravenous (IV) bolus injection, on day 19 post tumor implantation. Animals were weighed daily and tumors were measured 2 times weekly by caliper.

Toxicity and efficacy evaluation were performed as reported in example 10.1.

Results

Figure 23:
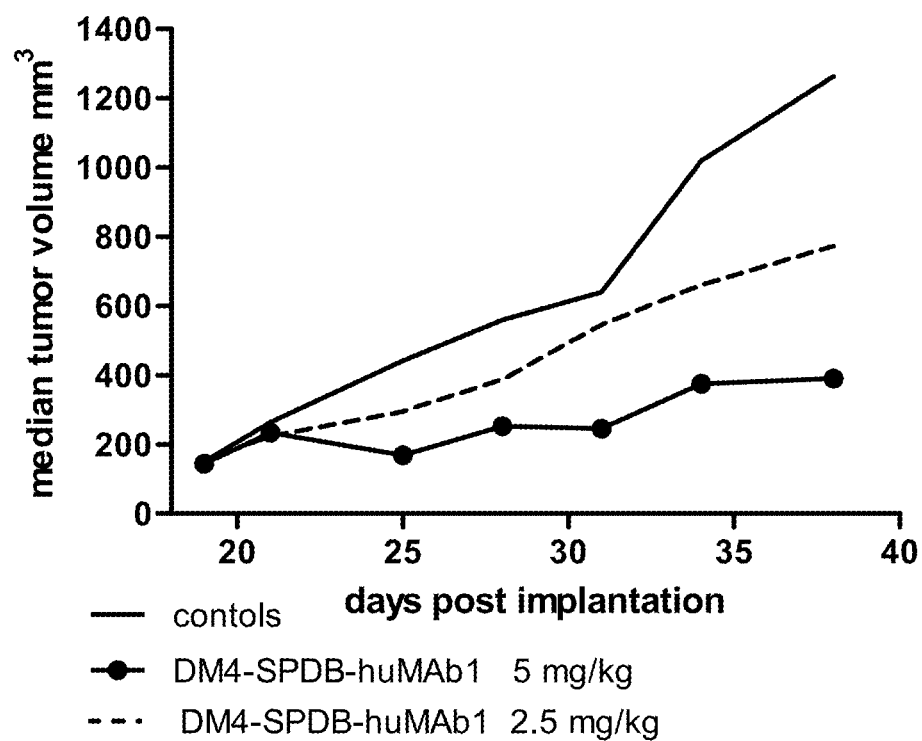
FIG. 23: Evaluation of the anti-tumor activity of DM4-SPDB-huMAb1_1 against primary human colon adenocarcinoma CR-LRB-010P in SCID female mice.

DM4-SPDB-huMAb1_1 given at 5.0 and 2.5 mg/kg was well tolerated with a maximal body weight loss of 4.4% at 2.5 mg/kg. After a single administration at 5.0 mg/kg DM4-SPDB-huMAb1_1 was active and statistically significant (p<0.0001), as compared to control, producing a $\Delta T/\Delta C=0$ without regressions. The dosage below 2.5 mg/kg yielded a $\Delta T/\Delta C=47\%$. (Table 34, FIG. 23)

TABLE 33

Evaluation of the antitumor activity of DM4-SPDB-chMAb1 against primary human lung tumor LUN-NIC-0014 in SCID female mice

| Agent[1] | Route/Dosage in mL/kg per injection | Dosage in mg/kg per injection | Average body weight change in % (on day of trough) | Median $\Delta T/\Delta c$ in % (on day 42) | Median % of regression (on day 42) | Regressions Partial | Regressions Complete |
|---|---|---|---|---|---|---|---|
| DM4-SPDB-chMAb1 | 10 mL/kg IV | Single dose day 26 | −2.52 (28) | <0 | 81 | 6/6 | 6/6 |
| DM4-SPDB-chMAb1 | 5 mL/kg IV | Single dose day 26 | −1.34 (28) | <0 | 65 | 5/6 | 0/6 |
| DM4-SPDB-chMAb1 | 2.5 mL/kg IV | Single dose day 26 | −3.32 (28) | 33 | | 0/6 | 0/6 |
| Control | | | −2.83 (27) | | | 0/6 | 0/6 |

Drug formulation: HGS buffer at pH 5.5 (10 mM histidine, 130 mM glycine, 5% (w/v) sucrose, 0.01% Tween 80)
Tumor doubling time = 7.5 days. Tumor size at start of therapy was 99-230 mm$^3$, with amedian tumor burden per group of 148-162 mm$^3$.

TABLE 34

Evaluation of the anti-tumor activity of DM4-SPDB-huMAb1_1 against
primary human colon adenocarcinoma CR-LRB-010P in SCID female mice.

| Agent | Route/ Dosage in mL/kg per injection | Dosage in mg/kg per injection (total dose) | Schedule in days | Drug death (Day of death) | Average body weight change in % per mouse at nadir (day of nadir) | Median $\Delta T/\Delta C$ in % day 25 | Median % of regression on day | Regressions Partial | Regressions Complete | Biostatistic p value (25) |
|---|---|---|---|---|---|---|---|---|---|---|
| DM4-SPDB-huMAb1_1 | IV 10 mL/kg | 5 (5) | 19 | 0/6 | −0.9 (21) | 0 | — | 0/6 | 0/6 | p < 0.0001 |
|  |  | 2.5 (2.5) |  | 0/6 | −4.4 (45) | 47 | — | 0/6 | 0/6 | p = 0.2258 |
| Control |  |  |  | 0/10 | −3.5 (37) | — | — | 0/6 | 0/6 | — |

Tumor doubling time = 6.0 days. Tumor size at start of therapy was 88-277 mm³, with a median tumor burden per group of 138-157 mm³.
Mice average weight range = 18.10-22.40 g dosages were adjusted to the individual body weights. Drug formulation: His-Gly-Sucrose buffer pH = 5.5; Statistical analysis: Dunnett's test versus control following a two-way Anova with repeated measures performed separately for each compounds on ranks of changes from baseline. A probability less than 5% (p < 0.05) was considered as significant.

Example 10.2.2: Evaluation of the Anti-Tumor Activity of DM4-SPDB-huMAb1_1 Against Primary Invasive Ductal Carcinoma BRE-IGR-0159

Material and Method

DM4-SPDB-huMAb1_1 was evaluated at four doses against measurable primary invasive ductal carcinoma BRE-IGR-0159 tumors implanted s.c in female SCID mice. Control groups were left untreated. DM4-SPDB-huMAb1_1 was administered at 5, 2.5, 1.25 and 0.62 mg/kg by an intravenous (IV) bolus injection, on day 17 post tumor implantation. Animals were weighed daily and tumors were measured 2 times weekly by caliper.

Toxicity and efficacy evaluation were performed as reported in example 10.1.

Results

Figure 24:
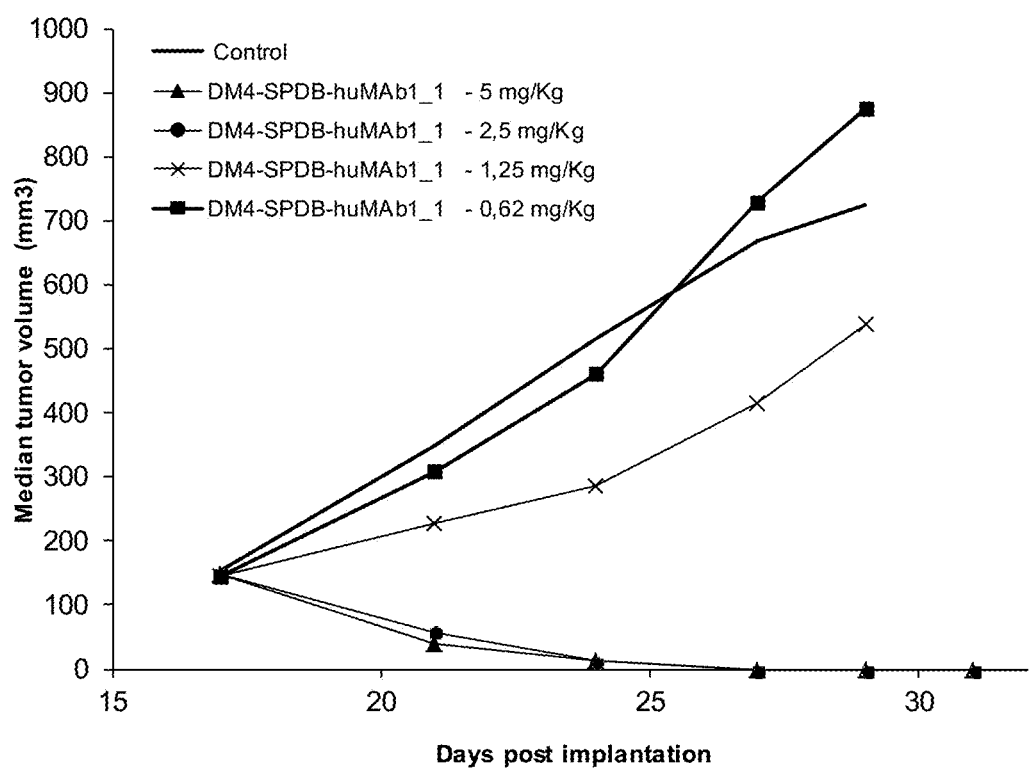
FIG. 24: Evaluation of the anti-tumor activity of DM4-SPDB-huMAb1_1 against human primary invasive ductal carcinoma BRE-IGR-0159 in SCID female mice.

After a single administration at 5.0 and 2.5 mg/kg, DM4-SPDB-huMAb1_1 was well tolerated and was active producing a $\Delta T/\Delta C<0$ and regressions of the initial tumor, volume of 100%, with 6/6 CR at 5 mg/kg and 4/6 CR at 2.5 mg/kg. The dosages below 1.25 mg/kg was active with $\Delta T/\Delta C=30\%$ (p=0.0015) and no regressions. The lower dose 0.62 mg/kg yielded a $\Delta T/\Delta C=86\%$ (Table 35, FIG. 24)

Example 10.2.3: Evaluation of the Anti-Tumor Activity of DM4-SPDB-huMAb1_1 Against Primary Human Lung Tumor LUN-NIC-0070

Material and Method

DM4-SPDB-huMAb1_1 was evaluated at 4 doses against measurable primary colon CR-LRB-010P tumors implanted s.c in female SCID mice. Control groups were left untreated. DM4-SPDB-chMAb2 was administered at 10, 5, 2.5 and 1.25 mg/kg by an intravenous (IV) bolus injection, on day 35 at 10, 5, 2.5 mg/kg and 49 at 1.25 mg/kg 19 post tumor implantation. Animals were weighed daily and tumors were measured 2 times weekly by caliper.

Toxicity and efficacy evaluation were performed as reported in example 10.1.

Results

Figure 25A:
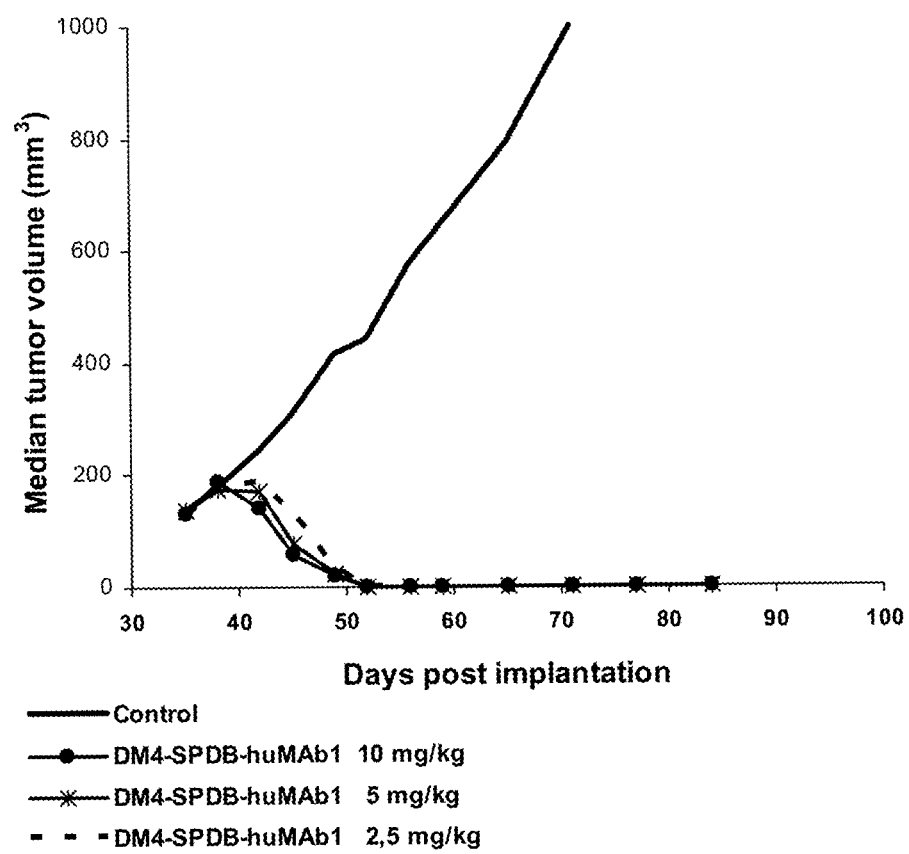
FIG. 25A and FIG. 25B: Evaluation of the anti-tumor activity of DM4-SPDB-huMAb1_1 against primary primary human lung tumor LUN-NIC-0070 in SCID female mice.
Figure 25B:
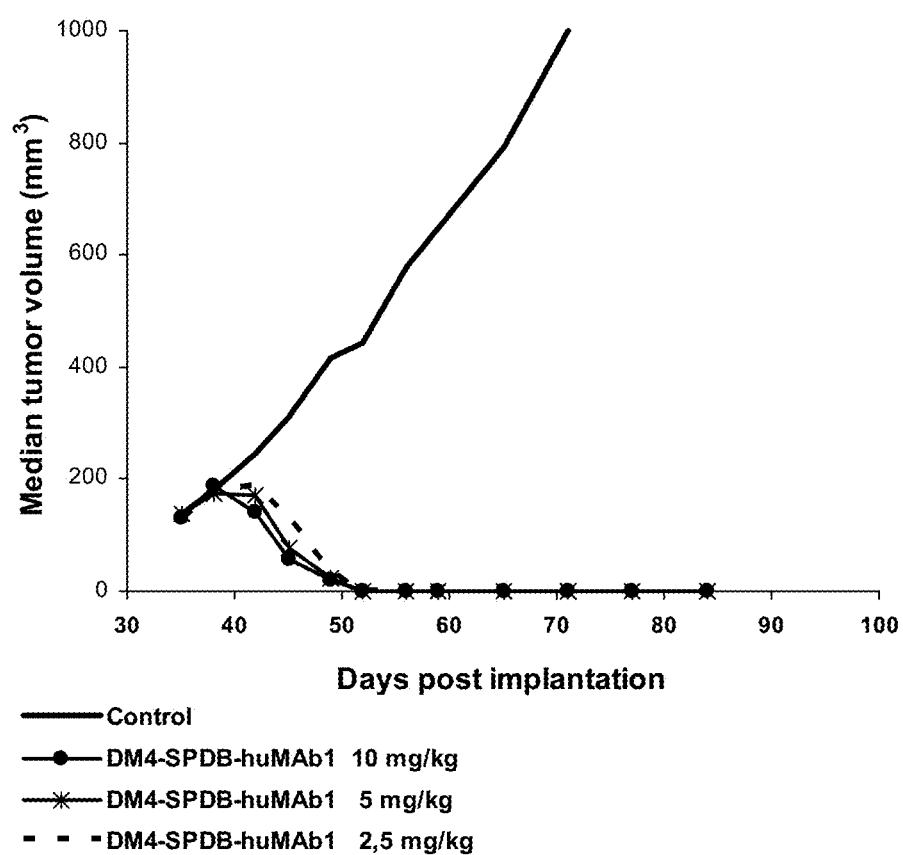

DM4-SPDB-huMAb1_1 given at 10.0; 5.0 2.5 and 1.25 mg/kg was well tolerated. After a single administration at 10; 5 and 2.5 mg/kg DM4-SPDB-huMAb1_1 was active with a $\Delta T/\Delta C<0$ ((p<0.0001) and 100% complete regressions. The dosage below 1.25 mg/kg was active with 2.5 mg/kg $\Delta T/\Delta C<0$ ((p<0.0001) and 4/6 PR (Table 36 a) and b), FIG. 25).

TABLE 35

Evaluation of the anti-tumor activity of DM4-SPDB-huMAb1_1 against
human primary invasive ductal carcinoma BRE-IGR-0159 in SCID female mice

| Agent | Route/ Dosage in mL/kg per injection | Dosage in mg/kg per injection (total dose) | Schedule in days | Drug death (Day of death) | Average body weight change in % per mouse at nadir (day of nadir) | Median $\Delta T/\Delta C$ in % day 24 | Median % of regression on day 27 | Regressions Partial | Regressions Complete | Tumor free survivors day 49 | Biostatistic p value 24 |
|---|---|---|---|---|---|---|---|---|---|---|---|
| DM4-SPDB-huMAb1_1 | IV 10 mL/kg | 5.0 (5.0) | 17 | 0/6 | −1.7 (18) | <0 | 100 | 6/6 | 6/6 | 6/6 | p < 0.0001 |
|  |  | 2.5 (2.5) | 17 | 0/6 | −3.0 (32) | <0 | 100 | 6/6 | 4/6 | 3/6 | p < 0.0001 |
|  |  | 1.25 (1.25) | 17 | 0/6 | −3.3 (34) | 30 | — | 0/6 | 0/6 | 0/6 | p = 0.0015 |
|  |  | 0.62 (0.62) | 17 | 0/6 | −8.1 (31) | 86 | — | 0/6 | 0/6 | 0/6 | p = 0.9232 |
| Control |  |  |  | 0/6 | −13 (31) |  |  |  |  |  |  |

Tumor doubling time = 5.3 days. Tumor size at start of therapy was 80-270 mm³, with a median tumor burden per group of 144-153 mm³. Mice average weight: Due to body weight heterogeneity (range: SAR428926 = 20.50-26.10 g) dosages were adjusted to the individual body weights. Drug formulation: HGS buffer pH = 5.5. Statistical analysis: Dunnett's test versus control following a two-way Anova with repeated measures performed separately for each compounds on ranks of changes from baseline. A probability less than 5% (p < 0.05) was considered as significant.

TABLE 36

Evaluation of the anti-tumor activity of DM4-SPDB-huMAb1 gainst primary human lung tumor LUN-NIC-0070 in SCID female mice.

a)

| Agent | Route/ Dosage in mL/kg per injection | Dosage in mg/kg per injection (total dose) | Schedule in days | Drug death (Day of death)c | Average body weight change in % per mouse at nadir (day of nadir) | Median $\Delta T/\Delta C$ in % day 59 | Median % of regression on day 59 | Regressions Partial | Regressions Complete | Tumor free survivors at day 84 | Biostatistic p value |
|---|---|---|---|---|---|---|---|---|---|---|---|
| DM4-SPDB-huMAb1 | IV/10 | 10 (10) | 35 | 0/6 | −4.1 (64) | <0 | 100 | 6/6 | 6/6 | 6/6 | p < 0.0001 |
|  |  | 5 (5) |  | 0/6[a)] | −4.9 (50) | <0 | 100 | 5/5 | 5/5 | 5/5 | p < 0.0001 |
|  |  | 2.5 (2.5) |  | 0/6 | −4.2 (64) | <0 | 100 | 6/6 | 6/6 | 5/6 | p < 0.0001 |
| controls |  |  |  | 0/9 | −2.0 (37) |  |  | 0/6 | 0/6 | 0/6 |  | b)

| Agent | Route/ Dosage in mL/kg per injection | Dosage in mg/kg per injection (total dose) | Schedule in days | Drug death (day of nadir) | Average body weight change in % per mouse at nadir (day of nadir) | Median $\Delta T/\Delta C$ in % day 59 | Median % of regression on day 59 | Regressions Partial | Regressions Complete | Tumor free survivors at day 84 | Biostatistic p value |
|---|---|---|---|---|---|---|---|---|---|---|---|
| DM4-SPDB-huMAb1 | IV/10 | 1.25 (1.25) | 49 | 0/6 | −4.3 (63) | <0 | (64 on day 71) | 4/6 | 0/6 | 0/6 | p < 0.0001 |
| controls |  |  |  | 0/6 | −2.8 (56) |  |  | 0/6 | 0/6 | 0/6 |  |

Tumor doubling time = 8.8 days. Tumor size at start of therapy was 96-218 mm³ with a median tumor burden per group of 132-138 mm³. Drug formulation: His-Gly-Sucrose buffer pH = 5.5; Statistical analysis: Dunnett's test versus control following a two-way Anova with repeated measures performed separately for each compounds on ranks of changes from baseline. A probability less than 5% (p < 0.05) was considered as significant.
Tumor doubling time = 10.3 days. Tumor size at start of therapy was 118-220 mm³ with a median tumor burden per group of 171-176 mm³. Drug formulation: His-Gly-Sucrose buffer pH = 5.5; Statistical analysis: Dunnett's test versus control following a two-way Anova with repeated measures performed separately for each compounds on ranks of changes from baseline. A probability less than 5% (p < 0.05) was considered as significant.

Example 10.3: In Vivo Efficacy of DM4-SPDB-chMAb2

Example 10.3.1: Evaluation of the Anti-Tumor Activity of DM4-SPDB-chMAb2 Against Primary Human Colon Adenocarcinoma CR-LRB-010P Material and Method DM4-SPDB-chMAb2 was evaluated at 3 doses against measurable primary colon CR-LRB-010P tumors implanted s.c in female SCID mice. Control groups were left untreated. DM4-SPDB-chMAb2 was administered at 10, 5 and 2.5 mg/kg by an intravenous (IV) bolus injection, on day 19 post tumor implantation. Animals were weighed daily and tumors were measured 2 times weekly by caliper.

Toxicity and efficacy evaluation were performed as reported in example 10.1.

Results

Figure 26:
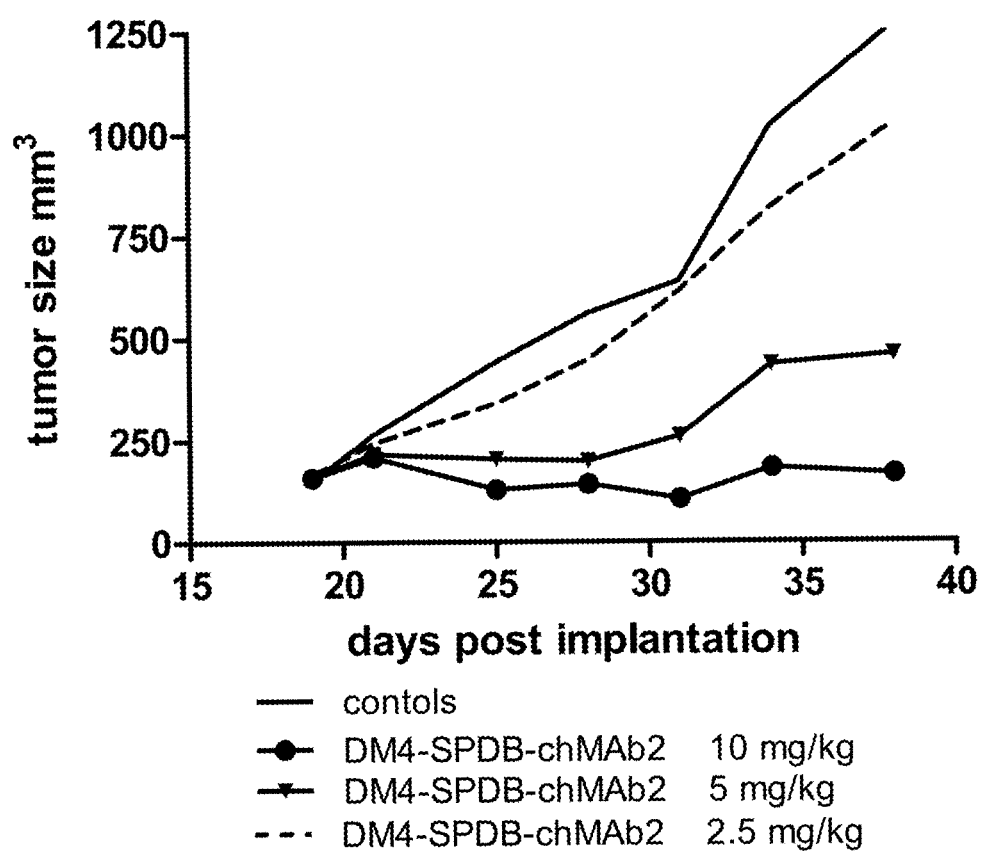
FIG. 26: Evaluation of the anti-tumor activity of DM4-SPDB-chMAb2 against primary human colon adenocarcinoma CR-LRB-010P in SCID female mice.

DM4-SPDB-chMAb2 given at 10.0; 5.0 and 2.5 mg/kg was well tolerated. After a single administration at 10 and 5 mg/kg DM4-SPDB-chMAb2 was active with a $\Delta T/\Delta C<0$ ((p<0.0001) and 1/6 PR and $\Delta T/\Delta C=10$ (p<0.0001) and no regressions respectively. The dosage below 2.5 mg/kg produced a $\Delta T/\Delta C=68\%$. (Table 37, FIG. 26)

TABLE 37

Evaluation of the anti-tumor activity of DM4-SPDB-chMAb2 against primary human colon adenocarcinoma CR-LRB-010P in SCID female mice.

| Agent | Route/ Dosage in mL/kg per injection | Dosage in mg/kg per injection (total dose) | Schedule in days | Drug death (Day of death) | Average body weight change in % per mouse at nadir (day of nadir) | Median $\Delta T/\Delta C$ in % day | Median % of regression on day | Regressions Partial | Regressions Complete | Biostatistic p value (day) |
|---|---|---|---|---|---|---|---|---|---|---|
| DM4-SPDB-chMAb2 | IV 10 mL/kg | 10 (10) | 19 | 0/6 | −1.6 (20) | <0 (31) | 36 (31) | 1/6 | 0/6 | p < 0.0001 (31) |
|  |  | 5 (5) | 19 | 0/6 | −2.4 (37) | 10 (28) | — | 0/6 | 0/6 | p < 0.0001 (28) |
|  |  | 2.5 (2.5) | 19 | 0/6 | −2.5 (36) | 66 (28) | — | 0/6 | 0/6 | p = 0.7711 (28) |
| Control |  |  |  | 0/10 | −3.5 (37) | — | — | 0/6 | 0/6 | — |

Tumor doubling time = 6.0 days. Tumor size at start of therapy was 88-277 mm³, with a median tumor burden per group of 138-157 mm³. Mice average weight range = 18.10-22.40 g dosages were adjusted to the individual body weights. Drug formulation: His-Gly-Sucrose buffer pH = 5.5; Statistical analysis: Dunnett's test versus control following a two-way Anova with repeated measures performed separately for each compounds on ranks of changes from baseline. A probability less than 5% (p < 0.05) was considered as significant.

Example 10.3.2: Evaluation of the Anti-Tumor Activity of DM4-SPDB-chMAb2 Against Human Primary Invasive Ductal Carcinoma BRE-IGR-0159 in SCID Female Mice Material and Method DM4-SPDB-chMAb2 was evaluated at 3 doses against measurable primary invasive ductal carcinoma BRE-IGR-0159 tumors implanted s.c in female SCID mice. Control groups were left untreated. DM4-SPDB-chMAb2 was administered at 10, 5 and 2.5 mg/kg by an intravenous (IV) bolus injection, on day 14 post tumor implantation. Animals were weighed daily and tumors were measured 2 times weekly by caliper.

Toxicity and efficacy evaluation were performed as reported in example 10.1.

Results

Figure 27:
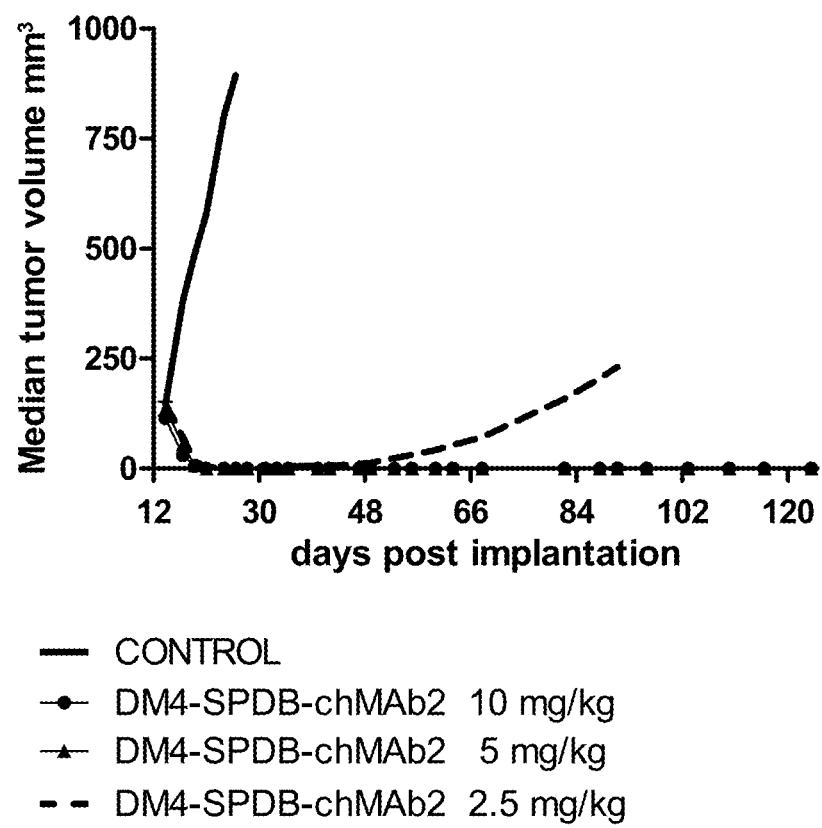
FIG. 27: Evaluation of the anti-tumor activity of DM4-SPDB-chMAb2 against human primary invasive ductal carcinoma BRE-IGR-0159 in SCID female mice.

DM4-SPDB-chMAb2 given at 10.0; 5.0 and 2.5 mg/kg was well tolerated. After a single administration at 10, 5 and 2.5 mg/kg DM4-SPDB-chMAb2 was active with a $\Delta T/\Delta C<0$ ((p<0.0001) and 100% complete regressions at all doses tested. (Table 38, FIG. 27)

TABLE 38

Evaluation of the anti-tumor activity of DM4-SPDB-chMAb2 against human primary invasive ductal carcinoma BRE-IGR-0159 in SCID female mice

| Agent (batch) | Route/ Dosage in mL/kg per injection | Dosage in mg/kg per injection (total dose) | Schedule in days | Drug death (Day of death) | Average body weight change in % per mouse at nadir (day of nadir) | Median $\Delta T/\Delta C$ in % day 24 | Median % of re-gression on day 24 | Regressions Partial | Regressions Complete | Biostatistic p value day 24 | Tumor Free survivor on day 124 |
|---|---|---|---|---|---|---|---|---|---|---|---|
| DM4-SPDB-chMAb2 | IV 10 mL/kg | 10.0 (10.0) | 14 | 0/6 | −5.2 (17) | <0 | 100 | 5/5 | 5/5 | p < 0.0001 | 5/5 |
|  |  | 5.0 (5.0) | 14 | 0/6 | −6.9 (17) | <0 | 100 | 6/6 | 6/6 | p < 0.0001 | 6/6 |
|  |  | 2.5 (2.5) | 14 | 0/6 | −4.2 (17) | <0 | 100 | 6/6 | 6/6 | p < 0.0001 | 4/6 |
| Control | — | — | — | 0/10 | −15.9 (24) | — | — | 0/6 | 0/6 |  | 0/6 |

Tumor doubling time = 2.9 days. Tumor size at start of therapy was 88-245 mm3, with a median tumor burden per group of 120-135 mm3. Statistical analysis: Dunnett's test versus control following a two-way Anova with repeated measures performed separately for each compounds on ranks of changes from baseline. A probability less than 5% (p < 0.05) was considered as significant.

Example 10.4: Efficacy of the Anti-Tumor Activity of DM4-SPDB-chMAb3 Against Human Primary Invasive Ductal Carcinoma BRE-IGR-0159 in SCID Female Mice Material and Method DM4-SPDB-chMAb3 was evaluated at 3 doses against measurable primary invasive ductal carcinoma BRE-IGR-0159 tumors implanted s.c in female SCID mice. Control groups were left untreated. DM4-SPDB-chMAb3 was administered at 5.0, 2.5 and 1.25 mg/kg by an intravenous (IV) bolus injection, on day 16 post tumor implantation. Animals were weighed daily and tumors were measured 2 times weekly by caliper.

Toxicity and efficacy evaluation were performed as reported in example 10.1.

Results

DM4-SPDB-chMAb3 given at 5.0, 2.5 and 1.25 mg/kg was well tolerated.

Figure 28:
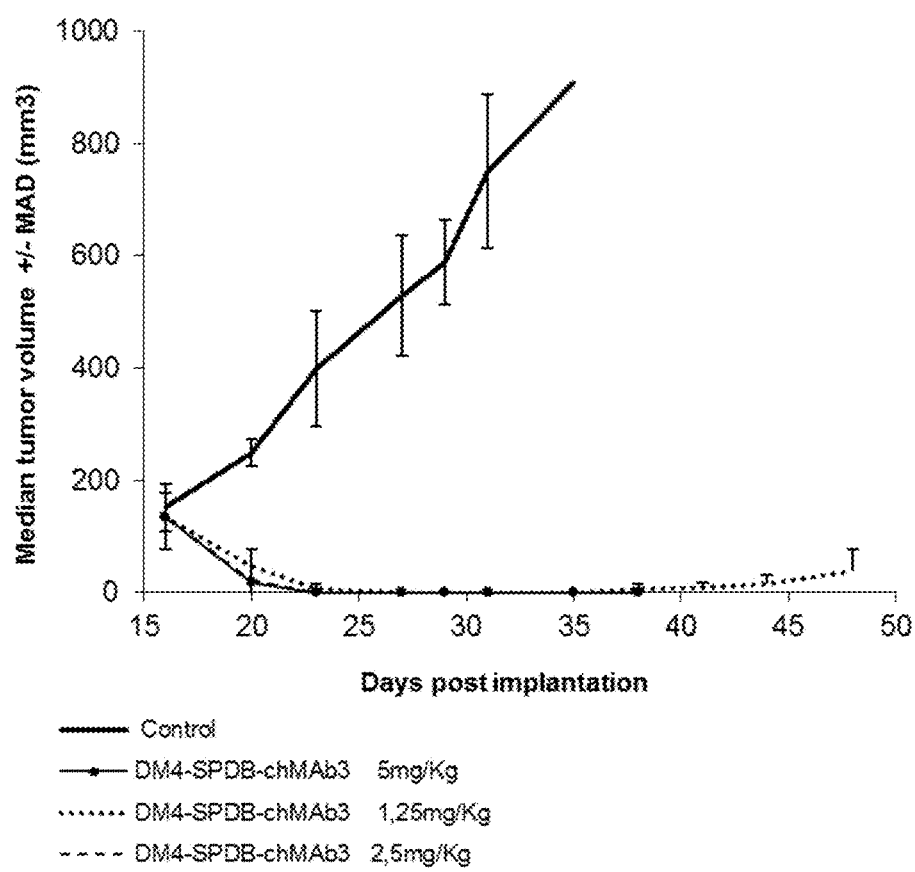
FIG. 28: Evaluation of the anti-tumor activity of DM4-SPDB-chMAb3 against human primary invasive ductal carcinoma BRE-IGR-0159 in SCID female mice.

After a single administration at 5.0, 2.5 and 1.25 mg/kg DM4-SPDB-chMAb3 was active with a $\Delta T/\Delta C<0$ ((p<0.0001) and 100% of regressions at all dose tested. (Table 39, FIG. 28)

TABLE 39

Evaluation of the anti-tumor activity of DM4-SPDB-chMAb3 against human primary invasive ductal carcinoma BRE-IGR-0159 in SCID female mice

| Agent | Route/ Dosage in mL/kg per injection | Dosage in mg/kg per injection (total dose) | Schedule in days | Drug death (Day of death) | Average body weight change in % per mouse at nadir (day of nadir) | Median $\Delta T/\Delta C$ in % (day) | Median % of re-gression on day 35 | Regressions Partial | Regressions Complete | Tumor free survivors day 76 | Biostatistic p value |
|---|---|---|---|---|---|---|---|---|---|---|---|
| DM4-SPDB-chMAb3 | IV 10 ml/kg | 5.0 (5.0) | 16 | 0/6 | −2.8 (17) | <0 (35) | 100 | 6/6 | 6/6 | 6/6 | p < 0.0001 |
|  |  | 2.5 (2.5) | 16 | 0/6 | −3.2 (17) | <0 (35) | 100 | 6/6 | 5/6 | 5/6 | p < 0.0001 |
|  |  | 1.25 (1.25) | 16 | 0/6 | −1.7 (17) | <0 (35) | 100 | 6/6 | 6/6 | 2/6 | p < 0.0001 |
| Control |  |  |  | 0/10 | −17.8 (32) | — |  | 0/6 | 0/6 | 0/6 |  |

Tumor doubling time = 7.4 days. Tumor size at start of therapy was 88-221 mm$^3$, with a median tumor burden per group of 135-151 mm$^3$. Mice average weight range = 18.10-22.40 g dosages were adjusted to the individual body weights. Drug formulation: His-Gly-Sucrose buffer pH = 5.5. Statistical analysis: Dunnett's test versus control following a two-way Anova with repeated measures performed separately for each compounds on ranks of changes from baseline. A probability less than 5% (p < 0.05) was considered as significant.

Example 11: In Vitro ADCC Activity

ADCC activity was evaluated using HCT116 huLAMP1 clone 8 (as described in example 9) as target cells and human natural killer (NK) cells as effector cells. A lactate dehydrogenase (LDH) release assay was used to measure cell lysis (R. L. Shields et al., 2001, *J Biol Chem*, 276: 6591-6604).

Peripheral Blood Mononuclear Cells Isolation

Blood was diluted 2-3-fold with phosphate-Buffered Saline (PBS). Thirty five mL of diluted blood was carefully layered over 15 mL of Ficoll-Paque Plus (GE healthcare) in a 50 mL conical tube and centrifuged at 400 g for 40 min at room temperature. The peripheral blood mononuclear cells (PBMC) were collected from the interface, transferred into a new conical 50 mL tube, and washed twice with PBS.

NK Isolation

According to Miltenyi NK cell isolation kit protocol (130-092-657, Miltenyi Biotech). The PBMC were suspended in NK-isolation buffer (40 µl of buffer for $10^7$ total cells), and then Biotin-Antibody Cocktail (10 µl for $10^7$ total cells) was added to the cell suspension. The Biotin-Antibody Cocktail contains biotinylated antibodies that bind to the mononuclear cells, except for NK cells. The mixture was incubated at 4° C. for 5 min, and then NK-isolation buffer (30 µl of buffer for $10^7$ total cells) and NK cells MicroBead cocktail (20 µl for $10^7$ total cells) were added. The cell-antibody mixture was incubated for another 10 min at 4° C. Next, cells were washed (centrifugation at 400 g for 10 min) once with 50 mL of NK-isolation buffer, suspended in 1 mL of NK-isolation buffer for 2.10E+8 cell and loaded on isolated by the autoMACS Pro Separator (Miltenyi) using the depletion program. Collected and pooled negative fractions (containing NK cells) were washed once (centrifugation at 400 g for 10 min) and suspended at $2.5 \times 10^6$/mL in RPMI-1640 supplemented with 10% fetal bovine serum, 2 mM of L-Glutamine, 1% of penicillin/streptomycin, 1% Hepes, 1% Na-pyruvate and 1% non-essential amino-acids.

ADCC Protocol 10-fold serial dilutions, from $1.5 \times 10^{-7}$ M to $1.5 \times 10^{-17}$ M of tested antibody as well as isotypic control antibody were prepared in RPMI-1640 medium supplemented with 0.1% BSA, 2 mM HEPES, pH 7.4 (denoted below as RHBP medium). Triplicate of each antibody concentration were distributed (50 µL/well) into a round bottom 96-well plate. HCT116 huLAMP1 clone 8 cells were suspended at $0.075 \times 10^6$ cells/mL in RHBP medium and added to each well (100 µL/well) containing antibody dilutions. The plate containing target cells and antibody dilutions was incubated for 10 min at room temperature. NK cells were washed and suspended in RHBP medium at $0.75 \times 10^6$ cells/mL, 50 µL of NK cells were then added to each well, leading to a typically ratio of 5 NK cells to 1 target cell. Control A consisted of wells containing only target cells (no antibody and no NK cells added) where RHBP medium (50 µL/well) was added instead of NK cells. Control B consisted of wells containing only target cells (no antibody and no NK cells added) where 20 µL of Triton X-100 solution (RPMI-1640 medium, 10% TritonX-100) was added, to determine the maximum possible LDH release of target cells. The mixtures were incubated at 37° C. for 4 h, and then centrifuged for 10 min at 1200 rpm, 100 µL of the supernatant was carefully transferred to a new flat-bottom 96-well plate. Freshly prepared LDH reaction mixture (100 µL/well) from Cytotoxicity Detection Kit (Roche 11644793001) was added to each well and incubated in dark at room temperature for 30 min.

The optical density of samples was measured at 490 mn (OD490). 100% of lysis corresponded to OD490 value of control B wells and 0% of lysis to the OD490 value of the control A wells. The percent specific lysis of each sample was determined by the following formula: (OD490 sample−OD490 of control A)/(OD490 control B−OD490 control A)*100

The samples containing only NK cells gave negligible OD490 readings.

Example 11.1: In Vitro ADCC Mediated by chMAb1, chMAb2 and chMAb3

Figure 29:
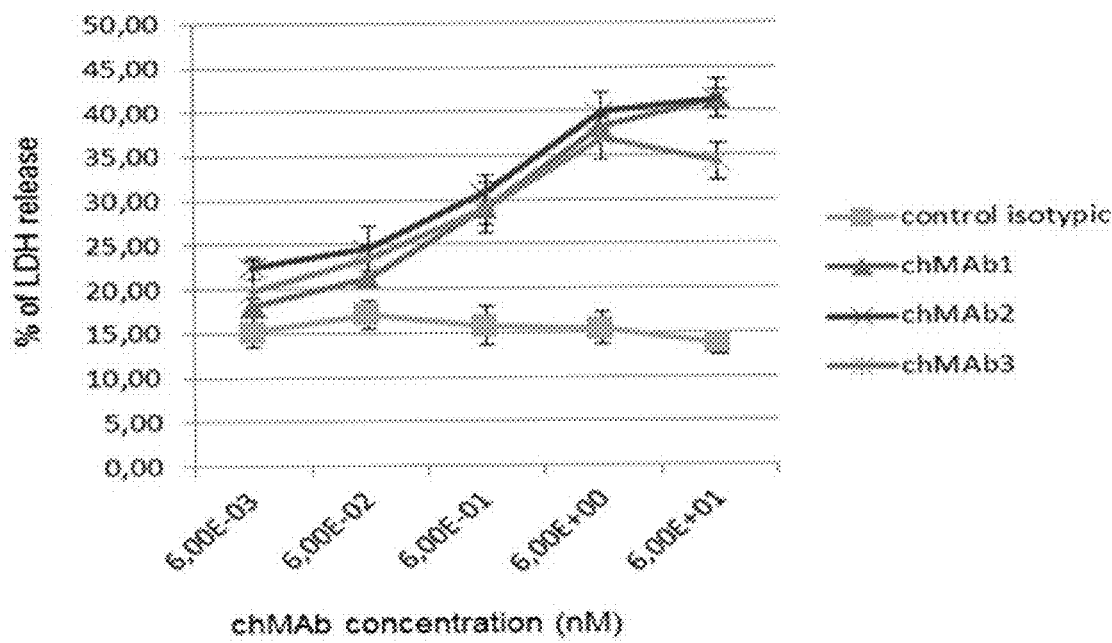
FIG. 29: Graphical representation of the in vitro ADCC mediated by chMAb1, chMAb2 and chMAb3.

The chMAb1, chMAb2 and chMAb3 antibodies specifically induced similar and potent ADCC activities as shown in FIG. 29. Isotype control antibody had no significant ADCC activity

Example 11.2: Variability of In Vitro ADCC

ADCC activities of chMAb1 or chMAb2 were evaluated for several batches of purified NK, each batch correspond to an individual blood donor. As depicted in table 40, ADCC activities varied from one batch of NK cells to the other. $EC_{50}$ values were estimated using BIOST@T-SPEED software.

TABLE 40

Maximum of ADCC and $EC_{50}$ for individual batches of isolated NK cells

|  | NK batch # | Highest ADCC value (% of maximal LDH release) | $EC_{50}$ (nM) | Comment |
|---|---|---|---|---|
| chMAb1 | 67125903091 | 36 | 0.76 | |
|  | 67125626389 | 51 | 0.05 | |
|  | 6712562616 | 44 | Not determined | $EC_{50}$ could not be determined as high plateau not reach for highest concentration of MAb assayed |
|  | 67130127373 | 33 | 0.009 | |
|  | 67130127429 | 60 | Not determined | $EC_{50}$ could not be determined as high plateau not reach for highest concentration of MAb assayed |
|  | 67130496259 | 20 | 0.6 | |
|  | 67130194552 | 33 | 0.2 | |
| chMAb2 | 67125903091 | 32 | 0.5 | |
|  | 67125626369 | 52 | 0.1 | |
|  | 6712562616 | 31 | 2 | |
|  | 67130127429 | 61 | Not determined | $EC_{50}$ could not be determined as high plateau not reach for highest concentration of MAb assayed |

Example 11.3: In Vitro ADCC Dependency on LAMP1 Antigen Density

Figure 30:
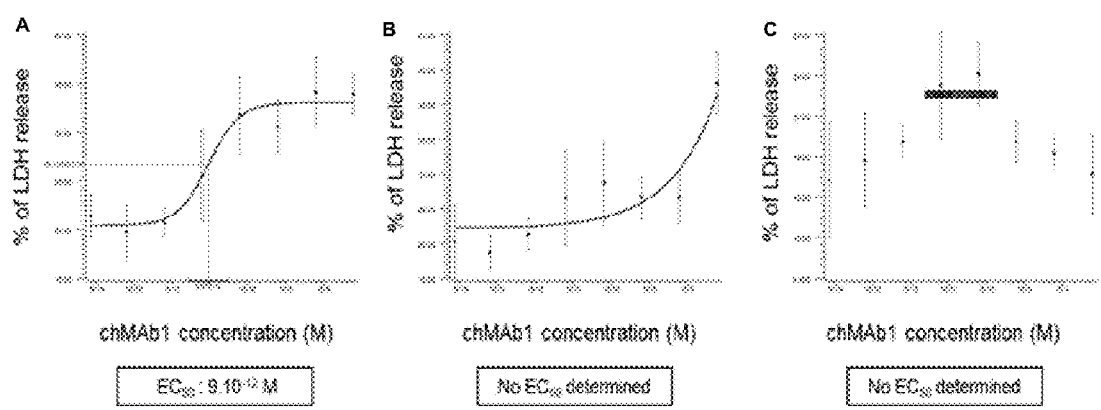
FIG. 30: Graphical representation of the in vitro ADCC dependency on LAMP1 antigen density with a) HCT hu LAMP1 clone 8 LAMP1 antigen density: 160000 b) HCT hu LAMP1 clone 4 LAMP1 antigen density: 2000 and c) HCT hu LAMP1 clone 12 LAMP1 antigen density: 5000.

Using the same NK batch, ADCC was analyzed for HCT116 huLAMP1 clones displaying different antigen densities. As illustrated by data of FIG. 30, antigen density >20 000 is required to lead to noticeable in vitro ADCC activity.

Example 11.4: Comparison of In Vitro ADCC of chMAb1 and DM4-SPDB-chMAb1 or chMAb2 and DM4-SPDB-chMAb2

Figure 31A:
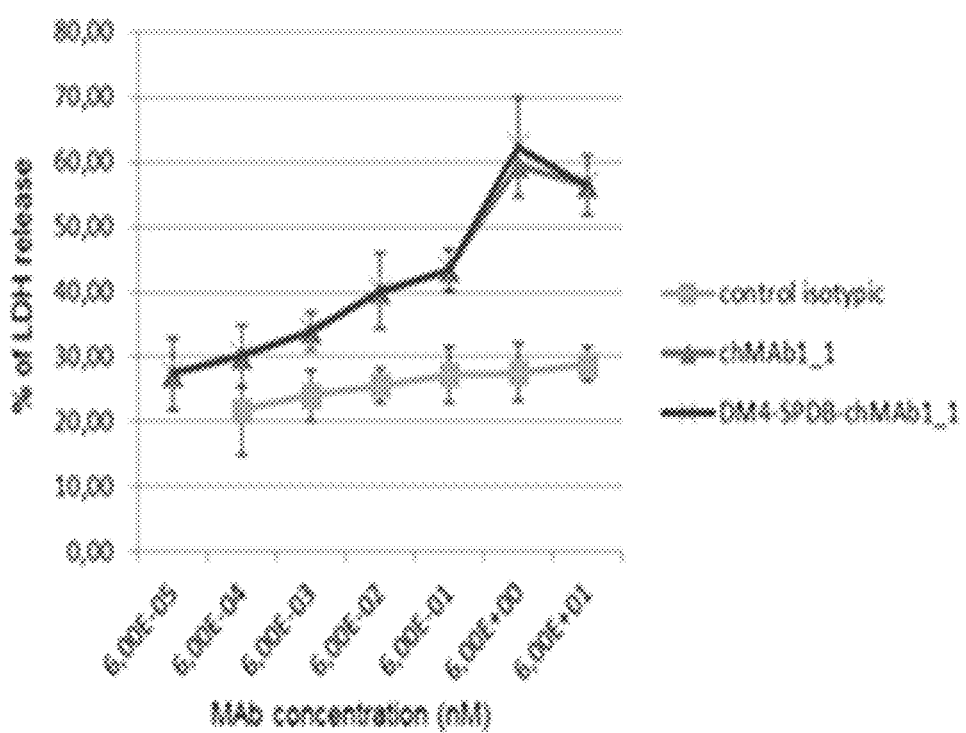
FIG. 31A: Comparison of in vitro ADCC of chMAb1 and DM4-SPDB-chMAb1.
Figure 31B:
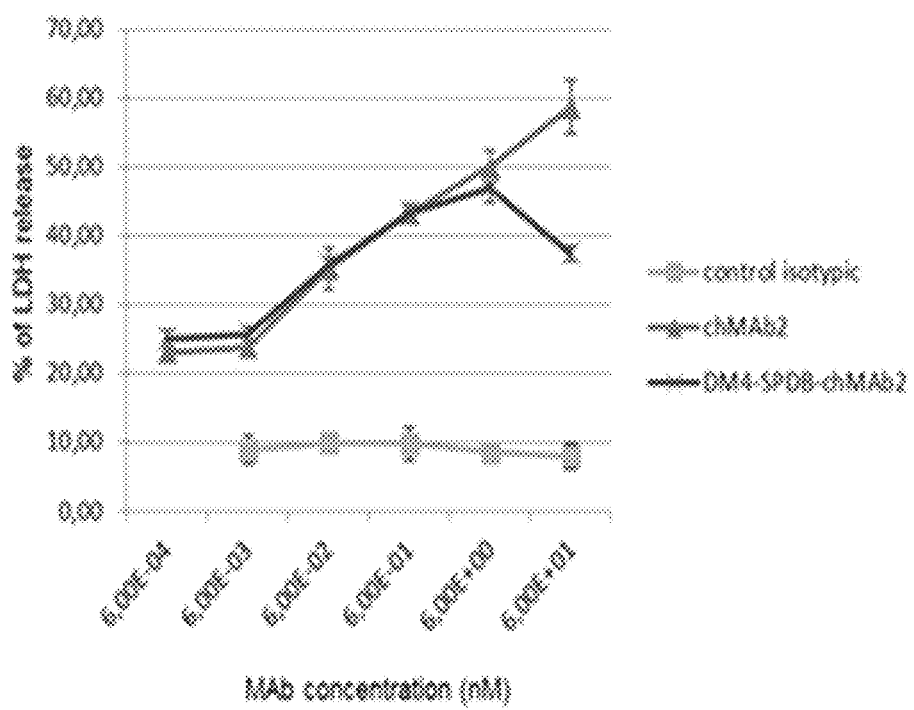
FIG. 31B: Comparison of in vitro ADCC of chMAb2 and DM4-SPDB-chMAb2.

DM4-SPDB conjugation did not significantly impacts ADCC activity of chMAb1 or chMAb2 (FIGS. 31a and b).

Example 11.5: In Vitro ADCC Mediated by huMAb1_1

Figure 32:
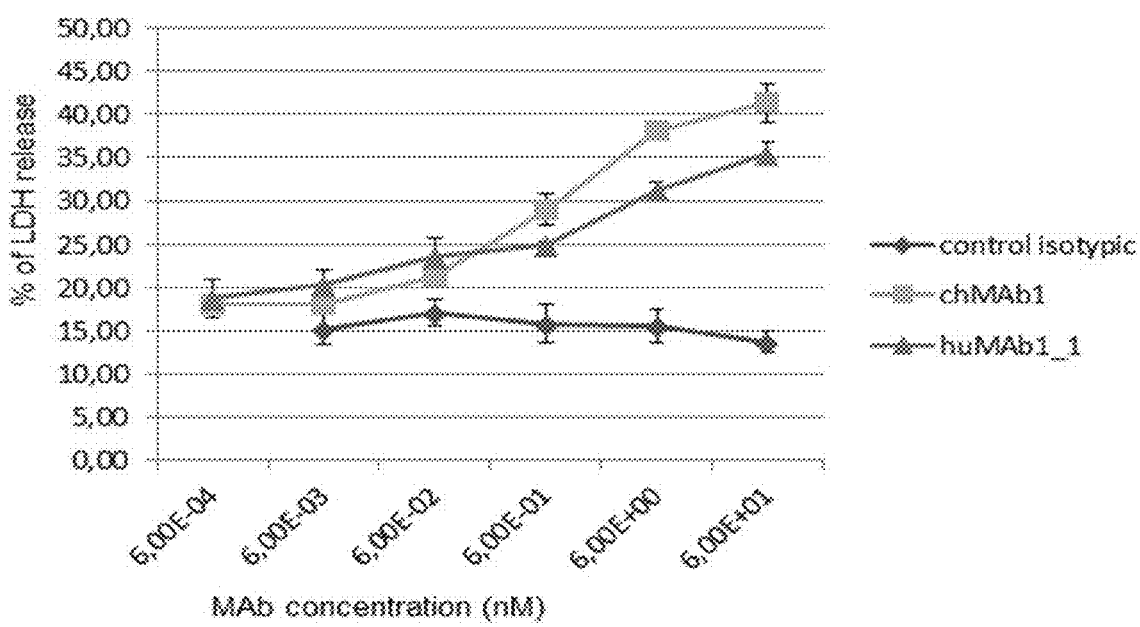
FIG. 32: In vitro ADCC mediated by huMAb1_1.

ChMAb1 was included in the experiments a reference comparator. HuMAb1_1 induced ADCC activity similar to chMAb1 as shown in FIG. 32.

Example 11.6: In Vitro ADCC Mediated by DM4-SPDB-huMAb1_1

Figure 33:
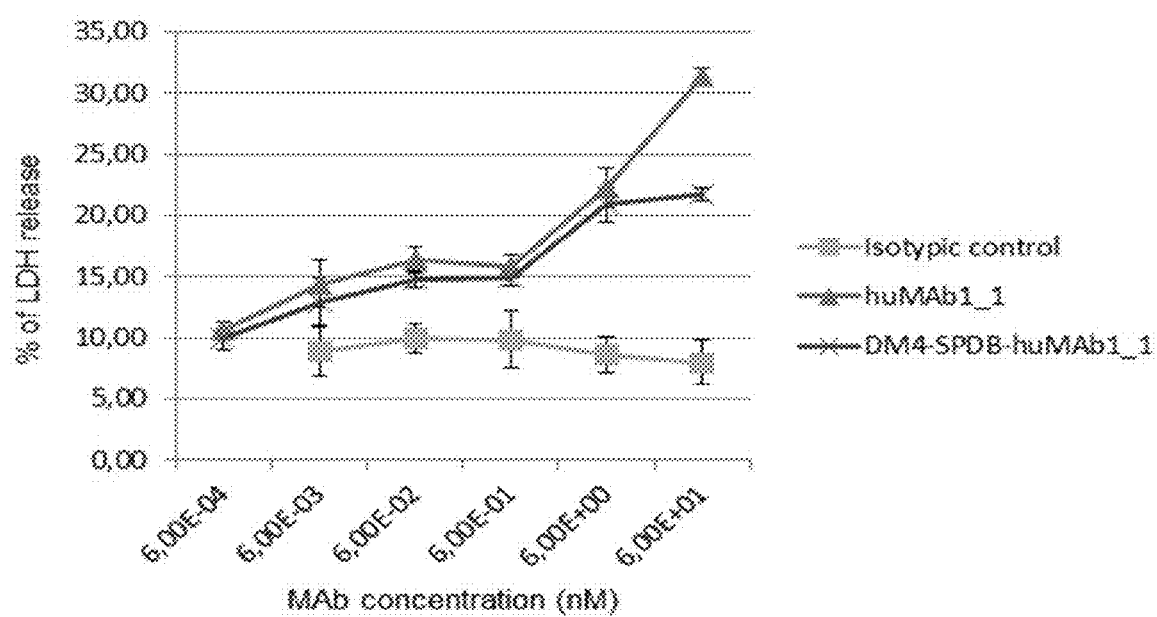
FIG. 33: In vitro ADCC mediated by DM4-SPDB-huMAb1_1.

HuMAb1_1 was included in the experiments a reference comparator. DM4-SPDB-huMAb1_1 induced ADCC activity similar to huMAb1 as shown in FIG. 33.

Example 12: In Vitro ADCP Activity

ADCP activity was evaluated using HCT116 huLAMP1 clones with different LAMP1 antigen densities as target cells and human macrophages as effector cells. HCT116 huLAMP1 clones were labeled by PKH67 fluorescent dye, macrophages were labeled by CD14-PC7 fluorescent dye.

Peripheral Blood Mononuclear Cells Isolation

The peripheral blood mononuclear cells (PBMC) were isolated as described in example 11.

Monocytes Isolation

From isolated PBMC and according to Miltenyi monocytes cell isolation kit protocol (130-050-201, Miltenyi Biotech). Cells labeled by CD14-MicroBead were isolated using the positive selection program of the autoMACS Pro Separator (Milteny Biotech). Collected fraction (containing monocytes cells) were suspended in 13.6 mL of RPMI-1640 supplemented with 10% fetal bovine serum, washed once (centrifugation at 400 g for 10 min) and suspended at a final concentration of $10^6$ cells/mL in 64 mL of RPMI-1640 supplemented with 10% fetal bovine serum, 1% of heat inactivated human serum (AB; #14-490E), 2 mM of L-glutamine and 50 ng/mL of GM-CSF (Miltenyi Biotech; #130-093-866).

Macrophages Differentiation

The 64 mL of isolated monocytes were added to T75 flasks (NUNC; #I56472), 10 mL per flasks. Flasks were put in a 37° C. 5% CO2 incubator where cells were allowed to adhere for 8 days. RPMI-1640 supplemented with 10% fetal bovine serum, 1% of heat inactivated human serum, 2 mM of L-glutamine and 50 ng/mL of GM-CSF was changed after 4 days of incubation.

ADCP Protocol

Macrophages were suspended by accutase (Invitrogen Stempro; #A111-0501), washed once (centrifugation at 400 g for 10 min) and suspended in RPMI-1640 medium supplemented with 2% fetal bovine serum and 2 mM L-glutamine at a concentration of $1.5 \times 10^6$ cells/mL for a ratio of 6/1 or $0.75 \times 10^6$ cells/mL for a ratio of 3/1. 100 µL of suspended macrophages were distributed into a round bottom 96-well polypropylene plate. $10^7$ of suspended target cells (HCT116 huLAMP1 clone 4; HCT116 huLAMP1 clone 5; HCT116 huLAMP1 clone 8 or HCT116 huLAMP1 clone 12) were labeled by PKH67 fluorescent dye following provider's procedure (SIGMA-ALDRICH; #MIDI67-1KT), then suspended at $5 \times 10^5$ cells/ml in RPMI-1640 supplemented with 2% fetal bovine serum and 2 mM of L-glutamine. ⅓ serial dilutions, from $9 \times 10^{-8}$ M to $3 \times 10^{-12}$ M of tested huMAb1_1 as well as isotypic control antibody were prepared in RPMI-1640 medium supplemented with 2% fetal bovine serum. Duplicate of each antibody concentration were distributed (150 µL/well) into a round bottom 96-well polypropylene plate. 150 µL of PKH67-labeled target cells were added to each well containing antibody dilutions. The plate containing target cells and antibody dilutions was incubated for 15 min at 37° C. 100 µL of mixture (target cells+antibody) were added to the 96-well plate containing macrophages which was then placed for 4 h to 17 h in a 37° C. 5% CO2 incubator. Cells were suspended by accutase (Invitrogen stempro; #A111-0501), washed twice (centrifugation at 400 g for 10 min) and suspended in buffer (PBS supplemented with 5% of heat inactivated human serum) containing CD14-PC7 antibody (Beckman Coulter; #PN A22331). After 20 minutes of incubation at 4° C., cells were washed once and suspended in 250 µL of PBS, washed once and suspended in 50 µL of fixing paraformaldehyde solution (PFA 4% in PBS, USB; #19943). Samples were stored at 4° C. up to cytometry analysis.

Cytometry Analysis

Figure 34:
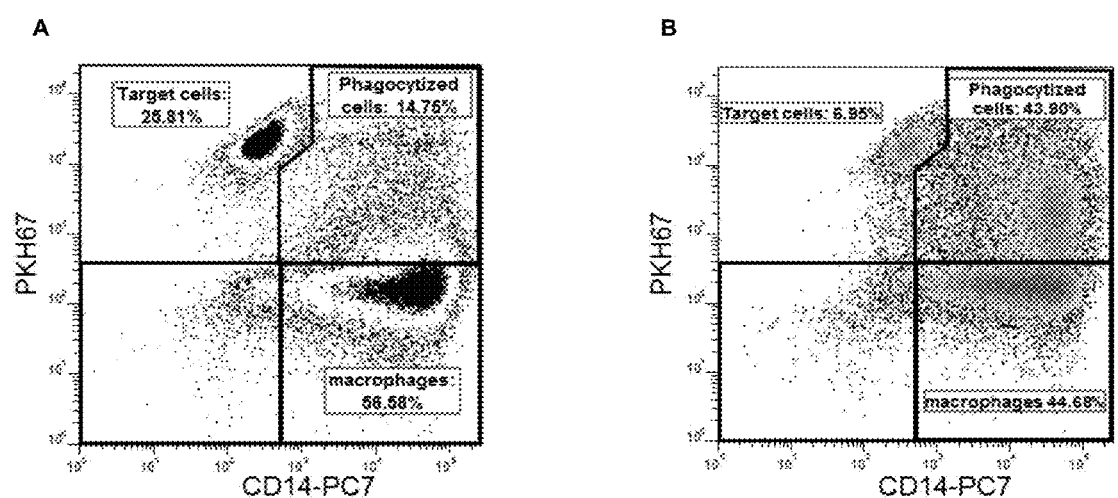
FIG. 34: Flow cytometry analysis of ADCP with a) Macrophages and target cells without Mab1_1 and b) Macrophages and target cells and Mab1_1.

Samples were analyzed using a MACSQUANT apparatus. Phagocytosis was determined as double-labeled cells (PKH67 positive and PC7 positive cells). Typical data obtained are shown in FIG. 34.

Example 12.1: In Vitro ADCP Mediated by huMAb1_1

Two ratios of macrophages/HCT116 huLAMP1 clone 8 were analyzed. $EC_{50}$ values were estimated using BIOST@T-SPEED software. HuMAb1_1 induces significant in vitro ADCP at a ratio macrophages/target cell of 3/1. Higher ratio, 6/1, did not lead to lower $EC_{50}$ or higher % of phagocytosis as shown in Table 41.

TABLE 41

In vitro ADCP mediated by huMAb1_1

| Ratio macrophages/ target cell | Batch of macrophages | $EC_{50}$ (nM) | Maximum of phagocytosis |
| --- | --- | --- | --- |
| 3/1 | 67131617438 | 0.28 | 32 |
|     | 67131617470 | 0.56 | 39 |
|     | 67131354967 | 0.5  | 43 |
|     | 67130713495 | 0.47 | 33 |
|     | 67130713495 | 0.36 | 34 |
| 6/1 | 67130713495 | 0.98 | 41 |
|     | 67130713495 | 0.34 | 40 |

Example 12.2: In Vitro ADCP Dependency on LAMP1 Cell Surface Expression

ADCP was analyzed for HCT116 huLAMP1 clones displaying different antigen densities. The level of in vitro ADCP induced by huMAb1_1 is linked to antigen density of LAMP1 as maximum of phagocytosis decreased as LAMP1 antigen density decreased as deducible from Table 42.

TABLE 42

In vitro ADCP dependency on LAMP1 cell surface expression

| Target cell | Antigen density | Mean EC$_{50}$ (nM) +/− STD | Mean Maximum of phagocytosis (%) +/− STD |
|---|---|---|---|
| HCT116 huLAMP1 clone 5 | 300 000 | 0.33 +/− 0.21 | 45.5 +/− 15.5 |
| HCT116 huLAMP1 clone 8 | 100 000 | 0.43 +/− 0.11 | 36.2 +/− 4.7 |
| HCT116 huLAMP1 clone 4 | 20 000 | 0.73 +/− 0.17 | 34.0 +/− 9.1 |
| HCT116 huLAMP1 clone 12 | 2500 | 0.65 +/− 0.49 | 8.7 +/− 4.1 |

Example 12.3: In Vitro ADCP for huMAb1_negB

Figure 35:
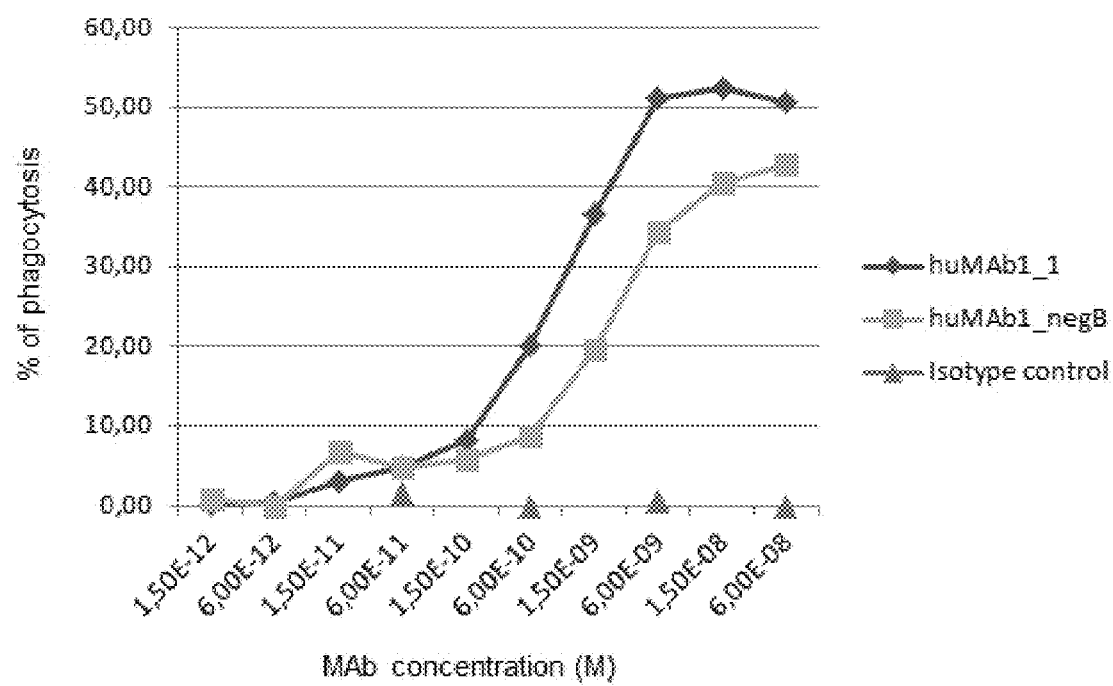
FIG. 35: In vitro ADCP of huMAb1_negB.

FCγRIIIa mediated phagocytosis was evaluated by assessing ADCP induced by huMAb1_negB (described in example 7.2). As expected (macrophages not being strictly dependent on FCγRIIIa for activation), huMAb1_negB leaded to lower ADCP than huMAb1_1, however ADCP still occurred when huMAb1_negB was used. Typical data obtained are displayed in FIG. 35.

Example 12.4: In Vitro ADCP for huMAb1_negA

Figure 36:
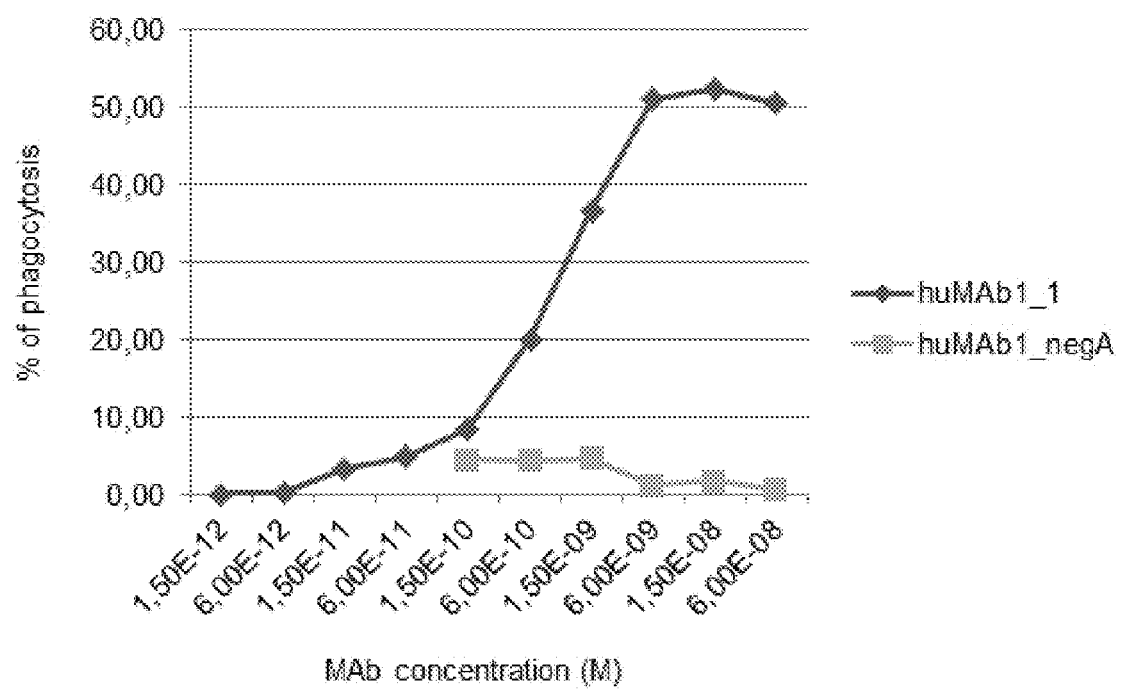
FIG. 36: Loss of in vitro ADCP for huMAB1_negA.

ADCP mediated by huMAb1_negA (described in example B7.2) was tested to evaluate antigen specificity mediated phagocytosis. As displayed in FIG. 36, huMAb1_negA did not induce any ADCP, validating specificity of data obtained for huMAb1_1.

Example 13: LAMP1 Gene Copy Number Change

Materials and Methods:
Array-Based Oligonucleotide Comparative Genomic Hybridization (aCGH)

Genomic DNA was analyzed using the Human Genome CGH Microarray 400k-(Agilent Technologies, Santa Clara, Calif., USA). Digestion, labeling and hybridization were performed using Agilent Oligo aCGH Bravo platform protocols for Human CGH 2×400K microarrays. In all experiments, sex-matched DNA from a human well-characterized normal female (NA12878) or one well-characterized normal male (NA10858) was used as reference DNA. The normal human genomic DNA used in these experiences is commercialized by Coriell Reference.

Oligonucleotide aCGH processing was performed as detailed in the manufacturer's protocol (version 6.2 Oct. 2009 on the world wide web at; agilent.com). The microarray required 600 ng of genomic DNA from the reference sample and from the experimental sample. Array was scanned with an Agilent DNA Microarray Scanner (G2565CA).

Data were extracted from scanned images and normalized using the Feature Extraction software (v10.7.3.1, Agilent).

The log 2 ratio and segmentation were generated using Array Studio software. Array Studio, Array Viewer and Array Server and all other Omicsoft products or service names are registered trademarks or trademarks of Omicsoft Corporation, Research Triangle Park, N.C., USA.

Centralization of the log 2 ratio distribution was verified and segmentation was performed using the CBS algorithm (Olshen et al.; *Biostatistics* (2004), 5(4): 557). Aberration status calling was automatically performed for each profile according to its internal noise (variation of log 2 ratio values across consecutive probes on the genome). All genomic coordinates were established on the UCSC human genome build hg19 (Karolchik D et al. Nucleic Acids Res 2003, 31: 51). The value log Ratio and Copy Number Change, for each region or gene, was introduced in an internal database for subsequent analysis.

Gene Expression

The gene expression analysis was performed using a GeneChip Expression 3'-Amplification Reagents Kit and U133Plus GeneChip arrays (Affymetrix, Santa Clara, Calif., USA), using the Expression Analysis Cia platforme. All data were imported into Resolver software (Rosetta Biosoftware, Kirkland, Wash., USA) for database management, quality controls and Analysis. Each mRNA is represented by one or more qualifier. The value of expression from each qualifier was downloaded in the Patient-Derived Tumor Xenograft Tumor Bank database (Tumor bank database) for analysis.

Animals

Animals were maintained in the animal facilities of each institution following standard animal regulation and strict health controls allowing transfer between members of the consortium. Swiss-nude and CB17-SCID female mice, as well as NIH-nude rats were bred at Charles River France (Les Oncins, France). Mouse weights were over 18 g and rat weights were over 160 g at the start of experiments. Their care and housing were in accordance with institutional guidelines, as well as national and European laws and regulations as put forth by the French Forest and Agriculture Ministry and the standards required by the UKCCCR guidelines.

Sample Preparation

Frozen fragments were cut in a cryostat at −20° C. then beginning and end sections were stained with HES (Haematoxylin-Eosin-Saffron) for histological control and evaluation of tumor cell percentage by pathologists. Genomic DNA was extracted according to QIAamp DNA Kit protocols v01 (Qiagen, Hilden, Germany). Total RNA was extracted from tumor samples and purified with an RNAeasy kit (Qiagen), using the RNA extraction Qiagen protocols v01.

Molecular Characterization of PDX

The molecular characterization (CGH, RNA expression and IHC) of each tumoral model of PDX was performed using the same Xenografts passage.

Immunohistochemistry

To associate genomic copy number aberration of LAMP1 gene and its region (13q34) with changes in the protein levels (Strong, medium, Faint and Negative) of the membrane localization of LAMP1 on PDXs (Frozen-Oct), specific staining (mAb1) was carried out on the same passage of PDX used for CGH and RNA expression characterization.

After avidin and biotin blocking (Endogenous Block, Ventana, 760-050), frozen sections (Frozen-OCT format) were incubated with murine monoclonal antibody MAb1 (final concentration 1 μg/mL (for human samples) and 1 and 5 μg/mL (for monkey samples) in Phosphate Buffer Saline, PBS) for 32 min at 37° C. A postfixation step with glutaraldehyde (0.05% in NaCl 0.9% w/v) for 4 min was done. The secondary goat anti-mouse IgG2a-biotinylated was incubated for 12 min at 37° C. (Southern Biotech, Ref 1080-08, dilution 1/200 in Ventana's diluent). Immunostaining was done with DAB Map chromogenic detection kit according to manufacturers recommendations. A couterstaining step was applied to the cryostat sections with hematoxylin II (790-2208, Ventana Medical Systems, Inc USA) and bluing reagent was applied for 4 min (760-2037).

Stained slides were dehydrated and coverslipped with Coverquick 2000 mounting medium (Labonord, Ref 05547530).

The negative controls used in this study consisted in omission of primary antibody and the use of IgG2a isotype (final concentration 1 µg/mL in PBS).

For data analysis sections immunostained with purified murine antibody MAb1 were scanned and digitized at a magnification of ×20 using Scan Scope XT system (Aperio Technologies, Vista Calif.). Digitized images were then captured using Image Scope software (v10.2.2.2319 Aperio, Technologies).

The positive samples were scored with a scale of intensity from 1 to 3. Ranges of intensities were described as negative (0), weak (1), moderate (2) and strong (3). Cell frequency was the percentage of immunostained cells and was estimated by the histologist observation as a median by sample. The cell frequency was ordered in 5 categories: 1 (0-5%), 2 (6-25%), 3 (26-50%), 4 (51-75%) and 5 (76-100%).

A global expression was calculated according the Allred Score (AS) description. AS was obtained by adding the intensity and the proportion scores to obtain a total score that ranged from 0-8. The AS was reported as a percent of the maximum global score and ranged in 5 categories: very low (0-25%), weak (26-50%), moderate (51-75%) and high (75-100%). The prevalence was defined as the percent of positive cases for the indication.

Basic descriptive statistics were calculated with Microsoft Excel 2003. For each indication, number of cases, positive cases number, prevalence, intensity score mean, frequency mean and Allred score were described.

Statistical Analyses

In order to study the relation between the mRNA expression and the LAMP1 gene change (gain or amplification), we applied a Student test on PDX data to compare the mRNA expression levels of the tumor PDX with or without Copy Number change. We also determined the correlation between mRNA expression levels of the CRC PDXs and their respective genomic copy number variation of LAMP1 gene and their region (13q34) by a Person correlation test.

In addition, a correlation analysis using a larger set of colorectal patients tissues samples (n=574) from the TCGA (The Cancer Genome Atlas) database, was performed between mRNA expression normalized and Copy Number using a Spearman correlation test. In order to study the association of LAMP1 expression or no expression at the plasma membrane of PDX tumors cells determined by IHC analysis and the Copy Number factor change or no change, a Cochran-Mantel-Haenszel statistics was performed. For colon PDX the test was performed using IHC score (Negative-Faint, Medium and Strong) versus Copy Number (CN<2.5 and CN≥2.5). For lung and stomach PDXs, a stratified Cochran-Mantel-Haenszel statistics was performed using IHC score (Negative-Faint, Medium-Strong) versus Copy Number (CN<2.5 and CN≥2.5). The statistical analyses were conducted using SAS 9.2; SAS Institute Inc. and Everstat V6 (Sanofi based on SAS 9 SAS Institute Inc.).

Bioinformatics Analyses: Copy Number Changes in the TCGA (the Cancer Genome Atlas)

DNA samples are analyzed using the GISTIC (Genomic Identification of Significant Targets in Cancer) methodology (Beroukhim, R. et al.; Nature 2010 463, 899; Beroukhim, R. et al.; Proc Natl Acad Sci USA (2007); 104, 20007). Briefly, each marker is scored according to the mean amplitude and frequency of focal amplification across the dataset, and significance values are computed by comparing to the distribution of scores obtained by random permutation of the markers across the genome. Significant peak regions of amplification (or deletion) are identified using an iterative peel-off procedure that distributes the score associated with amplified (or deleted) segments among all peaks that overlap them (weighted according to each peak's score) until no new region crosses the significance threshold of q-value 0.25 on each chromosome. Finally, by taking into account the autocorrelation within the GISTIC score profiles, a confidence interval is computed for each peak region that is predicted to contain the true driver gene or genes with at least 99 probability (TCGA Network. Nature 2008; 455: 1061).

The gene-based calls from GISTIC output were used. Genes were defined as possessing deep deletions, shallow deletions, neutral copy number, low gain, and high gain using specific thresholds, as follows. High gains are log 2 ratios that exceed 1.32; low gains are from 0.3 to the high gain threshold; neutral segments have copy numbers between −0.5 to 0.3; shallow losses have copy numbers between −0.5 and the deep deletion threshold; and deep deletions have copy numbers that are below −0.737.

Example 14: LAMP1 Gene Copy Number Change

Using CRC PDXs Tumors Samples

A total of 61 Colon tumor PDX were analyzed using whole genome high-density aCGH 400K-oligonucleotide arrays. As indicated in Table 44, 6 out of 61 (9.8%) colorectal cancer PDXs displays a high-level LAMP1 gene amplification (i.e: CN ≥5 or log 2 ratio ≥1.32) and 57.4% shows a LAMP1 gene gain (i.e: 2.5≤CN<5 or 0.32≤log 2 ratio <1.32).

Using Lung PDXs Tumor Samples

A total of 35 Lung tumor PDXs were analyzed using whole genome high-density aCGH 400K-oligonucleotide arrays. As depicted in Table 45; one Lung tumor PDX (3%) studied displays a high-level amplification of LAMP1 gene (CN=9.26) and 26% shows a LAMP1 gene gain (i.e: 2.5≤CN≤5 or 0.32≤log 2 ratio <1.32).

Using Commercial Tumor DNA Tissues Samples

The CGH analysis was performed also using whole genome high-density aCGH 400K-oligonucleotide arrays in the esophageal tumor DNA samples (Asterand). As indicated in Table 46 there is a gain or amplification of the LAMP1 gene in 2 out of 46 (4.3%) esophageal tumor samples studied, one of these (2%) shows a focal amplification of LAMP1 equal to 39.81 copy. This high level and focal amplification of LAMP1 is detected in an Asian female (ES01_F12), 64 years old; the biopsy contains 80% of tumor cells.

Using Patient Tumor Samples by the Cancer Genome Atlas (TCGA) Data

Figure 10A:
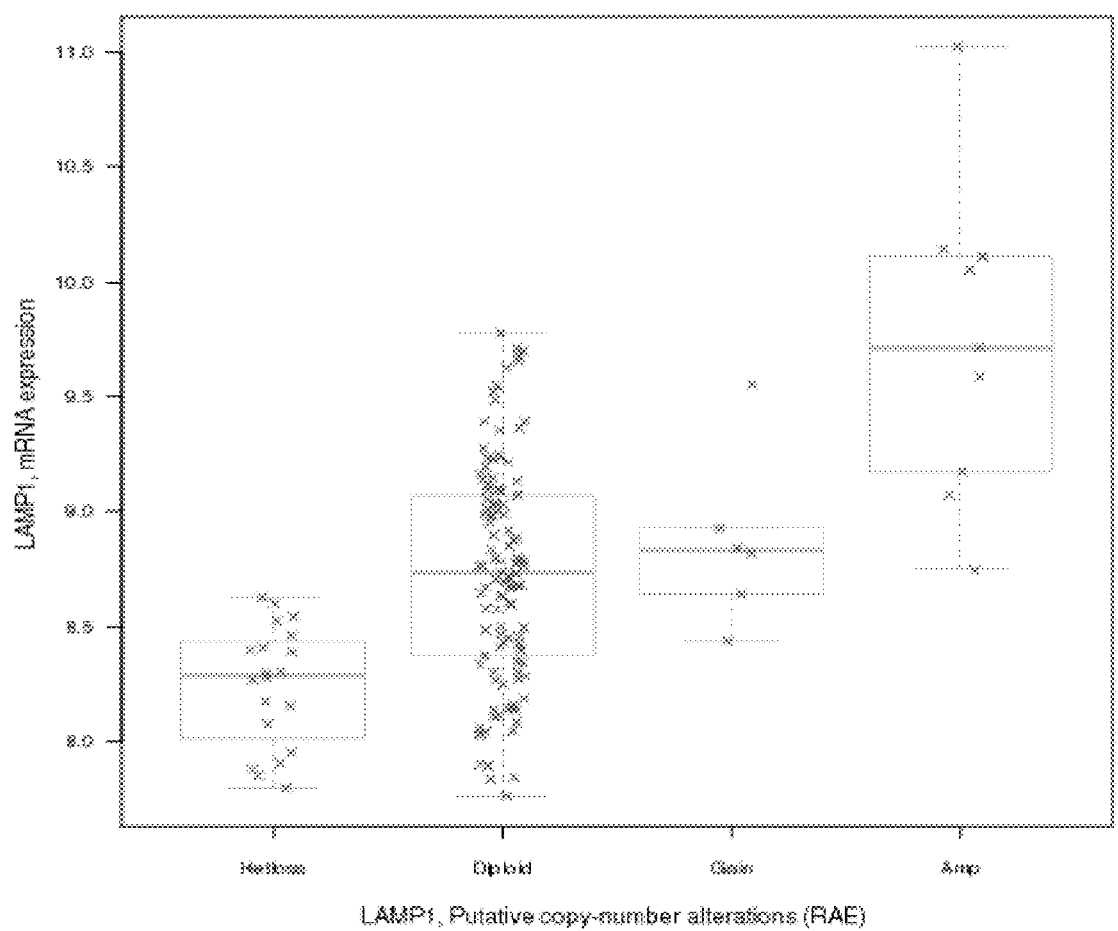
FIG. 10A: Box Plot of RNA Intensity expression and LAMP1 by Copy Number Change in Soft Tissue Sarcoma.
Figure 10B:
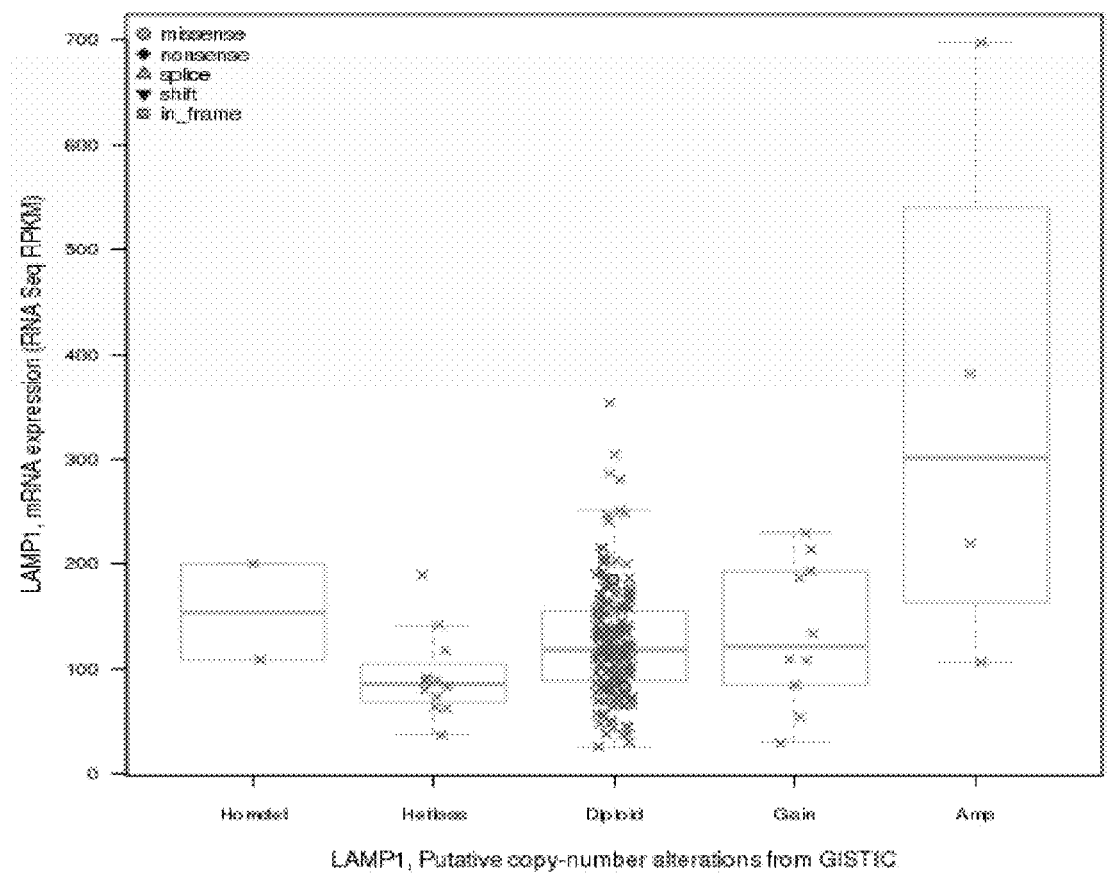
FIG. 10B: Box Plot of RNA Intensity expression and LAMP1 by Copy Number Change in Corpus Endometrioid Carcinoma.
Figure 10C:
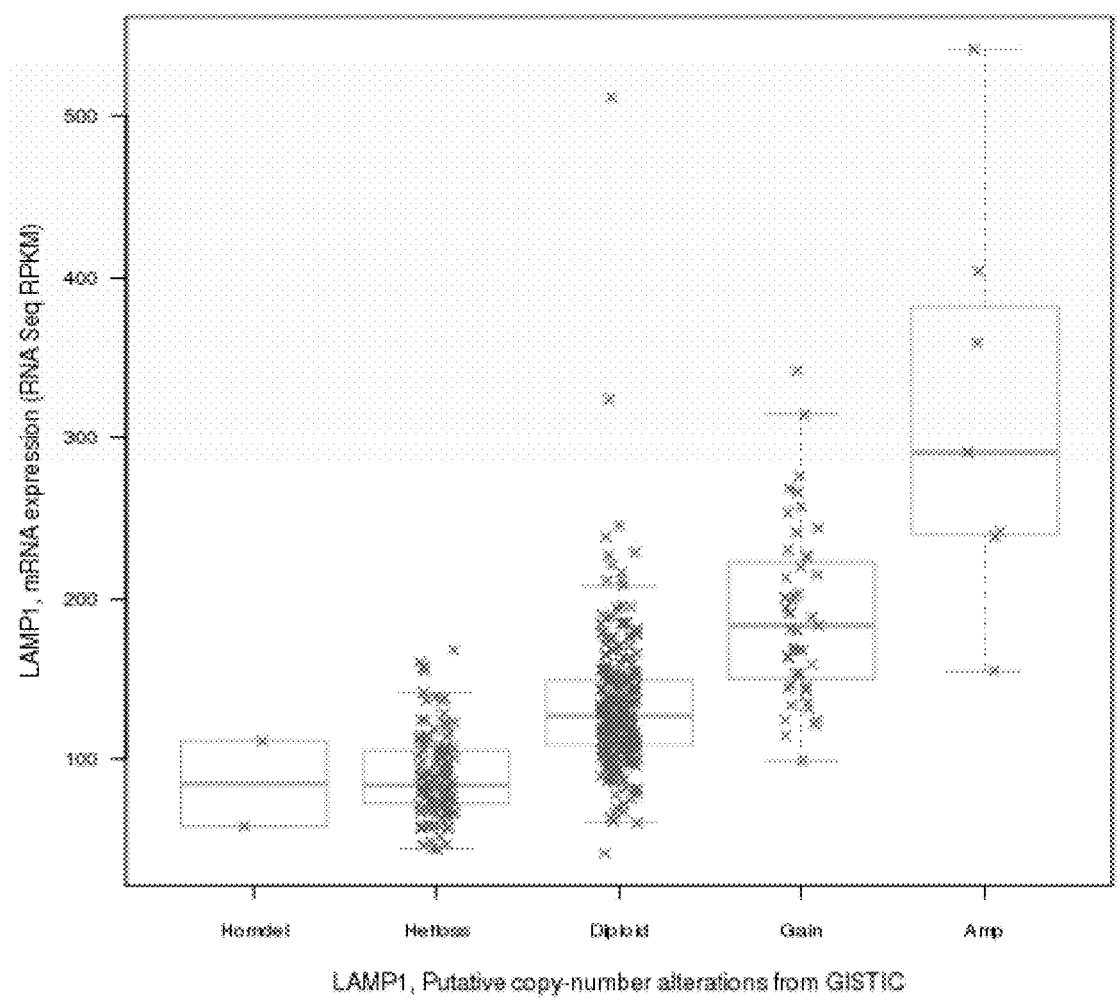
FIG. 10C: Box Plot of RNA Intensity expression and LAMP1 by Copy Number Change in Breast Invasive Carcinoma.

Following analyses of Copy number changes were performed using the TCGA (The Cancer Genome Atlas) data. Using a larger set of colorectal samples (n=574); the results are extremely similar with those obtained using internal data (CRC PDX). Colorectal and rectum human adenocarninoma analysis (the Cancer Genome Atlas) discloses 14.4% high amplification (HighAmp). Subsequent Copy Number Alteration analyses using TCGA data were performed to search other tumor types for which LAMP1 was amplified. In summary, LAMP1 DNA gene low-level gains (LowAmp; Log 2 Ratio=0.3<LowAmp<1.32) and high-gain (amplifications) (HighAmp, Log 2 Ratio≥1.32 (theoretically, overall 5.0 copies or more)) is detected in 28 tumor types, including Colorectal adenocarcionoma, Stomach, Liver, Lung (Adenocarcinoma and Squamous), Breast (Basal, BRCA, LUMA, LUMB and HER2), Ovary, Head & neck, Kidney (Kidney Chromophobe, Kidney Renal Clear Cell Carcinoma, Kidney Renal Papilliary Cell Carcinoma, Cervical squamous Cell, Pancreatic, Prostate, Bladder urothelial, Glioma (Low grade glyoma and Glioblastoma multiform), Uterus, Thyroid, Leukemia, Lymphoma, Esophageal, Melanoma and Soft tissue sarcoma, LAMP1 high gain or amplification data of 12 of these tumor types including colorectal adenocarcinoma, stomach, liver, lung, breast, ovary, head and neck, cervical squamous cell, glioblastoma, glioma, uterus, thyroid and soft tissue sarcoma are displayed in Table 43 and FIG. 10A.

TABLE 43

LAMP1 Genomic Alteration Summary: 18 TCGA tumor types

| % of HighAmp | Average <Log2> HighAmp | % of LowAmp | Average <Log2> LowAmp | Number of Cases | Tumor Type | Tumor |
|---|---|---|---|---|---|---|
| 0.000 | 0.000 | 16.071 | 0.688 | 56 | BLCA | Bladder Urothelial Carcinoma |
| 1.578 | 2.084 | 9.587 | 0.626 | 824 | BRCA | Breast Invasive Carcinoma |
| 1.471 | 1.347 | 10.294 | 0.504 | 68 | CESC | Cervical Squamous Cell |
| 14.460 | 1.892 | 41.463 | 0.714 | 574 | COADREAD | Colon and Rectum Adenocarcinoma |
| 0.536 | 4.495 | 1.964 | 0.642 | 560 | GBM | Glioblastoma |
| 0.694 | 4.058 | 11.111 | 0.526 | 288 | HNSC | Head and Neck Squamous Cell |
| 0.000 | 0.000 | 4.090 | 0.516 | 489 | KIRC | Kidney Renal Clear Cell |
| 0.000 | 0.000 | 13.333 | 0.673 | 75 | KIRP | Kidney Renal Papilliary Cell |
| 0.694 | 2.018 | 2.083 | 0.462 | 144 | LGG | Lower Grade Glioma |
| 1.754 | 3.268 | 15.789 | 0.620 | 57 | LIHC | Liver Hepatocellular carcinoma |
| 1.132 | 1.661 | 7.925 | 0.471 | 265 | LUAD | Lung adenocarcinoma |
| 1.418 | 4.565 | 6.383 | 0.581 | 282 | LUSC | Lung squamous cell |
| 1.792 | 2.061 | 15.950 | 0.601 | 558 | OV | Serous Ovarian |
| 0.000 | 0.000 | 7.143 | 0.329 | 14 | PAAD | Pancreatic adenocarinoma |
| 0.000 | 0.000 | 2.000 | 0.475 | 100 | PRAD | Prostate Adenocarcinoma |
| 2.273 | 1.430 | 23.485 | 0.517 | 132 | STAD | Stomach Adenocarcinoma |
| 0.000 | 0.000 | 0.877 | 0.450 | 228 | THCA | Thyroid adenocarcinoma |
| 0.234 | 2.780 | 7.009 | 0.659 | 428 | UCEC | Uterine Corpus Endometrioid Carcinoma |

Log2 = 1.32 ≤ HighAmp < ∞;
Log2 = 0.32 < LowAmp < 1.32

Genomic Definition of LAMP1 (13q34) Change (Gain/Amplification) on the PDXs

LAMP1 gene gain or amplification can be related to a focal somatic gain or amplification, a somatic large region gain or amplification on 13q, a somatic chromosome duplication, a somatic chromosome triplication or polyploidy.

In colon tumor PDX, the LAMP1 DNA gain or amplification is included in a larger amplicon involving: CUL4A, LAMP1, TFDP1, and GAS6. As show in the Table 44, for the Colon cancer PDX, the mean size segments are 8489.5 kb and 49292.7 kb for Amplification and gain, respectively. The minimum region involves 454 kb, which starts at base 113319683, ends at base 115107245 and contains others genes than LAMP1: ADPRHL1, CUL4A, DCUNID2, GRTP1, LOC100130463, PC1D2, PRO7, TFDP1, TMCO3 and F10. Most of DNA gain or amplification contains at least the genes: ADPRHL1, ATP11A, ATP4B, CUL4A, DCUNID2, F10, F7, FAM70B, FLJ41484, FLJ44054, GAS6, GRK1, GRTP1, LAMP1, LINC00552, LOC100128430, LOC100130463, LOC100506063, LOC100506394, MCF2L, MCF2L-AS1, PC1D2, PROZ, RASA3, TFDP1 and TMCO3C13orf35. The largest gain region covers 95.8 Mb (19,296,544-115,107,245).

TABLE 44

Description analysis of LAMP1 Copy number analysis of studied groups (LAMP1 Amplification, Gain, Diploid and Heteroloss (Complete or partial loss of one allele of LAMP1 gene) on Colon cancer PDX. Descriptive statistics for parameter Segment (size in kb)

| Status | N | Mean | Standard Deviation |
|---|---|---|---|
| Hetloss | 1 | 41152 | . |
| Diploid | 19 | 65768.5 | 31068.78 |
| Gain | 35 | 49292.7 | 37513.6 |
| Amplification | 6 | 8489.5 | 13016.03 |

In Lung Tumors PDX (Table 45), the mean of size segments is 14966.4 kb for gain. The minimum region covers 1186 kb.

TABLE 45

Description analysis of LAMP1 Copy number analysis of studied groups (LAMP1 Amplification, Gain, Diploid, Deletion and Heteroloss (Complete or partial loss of one allele of LAMP1 gene) on Lung cancer PDX.
Descriptive statistics for parameter Segment (size in kb)

| Status | N | Mean | Standard Deviation |
|---|---|---|---|
| Deletion | 1 | 1460 | . |
| Hetloss | 7 | 44592.4 | 39478.32 |
| Diploid | 17 | 26744.9 | 37016.96 |
| Gain | 9 | 14966.4 | 31033.29 |
| Amplification | 1 | 4874 | . |

Genomic Definition of LAMP1 (13q34) Gain on Esophageal Human Tumor Cancer

In the Esophageal cancer DNA samples (Asterand), the LAMP1 gain or amplification is also including in a large amplicon, the largest gain region involves 4523 kb (110584050-115107245) and the smallest region present a LAMP1 amplification (Chr13q34) equal to 39.81 copy number. This focal amplification of LAMP1 covers 378 kb and includes 10 genes: ADPRHL1, CUL4A, F10, F7, GRTP1, LAMP1, LOC100130463, PCID2, PROZ and MCF2L.

TABLE 46

Description analysis of LAMP1 Copy number analysis of studied groups (LAMP1 Amplification, Gain, Diploid and Heteroloss (Complete or partial loss of one allele of LAMP1 gene) on Eosophagus cancer tissues.
Descriptive statistics for parameter Segment (size in kb)

| Status | N | Mean | Standard Deviation |
|---|---|---|---|
| Loss | 5 | 70415 | 29317.91 |
| NoChange | 39 | 48109.4 | 37656.46 |
| Gain | 1 | 4523 | . |
| Amplification | 1 | 378 | . |

Example 15: Relation Between LAMP1 Gene Copy Number and mRNA Gene Expression

Figure 8A:
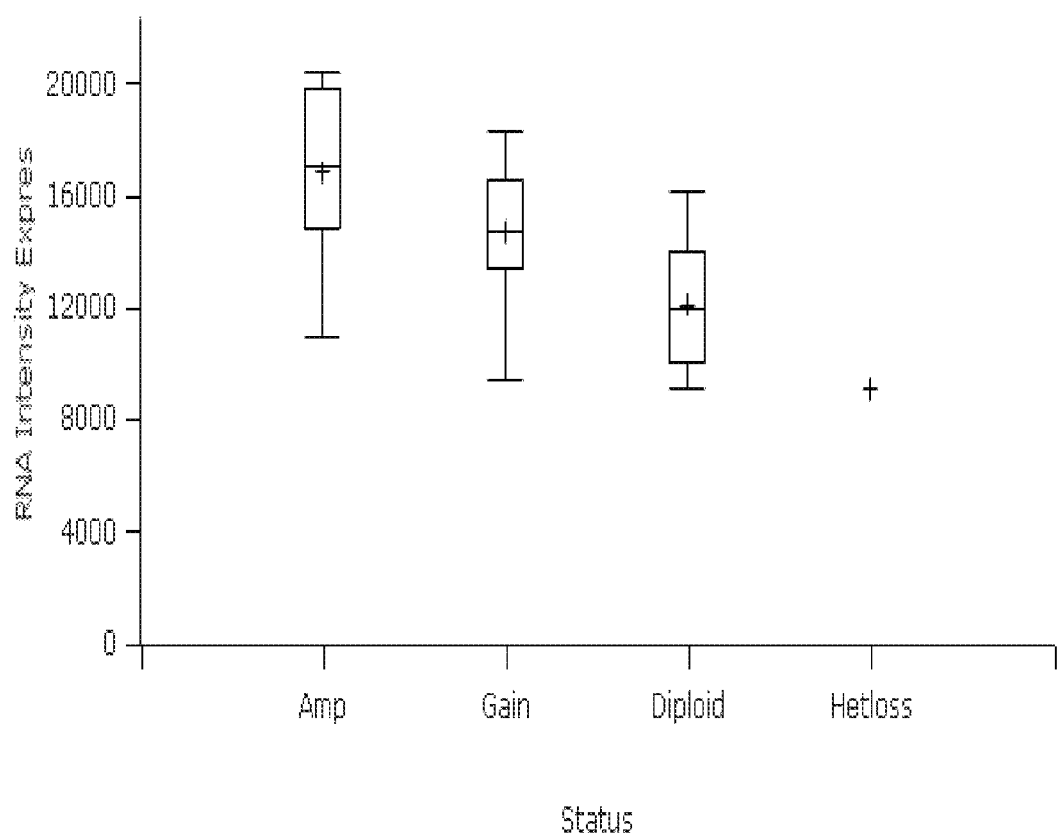
FIG. 8A: Box Plot of RNA Intensity expression of LAMP1 by Copy Number Changer category.
Figure 8B:
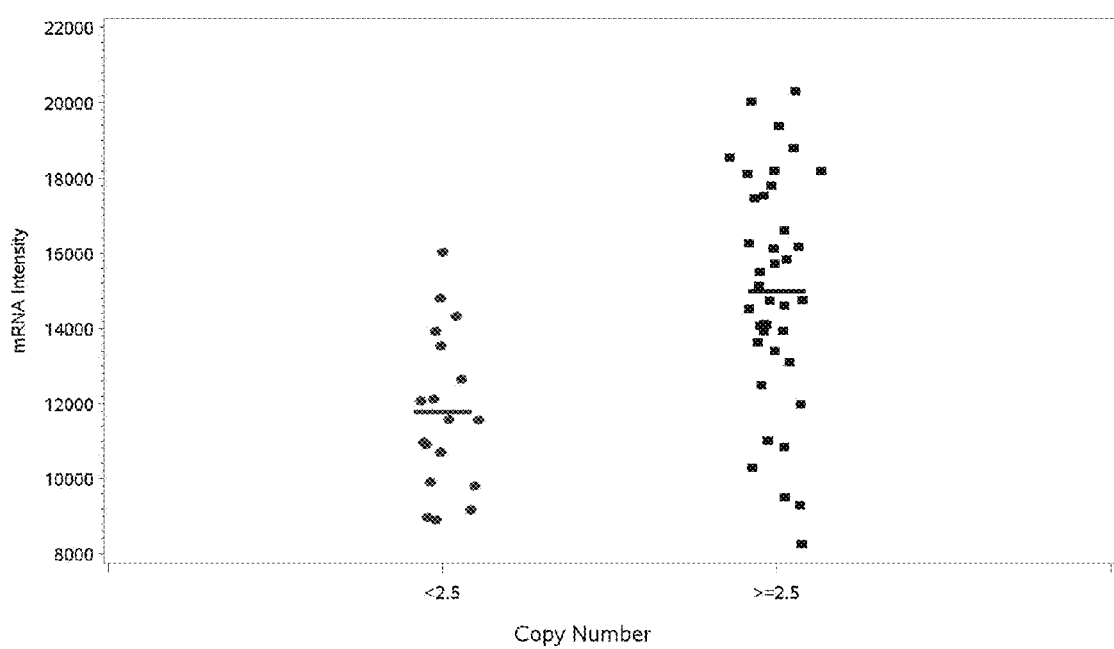
FIG. 8B: Plot of LAMP1 Copy Number according to LAMP1 mRNA expression on colon tumors. Points represent individual mRNA expression, bars corresponds to mean values.

Analyses of the mRNA Expression Level by Gene Expression Profile and the Copy Number Change at LAMP1 Region In addition to the analysis of LAMP1 Copy Number Change (amplification and gain), using the CRC tumors PDX, the correlation between LAMP1 amplification was evaluated by CGH analysis and LAMP1 expression by using mRNA (Affymetrix technology). Results from the mRNA analysis, using Pearson correlation test (Table 47) indicated high correlation ((r)=0.59; p<0.0001) between LAMP1 Copy Numbers and LAMP1 mRNA expression levels (FIG. 8A). For the Colon tumors PDX, a Student test is performed to compare LAMP1 gene copy number (with or without gain/amplification) and LAMP1 mRNA expression. mRNA expression analysis was performed using Affymetrix technology (Table 48 and FIG. 8B).

TABLE 47

LAMP1: Copy Number Alteration Data and correlation with mRNA data on CRC PDX

| Tumor Type | Total of models | Number of Gain cases | Number of gain cases >4.5 | Number of diploid | Number of Hetloss | Corr with mRNA (r) | P values |
|---|---|---|---|---|---|---|---|
| CRC PDX | 58 | 45161.2 +/− 6987.02(Kb) (n = 29) (50%) | 30710.7 +/− 11123.32 (Kb) (n = 9) (~15.5%) | 66942.5 +/− 6795.47 (Kb) (n = 19) (~33%) | 91670 +/− (n = 1) (<1%) | 0.59 | <0.0001 |

TABLE 48

Student t-test of mRNA expression for factor copy number
Student t-test for factor Copy Number

| | Mean +/− SEM | | | t | |
|---|---|---|---|---|---|
| Parameter | <2.5 | ≥2.5 | DF | value | p |
| RNA Intensity | 11785.30 +/− 496.501 (n = 18) | 14987.09 +/− 486.708 (n = 39) | 55 | −4.04 | p = 0.0002 |

If p < 0.05, the factor has significant influence on parameter

The mRNA expression is significantly higher for LAMP1 Copy Numbers change (CN≥2.5).

The correlation analysis, using Pearson test between LAMP1 amplification by CGH analysis and LAMP1 expression by using mRNA, shows a significantly correlation between these two parameter studied.

As shown in FIG. 8a, the group with LAMP1 high amplification (Amp) shows higher mRNA expression levels than groups with LAMP1 low amplification (Gain), Diploid and Hetloss.

The correlation analysis using a larger set of colorectal patients tissues samples (n=574) from the TCGA (The Cancer Genome Atlas) data, disclosed 14.4% amplification that correlates with mRNA expression ((r)=0.57; p<0.0001), this result is extremely similar with that observed on the CRC PDX.

Figure 9:
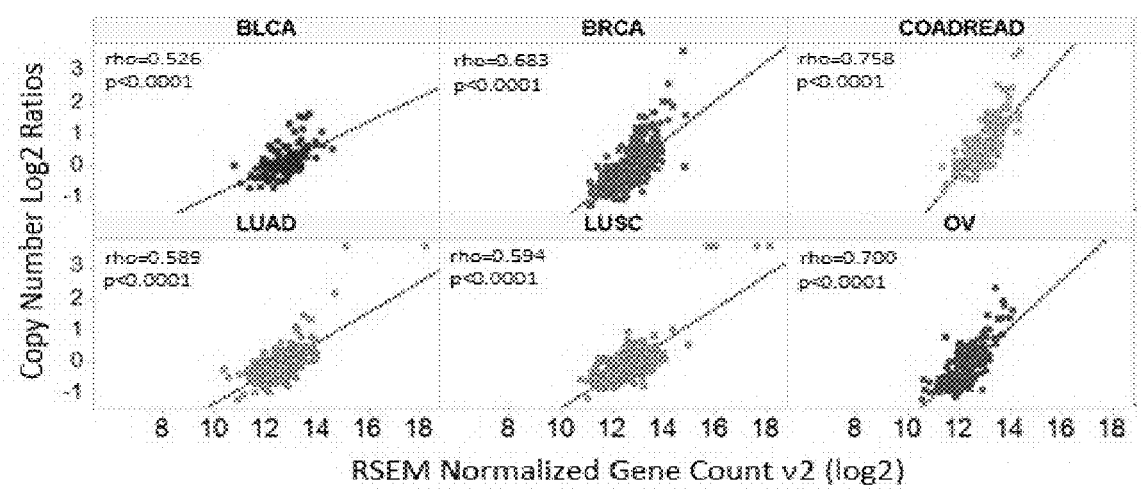
FIG. 9: A Sperman Correlation analysis of LAMP1 mRNA and Copy Number Change data.

Moreover, using the same dataset, a significant correlation of LAMP1 copy number change and mRNA expression level was evidenced for: Bladder Urothelial Carcinoma (BLCA), Breast Invasive Carcinoma (BRCA), Lung adenocarcinoma (LUAD), Lung squamous cell (LUSC) and Ovary (OV) (FIG. 9).

Example 16: LAMP1 Copy Number Variation and its Impact on the LAMP1 Protein Cell Membrane Expression Level Association of LAMP1 Copy Number Change and the Protein Cell Membrane Expression Level Detected by Immunohistochemistry (IHC).

In addition to the analysis of LAMP1 gain and its relation with the LAMP1 RNA expression, we also evaluated association of LAMP1 copy number change (gain or amplification) to cell membrane LAMP1 protein localization, using IHC expression scoring (strong, medium, faint and negative) with antibody mAb1 for colon, lung and stomach tumor PDXs.

Figure 11A:
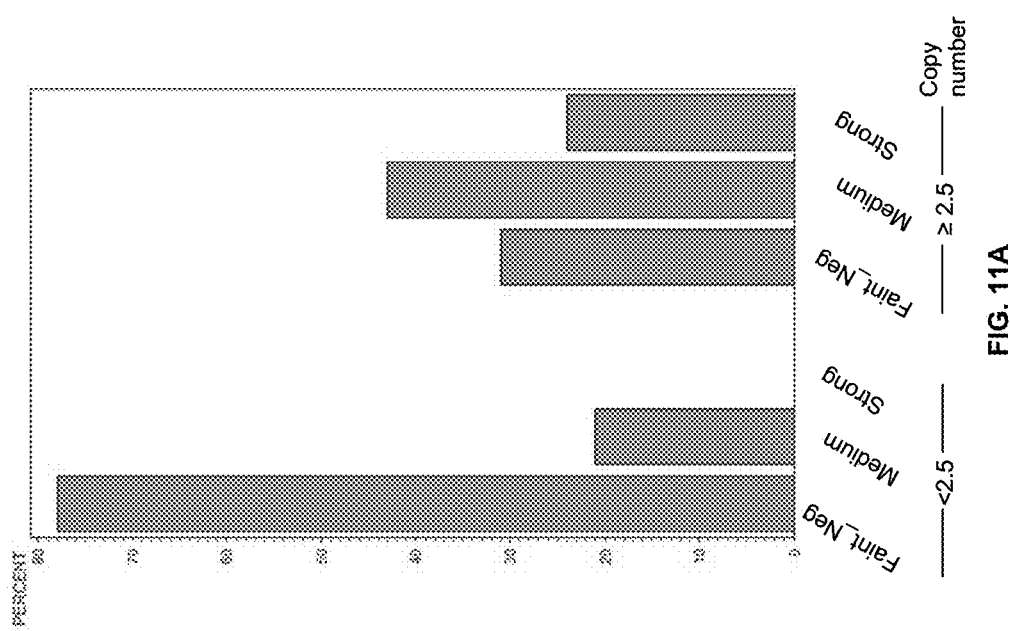
FIG. 11A: Histogram of LAMP1 Copy number by LAMP1 membrane expression (IHC category scoring) for colon tumor PDX.
Figure 11B:
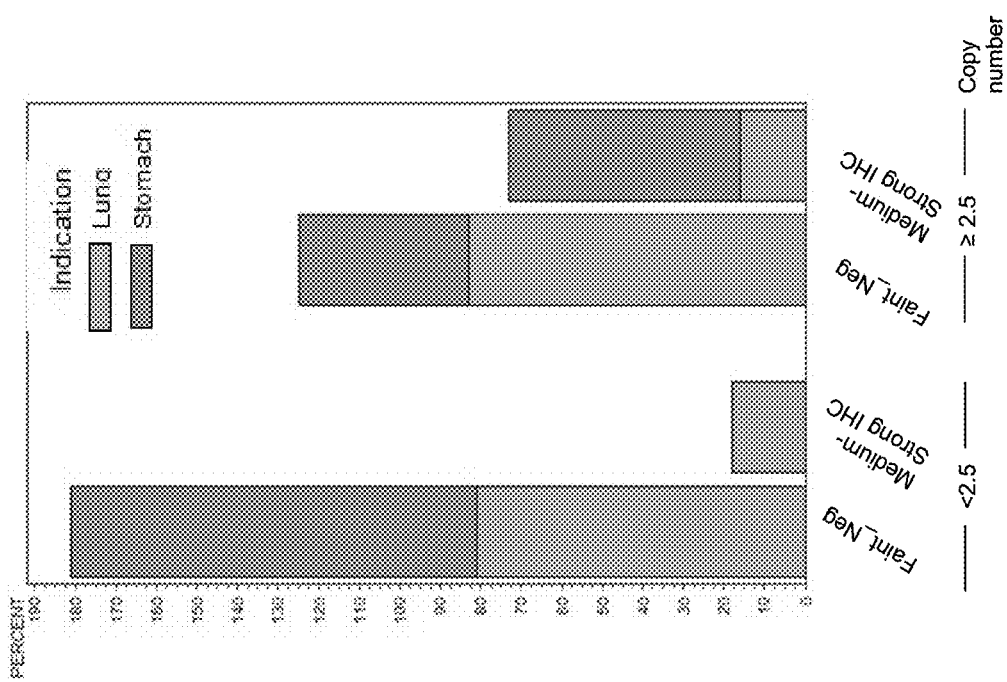
FIG. 11B: Histogram of LAMP1 Copy number by LAMP1 membrane expression (IHC category scoring) for lung and stomach tumor PDXs.

As shown in tables 49 and 50 below, and FIG. 11, analysis of IHC cell membrane expression in colon, lung and stomach PDXs samples shows that LAMP1 protein is expressed in the membrane cells in 39 out of 95 PDXs (41.1%) models studied; 33 of these PDXs samples positive for LAMP1 membrane expression (33 out of 39; 85%) present also LAMP1 gain or amplification, most of these are Colon PDX.

TABLE 49

Frequency of LAMP1 Copy Number data and IHC scoring data of colon tumor PDX

| Copy Number Frequency | Neg_Faint | IHC Medium | Strong | Total |
|---|---|---|---|---|
| <2.5 | 15 | 4 | 0 | 19 |
| ≥2.5 | 13 | 18 | 10 | 41 |
| Total | 28 | 22 | 10 | 60 |

TABLE 50

Frequency of LAMP1 Copy number data and IHC scoring data of lung and stomach tumor PDXs

| Copy Number Frequency | Tumor Type | Neg_Faint | IHC Medium_Strong | Total |
|---|---|---|---|---|
| <2.5 | Lung | 9 | 2 | 11 |
|  | Stomach | 11 | 0 | 11 |

TABLE 50-continued

Frequency of LAMP1 Copy number data and IHC scoring data of lung and stomach tumor PDXs

| Copy Number Frequency | Tumor Type | Neg_Faint | IHC Medium_Strong | Total |
|---|---|---|---|---|
| ≥2.5 | Lung | 5 | 1 | 6 |
|  | Stomach | 3 | 4 | 7 |

The association between IHC membrane expression and the copy number change was studied using Cochran-Mantel-Haenszel statistics (Tables 51 and 52).

TABLE 51

Cochran-Mantel-Haenszel statistics of LAMP1 IHC membrane expression by the Copy Number of LAMP1 in the Colon PDX tumor samples.
Cochran-Mantel-Haenszel Statistics (Based on Rank Scores)

| Alternative Hypothesis | DF | Value | Prob |
|---|---|---|---|
| Nonzero Correlation | 1 | 12.4418 | 0.0004 |

In Colon tumor PDX, the association between LAMP1 IHC membrane expression and Copy Number of LAMP1 is significant.

TABLE 52

Cochran-Mantel-Haenszel statistics of LAMP1 IHC membrane expression by the Copy Number of LAMP1 in Lung and Stomach PDX tumor samples.
Cochran-Mantel-Haenszel Statistics (Based on Rank Scores)

| Alternative Hypothesis | DF | Value | Prob |
|---|---|---|---|
| Nonzero Correlation | 1 | 4.5416 | 0.0331 |

After adjusting for tumor type, the association between LAMP1 IHC membrane expression and Copy Number of LAMP1 is significant.

We conclude that the level of LAMP1 cell surface localization (Strong and medium) is associated with copy number change on tumor PDX samples. Most of cell surface localization of LAMP1 appears to be a consequence of LAMP1 gain or amplification.

TABLE 53

Table summarizing LAMP1 gene gain and LAMP1 expression

| Sample Name | Indication | Status | Class | Segment (size in kb) | Log2 ratio (Mean) | Copynumber | IHC_Score | IHC_Level2 | Membrane-Expression |
|---|---|---|---|---|---|---|---|---|---|
| LUN-NIC-0070 | Lung | Amplification | Gain | 4874 | 2.21 | 9.26 | ** | Medium | Yes |
| CR-LRB-0010-P | Colon | Amplification | Gain | 1029 | 2.15 | 8.88 | *** | Strong | Yes |
| CR-LRB-0011-M | Colon | Amplification | Gain | 34252 | 1.78 | 6.85 | *** | Strong | Yes |
| IMM-COLO-0010 | Colon | Amplification | Gain | 454 | 1.75 | 6.73 | ** | Medium | Yes |
| CR-IGR-0002-C | Colon | Amplification | Gain | 4451 | 1.62 | 6.14 | ** | Medium | Yes |
| CR-IC-0029-P | Colon | Amplification | Gain | 9080 | 1.58 | 5.99 | *** | Strong | Yes |
| IMM-COLO-0020 | Colon | Amplification | Gain | 1671 | 1.41 | 5.32 | neg | neg | No |
| CR-IC-0028-M | Colon | Gain | Gain | 95810 | 1.27 | 4.84 | ** | Medium | Yes |
| CR-LRB-0017-P | Colon | Gain | Gain | 56497 | 1.27 | 4.83 | neg | neg | No |
| CR-IGR-0025-P | Colon | Gain | Gain | 14032 | 1.27 | 4.82 | ** | Medium | Yes |
| CR-IGR-0002-P | Colon | Gain | Gain | 59574 | 1.23 | 4.69 | ** | Medium | Yes |
| GAS0232 | Stomach | Gain | Gain | 1787 | 1.19 | 4.57096889 | *** | Strong | Yes |
| CR-IGR-0052-M | Colon | Gain | Gain | 17965 | 1.16 | 4.47 | ** | Medium | Yes |
| IMM-COLO-0006 | Colon | Gain | Gain | 95810 | 1.04 | 4.12 | ** | Medium | Yes |
| CR-IC-0010-P | Colon | Gain | Gain | 92308 | 1.04 | 4.11 | neg | neg | No |
| CR-IGR-0007-P | Colon | Gain | Gain | 85070 | 0.99 | 3.97 | *** | Strong | Yes |
| CR-IGR-0047-P | Colon | Gain | Gain | 45330 | 0.97 | 3.91 | ** | Medium | Yes |
| CR-LRB-0013-P | Colon | Gain | Gain | 1575 | 0.89 | 3.71 | ** | Medium | Yes |
| LUN-NIC-0004 | Lung | Gain | Gain | 4305 | 0.89 | 3.7 | neg | neg | No |

TABLE 53-continued

Table summarizing LAMP1 gene gain and LAMP1 expression

| Sample Name | Indication | Status | Class | Segment (size in kb) | Log2 ratio (Mean) | Copynumber | IHC_Score | IHC_Level2 | Membrane-Expression |
|---|---|---|---|---|---|---|---|---|---|
| CR-IGR-0014-P | Colon | Gain | Gain | 95810 | 0.89 | 3.7 | * | Faint | No |
| CR-IGR-0016-P | Colon | Gain | Gain | 20181 | 0.82 | 3.54 | ** | Medium | Yes |
| CR-LRB-0019-C | Colon | Gain | Gain | 941 | 0.8 | 3.49 | *** | Strong | Yes |
| LUN-NIC-0040 | Lung | Gain | Gain | 5329 | 0.79 | 3.46 | neg | neg | No |
| LUN-NIC-0047 | Lung | Gain | Gain | 1560 | 0.77 | 3.42 | neg | neg | No |
| CR-IC-0007-M | Colon | Gain | Gain | 25657 | 0.76 | 3.39 | * | Faint | No |
| CR-IC-0006-M | Colon | Gain | Gain | 4915 | 0.74 | 3.33 | neg | neg | No |
| CR-IC-0008-P | Colon | Gain | Gain | 19106 | 0.71 | 3.27 | ** | Medium | Yes |
| CR-IGR-0048-M | Colon | Gain | Gain | 95810 | 0.71 | 3.26 | * | Faint | No |
| CR-LRB-0014-P | Colon | Gain | Gain | 16868 | 0.69 | 3.22 | ** | Medium | Yes |
| SA-STO-0073 | Stomach | Gain | Gain | 3160 | 0.67 | 3.19 | *** | Strong | Yes |
| CR-IGR-0008-P | Colon | Gain | Gain | 523 | 0.64 | 3.12 | neg | neg | No |
| GAS0081 | Stomach | Gain | Gain | 209 | 0.63 | 3.100283186 | neg | neg | No |
| SA-STO-0043 | Stomach | Gain | Gain | 1984 | 0.61 | 3.05 | ** | Medium | Yes |
| CR-IGR-0009-P | Colon | Gain | Gain | 73073 | 0.59 | 3 | *** | Strong | Yes |
| CR-IGR-0038-C | Colon | Gain | Gain | 14246 | 0.58 | 2.99 | ** | Medium | Yes |
| CR-LRB-0009-C | Colon | Gain | Gain | 54677 | 0.55 | 2.93 | ** | Medium | Yes |
| GAS0080 | Stomach | Gain | Gain | 1773 | 0.546 | 2.920671295 | ** | Medium | Yes |
| CR-IGR-0023-M | Colon | Gain | Gain | 95810 | 0.54 | 2.91 | * | Faint | No |
| IMM-COLO-0004 | Colon | Gain | Gain | 95810 | 0.47 | 2.78 | *** | Strong | Yes |
| GAS0832 | Stomach | Gain | Gain | 57217 | 0.47 | 2.767915691 | neg | neg | No |
| CR-IC-0005-P | Colon | Gain | Gain | 95810 | 0.47 | 2.76 | *** | Strong | Yes |
| LUN-NIC-0002 | Lung | Gain | Gain | 1590 | 0.45 | 2.73 | neg | neg | No |
| IMM-COLO-0023 | Colon | Gain | Gain | 10757 | 0.45 | 2.72 | *** | Strong | Yes |
| CR-IC-0020-P | Colon | Gain | Gain | 4364 | 0.44 | 2.71 | ** | Medium | Yes |
| CR-IC-0019-P | Colon | Gain | Gain | 95810 | 0.44 | 2.71 | * | Faint | No |
| CR-IC-0013-M | Colon | Gain | Gain | 39036 | 0.43 | 2.69 | ** | Medium | Yes |
| GAS0819 | Stomach | Gain | Gain | 1994 | 0.41 | 2.665858119 | neg | neg | No |
| CR-IGR-0011-C | Colon | Gain | Gain | 45835 | 0.38 | 2.6 | ** | Medium | Yes |
| CR-IC-0009-M | Colon | Gain | Gain | 45566 | 0.38 | 2.6 | *** | Strong | Yes |
| CR-LRB-0022-P | Colon | Gain | Gain | 4874 | 0.37 | 2.59 | * | Faint | No |
| CR-IGR-0034-P | Colon | Gain | Gain | 16139 | 0.36 | 2.56 | ** | Medium | Yes |
| LUN-NIC-0051 | Lung | Gain | Gain | 95810 | 0.33 | 2.51 | neg | neg | No |
| CR-LRB-0007-P | Colon | Gain | Gain | 94994 | 0.32 | 2.5 | * | Faint | No |
| CR-IC-0016-M | Colon | Gain | Gain | 94661 | 0.32 | 2.5 | * | Faint | No |
| CR-IC-0032-P | Colon | NoChange | NoGain | 41073 | 0.3 | 2.47 | * | Faint | No |
| LUN-NIC-0011 | Lung | NoChange | NoGain | 1560 | 0.3 | 2.46 | neg | neg | No |
| CR-IC-0025-M | Colon | NoChange | NoGain | 57313 | 0.3 | 2.46 | ** | Medium | Yes |
| CR-IC-0002-P | Colon | NoChange | NoGain | 86532 | 0.29 | 2.44 | ** | Medium | Yes |
| LUN-NIC-0006 | Lung | NoChange | NoGain | 1587 | 0.28 | 2.42 | ** | Medium | Yes |
| CR-IC-0021-M | Colon | NoChange | NoGain | 57313 | 0.23 | 2.35 | * | Faint | No |
| LUN-NIC-0034 | Lung | NoChange | NoGain | 5334 | 0.22 | 2.33 | neg | neg | No |
| LUN-NIC-0041 | Lung | NoChange | NoGain | 1753 | 0.2 | 2.29 | neg | neg | No |
| GAS0773 | Stomach | NoChange | NoGain | 46737 | 0.17 | 2.25 | neg | neg | No |
| CR-IC-0003-P | Colon | NoChange | NoGain | 95810 | 0.16 | 2.24 | * | Faint | No |
| CR-IC-0004-M | Colon | NoChange | NoGain | 14209 | 0.14 | 2.2 | * | Faint | No |
| CR-IGR-0032-P | Colon | NoChange | NoGain | 95810 | 0.1 | 2.15 | * | Faint | No |
| SA-STO-0014 | Stomach | NoChange | NoGain | 7816 | 0.1 | 2.14 | neg | neg | No |
| GAS0720 | Stomach | NoChange | NoGain | 4061 | 0.099 | 2.14 | neg | neg | No |
| CR-IGR-0029-P | Colon | NoChange | NoGain | 57313 | 0.07 | 2.11 | neg | neg | No |
| IMM-COLO-0018 | Colon | NoChange | NoGain | 4936 | 0.06 | 2.09 | neg | neg | No |
| IMM-COLO-0008 | Colon | NoChange | NoGain | 95810 | 0.04 | 2.05 | * | Faint | No |
| IMM-COLO-0001 | Colon | NoChange | NoGain | 95810 | 0.03 | 2.05 | neg | neg | No |
| LUN-NIC-0060 | Lung | NoChange | NoGain | 33461 | 0.02 | 2.03 | neg | neg | No |
| GAS0517 | Stomach | NoChange | NoGain | 1739 | 0.001 | 2.001 | neg | neg | No |
| STO-IND-0006 | Stomach | NoChange | NoGain | 95810 | 0 | 2 | neg | neg | No |
| SA-STO-0039 | Stomach | NoChange | NoGain | 14361 | 0 | 2 | neg | neg | No |
| CR-LRB-0018-P | Colon | NoChange | NoGain | 62941 | −0.02 | 1.97 | neg | neg | No |
| CR-LRB-0003-P | Colon | NoChange | NoGain | 57313 | −0.02 | 1.97 | ** | Medium | Yes |
| SA-STO-0024 | Stomach | NoChange | NoGain | 7831 | −0.03 | 1.96 | neg | neg | No |
| CR-LRB-0004-P | Colon | NoChange | NoGain | 57313 | −0.03 | 1.96 | ** | Medium | Yes |
| CR-IGR-0012-P | Colon | NoChange | NoGain | 78930 | −0.03 | 1.96 | * | Faint | No |
| IMM-COLO-0009 | Colon | NoChange | NoGain | 95810 | −0.04 | 1.95 | * | Faint | No |
| CR-IC-0022-P | Colon | NoChange | NoGain | 7897 | −0.08 | 1.89 | * | Faint | No |
| GAS0928 | Stomach | NoChange | NoGain | 95810 | −0.107 | 1.86 | neg | neg | No |
| LUN-NIC-0001 | Lung | NoChange | NoGain | 1567 | −0.19 | 1.75 | neg | neg | No |
| GAS0680 | Stomach | NoChange | NoGain | 1217 | −0.31 | 1.61 | neg | neg | No |
| LUN-NIC-0007 | Lung | NoChange | NoGain | 1481 | −0.32 | 1.6 | neg | neg | No |
| CR-IGR-0003-P | Colon | NoChange | NoGain | 91670 | −0.34 | 1.58 | * | Faint | No |
| LUN-NIC-0066 | Lung | Loss | NoGain | 20716 | −0.53 | 1.38 | neg | neg | No |

TABLE 53-continued

Table summarizing LAMP1 gene gain and LAMP1 expression

| Sample Name | Indication | Status | Class | Segment (size in kb) | Log2 ratio (Mean) | Copynumber | IHC_Score | IHC_Level2 | Membrane-Expression |
|---|---|---|---|---|---|---|---|---|---|
| GAS0248 | Stomach | Loss | NoGain | 57313 | −0.5852 | 1.333113855 | neg | neg | No |
| LUN-NIC-0081 | Lung | Loss | NoGain | 52860 | −0.59 | 1.33 | neg | neg | No |
| CR-IGR-0043-P | Colon | Loss | NoGain | 41152 | −0.83 | 1.12 | neg | neg | No |
| LUN-NIC-0030 | Lung | Loss | NoGain | 95810 | −0.85 | 1.11 | ** | Medium | Yes |
| GAS0707 | Stomach | Loss | NoGain | 3462 | −0.9479 | 1.036772962 | neg | neg | No |
| LUN-NIC-0033 | Lung | Deletion | NoGain | 1460 | −1.16 | 0.89 | neg | neg | No |

Example 17:—Specific Peptide and mAb to Detect LAMP1 Membrane Reinforcement on FFPE Tumor Tissue by Immunohistochemistry (IHC)

IHC analysis of tumor tissues from biobanks or from hospitals before or during patient treatment is routinely done with formalin-fixed paraffin-embedded (FFPE) samples. Although commercially available mAbs and the three mAbs described previously (MAb1, MAb2 and MAb3) can allow intracellular detection of LAMP1 and some of them, including MAb1, 2 and 3, LAMP1 membrane reinforcement in frozen-OCT and AFA (Alcohol Formalin Acetic acid Fixative) sample format, none can lead to the detection of LAMP1 reinforcement in FFPE format. One of the reasons is probably the effect of the formalin fixative combined to the complexity of the protein. Samples processed in frozen OCT or AFA are not routinely prepared in hospitals. Therefore, there is a need to have a mAb that would allow complete and fast coverage of the FFPE tumor biobanks and hospital samples.

It is shown in the examples below that it was possible to overcome the difficulties by identifying a peptide (peptide 4) located in the second luminal domain at positions 360 to 375 of SEQ ID NO: 24, and having the amino acid sequence of SEQ ID NO: 82. Said peptide permitted the obtention of rabbit polyclonal antibodies and mouse monoclonal antibody that led to the detection of LAMP1 membrane reinforcement in FFPE tissues.

TABLE 54

List of antiLAMP1 mAb tested and showing no LAMP1 membrane reinforcement on FFPE tissues by IHC

| | Species | clone number |
|---|---|---|
| MAbs obtained from the following supplier | | |
| Epitomics | Rabbit | ERP4204 |
| Novus Biologicals | Mouse | B-T47 |
| Biolegend | Mouse | H4A3 |
| United States Biol | Mouse | 5K76 |
| Santa Cruz | Mouse | E-5 |
| Santa Cruz | Mouse | H5G11 |
| Biorbyt | Mouse | monoclonal |
| Biorbyt | Rabbit | monoclonal |
| MAbs described in this application | | |
| MAb1 | Mouse | monoclonal |
| MAb2 | Mouse | monoclonal |
| MAb3 | Mouse | monoclonal |

Example 17.1: Production of Rabbit Polyclonal Antibodies that LED to LAMP1 Membrane Reinforcement on FFPE Tumor Tissues This example describes the selection of peptides in the human LAMP1 luminal domains, the generation of polyclonal antibodies and the IHC screening. It demonstrates the feasibility to obtain polyclonal antibodies that allow the detection of LAMP1 membrane reinforcement on formalin-fixed paraffin-embedded tissues when using the specific peptide ("peptide 4") of SEQ ID NO:82 corresponding to the amino acids at positions 360 to 375 on the human LAMP1 sequence of SEQ ID NO:24.

Example 17.1.1: Rabbit Immunisation with Peptides or Soluble LAMP1 Protein. Purification of Polyclonal Antibodies Peptide Preparation:

Peptides of 15-16 amino acids were selected within the two luminal domains without a N-glycosylation site and no internal cysteine. A total of four peptides were chemically synthesised and coupled to the Keyhole Limpet Hemocyanin (KLH) carrier protein. When needed, a terminal cysteine was previously added to the peptide so that coupling occurred via its thiol group to maleimide activated KLH protein.

TABLE 55

Description of the four selected peptides

| Localisation on human LAMP1 sequence of SEQ ID NO: 24 | Immunogen | SEQ ID |
|---|---|---|
| 47-61 | Peptide 1-KLH | SEQ ID NO: 90 |
| 140-155 | Peptide 2-KLH | SEQ ID NO: 91 |
| 307-321 | Peptide 3-KLH | SEQ ID NO: 92 |
| 360-375 | Peptide 4-KLH | SEQ ID NO: 82 |

Immunisation and Obtention of Polyclonal Antibodies.

A total of three programs of rabbit immunisations were performed. Rabbits were immunized in the first program, with peptide 1 SEQ ID NO: 90 and peptide 2 of SEQ ID NO: 91, in the second program with peptide 4 of SEQ ID NO: 82 and peptide 3 of SEQ ID NO: 92 and in the third program with heated denatured human LAMP1::histag protein produced as described in example 6.2. In brief, the immunisation schedule comprised four injections and a final bleed after 28 days. Polyclonal response was determined by ELISA on a sample from the final bleeds.

Purifications of Polyclonal Antibodies.

Reactive AF-aminoTOYOPEARL was used to couple each peptide described on Table 55 and to generate four affinity chromatography columns. The serum final bleeds on rabbits immunized with the respective peptides were purified by peptide affinity chromatography. The purified polyclonal batches were then characterized by SDS-PAGE and ELISA.

The serum final bleed on the rabbit immunized with LAMP1 protein was purified by protein G affinity chromatography. The purified polyclonal batch was then characterized by SDS-PAGE.

Figure 38:
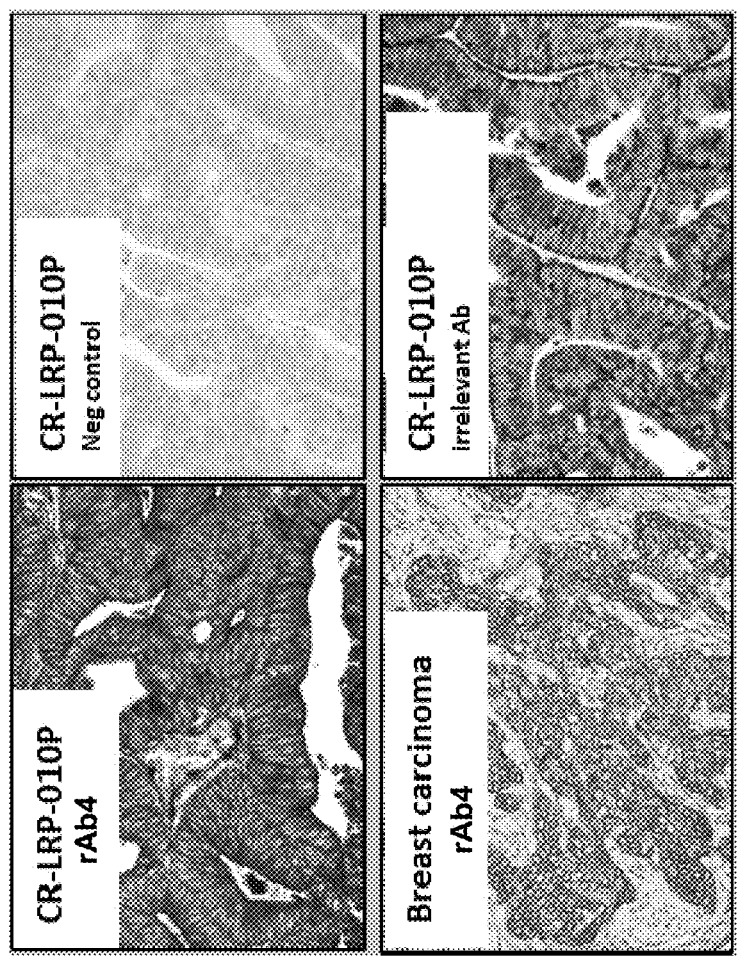
FIG. 38: Immunohistochemistry staining (IHC) on FFPE sample of colon adenocarcinoma patient derived xenograft CR-LRB-010P and human breast carcinoma with the polyclonal rabbit rAb4 Antibody. The Negative controls were performed by omission of the primary antibody. Furthermore, other irrelevant antibodies were negative or displayed intracellular immunostaining.

Example 17.1.2: IHC Screening and Identification of Polyclonal rAb4 (Rabbit Antibody 4) Obtained by Peptide 4 Immunization Rabbit polyclonal antibodies generated with peptides described in example 17.1.1 were tested by IHC on FFPE sample of colon adenocarcinoma patient derived xenograft CR-LRB-010P and human breast carcinoma. After antigen retrieval procedure and endogen biotins blocking steps, slides were incubated with the primary anti-antibody for 1 hour at 24° C. Negative controls were performed by omission of the primary antibody. The biotin free anti-rabbit UltraMap™ horseradish peroxidase (HRP) conjugate (760-4315, Ventana Medical Systems, Inc, USA) was used as secondary antibody system according to manufacturer's recommendations. Negative controls were performed by omission of the primary antibody. A couterstaining step was done with hematoxylin (760-2037, Ventana Medical Systems, Inc, USA) and bluing reagent was applied (760-2037, Ventana Medical Systems, Inc, USA). Stained slides were dehydrated and coverslipped with cytoseal XYL (8312-4, Richard-Allan Scientific, USA). Only antibodies from peptide 4 of SEQ ID NO: 82 immunization displayed LAMP1 membrane reinforcement in FFPE samples as shown in FIG. 38.

Example 17.1.3: Validation of Polyclonal Rabbit (rAb4) Batch

Figure 39:
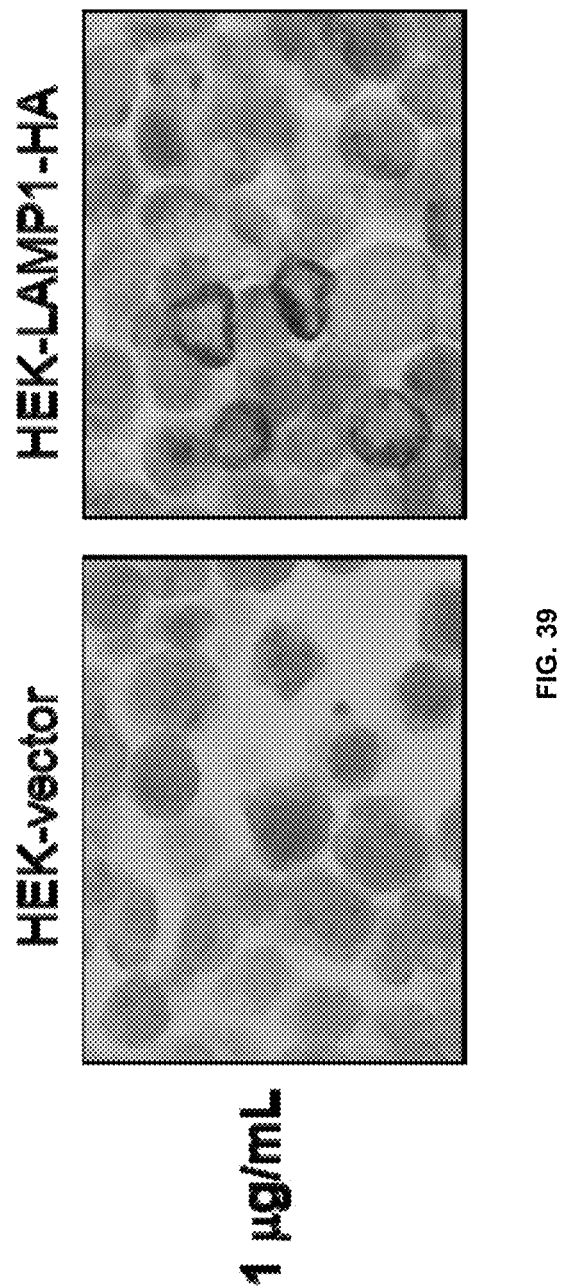
FIG. 39: Immunocytochemistry (ICC) in FFPE format with the polyclonal rabbit rAb4 Antibody at 1 µg/mL.

ICC with Cells Expressing or not LAMP1 at the Membrane
Human-LAMP1 and empty-vector HEK transfected cells were tested with the polyclonal rabbit rAb4 Antibody by immunocytochemistry (ICC) in FFPE format. High level of intracellular and surface cell LAMP1 immunostaining was obtained using the polyclonal rabbit rAb4 Antibody Ab at 1 µg/mL as shown in FIG. 39.
Affinity to LAMP1 Protein
Secreted LAMP1::histag (29-382) with SEQ ID NO: 28 described in example 6.2 was used to determine the affinity of the polyclonal antibodies poly rAb4 by ELISA as described in example 6.3. The polyclonal rabbit antibody poly rAb4 binds to LAMP1 with an $EC_{50}$ of around 3 nM whereas MAb1 binds with an $EC_{50}$ of 0.16 nM.

Example 17.2: Obtention and Characterization of Mouse Monoclonal Antibodies that LED to LAMP1 Membrane Reinforcement on FFPE Tumor Tissues

Example 17.2.1: Mouse Immunisation and Selection of Mature IgG LAMP1-Secreting Hybridoma While immunizations have been performed with diverse protein antigens including recombinant chimer human/mouse LAMP1 protein, recombinant denatured human LAMP1 protein or recombinant human LAMP1 protein, these approaches were not successful in identifying antibody able to detect LAMP1 membrane reinforcement on FFPE tumor tissues. These approaches used immunization protocol described in example 2 for generation of anti-LAMP1 monoclonal antibodies and LAMP1 proteins described in example 6.2. On the contrary, the peptide 4-based immunization strategy has been shown to identify an antibody eligible to detect LAMP1 membrane reinforcement on FFPE tumor tissues.

Therefore mouse were immunised with peptide 4 and anti-LAMP1-secreting hybridomas were selected as described below.
Generation of Anti-LAMP1 Monoclonal Antibodies
Five BALB/cJ mice, about 6-8 weeks old (Charles River) were immunized with 40 µg of peptide peptide 4 of SEQ ID NO: 82 using RIMMS approach as described by Kilpatrick et al.; hybridoma, 1997: volume 16, number4. B cells immortalization using P3X63-AG8.653 (ATCC, ref CRL-1580) as fusion partner and hybridoma selection was performed as described in example 2.
Selection of Anti-LAMP1 Antibodies by ELISA
The primary screen was an enzyme-linked immunosorbent assay (ELISA) assay (described in example 6.3 for anti-LAMP1 IgG production) using the LAMP1::histag protein described in example 6.2 as capturing antigen.

Example 17.2.2: IHC Screening and Identification of MAb4

As the same manner as in example 17.1.2, IHC screening was performed with the hybridoma supernatant to identify mouse monoclonal antibody showing LAMP1 membrane reinforcement on FFPE sample of colon adenocarcinoma patient derived xenograft CR-LRB-010P. The biotin free anti-mouse UltraMap™ horseradish peroxidase (HRP) conjugate (760-152, Ventana Medical Systems, Inc, USA) was used as secondary antibody system according to manufacturer's recommendations.

Figure 40:
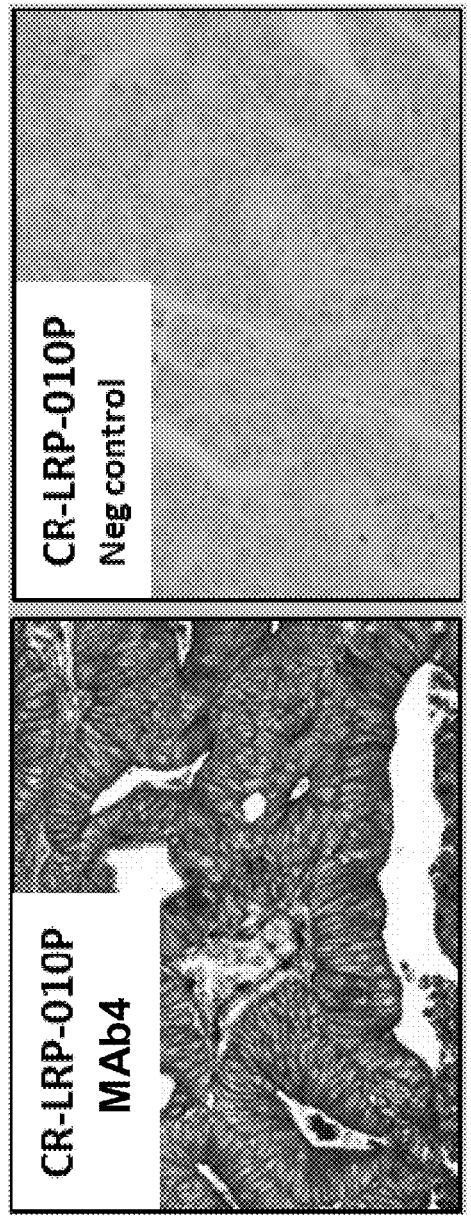
FIG. 40: Immunohistochemistry (IHC) on FFPE sample of adenocarcinoma patient derived xenograft CR-LRB-010P with MAb4 obtained from hybridoma 88LAMP1-2. The negative control was performed by omission of the primary antibody.

The supernatant of the selected hybridoma 88LAMP1-2 displayed membrane reinforcement immunostaining in FFPE sample of colon adenocarcinoma patient derived xenograft CR-LRB-010P. Other irrelevant antibodies were negative or displayed intracellular immunostaining as shown in FIG. 40.

Example 17.2.3: Validation of Hybridoma 88LAMP1-2

Purification and Characterisation of Mab4 Obtained from Hybridoma 88LAMP1-2
Hybridoma 88LAMP1-2 was produced in medium A Clonacell-Hy (StemCell Technologies #03801) supplemented with 5% HCS (PAA; #F05-009) at the 400 mL scale and purified by protein A affinity chromatography. The purified antibody MAb4 was characterized by SDS-PAGE, and Mass Spectrometry. Masses of heavy and light chains from MAb4 were identified as reported in example 7 and are reported on the Table 55 below. Nucleic acid sequences encoding the variable domains were retrieved from hybridoma cells by RT-PCR as described in example 7. The corresponding amino acids from the heavy and light chains led to masses in agreement with the respective masses from MAb4.

TABLE 56

Mass characterization of MAb4

| mAb4 | Isotype | Mass obtained by Mass Spectrometry | Mass calculated from amino acid sequence |
|---|---|---|---|
| Heavy chain | mIgG1 | (G0F) 50 169 Da | 50 168 Da |
| Light chain | mCk | 23651 Da | 23 650 Da |

Example 17.3: In Vitro Characterisation of MAb4

Example 17.3.1: Apparent Affinity to Human LAMP1 and Cynomolgus LAMP1 by ELISA Antibody MAb4 was assessed for its ability to bind primate LAMP1 protein by enzyme-linked immunosorbent assay (ELISA) assay as described in example 4.7 and EC50 values determined as described in example 6.2. Antibody MAb4 binds to human LAMP1 and cynomolgus LAMP1 with similar affinity in range of 0.2 to 0.4 nM as shown in Table 57 below.

TABLE 57

$EC_{50}$ determined by ELISA values on recombinant human LAMP1 and cynomolgus LAMP1

| LAMP1 protein | $EC_{50}$ |
|---|---|
| Human LAMP1 | 0.39 nM |
| cynomolgus LAMP1 | 0.22 nM |

Example 17.3.2: Specificity to LAMP1

Figure 41:
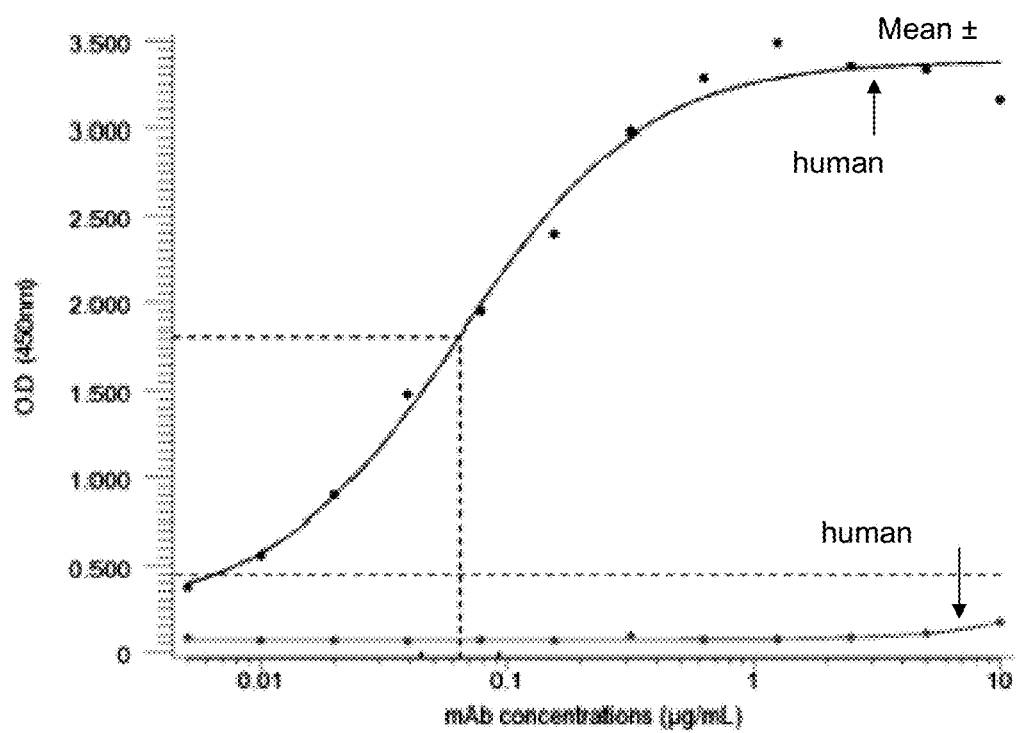
FIG. 41: Binding affinity by ELISA of MAb4 towards LAMP1 (black) or LAMP2 (grey).

LAMP2 is the closest member of the LAMP family with 35% sequence identity to LAMP1. Specificity of MAb4 was evaluated by ELISA as described in example 4.6 with either LAMP1 or LAMP2 soluble proteins, as shown in FIG. 41. No binding to LAMP2 was detected with MAb4 and a difference of more than 100 fold is observed between the $EC_{50}$ of MAb4 towards LAMP1 versus LAMP2.

Example 17.3.3: Binding of Antibody MAb4 to Multiple Cancer Cells and Determination of Antibody Binding Capacity by Flow Cytometry Antibody MAb4 was found to be able of binding to multiple tumor cells by Flow Cytometry using the conditions described in example 4.1. The panel of tumor cells comprises Patient-derived tumor xenografts from different origins and tumor cell lines. The Mean Fluorescence Intensity (MFI) obtained from the flow cytometry analysis is reported in Table 58. Table 59 summarizes the antibody binding capacity results.

TABLE 58

Mean Florescence Intensity by FACS on Patient-derived xenografts

| | Mean Florescence Intensity (MFI) |
|---|---|
| CR-IGR-034P/colorectal | 424 |
| LUN-NIC-006/lung | 162 |
| LUN-NIC-033/lung | 154 |
| BRE-IGR-0159/breast | 400 |
| Colo205/colon | 7 |

TABLE 59

Antibody Binding Capacity by FACS on Patient-derived xenograft

| | Antibody Binding Capacity (ABC) MAb4 |
|---|---|
| PDX/origin | |
| CR-IGR-034P/colorectal | 260 000 |
| LUN-NIC-006/lung | 92 000 |
| LUN-NIC-033/lung | 87 000 |
| Cell lines/origin | |
| Colo205/colon | 3000 |

Example 17.3.4: Apparent Affinity of Antibody MAb4 to Human Primary Colon Tumor PDX (CR-IGR-034P) by Flow Cytometry Apparent affinity of antibody MAb4 was evaluated to human primary colon tumor PDX CR-IGR-034P by Flow Cytometry using the conditions described in example 4.1. $EC_{50}$ obtained with CR-IGR-034P with MAb4 was 1.3 nM.

Example 17.3.5: IHC Validation

Results obtained with purified batch are similar to those obtained in example 17.2.2 with none purified MAb4.

The invention claimed is:
1. An immunoconjugate comprising a) an antibody or antigen binding fragment thereof wherein said antibody or antigen binding fragment thereof binds to a first lumenal domain of human LAMP1 protein and
   b) at least one growth inhibitory agent, wherein the at least one growth inhibitory agent is linked to the antibody or antigen binding fragment thereof.
2. The immunoconjugate according to claim 1, wherein the antibody or antigen binding fragment thereof comprises:
   (i) a CDR1-H having an amino acid sequence of SEQ ID NO: 2, a CDR2-H having an amino acid sequence of SEQ ID NO: 3, a CDR3-H having an amino acid sequence of SEQ ID NO: 4, a CDR1-L having an amino acid sequence of SEQ ID NO: 6, a CDR2-L having an amino acid sequence of DTS, and a CDR3-L having an amino acid sequence of SEQ ID NO: 7; or
   (ii) a CDR1-H having an amino acid sequence of SEQ ID NO: 9, a CDR2-H having an amino acid sequence of SEQ ID NO: 10, a CDR3-H having an amino acid sequence of SEQ ID NO: 11, a CDR1-L having an amino acid sequence of SEQ ID NO: 13, a CDR2-L having an amino acid sequence of AAS, and a CDR3-L having an amino acid sequence of SEQ ID NO: 14; or
   (iii) a CDR1-H having an amino acid sequence of SEQ ID NO: 43, a CDR2-H having an amino acid sequence of SEQ ID NO: 44, a CDR3-H having an amino acid sequence of SEQ ID NO: 45, a CDR1-L having an amino acid sequence of SEQ ID NO: 47, a CDR2-L having an amino acid sequence of YTS, and a CDR3-L having an amino acid sequence of SEQ ID NO: 48 or SEQ ID NO: 52.
3. The immunoconjugate according to claim 1 wherein the antibody is a chimeric or a humanised antibody.
4. The immunoconjugate according to claim 1, wherein the antibody comprises:
   i) a heavy chain having an amino acid sequence of SEQ ID NO: 17 and a light chain having an amino acid sequence of SEQ ID NO: 18; or
   ii) a heavy chain having an amino acid sequence of SEQ ID NO: 19 and a light chain having an amino acid sequence of SEQ ID NO: 20; or
   iii) a heavy chain having an amino acid sequence of SEQ ID NO: 21 and a light chain having an amino acid sequence of SEQ ID NO: 22; or
   iv) a heavy chain having an amino acid sequence of SEQ ID NO: 49 and a light chain having an amino acid sequence of SEQ ID NO: 50; or
   v) a heavy chain having an amino acid sequence of SEQ ID NO: 49 and a light chain having an amino acid sequence of SEQ ID NO: 81, or
   vi) a heavy chain having an amino acid sequence of ence SEQ ID NO: 60 and a light chain having an amino acid sequence of SEQ ID NO: 59; or
   vii) a heavy chain having an amino acid sequence of SEQ ID NO: 62 and a light chain having an amino acid sequence of SEQ ID NO: 61; or
   Viii) a heavy chain having an amino acid sequence of SEQ ID NO: 64 and a light chain having an amino acid sequence of SEQ ID NO: 63.
5. The immunoconjugate according to claim 1, wherein said at least one growth inhibitory agent is a cytotoxic agent or a radioactive isotope.
6. The immunoconjugate conjugate according to claim 5, wherein said growth inhibitory agent is ($N^{2'}$-deacetyl-$N^{2'}$-(3-mercapto-1-oxopropyl)-maytansine) DM1 or $N^{2'}$-deacetyl-$N^{2'}$(4-methyl-4-mercapto-1-oxopentyl)-maytansine (DM4).
7. The immunoconjugate according to claim 1, wherein said growth inhibitory agent is covalently attached to the antibody or antigen binding fragment thereof via a linker selected from the group consisting of N-succinimidyl pyridyldithiobutyrate (SPDB), 4-(Pyridin-2-yldisulfanyl)-2-sulfo-butyric acid (sulfo-SPDB), and succinimidyl (N-maleimidomethyl) cyclohexane-1-carboxylate (SMCC).
8. The immunoconjugate according to claim 7, wherein said linker is N-succinimidyl pyridyldithiobutyrate (SPDB) and the growth inhibitory agent is $N^{2'}$-deacetyl-$N^{2'}$-(4-methyl-4-mercapto-1-oxopentyl)-maytansine (DM4).
9. The immunoconjugate according to claim 7, wherein said linker is 4-(Pyridin-2-yldisulfanyl)-2-sulfo-butyric acid (sulfo-SPDB) and the growth inhibitory agent is $N^{2'}$-deacetyl-$N^{2'}$-(4-methyl-4-mercapto-1-oxopentyl)-maytansine (DM4).
10. The immunoconjugate according to claim 7, wherein said linker is succinimidyl (N-maleimidomethyl) cyclohexane-1-carboxylate (SMCC) and the growth inhibitory agent is $N^{2'}$-deacetyl-$N^{2'}$-(3-mercapto-1-oxopropyl)-maytansine (DM1).
11. The immunoconjugate according to claim 6, wherein the immunoconjugate is characterised by a drug-to-antibody ratio (DAR) ranging from 1 to 10, the DAR being calculated from the ratio of the drug concentration to that of the antibody:

$$DAR = c_D/c_A$$

wherein $$c_D = [(\epsilon_{A280} \times A_{252}) - (\epsilon_{A252} \times A_{280})] / [(\epsilon_{D252} \times \epsilon_{A280}) - (\epsilon_{A252} \times \epsilon_{D280})]$$

$$c_A = [A_{280} - (c_D \times \epsilon_{D280})] / \epsilon_{A280}$$

and $\epsilon_{D252}$ and $\epsilon_{D280}$ are respectively the molar extinction coefficients of the drug at 252 nm and 280 nm;

$\epsilon_{A252}$ and $\epsilon_{A280}$ are respectively the molar extinction coefficients of the antibody at 252 nm and 280 nm;

($A_{252}$) and $A_{280}$ are respectively the absorbances for the conjugate at 252 nm ($A_{252}$) and at 280 nm ($A_{280}$), measured using a classic spectrophotometer apparatus.

12. An isolated antibody or antigen binding fragment thereof, wherein said antibody or antigen binding fragment thereof binds to a first lumenal domain of human LAMP1 protein.
13. An isolated anti-LAMP-1 antibody or antigen binding fragment thereof according to claim 12, wherein said antibody or antigen binding fragment thereof comprises:
   (i) a CDR1-H having an amino acid sequence of SEQ ID NO: 2, a CDR2-H having an amino acid sequence of SEQ ID NO: 3, and a CDR3-H having an amino acid sequence of SEQ ID NO: 4; and
   a CDR1-L having an amino acid sequence of SEQ ID NO: 6, a CDR2-L having an amino acid sequence of DTS, and a CDR3-L having an amino acid sequence of SEQ ID NO: 7; or
   (ii) a CDR1-H having an amino acid sequence of SEQ ID NO: 9, a CDR2-H having an amino acid sequence of SEQ ID NO: 10, a CDR3-H having an amino acid sequence of SEQ ID NO: 11; and
   a CDR1-L having an amino acid sequence of SEQ ID NO: 13, a CDR2-L having an amino acid sequence of AAS, and a CDR3-L having an amino acid sequence of SEQ ID NO: 14; or
(iii) a CDR1-H having an amino acid sequence of SEQ ID NO: 43, a CDR2-H having an amino acid sequence of SEQ ID NO: 44, and a CDR3-H having an amino acid sequence of SEQ ID NO: 45, and
a CDR1-L having an amino acid sequence of SEQ ID NO: 47, a CDR2-L having an amino acid sequence of YTS, and a CDR3-L having an amino acid sequence of SEQ ID NO: 48 or SEQ ID NO: 52.

14. A pharmaceutical composition comprising an immunoconjugate according to claim 1 and a pharmaceutically acceptable carrier.

15. An immunoconjugate comprising a) an antibody or antigen binding fragment thereof wherein said antibody or antigen binding fragment thereof comprises a CDR1-H having an amino acid sequence of SEQ ID NO: 2, a CDR2-H having an amino acid sequence of SEQ ID NO: 3, a CDR3-H having an amino acid sequence of SEQ ID NO: 4, a CDR1-L having an amino acid sequence of SEQ ID NO: 6, a CDR2-L having an amino acid sequence DTS, and a CDR3-L having an amino acid sequence of SEQ ID NO: 7; and
b) at least one growth inhibitory agent, wherein the at least one growth inhibitory agent is covalently attached to the antibody or antigen binding fragment thereof via a linker linked to the antibody or antigen binding fragment thereof and wherein said linker is N-succinimidyl pyridyldithiobutyrate (SPDB) and said growth inhibitory agent is $N^{2'}$-deacetyl-$N^{2'}$-(4-methyl-4-mercapto-1-oxopentyl)-maytansine (DM4).

16. The immunoconjugate of claim 15, wherein the antibody or antigen binding fragment thereof comprises
i) a heavy chain variable domain having an amino acid sequence of SEQ ID NO: 1 and a light chain variable domain having an amino acid sequence of SEQ ID NO: 5; or
ii) a heavy chain variable domain having an amino acid sequence of SEQ ID NO: 8 and a light chain variable domain having an amino acid sequence of SEQ ID NO: 12; or
iii) a heavy chain variable domain having an amino acid sequence of SEQ ID NO: 15 and a light chain variable domain having an amino acid sequence of SEQ ID NO: 16; or
iv) a heavy chain variable domain having an amino acid sequence of SEQ ID NO: 42 and a light chain variable domain having an amino acid sequence of SEQ ID NO: 46; or
v) a heavy chain variable domain having an amino acid sequence of SEQ ID NO: 42 and a light chain variable domain having an amino acid sequence of SEQ ID NO: 51; or
vi) a heavy chain variable domain having an amino acid sequence of SEQ ID NO: 53 and a light chain variable domain having an amino acid sequence of SEQ ID NO: 56, or
viii) a heavy chain variable domain having an amino acid sequence of SEQ ID NO: 54 and a light chain variable domain having an amino acid sequence of SEQ ID NO: 57, or
ix) a heavy chain variable domain having an amino acid sequence of SEQ ID NO: 55 and a light chain variable domain having an amino acid sequence of SEQ ID NO: 58.

17. The immunoconjugate of claim 15, wherein the antibody comprises
i) a heavy chain having an amino acid sequence of SEQ ID NO: 17 and a light chain having an amino acid sequence of SEQ ID NO: 18; or
ii) a heavy chain having an amino acid sequence of SEQ ID NO: 19 and a light chain having an amino acid sequence of SEQ ID NO: 20; or
iii) a heavy chain having an amino acid sequence of SEQ ID NO: 21 and a light chain having an amino acid sequence of SEQ ID NO: 22; or
iv) a heavy chain having an amino acid sequence of SEQ ID NO: 49 and a light chain having an amino acid sequence of SEQ ID NO: 50; or
v) a heavy chain having an amino acid sequence of SEQ ID NO: 49 and a light chain having an amino acid sequence of SEQ ID NO: 81, or
vi) a heavy chain having an amino acid sequence of ence SEQ ID NO: 60 and a light chain having an amino acid sequence of SEQ ID NO: 59; or
vii) a heavy chain having an amino acid sequence of SEQ ID NO: 62 and a light chain having an amino acid sequence of SEQ ID NO: 61; or
viii) a heavy chain having an amino acid sequence of SEQ ID NO: 64 and a light chain having an amino acid sequence of SEQ ID NO: 63.

* * * * *

SEQUENCE LISTING

```
<160> NUMBER OF SEQ ID NOS: 99

<210> SEQ ID NO 1
<211> LENGTH: 118
<212> TYPE: PRT
<213> ORGANISM: Artificial Sequence
<220> FEATURE:
<223> OTHER INFORMATION: Antibody Fragment

<400> SEQUENCE: 1

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Ile His Trp Val Lys Ser Pro Gly Gln Gly Leu Glu Trp Ile
        35                  40                  45

Gly Ala Ile Tyr Pro Gly Asn Gly Asp Ala Pro Tyr Ser Gln Lys Phe
```

```
                50                  55                  60
Lys Asp Lys Ala Thr Leu Thr Ala Asp Lys Ser Ser Thr Thr Tyr
 65                  70                  75                  80

Met Gln Leu Ser Arg Leu Thr Ser Glu Asp Ser Ala Val Tyr Tyr Cys
                 85                  90                  95

Val Arg Ala Asn Trp Asp Val Ala Phe Ala Tyr Trp Gly Gln Gly Thr
            100                 105                 110

Leu Val Ser Val Ser Ala
        115

<210> SEQ ID NO 2
<211> LENGTH: 8
<212> TYPE: PRT
<213> ORGANISM: Artificial Sequence
<220> FEATURE:
<223> OTHER INFORMATION: antibody fragment

<400> SEQUENCE: 2

Gly Tyr Ile Phe Thr Asn Tyr Asn
 1               5

<210> SEQ ID NO 3
<211> LENGTH: 8
<212> TYPE: PRT
<213> ORGANISM: Artificial Sequence
<220> FEATURE:
<223> OTHER INFORMATION: antibody fragment

<400> SEQUENCE: 3

Ile Tyr Pro Gly Asn Gly Asp Ala
 1               5

<210> SEQ ID NO 4
<211> LENGTH: 11
<212> TYPE: PRT
<213> ORGANISM: Artificial Sequence
<220> FEATURE:
<223> OTHER INFORMATION: antibody fragment

<400> SEQUENCE: 4

Val Arg Ala Asn Trp Asp Val Ala Phe Ala Tyr
 1               5                  10

<210> SEQ ID NO 5
<211> LENGTH: 106
<212> TYPE: PRT
<213> ORGANISM: Artificial Sequence
<220> FEATURE:
<223> OTHER INFORMATION: antibody fragment

<400> SEQUENCE: 5

Asp Ile Gln Met Thr Gln Ser Pro Pro Ser Leu Ser Ala Ser Leu Gly
 1               5                  10                  15

Gly Lys Val Thr Ile Thr Cys Lys Ala Ser Gln Asp Ile Asp Arg Tyr
             20                  25                  30

Met Ala Trp Tyr Gln Asp Lys Pro Gly Lys Gly Pro Arg Leu Leu Ile
         35                  40                  45

His Asp Thr Ser Thr Leu Gln Pro Gly Ile Pro Ser Arg Phe Ser Gly
     50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Trp Thr
```

Phe Gly Gly Gly Thr Lys Leu Glu Ile Lys
              100                 105

<210> SEQ ID NO 6
<211> LENGTH: 6
<212> TYPE: PRT
<213> ORGANISM: Artificial Sequence
<220> FEATURE:
<223> OTHER INFORMATION: antibody fragment

<400> SEQUENCE: 6

Gln Asp Ile Asp Arg Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: antibody fragment

<400> SEQUENCE: 7

Leu Gln Tyr Asp Asn Leu Trp Thr
1               5

<210> SEQ ID NO 8
<211> LENGTH: 122
<212> TYPE: PRT
<213> ORGANISM: Artificial Sequence
<220> FEATURE:
<223> OTHER INFORMATION: antibod fragment

<400> SEQUENCE: 8

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Phe Asn Pro Ser Ser Gly Tyr Pro Glu Tyr Asn Gln Lys Phe
    50                  55                  60

Lys Asp Lys Thr Thr Leu Thr Ala Asp Lys Ser Ser Asn Thr Ala Phe
65                  70                  75                  80

Ile Gln Leu Asn Ser Leu Thr Ser Glu Asp Ser Ala Val Tyr Tyr Cys
                85                  90                  95

Ser Arg Gly Tyr Tyr Tyr Gly Ser Arg Gly Tyr Ala Leu Asp Phe Trp
            100                 105                 110

Gly Gln Gly Ala Ser Val Thr Val Ser Ser
        115                 120

<210> SEQ ID NO 9
<211> LENGTH: 8
<212> TYPE: PRT
<213> ORGANISM: Artificial Sequence
<220> FEATURE:
<223> OTHER INFORMATION: antibody fragment

<400> SEQUENCE: 9

Gly Tyr Thr Phe Thr Ser Tyr Thr
1               5

-continued

```
<210> SEQ ID NO 10
<211> LENGTH: 8
<212> TYPE: PRT
<213> ORGANISM: Artificial Sequence
<220> FEATURE:
<223> OTHER INFORMATION: antibody fragment

<400> SEQUENCE: 10

Phe Asn Pro Ser Ser Gly Tyr Pro
1               5

<210> SEQ ID NO 11
<211> LENGTH: 15
<212> TYPE: PRT
<213> ORGANISM: Artificial Sequence
<220> FEATURE:
<223> OTHER INFORMATION: antibody fragment

<400> SEQUENCE: 11

Ser Arg Gly Tyr Tyr Tyr Gly Ser Arg Gly Tyr Ala Leu Asp Phe
1               5                   10                  15

<210> SEQ ID NO 12
<211> LENGTH: 111
<212> TYPE: PRT
<213> ORGANISM: Artificial Sequence
<220> FEATURE:
<223> OTHER INFORMATION: antibody fragment

<400> SEQUENCE: 12

Asn Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Ile Asn
            20                  25                  30

Gly Asn Thr Phe Met His Trp Tyr Gln Gln Lys Pro Gly Gln Ser Pro
        35                  40                  45

Lys Leu Val Ile Tyr Ala Ala Ser Asn Ile Glu Ser Gly Val Pro Ala
    50                  55                  60

Arg Phe Ser Gly Ser Gly Ser Ser Thr Asp Phe Thr Phe Thr Ile Asp
65                  70                  75                  80

Pro Val Glu Ala Asp Asp Val Ala Thr Tyr Tyr Cys Gln Gln Asn Ile
                85                  90                  95

Glu Asp Pro Trp Thr Phe Gly Gly Gly Thr Lys Val Glu Ile Lys
            100                 105                 110

<210> SEQ ID NO 13
<211> LENGTH: 10
<212> TYPE: PRT
<213> ORGANISM: Artificial Sequence
<220> FEATURE:
<223> OTHER INFORMATION: antibody fragment

<400> SEQUENCE: 13

Glu Ser Val Asp Ile Asn Gly Asn Thr Phe
1               5                   10

<210> SEQ ID NO 14
<211> LENGTH: 9
<212> TYPE: PRT
<213> ORGANISM: Artificial Sequence
<220> FEATURE:
<223> OTHER INFORMATION: antibody fragment

<400> SEQUENCE: 14
```

Gln Gln Asn Ile Glu Asp Pro Trp Thr
1               5

<210> SEQ ID NO 15
<211> LENGTH: 122
<212> TYPE: PRT
<213> ORGANISM: Artificial Sequence
<220> FEATURE:
<223> OTHER INFORMATION: antibody fragment

<400> SEQUENCE: 15

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Phe Asn Pro Ser Ser Gly Tyr Pro Glu Tyr Asn Gln Lys Phe
    50                  55                  60

Lys Asp Lys Thr Thr Leu Thr Ala Asp Lys Ser Ser Asn Thr Ala Phe
65                  70                  75                  80

Ile Gln Leu Asn Ser Leu Thr Ser Glu Asp Ser Ala Val Tyr Tyr Cys
                85                  90                  95

Ser Arg Gly Tyr Tyr Tyr Gly Ser Arg Gly Tyr Ala Leu Asp Phe Trp
            100                 105                 110

Gly Gln Gly Thr Ser Val Thr Val Ser Ser
        115                 120

<210> SEQ ID NO 16
<211> LENGTH: 111
<212> TYPE: PRT
<213> ORGANISM: Artificial Sequence
<220> FEATURE:
<223> OTHER INFORMATION: antibody fragment

<400> SEQUENCE: 16

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ile Asn
            20                  25                  30

Gly Asn Thr Phe Met His Trp Tyr Gln Gln Lys Pro Gly Gln Ser Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Phe Thr Ile Asp
65                  70                  75                  80

Pro Val Glu Ala Asp Asp Val Ala Thr Tyr Tyr Cys Gln Gln Asn Ile
                85                  90                  95

Glu Asp Pro Trp Thr Phe Gly Gly Gly Thr Lys Leu Glu Ile Lys
            100                 105                 110

<210> SEQ ID NO 17
<211> LENGTH: 447
<212> TYPE: PRT
<213> ORGANISM: Artificial Sequence
<220> FEATURE:
<223> OTHER INFORMATION: antibody fragment

<400> SEQUENCE: 17

Gln Val Gln Leu Gln Gln Ser Gly Ala Glu Leu Val Lys Pro Gly Ala

-continued

```
1               5                   10                  15
Ser Val Lys Met Ser Cys Lys Ala Ser Gly Tyr Ile Phe Thr Asn Tyr
            20                  25                  30
Asn Ile His Trp Val Lys Lys Ser Pro Gly Gln Gly Leu Glu Trp Ile
            35                  40                  45
Gly Ala Ile Tyr Pro Gly Asn Gly Asp Ala Pro Tyr Ser Gln Lys Phe
            50                  55                  60
Lys Asp Lys Ala Thr Leu Thr Ala Asp Lys Ser Ser Thr Thr Tyr
65                  70                  75                  80
Met Gln Leu Ser Arg Leu Thr Ser Glu Asp Ser Ala Val Tyr Cys
            85                  90                  95
Val Arg Ala Asn Trp Asp Val Ala Phe Ala Tyr Trp Gly Gln Gly Thr
            100                 105                 110
Leu Val Ser Val Ser Ala Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
            245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
```

-continued

Leu His Asn His Tyr Thr Gln Lys Ser Leu Ser Leu Ser Pro Gly
        435                 440                 445

<210> SEQ ID NO 18
<211> LENGTH: 213
<212> TYPE: PRT
<213> ORGANISM: Artificial Sequence
<220> FEATURE:
<223> OTHER INFORMATION: antibody fragment

<400> SEQUENCE: 18

Asp Ile Gln Met Thr Gln Ser Pro Ser Leu Ser Ala Ser Leu Gly
1               5                   10                  15

Gly Lys Val Thr Ile Thr Cys Lys Ala Ser Gln Asp Ile Asp Arg Tyr
            20                  25                  30

Met Ala Trp Tyr Gln Asp Lys Pro Gly Lys Pro Arg Leu Leu Ile
        35                  40                  45

His Asp Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 451
<212> TYPE: PRT
<213> ORGANISM: Artificial Sequence
<220> FEATURE:
<223> OTHER INFORMATION: antibody fragment

<400> SEQUENCE: 19

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Phe Asn Pro Ser Ser Gly Tyr Pro Glu Tyr Asn Gln Lys Phe
    50                  55                  60

Lys Asp Lys Thr Thr Leu Thr Ala Asp Lys Ser Ser Asn Thr Ala Phe

```
                65                  70                  75                  80
Ile Gln Leu Asn Ser Leu Thr Ser Glu Asp Ser Ala Val Tyr Tyr Cys
                    85                  90                  95

Ser Arg Gly Tyr Tyr Gly Ser Arg Gly Tyr Ala Leu Asp Phe Trp
                100                 105                 110

Gly Gln Gly Ala Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 20
<211> LENGTH: 218
<212> TYPE: PRT
<213> ORGANISM: Artificial Sequence
```

```
<220> FEATURE:
<223> OTHER INFORMATION: antibody fragment

<400> SEQUENCE: 20

Asn Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Ile Asn
            20                  25                  30

Gly Asn Thr Phe Met His Trp Tyr Gln Gln Lys Pro Gly Gln Ser Pro
        35                  40                  45

Lys Leu Val Ile Tyr Ala Ala Ser Asn Ile Glu Ser Gly Val Pro Ala
    50                  55                  60

Arg Phe Ser Gly Ser Gly Ser Ser Thr Asp Phe Thr Phe Thr Ile Asp
65                  70                  75                  80

Pro Val Glu Ala Asp Asp Val Ala Thr Tyr Tyr Cys Gln Gln Asn Ile
                85                  90                  95

Glu Asp Pro Trp Thr Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 451
<212> TYPE: PRT
<213> ORGANISM: Artificial Sequence
<220> FEATURE:
<223> OTHER INFORMATION: antibody fragment

<400> SEQUENCE: 21

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Phe Asn Pro Ser Ser Gly Tyr Pro Glu Tyr Asn Gln Lys Phe
    50                  55                  60

Lys Asp Lys Thr Thr Leu Thr Ala Asp Lys Ser Ser Asn Thr Ala Phe
65                  70                  75                  80

Ile Gln Leu Asn Ser Leu Thr Ser Glu Asp Ser Ala Val Tyr Tyr Cys
                85                  90                  95

Ser Arg Gly Tyr Tyr Gly Ser Arg Gly Tyr Ala Leu Asp Phe Trp
            100                 105                 110

Gly Gln Gly Thr Ser Val Thr Val Ser Ser Ala Ser Thr Lys Gly Pro
```

```
            115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 22
<211> LENGTH: 218
<212> TYPE: PRT
<213> ORGANISM: Artificial Sequence
<220> FEATURE:
<223> OTHER INFORMATION: antibody fragment

<400> SEQUENCE: 22

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ile Asn
```

|   |   |   | 20 |   |   |   | 25 |   |   |   | 30 |   |
|---|---|---|---|---|---|---|---|---|---|---|---|---|

Gly Asn Thr Phe Met His Trp Tyr Gln Gln Lys Pro Gly Gln Ser Pro
        35                  40                 45

Lys Leu Leu Ile Tyr Ala Ala Ser Asn Leu Glu Ser Gly Val Pro Ala
  50                  55                60

Arg Phe Ser Gly Ser Gly Ser Gly Thr Asp Phe Thr Phe Thr Ile Asp
65                  70                75                80

Pro Val Glu Ala Asp Asp Val Ala Thr Tyr Tyr Cys Gln Gln Asn Ile
                85                90                95

Glu Asp Pro Trp Thr Phe Gly Gly Thr Lys Leu Glu Ile Lys Arg
           100              105             110

Thr Val Ala Ala Pro Ser Val Phe Ile Phe Pro Pro Ser Asp Glu Gln
         115               120             125

Leu Lys Ser Gly Thr Ala Ser Val Val Cys Leu Leu Asn Asn Phe Tyr
       130               135             140

Pro Arg Glu Ala Lys Val Gln Trp Lys Val Asp Asn Ala Leu Gln Ser
145                150              155           160

Gly Asn Ser Gln Glu Ser Val Thr Glu Gln Asp Ser Lys Asp Ser Thr
         165               170             175

Tyr Ser Leu Ser Ser Thr Leu Thr Leu Ser Lys Ala Asp Tyr Glu Lys
       180               185             190

His Lys Val Tyr Ala Cys Glu Val Thr His Gln Gly Leu Ser Ser Pro
       195               200             205

Val Thr Lys Ser Phe Asn Arg Gly Glu Cys
     210              215

<210> SEQ ID NO 23
<211> LENGTH: 1254
<212> TYPE: DNA
<213> ORGANISM: Homo sapiens

<400> SEQUENCE: 23

```
atggcggccc ccggcagcgc ccggcgaccc ctgctgctgc tactgctgtt gctgctgctc    60
ggcctcatgc attgtgcgtc agcagcaatg tttatggtga aaaatggcaa cgggaccgcg   120
tgcataatgg ccaacttctc tgctgccttc tcagtgaact acgacaccaa gagtggccct   180
aagaacatga cctttgacct gccatcagat gccacagtgg tgctcaaccg cagctcctgt   240
ggaaaagaga cacttctga cccccagtctc gtgattgctt ttggaagagg acatacactc   300
actctcaatt tcacgagaaa tgcaacacgt tacagcgtcc agctcatgag ttttgtttat   360
aacttgtcag acacacacct tttccccaat gcgagctcca agaaaatcaa gactgtggaa   420
tctataactg catcaggggc agatatagat aaaaaataca gatgtgttag tggcacccag   480
gtccacatga acaacgtgac cgtaacgctc catgatgcca ccatccaggc gtaccttcc    540
aacagcagct tcagcagggg agagacacgc tgtgaacaag acaggccttc cccaaccaca   600
gcgcccctg cgccacccag ccctcgccc tcaccgtgc caagagccc ctctgtggac   660
aagtacaacg tgagcggcac caacgggacc tgcctgctgg ccagcatggg gctgcagctg   720
aacctcacct atgagaggaa ggacaacacg acggtgacaa ggcttctcaa catcaacccc   780
aacaagacct cggccagcgg gagctgcggc gccacctgg tgactctgga gctgcacagc   840
gagggcacca ccgtcctgct cttccagttc gggatgaatg caagttctag ccggtttttc   900
ctacaaggaa tccagttgaa tacaattctt cctgacgcca gagaccctgc ctttaaagct   960
gccaacggct ccctgcgagc gctgcaggcc acagtcggca attcctacaa gtgcaacgcg  1020
```

```
gaggagcacg tccgtgtcac gaaggcgttt tcagtcaata tattcaaagt gtgggtccag    1080
gctttcaagg tggaaggtgg ccagtttggc tctgtggagg agtgtctgct ggacgagaac    1140
agcatgctga tccccatcgc tgtgggtggt gccctggcgg ggctggtcct catcgtcctc    1200
atcgcctacc tcgtcggcag gaagaggagt cacgcaggct accagactat ctag          1254
```

<210> SEQ ID NO 24
<211> LENGTH: 417
<212> TYPE: PRT
<213> ORGANISM: Homo sapiens

<400> SEQUENCE: 24

```
Met Ala Ala Pro Gly Ser Ala Arg Arg Pro Leu Leu Leu Leu Leu
1               5                   10                  15

Leu Leu Leu Leu Gly Leu Met His Cys Ala Ser Ala Ala Met Phe Met
            20                  25                  30

Val Lys Asn Gly Asn Gly Thr Ala Cys Ile Met Ala Asn Phe Ser Ala
        35                  40                  45

Ala Phe Ser Val Asn Tyr Asp Thr Lys Ser Gly Pro Lys Asn Met Thr
    50                  55                  60

Phe Asp Leu Pro Ser Asp Ala Thr Val Val Leu Asn Arg Ser Ser Cys
65                  70                  75                  80

Gly Lys Glu Asn Thr Ser Asp Pro Ser Leu Val Ile Ala Phe Gly Arg
                85                  90                  95

Gly His Thr Leu Thr Leu Asn Phe Thr Arg Asn Ala Thr Arg Tyr Ser
            100                 105                 110

Val Gln Leu Met Ser Phe Val Tyr Asn Leu Ser Asp Thr His Leu Phe
        115                 120                 125

Pro Asn Ala Ser Ser Lys Glu Ile Lys Thr Val Glu Ser Ile Thr Asp
    130                 135                 140

Ile Arg Ala Asp Ile Asp Lys Lys Tyr Arg Cys Val Ser Gly Thr Gln
145                 150                 155                 160

Val His Met Asn Asn Val Thr Val Thr Leu His Asp Ala Thr Ile Gln
                165                 170                 175

Ala Tyr Leu Ser Asn Ser Ser Phe Ser Arg Gly Glu Thr Arg Cys Glu
            180                 185                 190

Gln Asp Arg Pro Ser Pro Thr Thr Ala Pro Pro Ala Pro Pro Ser Pro
        195                 200                 205

Ser Pro Ser Pro Val Pro Lys Ser Pro Ser Val Asp Lys Tyr Asn Val
210                 215                 220

Ser Gly Thr Asn Gly Thr Cys Leu Leu Ala Ser Met Gly Leu Gln Leu
225                 230                 235                 240

Asn Leu Thr Tyr Glu Arg Lys Asp Asn Thr Thr Val Thr Arg Leu Leu
                245                 250                 255

Asn Ile Asn Pro Asn Lys Thr Ser Ala Ser Gly Ser Cys Gly Ala His
            260                 265                 270

Leu Val Thr Leu Glu Leu His Ser Glu Gly Thr Thr Val Leu Leu Phe
        275                 280                 285

Gln Phe Gly Met Asn Ala Ser Ser Ser Arg Phe Phe Leu Gln Gly Ile
    290                 295                 300

Gln Leu Asn Thr Ile Leu Pro Asp Ala Arg Asp Pro Ala Phe Lys Ala
305                 310                 315                 320

Ala Asn Gly Ser Leu Arg Ala Leu Gln Ala Thr Val Gly Asn Ser Tyr
                325                 330                 335
```

```
Lys Cys Asn Ala Glu Glu His Val Arg Val Thr Lys Ala Phe Ser Val
            340                 345                 350

Asn Ile Phe Lys Val Trp Val Gln Ala Phe Lys Val Glu Gly Gly Gln
            355                 360                 365

Phe Gly Ser Val Glu Glu Cys Leu Leu Asp Glu Asn Ser Met Leu Ile
370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
            405                 410                 415

Ile

<210> SEQ ID NO 25
<211> LENGTH: 406
<212> TYPE: PRT
<213> ORGANISM: Mus musculus

<400> SEQUENCE: 25

Met Ala Ala Pro Gly Ala Arg Arg Pro Leu Leu Leu Leu Leu Leu Ala
1               5                   10                  15

Gly Leu Ala His Gly Ala Ser Ala Leu Phe Glu Val Lys Asn Asn Gly
            20                  25                  30

Thr Thr Cys Ile Met Ala Ser Phe Ser Ala Ser Phe Leu Thr Thr Tyr
            35                  40                  45

Glu Thr Ala Asn Gly Ser Gln Ile Val Asn Ile Ser Leu Pro Ala Ser
    50                  55                  60

Ala Glu Val Leu Lys Asn Gly Ser Ser Cys Gly Lys Glu Asn Val Ser
65                  70                  75                  80

Asp Pro Ser Leu Thr Ile Thr Phe Gly Arg Gly Tyr Leu Leu Thr Leu
                85                  90                  95

Asn Phe Thr Lys Asn Thr Thr Arg Tyr Ser Val Gln His Met Tyr Phe
            100                 105                 110

Thr Tyr Asn Leu Ser Asp Thr Glu His Phe Pro Asn Ala Ile Ser Lys
        115                 120                 125

Glu Ile Tyr Thr Met Asp Ser Thr Thr Asp Ile Lys Ala Asp Ile Asn
    130                 135                 140

Lys Ala Tyr Arg Cys Val Ser Asp Ile Arg Val Tyr Met Lys Asn Val
145                 150                 155                 160

Thr Val Val Leu Arg Asp Ala Thr Ile Gln Ala Tyr Leu Ser Ser Gly
                165                 170                 175

Asn Phe Ser Lys Glu Glu Thr His Cys Thr Gln Asp Gly Pro Ser Pro
            180                 185                 190

Thr Thr Gly Pro Pro Ser Pro Ser Pro Pro Leu Val Pro Thr Asn Pro
        195                 200                 205

Thr Val Ser Lys Tyr Asn Val Thr Gly Asn Asn Gly Thr Cys Leu Leu
    210                 215                 220

Ala Ser Met Ala Leu Gln Leu Asn Ile Thr Tyr Leu Lys Lys Asp Asn
225                 230                 235                 240

Lys Thr Val Thr Arg Ala Phe Asn Ile Ser Pro Asn Asp Thr Ser Ser
                245                 250                 255

Gly Ser Cys Gly Ile Asn Leu Val Thr Leu Lys Val Glu Asn Lys Asn
            260                 265                 270

Arg Ala Leu Glu Leu Gln Phe Gly Met Asn Ala Ser Ser Ser Leu Phe
        275                 280                 285
```

```
Phe Leu Gln Gly Val Arg Leu Asn Met Thr Leu Pro Asp Ala Leu Val
        290                 295                 300

Pro Thr Phe Ser Ile Ser Asn His Ser Leu Lys Ala Leu Gln Ala Thr
305                 310                 315                 320

Val Gly Asn Ser Tyr Lys Cys Asn Thr Glu Glu His Ile Phe Val Ser
            325                 330                 335

Lys Met Leu Ser Leu Asn Val Phe Ser Val Gln Val Gln Ala Phe Lys
            340                 345                 350

Val Asp Ser Asp Arg Phe Gly Ser Val Glu Glu Cys Val Gln Asp Gly
        355                 360                 365

Asn Asn Met Leu Ile Pro Ile Ala Val Gly Gly Ala Leu Ala Gly Leu
    370                 375                 380

Val Leu Ile Val Leu Ile Ala Tyr Leu Ile Gly Arg Lys Arg Ser His
385                 390                 395                 400

Ala Gly Tyr Gln Thr Ile
            405

<210> SEQ ID NO 26
<211> LENGTH: 407
<212> TYPE: PRT
<213> ORGANISM: Rattus norvegicus

<400> SEQUENCE: 26

Met Ala Ala Pro Gly Ala Arg Arg Pro Leu Leu Leu Leu Leu Leu Ala
1               5                   10                  15

Gly Leu Ala His Ser Ala Pro Ala Leu Phe Glu Val Lys Asp Asn Asn
            20                  25                  30

Gly Thr Ala Cys Ile Met Ala Ser Phe Ser Ala Ser Phe Leu Thr Thr
        35                  40                  45

Tyr Asp Ala Gly His Val Ser Lys Val Ser Asn Met Thr Leu Pro Ala
    50                  55                  60

Ser Ala Glu Val Leu Lys Asn Ser Ser Ser Cys Gly Glu Lys Asn Ala
65                  70                  75                  80

Ser Glu Pro Thr Leu Ala Ile Thr Phe Gly Glu Gly Tyr Leu Leu Lys
                85                  90                  95

Leu Thr Phe Thr Lys Asn Thr Thr Arg Tyr Ser Val Gln His Met Tyr
            100                 105                 110

Phe Thr Tyr Asn Leu Ser Asp Thr Gln Phe Phe Pro Asn Ala Ser Ser
        115                 120                 125

Lys Gly Pro Asp Thr Val Asp Ser Thr Thr Asp Ile Lys Ala Asp Ile
130                 135                 140

Asn Lys Thr Tyr Arg Cys Val Ser Asp Ile Arg Val Tyr Met Lys Asn
145                 150                 155                 160

Val Thr Ile Val Leu Trp Asp Ala Thr Ile Gln Ala Tyr Leu Pro Ser
                165                 170                 175

Ser Asn Phe Ser Lys Glu Glu Thr Arg Cys Pro Gln Asp Gln Pro Ser
            180                 185                 190

Pro Thr Thr Gly Pro Pro Ser Pro Ser Pro Leu Val Pro Thr Asn
        195                 200                 205

Pro Ser Val Ser Lys Tyr Asn Val Thr Gly Asp Asn Gly Thr Cys Leu
    210                 215                 220

Leu Ala Ser Met Ala Leu Gln Leu Asn Ile Thr Tyr Met Lys Lys Asp
225                 230                 235                 240

Asn Thr Thr Val Thr Arg Ala Phe Asn Ile Asn Pro Ser Asp Lys Tyr
```

```
                    245                 250                 255
Ser Gly Thr Cys Gly Ala Gln Leu Val Thr Leu Lys Val Gly Asn Lys
            260                 265                 270

Ser Arg Val Leu Glu Leu Gln Phe Gly Met Asn Ala Thr Ser Ser Leu
            275                 280                 285

Phe Phe Leu Gln Gly Val Gln Leu Asn Met Thr Leu Pro Asp Ala Ile
            290                 295                 300

Glu Pro Thr Phe Ser Thr Ser Asn Tyr Ser Leu Lys Ala Leu Gln Ala
305                 310                 315                 320

Ser Val Gly Asn Ser Tyr Lys Cys Asn Ser Glu Glu His Ile Phe Val
            325                 330                 335

Ser Lys Ala Leu Ala Leu Asn Val Phe Ser Val Gln Val Gln Ala Phe
            340                 345                 350

Arg Val Glu Ser Asp Arg Phe Gly Ser Val Glu Cys Val Gln Asp
            355                 360                 365

Gly Asn Asn Met Leu Ile Pro Ile Ala Val Gly Gly Ala Leu Ala Gly
            370                 375                 380

Leu Val Leu Ile Val Leu Ile Ala Tyr Leu Ile Gly Arg Lys Arg Ser
385                 390                 395                 400

His Ala Gly Tyr Gln Thr Ile
                405

<210> SEQ ID NO 27
<211> LENGTH: 416
<212> TYPE: PRT
<213> ORGANISM: Macaca mulatta

<400> SEQUENCE: 27

Met Ala Ala Pro Gly Ser Ala Arg Arg Ser Leu Leu Leu Leu Leu Leu
1               5                   10                  15

Leu Leu Leu Gly Leu Thr His Cys Ala Ser Ala Ala Met Phe Ile Val
            20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Phe
50                  55                  60

Asp Leu Pro Ser Asp Ala Lys Val Val Leu Asn Ser Ser Ser Cys Gly
65                  70                  75                  80

Lys Glu Asn Thr Ser Asp Pro Ser Leu Val Ile Ala Phe Gly Arg Gly
            85                  90                  95

Gln Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
            165                 170                 175

Tyr Leu Ser Asn Ser Ser Phe Ser Arg Glu Glu Thr Arg Cys Glu Gln
            180                 185                 190

Asp Arg Pro Ser Pro Thr Thr Ala Pro Pro Ala Pro Pro Ser Pro Ser
            195                 200                 205
```

-continued

```
Pro Ser Pro Val Pro Glu Ser Pro Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Val Thr Arg Leu Leu Asn
                245                 250                 255

Ile Asn Pro Asn Lys Thr Leu Ala Ser Gly Ser Cys Gly Ala His Leu
                260                 265                 270

Val Thr Leu Glu Leu His Ser Glu Gly Ser Thr Val Leu Leu Phe Gln
                275                 280                 285

Phe Gly Met Asn Ala Ser Ser Ser Arg Phe Phe Leu Gln Gly Ile Gln
290                 295                 300

Leu Asn Thr Thr Leu Pro Asp Ala Arg Asp Pro Ala Phe Lys Ala Ala
305                 310                 315                 320

Asn Ser Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
                340                 345                 350

Ile Phe Lys Val Trp Val Gln Ala Phe Lys Val Glu Gly Gly Gln Phe
                355                 360                 365

Gly Ser Val Glu Glu Cys Leu Leu Asp Glu Asn Asn Met Leu Ile Pro
370                 375                 380

Ile Ala Val Gly Gly Ala Leu Ala Gly Leu Val Leu Ile Val Leu Ile
385                 390                 395                 400

Ala Tyr Leu Val Gly Arg Lys Arg Ser His Ala Gly Tyr Gln Thr Ile
                405                 410                 415

<210> SEQ ID NO 28
<211> LENGTH: 360
<212> TYPE: PRT
<213> ORGANISM: Artificial Sequence
<220> FEATURE:
<223> OTHER INFORMATION: human LAMP1 expression construct

<400> SEQUENCE: 28

Ala Met Phe Met Val Lys Asn Gly Asn Gly Thr Ala Cys Ile Met Ala
1               5                   10                  15

Asn Phe Ser Ala Ala Phe Ser Val Asn Tyr Asp Thr Lys Ser Gly Pro
                20                  25                  30

Lys Asn Met Thr Phe Asp Leu Pro Ser Asp Ala Thr Val Val Leu Asn
                35                  40                  45

Arg Ser Ser Cys Gly Lys Glu Asn Thr Ser Asp Pro Ser Leu Val Ile
    50                  55                  60

Ala Phe Gly Arg Gly His Thr Leu Thr Leu Asn Phe Thr Arg Asn Ala
65                  70                  75                  80

Thr Arg Tyr Ser Val Gln Leu Met Ser Phe Val Tyr Asn Leu Ser Asp
                85                  90                  95

Thr His Leu Phe Pro Asn Ala Ser Ser Lys Glu Ile Lys Thr Val Glu
                100                 105                 110

Ser Ile Thr Asp Ile Arg Ala Asp Ile Asp Lys Lys Tyr Arg Cys Val
                115                 120                 125

Ser Gly Thr Gln Val His Met Asn Asn Val Thr Val Thr Leu His Asp
    130                 135                 140

Ala Thr Ile Gln Ala Tyr Leu Ser Asn Ser Ser Phe Ser Arg Gly Glu
145                 150                 155                 160
```

```
Thr Arg Cys Glu Gln Asp Arg Pro Ser Pro Thr Ala Pro Pro Ala
            165                 170                 175

Pro Pro Ser Pro Ser Pro Ser Pro Val Pro Lys Ser Pro Ser Val Asp
        180                 185                 190

Lys Tyr Asn Val Ser Gly Thr Asn Gly Thr Cys Leu Leu Ala Ser Met
        195                 200                 205

Gly Leu Gln Leu Asn Leu Thr Tyr Glu Arg Lys Asp Asn Thr Thr Val
        210                 215                 220

Thr Arg Leu Leu Asn Ile Asn Pro Asn Lys Thr Ser Ala Ser Gly Ser
225                 230                 235                 240

Cys Gly Ala His Leu Val Thr Leu Glu Leu His Ser Glu Gly Thr Thr
                245                 250                 255

Val Leu Leu Phe Gln Phe Gly Met Asn Ala Ser Ser Ser Arg Phe Phe
            260                 265                 270

Leu Gln Gly Ile Gln Leu Asn Thr Ile Leu Pro Asp Ala Arg Asp Pro
            275                 280                 285

Ala Phe Lys Ala Ala Asn Gly Ser Leu Arg Ala Leu Gln Ala Thr Val
            290                 295                 300

Gly Asn Ser Tyr Lys Cys Asn Ala Glu Glu His Val Arg Val Thr Lys
305                 310                 315                 320

Ala Phe Ser Val Asn Ile Phe Lys Val Trp Val Gln Ala Phe Lys Val
                325                 330                 335

Glu Gly Gly Gln Phe Gly Ser Val Glu Glu Cys Leu Leu Asp Glu Asn
            340                 345                 350

Ser Met His His His His His His
            355                 360

<210> SEQ ID NO 29
<211> LENGTH: 362
<212> TYPE: PRT
<213> ORGANISM: Artificial Sequence
<220> FEATURE:
<223> OTHER INFORMATION: cynomologous protein expression construct

<400> SEQUENCE: 29

Ala Met Phe Ile Val Lys Asn Gly Asn Gly Thr Ala Cys Ile Met Ala
1               5                   10                  15

Asn Phe Ser Ala Ala Phe Ser Val Asn Tyr Asp Thr Lys Ser Gly Pro
            20                  25                  30

Lys Asn Met Thr Phe Asp Leu Pro Ser Asp Ala Lys Val Val Leu Asn
        35                  40                  45

Ser Ser Ser Cys Gly Lys Glu Asn Thr Ser Asp Pro Ser Leu Val Ile
    50                  55                  60

Ala Phe Gly Arg Gly Gln Thr Leu Thr Leu Asn Phe Thr Arg Asn Ala
65                  70                  75                  80

Thr Arg Tyr Ser Val Gln Leu Met Ser Phe Val Tyr Asn Leu Ser Asp
                85                  90                  95

Thr His Leu Phe Pro Asn Ala Ser Ser Lys Glu Ile Lys Thr Val Glu
            100                 105                 110

Ser Ile Thr Asp Ile Arg Ala Asp Ile Asp Lys Lys Tyr Arg Cys Val
        115                 120                 125

Ser Gly Thr Gln Val His Met Asn Asn Val Thr Val Thr Leu His Asp
    130                 135                 140

Ala Thr Ile Gln Ala Tyr Leu Ser Asn Ser Ser Phe Ser Arg Glu Glu
145                 150                 155                 160
```

```
Thr Arg Cys Glu Gln Asp Arg Pro Ser Pro Thr Ala Pro Pro Ala
            165                 170                 175

Pro Pro Ser Pro Ser Pro Ser Pro Val Pro Glu Ser Pro Ser Val Asp
        180                 185                 190

Lys Tyr Asn Val Ser Gly Thr Asn Gly Thr Cys Leu Leu Ala Ser Met
        195                 200                 205

Gly Leu Gln Leu Asn Leu Thr Tyr Glu Arg Lys Asp Asn Thr Thr Val
        210                 215                 220

Thr Arg Leu Leu Asn Ile Asn Pro Asn Lys Thr Leu Ala Ser Gly Ser
225                 230                 235                 240

Cys Gly Ala His Leu Val Thr Leu Glu Leu His Ser Glu Gly Ser Thr
                245                 250                 255

Val Leu Leu Phe Gln Phe Gly Met Asn Ala Ser Ser Ser Arg Phe Phe
            260                 265                 270

Leu Gln Gly Ile Gln Leu Asn Thr Thr Leu Pro Asp Ala Arg Asp Pro
        275                 280                 285

Ala Phe Lys Ala Ala Asn Ser Ser Leu Arg Ala Leu Gln Ala Thr Val
        290                 295                 300

Gly Asn Ser Tyr Lys Cys Asn Ala Glu Glu His Val Arg Val Thr Lys
305                 310                 315                 320

Ala Phe Ser Val Asn Ile Phe Lys Val Trp Val Gln Ala Phe Lys Val
                325                 330                 335

Glu Gly Gly Gln Phe Gly Ser Val Glu Glu Cys Leu Leu Asp Glu Asn
            340                 345                 350

Asn Met Ala Ser His His His His His His
        355                 360

<210> SEQ ID NO 30
<211> LENGTH: 358
<212> TYPE: PRT
<213> ORGANISM: Artificial Sequence
<220> FEATURE:
<223> OTHER INFORMATION: protein expression construct

<400> SEQUENCE: 30

Leu Phe Glu Val Lys Asn Asn Gly Thr Thr Cys Ile Met Ala Ser Phe
1               5                   10                  15

Ser Ala Ser Phe Leu Thr Thr Tyr Glu Thr Ala Asn Gly Ser Gln Ile
            20                  25                  30

Val Asn Ile Ser Leu Pro Ala Ser Ala Glu Val Leu Lys Asn Gly Ser
        35                  40                  45

Ser Cys Gly Lys Glu Asn Val Ser Asp Pro Ser Leu Thr Ile Thr Phe
    50                  55                  60

Gly Arg Gly Tyr Leu Leu Thr Leu Asn Phe Thr Arg Asn Ala Thr Arg
65                  70                  75                  80

Tyr Ser Val Gln Leu Met Ser Phe Val Tyr Asn Leu Ser Asp Thr His
                85                  90                  95

Leu Phe Pro Asn Ala Ser Ser Lys Glu Ile Lys Thr Val Glu Ser Ile
            100                 105                 110

Thr Asp Ile Arg Ala Asp Ile Asp Lys Lys Tyr Arg Cys Val Ser Gly
        115                 120                 125

Thr Gln Val His Met Asn Asn Val Thr Val Thr Leu His Asp Ala Thr
    130                 135                 140

Ile Gln Ala Tyr Leu Ser Asn Ser Ser Phe Ser Arg Gly Glu Thr Arg
145                 150                 155                 160
```

-continued

```
Cys Glu Gln Asp Arg Pro Ser Pro Thr Thr Ala Pro Pro Ala Pro Pro
            165                 170                 175

Ser Pro Ser Pro Ser Pro Val Pro Lys Ser Pro Ser Val Asp Lys Tyr
        180                 185                 190

Asn Val Ser Gly Thr Asn Gly Thr Cys Leu Leu Ala Ser Met Gly Leu
        195                 200                 205

Gln Leu Asn Leu Thr Tyr Glu Arg Lys Asp Asn Thr Thr Val Thr Arg
    210                 215                 220

Leu Leu Asn Ile Asn Pro Asn Lys Thr Ser Ala Ser Gly Ser Cys Gly
225                 230                 235                 240

Ala His Leu Val Thr Leu Glu Leu His Ser Glu Gly Thr Thr Val Leu
                245                 250                 255

Leu Phe Gln Phe Gly Met Asn Ala Ser Ser Ser Arg Phe Phe Leu Gln
            260                 265                 270

Gly Ile Gln Leu Asn Thr Ile Leu Pro Asp Ala Arg Asp Pro Ala Phe
        275                 280                 285

Lys Ala Ala Asn Gly Ser Leu Arg Ala Leu Gln Ala Thr Val Gly Asn
        290                 295                 300

Ser Tyr Lys Cys Asn Ala Glu Glu His Val Arg Val Thr Lys Ala Phe
305                 310                 315                 320

Ser Val Asn Ile Phe Lys Val Trp Val Gln Ala Phe Lys Val Glu Gly
                325                 330                 335

Gly Gln Phe Gly Ser Val Glu Glu Cys Leu Leu Asp Glu Asn Ser Met
            340                 345                 350

His His His His His His
        355

<210> SEQ ID NO 31
<211> LENGTH: 358
<212> TYPE: PRT
<213> ORGANISM: Artificial Sequence
<220> FEATURE:
<223> OTHER INFORMATION: protein expression construct

<400> SEQUENCE: 31

Leu Phe Glu Val Lys Asn Asn Gly Thr Thr Cys Ile Met Ala Ser Phe
1               5                   10                  15

Ser Ala Ser Phe Leu Thr Thr Tyr Glu Thr Ala Asn Gly Ser Gln Ile
            20                  25                  30

Val Asn Ile Ser Leu Pro Ala Ser Ala Glu Val Leu Lys Asn Gly Ser
        35                  40                  45

Ser Cys Gly Lys Glu Asn Val Ser Asp Pro Ser Leu Thr Ile Thr Phe
    50                  55                  60

Gly Arg Gly Tyr Leu Leu Thr Leu Asn Phe Thr Lys Asn Thr Thr Arg
65                  70                  75                  80

Tyr Ser Val Gln His Met Tyr Phe Thr Tyr Asn Leu Ser Asp Thr Glu
                85                  90                  95

His Phe Pro Asn Ala Ile Ser Lys Glu Ile Tyr Thr Met Asp Ser Thr
            100                 105                 110

Thr Asp Ile Lys Ala Asp Ile Asn Lys Ala Tyr Arg Cys Val Ser Asp
        115                 120                 125

Ile Arg Val Tyr Met Lys Asn Val Thr Val Val Leu Arg Asp Ala Thr
    130                 135                 140

Ile Gln Ala Tyr Leu Ser Ser Gly Asn Phe Ser Lys Glu Glu Thr His
145                 150                 155                 160
```

-continued

Cys Thr Gln Asp Gly Pro Ser Pro Thr Thr Ala Pro Ala Pro Pro
            165                 170                 175

Ser Pro Ser Pro Ser Pro Val Pro Lys Ser Pro Ser Val Asp Lys Tyr
        180                 185                 190

Asn Val Ser Gly Thr Asn Gly Thr Cys Leu Leu Ala Ser Met Gly Leu
        195                 200                 205

Gln Leu Asn Leu Thr Tyr Glu Arg Lys Asp Asn Thr Thr Val Thr Arg
    210                 215                 220

Leu Leu Asn Ile Asn Pro Asn Lys Thr Ser Ala Ser Gly Ser Cys Gly
225                 230                 235                 240

Ala His Leu Val Thr Leu Glu Leu His Ser Glu Gly Thr Thr Val Leu
            245                 250                 255

Leu Phe Gln Phe Gly Met Asn Ala Ser Ser Ser Arg Phe Phe Leu Gln
            260                 265                 270

Gly Ile Gln Leu Asn Thr Ile Leu Pro Asp Ala Arg Asp Pro Ala Phe
            275                 280                 285

Lys Ala Ala Asn Gly Ser Leu Arg Ala Leu Gln Ala Thr Val Gly Asn
        290                 295                 300

Ser Tyr Lys Cys Asn Ala Glu Glu His Val Arg Val Thr Lys Ala Phe
305                 310                 315                 320

Ser Val Asn Ile Phe Lys Val Trp Val Gln Ala Phe Lys Val Glu Gly
                325                 330                 335

Gly Gln Phe Gly Ser Val Glu Glu Cys Leu Leu Asp Glu Asn Ser Met
            340                 345                 350

His His His His His His
        355

<210> SEQ ID NO 32
<211> LENGTH: 355
<212> TYPE: PRT
<213> ORGANISM: Artificial Sequence
<220> FEATURE:
<223> OTHER INFORMATION: protein expression construct

<400> SEQUENCE: 32

Ala Met Phe Met Val Lys Asn Gly Asn Gly Thr Ala Cys Ile Met Ala
1               5                   10                  15

Asn Phe Ser Ala Ala Phe Ser Val Asn Tyr Asp Thr Lys Ser Gly Pro
            20                  25                  30

Lys Asn Met Thr Phe Asp Leu Pro Ser Asp Ala Thr Val Val Leu Asn
        35                  40                  45

Arg Ser Ser Cys Gly Lys Glu Asn Thr Ser Asp Pro Ser Leu Val Ile
    50                  55                  60

Ala Phe Gly Arg Gly His Thr Leu Thr Leu Asn Phe Thr Arg Asn Ala
65                  70                  75                  80

Thr Arg Tyr Ser Val Gln Leu Met Ser Phe Val Tyr Asn Leu Ser Asp
                85                  90                  95

Thr His Leu Phe Pro Asn Ala Ser Ser Lys Glu Ile Lys Thr Val Glu
            100                 105                 110

Ser Ile Thr Asp Ile Arg Ala Asp Ile Asp Lys Lys Tyr Arg Cys Val
        115                 120                 125

Ser Gly Thr Gln Val His Met Asn Asn Val Thr Val Thr Leu His Asp
    130                 135                 140

Ala Thr Ile Gln Ala Tyr Leu Ser Asn Ser Ser Phe Ser Arg Gly Glu
145                 150                 155                 160

```
Thr Arg Cys Glu Gln Asp Arg Pro Ser Pro Thr Gly Pro Pro Ser
            165                 170                 175
Pro Ser Pro Pro Leu Val Pro Thr Asn Pro Thr Val Ser Lys Tyr Asn
        180                 185                 190
Val Thr Gly Asn Asn Gly Thr Cys Leu Leu Ala Ser Met Ala Leu Gln
        195                 200                 205
Leu Asn Ile Thr Tyr Leu Lys Lys Asp Asn Lys Thr Val Thr Arg Ala
    210                 215                 220
Phe Asn Ile Ser Pro Asn Asp Thr Ser Ser Gly Ser Cys Gly Ile Asn
225                 230                 235                 240
Leu Val Thr Leu Lys Val Glu Asn Lys Asn Arg Ala Leu Glu Leu Gln
                245                 250                 255
Phe Gly Met Asn Ala Ser Ser Ser Leu Phe Phe Leu Gln Gly Val Arg
            260                 265                 270
Leu Asn Met Thr Leu Pro Asp Ala Leu Val Pro Thr Phe Ser Ile Ser
        275                 280                 285
Asn His Ser Leu Lys Ala Leu Gln Ala Thr Val Gly Asn Ser Tyr Lys
    290                 295                 300
Cys Asn Thr Glu Glu His Ile Phe Val Ser Lys Met Leu Ser Leu Asn
305                 310                 315                 320
Val Phe Ser Val Gln Val Gln Ala Phe Lys Val Asp Ser Asp Arg Phe
                325                 330                 335
Gly Ser Val Glu Glu Cys Val Gln Asp Gly Asn Ser Met His His His
            340                 345                 350
His His His
        355

<210> SEQ ID NO 33
<211> LENGTH: 360
<212> TYPE: PRT
<213> ORGANISM: Artificial Sequence
<220> FEATURE:
<223> OTHER INFORMATION: protein expression construct

<400> SEQUENCE: 33

Ala Met Phe Met Val Lys Asn Gly Asn Gly Thr Ala Cys Ile Met Ala
1               5                   10                  15
Asn Phe Ser Ala Ala Phe Ser Val Asn Tyr Asp Thr Lys Ser Gly Pro
            20                  25                  30
Lys Asn Met Thr Phe Asp Leu Pro Ser Asp Ala Thr Val Val Leu Asn
        35                  40                  45
Arg Ser Ser Cys Gly Lys Glu Asn Thr Ser Asp Pro Ser Leu Val Ile
    50                  55                  60
Ala Phe Gly Arg Gly His Thr Leu Thr Leu Asn Phe Thr Arg Asn Ala
65                  70                  75                  80
Thr Arg Tyr Ser Val Gln Leu Met Ser Phe Val Tyr Asn Leu Ser Asp
                85                  90                  95
Thr His Leu Phe Pro Asn Ala Ser Ser Lys Glu Ile Lys Thr Val Glu
            100                 105                 110
Ser Ile Thr Asp Ile Arg Ala Asp Ile Asp Lys Lys Tyr Arg Cys Val
        115                 120                 125
Ser Gly Thr Gln Val His Met Asn Asn Val Thr Val Thr Leu His Asp
    130                 135                 140
Ala Thr Ile Gln Ala Tyr Leu Ser Asn Ser Ser Phe Ser Arg Gly Glu
145                 150                 155                 160
```

```
Thr Arg Cys Glu Gln Asp Arg Pro Ser Pro Thr Thr Ala Pro Pro Ala
                165                 170                 175

Pro Pro Ser Pro Ser Pro Ser Pro Val Pro Lys Ser Pro Ser Val Asp
            180                 185                 190

Lys Tyr Asn Val Ser Gly Thr Asn Gly Thr Cys Leu Leu Ala Ser Met
        195                 200                 205

Gly Leu Gln Leu Asn Leu Thr Tyr Glu Arg Lys Asp Asn Thr Thr Val
    210                 215                 220

Thr Arg Leu Leu Asn Ile Asn Pro Asn Lys Thr Ser Ala Ser Gly Ser
225                 230                 235                 240

Cys Gly Ala His Leu Val Thr Leu Glu Leu His Ser Glu Gly Thr Thr
                245                 250                 255

Val Leu Leu Phe Gln Phe Gly Met Asn Ala Ser Ser Ser Arg Phe Phe
            260                 265                 270

Leu Gln Gly Ile Gln Leu Asn Thr Ile Leu Pro Asp Ala Leu Val Pro
        275                 280                 285

Thr Phe Ser Ile Ser Asn His Ser Leu Lys Ala Leu Gln Ala Thr Val
    290                 295                 300

Gly Asn Ser Tyr Lys Cys Asn Thr Glu Glu His Ile Phe Val Ser Lys
305                 310                 315                 320

Met Leu Ser Leu Asn Val Phe Ser Val Gln Val Gln Ala Phe Lys Val
                325                 330                 335

Asp Ser Asp Arg Phe Gly Ser Val Glu Glu Cys Val Gln Asp Gly Asn
            340                 345                 350

Ser Met His His His His His His
        355                 360

<210> SEQ ID NO 34
<211> LENGTH: 353
<212> TYPE: PRT
<213> ORGANISM: Artificial Sequence
<220> FEATURE:
<223> OTHER INFORMATION: protein expression construct

<400> SEQUENCE: 34

Leu Phe Glu Val Lys Asn Asn Gly Thr Thr Cys Ile Met Ala Ser Phe
1               5                   10                  15

Ser Ala Ser Phe Leu Thr Thr Tyr Glu Thr Ala Asn Gly Ser Gln Ile
            20                  25                  30

Val Asn Ile Ser Leu Pro Ala Ser Ala Glu Val Leu Lys Asn Gly Ser
        35                  40                  45

Ser Cys Gly Lys Glu Asn Val Ser Asp Pro Ser Leu Thr Ile Thr Phe
    50                  55                  60

Gly Arg Gly Tyr Leu Leu Thr Leu Asn Phe Thr Lys Asn Thr Thr Arg
65                  70                  75                  80

Tyr Ser Val Gln His Met Tyr Phe Thr Tyr Asn Leu Ser Asp Thr Glu
                85                  90                  95

His Phe Pro Asn Ala Ile Ser Lys Glu Ile Tyr Thr Met Asp Ser Thr
            100                 105                 110

Thr Asp Ile Lys Ala Asp Ile Asn Lys Ala Tyr Arg Cys Val Ser Asp
        115                 120                 125

Ile Arg Val Tyr Met Lys Asn Val Thr Val Val Leu Arg Asp Ala Thr
    130                 135                 140

Ile Gln Ala Tyr Leu Ser Ser Gly Asn Phe Ser Lys Glu Glu Thr His
145                 150                 155                 160
```

```
Cys Thr Gln Asp Gly Pro Ser Pro Thr Thr Gly Pro Pro Ser Pro Ser
                165                 170                 175

Pro Pro Leu Val Pro Thr Asn Pro Thr Val Ser Lys Tyr Asn Val Thr
            180                 185                 190

Gly Asn Asn Gly Thr Cys Leu Leu Ala Ser Met Ala Leu Gln Leu Asn
            195                 200                 205

Ile Thr Tyr Leu Lys Lys Asp Asn Lys Thr Val Thr Arg Ala Phe Asn
    210                 215                 220

Ile Ser Pro Asn Asp Thr Ser Ser Gly Ser Cys Gly Ile Asn Leu Val
225                 230                 235                 240

Thr Leu Lys Val Glu Asn Lys Asn Arg Ala Leu Glu Leu Gln Phe Gly
                245                 250                 255

Met Asn Ala Ser Ser Ser Leu Phe Phe Leu Gln Gly Val Arg Leu Asn
            260                 265                 270

Met Thr Leu Pro Asp Ala Leu Val Pro Thr Phe Ser Ile Ser Asn His
            275                 280                 285

Ser Leu Lys Ala Leu Gln Ala Thr Val Gly Asn Ser Tyr Lys Cys Asn
    290                 295                 300

Thr Glu Glu His Ile Phe Val Ser Lys Met Leu Ser Leu Asn Val Phe
305                 310                 315                 320

Ser Val Gln Val Gln Ala Phe Lys Val Asp Ser Asp Arg Phe Gly Ser
                325                 330                 335

Val Glu Glu Cys Val Gln Asp Gly Asn Ser Met His His His His His
            340                 345                 350

His

<210> SEQ ID NO 35
<211> LENGTH: 213
<212> TYPE: PRT
<213> ORGANISM: Artificial Sequence
<220> FEATURE:
<223> OTHER INFORMATION: antibody fragment

<400> SEQUENCE: 35

Asp Ile Gln Met Thr Gln Ser Pro Pro Ser Leu Ser Ala Ser Leu Gly
1               5                   10                  15

Gly Lys Val Thr Ile Thr Cys Lys Ala Ser Gln Asp Ile Asp Arg Tyr
            20                  25                  30

Met Ala Trp Tyr Gln Asp Lys Pro Gly Lys Pro Arg Leu Leu Ile
            35                  40                  45

His Asp Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
```

```
                    165                 170                 175
Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 36
<211> LENGTH: 448
<212> TYPE: PRT
<213> ORGANISM: Artificial Sequence
<220> FEATURE:
<223> OTHER INFORMATION: antibody fragment

<400> SEQUENCE: 36

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Ile His Trp Val Lys Lys Ser Pro Gly Gln Gly Leu Glu Trp Ile
        35                  40                  45

Gly Ala Ile Tyr Pro Gly Asn Gly Asp Ala Pro Tyr Ser Gln Lys Phe
    50                  55                  60

Lys Asp Lys Ala Thr Leu Thr Ala Asp Lys Ser Ser Thr Thr Tyr
65                  70                  75                  80

Met Gln Leu Ser Arg Leu Thr Ser Glu Asp Ser Ala Val Tyr Tyr Cys
                85                  90                  95

Val Arg Ala Asn Trp Asp Val Ala Phe Ala Tyr Trp Gly Gln Gly Thr
            100                 105                 110

Leu Val Ser Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
```

```
            305                 310                 315                 320
Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
                340                 345                 350

Pro Pro Pro Glu Glu Met Thr Lys Lys Gln Val Thr Leu Thr Cys
                355                 360                 365

Met Val Thr Asp Phe Met Pro Glu Asp Ile Tyr Val Glu Trp Thr Asn
                370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
                420                 425                 430

Leu His Asn His His Thr Thr Lys Ser Phe Ser Arg Thr Pro Gly Lys
                435                 440                 445

<210> SEQ ID NO 37
<211> LENGTH: 218
<212> TYPE: PRT
<213> ORGANISM: Artificial Sequence
<220> FEATURE:
<223> OTHER INFORMATION: antibody fragment

<400> SEQUENCE: 37

Asn Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Ile Asn
                20                  25                  30

Gly Asn Thr Phe Met His Trp Tyr Gln Gln Lys Pro Gly Gln Ser Pro
            35                  40                  45

Lys Leu Val Ile Tyr Ala Ala Ser Asn Ile Glu Ser Gly Val Pro Ala
    50                  55                  60

Arg Phe Ser Gly Ser Gly Ser Ser Thr Asp Phe Thr Phe Thr Ile Asp
65                  70                  75                  80

Pro Val Glu Ala Asp Asp Val Ala Thr Tyr Tyr Cys Gln Gln Asn Ile
                85                  90                  95

Glu Asp Pro Trp Thr Phe Gly Gly Gly Thr Lys Val Glu Ile Lys Arg
                100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
                195                 200                 205

Ile Val Lys Ser Phe Asn Arg Asn Glu Cys
                210                 215
```

```
<210> SEQ ID NO 38
<211> LENGTH: 446
<212> TYPE: PRT
<213> ORGANISM: Artificial Sequence
<220> FEATURE:
<223> OTHER INFORMATION: antibody fragment

<400> SEQUENCE: 38
```

| | | | | | | | | | | | | | | | |
|---|---|---|---|---|---|---|---|---|---|---|---|---|---|---|---|
| Gln | Val | Gln | Leu | Gln | Gln | Ser | Ala | Ala | Glu | Leu | Ala | Arg | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Thr | Met | His | Trp | Val | Lys | Gln | Arg | Pro | Gly | Gln | Gly | Leu | Glu | Trp | Ile |
| | | 35 | | | | | 40 | | | | | 45 | | | |
| Gly | Tyr | Phe | Asn | Pro | Ser | Ser | Gly | Tyr | Pro | Glu | Tyr | Asn | Gln | Lys | Phe |
| 50 | | | | | 55 | | | | | 60 | | | | | |
| Lys | Asp | Lys | Thr | Thr | Leu | Thr | Ala | Asp | Lys | Ser | Ser | Asn | Thr | Ala | Phe |
| 65 | | | | 70 | | | | | 75 | | | | | 80 | |
| Ile | Gln | Leu | Asn | Ser | Leu | Thr | Ser | Glu | Asp | Ser | Ala | Val | Tyr | Tyr | Cys |
| | | | | 85 | | | | | 90 | | | | | 95 | |
| Ser | Arg | Gly | Tyr | Tyr | Gly | Ser | Arg | Gly | Tyr | Ala | Leu | Asp | Phe | Trp |
| | | | 100 | | | | | 105 | | | | | 110 | | |
| Gly | Gln | Gly | Ala | Ser | Val | Thr | Val | Ser | Ser | Ala | Lys | Thr | Thr | Pro | Pro |
| | | 115 | | | | | 120 | | | | | 125 | | | |
| Ser | Val | Tyr | Pro | Leu | Ala | Pro | Gly | Ser | Ala | Ala | Gln | Thr | Asn | Ser | Met |
| | 130 | | | | | 135 | | | | | 140 | | | | |
| Val | Thr | Leu | Gly | Cys | Leu | Val | Lys | Gly | Tyr | Phe | Pro | Glu | Pro | Val | Thr |
| 145 | | | | | 150 | | | | | 155 | | | | | 160 |
| Val | Thr | Trp | Asn | Ser | Gly | Ser | Leu | Ser | Ser | Gly | Val | His | Thr | Phe | Pro |
| | | | | 165 | | | | | 170 | | | | | 175 | |
| Ala | Val | Leu | Gln | Ser | Asp | Leu | Tyr | Thr | Leu | Ser | Ser | Ser | Val | Thr | Val |
| | | | 180 | | | | | 185 | | | | | 190 | | |
| Pro | Ser | Ser | Thr | Trp | Pro | Ser | Glu | Thr | Val | Thr | Cys | Asn | Val | Ala | His |
| | | 195 | | | | | 200 | | | | | 205 | | | |
| Pro | Ala | Ser | Ser | Thr | Lys | Val | Asp | Lys | Lys | Ile | Val | Pro | Arg | Asp | Cys |
| | 210 | | | | | 215 | | | | | 220 | | | | |
| Gly | Cys | Lys | Pro | Cys | Ile | Cys | Thr | Val | Pro | Glu | Val | Ser | Ser | Val | Phe |
| 225 | | | | | 230 | | | | | 235 | | | | | 240 |
| Ile | Phe | Pro | Pro | Lys | Pro | Lys | Asp | Val | Leu | Thr | Ile | Thr | Leu | Thr | Pro |
| | | | | 245 | | | | | 250 | | | | | 255 | |
| Lys | Val | Thr | Cys | Val | Val | Val | Asp | Ile | Ser | Lys | Asp | Asp | Pro | Glu | Val |
| | | | 260 | | | | | 265 | | | | | 270 | | |
| Gln | Phe | Ser | Trp | Phe | Val | Asp | Asp | Val | Glu | Val | His | Thr | Ala | Gln | Thr |
| | | 275 | | | | | 280 | | | | | 285 | | | |
| Gln | Pro | Arg | Glu | Glu | Gln | Phe | Asn | Ser | Thr | Phe | Arg | Ser | Val | Ser | Glu |
| | 290 | | | | | 295 | | | | | 300 | | | | |
| Leu | Pro | Ile | Met | His | Gln | Asp | Trp | Leu | Asn | Gly | Lys | Glu | Phe | Lys | Cys |
| 305 | | | | | 310 | | | | | 315 | | | | | 320 |
| Arg | Val | Asn | Ser | Ala | Ala | Phe | Pro | Ala | Pro | Ile | Glu | Lys | Thr | Ile | Ser |
| | | | | 325 | | | | | 330 | | | | | 335 | |
| Lys | Thr | Lys | Gly | Arg | Pro | Lys | Ala | Pro | Gln | Val | Tyr | Thr | Ile | Pro | Pro |
| | | | 340 | | | | | 345 | | | | | 350 | | |
| Pro | Lys | Glu | Gln | Met | Ala | Lys | Asp | Lys | Val | Ser | Leu | Thr | Cys | Met | Ile |
| | | 355 | | | | | 360 | | | | | 365 | | | |
| Thr | Asp | Phe | Phe | Pro | Glu | Asp | Ile | Thr | Val | Glu | Trp | Gln | Trp | Asn | Gly |

```
                    370                 375                 380
Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430

Asn His His Thr Glu Lys Ser Leu Ser His Ser Pro Gly Lys
                435                 440                 445

<210> SEQ ID NO 39
<211> LENGTH: 415
<212> TYPE: PRT
<213> ORGANISM: Macaca fascicularis

<400> SEQUENCE: 39

Met Ala Ala Pro Gly Ser Ala Arg Arg Ser Leu Leu Leu Leu Leu Leu
1               5                   10                  15

Leu Leu Gly Leu Thr His Cys Ala Ser Ala Ala Met Phe Ile Val Lys
                20                  25                  30

Asn Gly Asn Gly Thr Ala Cys Ile Met Ala Asn Phe Ser Ala Ala Phe
            35                  40                  45

Ser Val Asn Tyr Asp Thr Lys Ser Gly Pro Lys Asn Met Thr Phe Asp
50                  55                  60

Leu Pro Ser Asp Ala Lys Val Val Leu Asn Ser Ser Cys Gly Lys
65                  70                  75                  80

Glu Asn Thr Ser Asp Pro Ser Leu Val Ile Ala Phe Gly Arg Gly Gln
                85                  90                  95

Thr Leu Thr Leu Asn Phe Thr Arg Asn Ala Thr Arg Tyr Ser Val Gln
                100                 105                 110

Leu Met Ser Phe Val Tyr Asn Leu Ser Asp Thr His Leu Phe Pro Asn
            115                 120                 125

Ala Ser Ser Lys Glu Ile Lys Thr Val Glu Ser Ile Thr Asp Ile Arg
130                 135                 140

Ala Asp Ile Asp Lys Lys Tyr Arg Cys Val Ser Gly Thr Gln Val His
145                 150                 155                 160

Met Asn Asn Val Thr Val Thr Leu His Asp Ala Thr Ile Gln Ala Tyr
                165                 170                 175

Leu Ser Asn Ser Ser Phe Ser Arg Glu Glu Thr Arg Cys Glu Gln Asp
            180                 185                 190

Arg Pro Ser Pro Thr Thr Ala Pro Ala Pro Pro Ser Pro Ser Pro
            195                 200                 205

Ser Pro Val Pro Glu Ser Pro Ser Val Asp Lys Tyr Asn Val Ser Gly
            210                 215                 220

Thr Asn Gly Thr Cys Leu Leu Ala Ser Met Gly Leu Gln Leu Asn Leu
225                 230                 235                 240

Thr Tyr Glu Arg Lys Asp Asn Thr Thr Val Thr Arg Leu Leu Asn Ile
                245                 250                 255

Asn Pro Asn Lys Thr Leu Ala Ser Gly Ser Cys Gly Ala His Leu Val
            260                 265                 270

Thr Leu Glu Leu His Ser Glu Gly Ser Thr Val Leu Leu Phe Gln Phe
            275                 280                 285

Gly Met Asn Ala Ser Ser Ser Arg Phe Phe Leu Gln Gly Ile Gln Leu
            290                 295                 300
```

```
Asn Thr Thr Leu Pro Asp Ala Arg Asp Pro Ala Phe Lys Ala Ala Asn
305                 310                 315                 320

Ser Ser Leu Arg Ala Leu Gln Ala Thr Val Gly Asn Ser Tyr Lys Cys
            325                 330                 335

Asn Ala Glu Glu His Val Arg Val Thr Lys Ala Phe Ser Val Asn Ile
            340                 345                 350

Phe Lys Val Trp Val Gln Ala Phe Lys Val Glu Gly Gln Phe Gly
            355                 360                 365

Ser Val Glu Glu Cys Leu Leu Asp Glu Asn Asn Met Leu Ile Pro Ile
        370                 375                 380

Ala Val Gly Gly Ala Leu Ala Gly Leu Val Leu Ile Val Leu Ile Ala
385                 390                 395                 400

Tyr Leu Val Gly Arg Lys Arg Ser His Ala Gly Tyr Gln Thr Ile
                405                 410                 415

<210> SEQ ID NO 40
<211> LENGTH: 357
<212> TYPE: PRT
<213> ORGANISM: Artificial Sequence
<220> FEATURE:
<223> OTHER INFORMATION: Protein expression construct human LAMP2
      (AA29-375)

<400> SEQUENCE: 40

Leu Glu Leu Asn Leu Thr Asp Ser Glu Asn Ala Thr Cys Leu Tyr Ala
1               5                   10                  15

Lys Trp Gln Met Asn Phe Thr Val Arg Tyr Glu Thr Thr Asn Lys Thr
            20                  25                  30

Tyr Lys Thr Val Thr Ile Ser Asp His Gly Thr Val Thr Tyr Asn Gly
        35                  40                  45

Ser Ile Cys Gly Asp Asp Gln Asn Gly Pro Lys Ile Ala Val Gln Phe
    50                  55                  60

Gly Pro Gly Phe Ser Trp Ile Ala Asn Phe Thr Lys Ala Ala Ser Thr
65                  70                  75                  80

Tyr Ser Ile Asp Ser Val Ser Phe Ser Tyr Asn Thr Gly Asp Asn Thr
                85                  90                  95

Thr Phe Pro Asp Ala Glu Asp Lys Gly Ile Leu Thr Val Asp Glu Leu
            100                 105                 110

Leu Ala Ile Arg Ile Pro Leu Asn Asp Leu Phe Arg Cys Asn Ser Leu
        115                 120                 125

Ser Thr Leu Glu Lys Asn Asp Val Val Gln His Tyr Trp Asp Val Leu
130                 135                 140

Val Gln Ala Phe Val Gln Asn Gly Thr Val Ser Thr Asn Glu Phe Leu
145                 150                 155                 160

Cys Asp Lys Asp Lys Thr Ser Thr Val Ala Pro Thr Ile His Thr Thr
                165                 170                 175

Val Pro Ser Pro Thr Thr Thr Pro Thr Pro Lys Glu Lys Pro Glu Ala
            180                 185                 190

Gly Thr Tyr Ser Val Asn Asn Gly Asn Asp Thr Cys Leu Leu Ala Thr
        195                 200                 205

Met Gly Leu Gln Leu Asn Ile Thr Gln Asp Lys Val Ala Ser Val Ile
    210                 215                 220

Asn Ile Asn Pro Asn Thr Thr His Ser Thr Gly Ser Cys Arg Ser His
225                 230                 235                 240

Thr Ala Leu Leu Arg Leu Asn Ser Ser Thr Ile Lys Tyr Leu Asp Phe
                245                 250                 255
```

```
Val Phe Ala Val Lys Asn Glu Asn Arg Phe Tyr Leu Lys Glu Val Asn
            260                 265                 270

Ile Ser Met Tyr Leu Val Asn Gly Ser Val Phe Ser Ile Ala Asn Asn
        275                 280                 285

Asn Leu Ser Tyr Trp Asp Ala Pro Leu Gly Ser Ser Tyr Met Cys Asn
    290                 295                 300

Lys Glu Gln Thr Val Ser Val Ser Gly Ala Phe Gln Ile Asn Thr Phe
305                 310                 315                 320

Asp Leu Arg Val Gln Pro Phe Asn Val Thr Gln Gly Lys Tyr Ser Thr
                325                 330                 335

Ala Gln Asp Cys Ser Ala Asp Asp Asn Phe His His His His
            340                 345                 350

His His His His His
        355
```

<210> SEQ ID NO 41
<211> LENGTH: 410
<212> TYPE: PRT
<213> ORGANISM: Homo sapiens

<400> SEQUENCE: 41

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
                20                  25                  30

Leu Thr Asp Ser Glu Asn Ala Thr Cys Leu Tyr Ala Lys Trp Gln Met
            35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
    115                 120                 125

Ala Glu Asp Lys Gly Ile Leu Thr Val Asp Glu Leu Leu Ala Ile Arg
            130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
            195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
```

```
                 260                 265                 270
Arg Leu Asn Ser Ser Thr Ile Lys Tyr Leu Asp Phe Val Phe Ala Val
            275                 280                 285
Lys Asn Glu Asn Arg Phe Tyr Leu Lys Glu Val Asn Ile Ser Met Tyr
        290                 295                 300
Leu Val Asn Gly Ser Val Phe Ser Ile Ala Asn Asn Leu Ser Tyr
305                 310                 315                 320
Trp Asp Ala Pro Leu Gly Ser Ser Tyr Met Cys Asn Lys Glu Gln Thr
                325                 330                 335
Val Ser Val Ser Gly Ala Phe Gln Ile Asn Thr Phe Asp Leu Arg Val
            340                 345                 350
Gln Pro Phe Asn Val Thr Gln Gly Lys Tyr Ser Thr Ala Gln Asp Cys
        355                 360                 365
Ser Ala Asp Asp Asn Phe Leu Val Pro Ile Ala Val Gly Ala Ala
370                 375                 380
Leu Ala Gly Val Leu Ile Leu Val Leu Leu Ala Tyr Phe Ile Gly Leu
385                 390                 395                 400
Lys His His His Ala Gly Tyr Glu Gln Phe
                405                 410

<210> SEQ ID NO 42
<211> LENGTH: 122
<212> TYPE: PRT
<213> ORGANISM: Artificial Sequence
<220> FEATURE:
<223> OTHER INFORMATION: VH MAb3

<400> SEQUENCE: 42

Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Ile Phe Thr Asn Tyr
            20                  25                  30
Gly Met Asn Trp Val Lys Gln Ala Pro Gly Lys Gly Leu Lys Trp Met
        35                  40                  45
Gly Trp Ile Asn Thr Tyr Thr Gly Glu Ser Arg Tyr Ala Asp Asp Phe
    50                  55                  60
Lys Gly Arg Phe Ala Leu Ser Leu Glu Thr Ser Ala Ser Thr Ala Tyr
65                  70                  75                  80
Leu Gln Ile Asn Asn Leu Glu Asn Glu Asp Met Ala Thr Tyr Phe Cys
                85                  90                  95
Ala Arg Glu Asp Tyr Tyr Gly Asn Ser Pro Trp Phe Phe Asp Val Trp
            100                 105                 110
Gly Ala Gly Thr Thr Val Thr Val Ser Ser
        115                 120

<210> SEQ ID NO 43
<211> LENGTH: 8
<212> TYPE: PRT
<213> ORGANISM: Artificial Sequence
<220> FEATURE:
<223> OTHER INFORMATION: CDR1-H MAb3

<400> SEQUENCE: 43

Gly Tyr Ile Phe Thr Asn Tyr Gly
1               5

<210> SEQ ID NO 44
<211> LENGTH: 8
```

```
<212> TYPE: PRT
<213> ORGANISM: Artificial Sequence
<220> FEATURE:
<223> OTHER INFORMATION: CDR2-H MAb3

<400> SEQUENCE: 44

Ile Asn Thr Tyr Thr Gly Glu Ser
1               5

<210> SEQ ID NO 45
<211> LENGTH: 15
<212> TYPE: PRT
<213> ORGANISM: Artificial Sequence
<220> FEATURE:
<223> OTHER INFORMATION: CDR3H MAb3

<400> SEQUENCE: 45

Ala Arg Glu Asp Tyr Tyr Gly Asn Ser Pro Trp Phe Phe Asp Val
1               5                   10                  15

<210> SEQ ID NO 46
<211> LENGTH: 107
<212> TYPE: PRT
<213> ORGANISM: Artificial Sequence
<220> FEATURE:
<223> OTHER INFORMATION: VL MAb3

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Asn Ala Ser Gln Gly Ile Asn Lys Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Asn Asn Leu Glu Pro
65                  70                  75                  80

Glu Asp Ile Ala Thr Tyr Tyr Cys Gln Gln Tyr Thr Lys Leu Pro Phe
                85                  90                  95

Thr Phe Gly Ser Gly Thr Lys Leu Glu Ile Lys
            100                 105

<210> SEQ ID NO 47
<211> LENGTH: 6
<212> TYPE: PRT
<213> ORGANISM: Artificial Sequence
<220> FEATURE:
<223> OTHER INFORMATION: CDR1-L MAb3 154L4

<400> SEQUENCE: 47

Gln Gly Ile Asn Lys Tyr
1               5

<210> SEQ ID NO 48
<211> LENGTH: 9
<212> TYPE: PRT
<213> ORGANISM: Artificial Sequence
<220> FEATURE:
<223> OTHER INFORMATION: CDR3-L MAb3

<400> SEQUENCE: 48

Gln Gln Tyr Thr Lys Leu Pro Phe Thr
1               5
```

```
<210> SEQ ID NO 49
<211> LENGTH: 451
<212> TYPE: PRT
<213> ORGANISM: Artificial Sequence
<220> FEATURE:
<223> OTHER INFORMATION: HC chMAb3

<400> SEQUENCE: 49

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Ser Arg Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Ile Asn Asn Leu Glu Asn Glu Asp Met Ala Thr Tyr Phe Cys
                85                  90                  95

Ala Arg Glu Asp Tyr Tyr Gly Asn Ser Pro Trp Phe Phe Asp Val Trp
            100                 105                 110

Gly Ala Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
        450

<210> SEQ ID NO 50
<211> LENGTH: 214
<212> TYPE: PRT
<213> ORGANISM: Artificial Sequence
<220> FEATURE:
<223> OTHER INFORMATION: LC chMAb3

<400> SEQUENCE: 50

Asp Ile Gln Met Thr Gln Thr Thr Ser Ser Leu Ser Ala Ser Leu Gly
1               5                   10                  15

Asp Arg Val Thr Ile Ser Cys Asn Ala Ser Gln Gly Ile Asn Lys Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Asn Asn Leu Glu Pro
65                  70                  75                  80

Glu Asp Ile Ala Thr Tyr Tyr Cys Gln Gln Tyr Thr Lys Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 107
<212> TYPE: PRT
<213> ORGANISM: Artificial Sequence
<220> FEATURE:
<223> OTHER INFORMATION: VL MAb3 R24R93
```

<400> SEQUENCE: 51

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Gly Ile Asn Lys Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
50                  55                  60

Ser Gly Ser Gly Thr Asp Tyr Ser Leu Thr Ile Asn Asn Leu Glu Pro
65                  70                  75                  80

Glu Asp Ile Ala Thr Tyr Tyr Cys Gln Gln Tyr Thr Arg Leu Pro Phe
                85                  90                  95

Thr Phe Gly Ser Gly Thr Lys Leu Glu Ile Lys
            100                 105
```

<210> SEQ ID NO 52
<211> LENGTH: 9
<212> TYPE: PRT
<213> ORGANISM: Artificial Sequence
<220> FEATURE:
<223> OTHER INFORMATION: CDR3-L MAb3 R24R93

<400> SEQUENCE: 52

```
Gln Gln Tyr Thr Arg Leu Pro Phe Thr
1               5
```

<210> SEQ ID NO 53
<211> LENGTH: 118
<212> TYPE: PRT
<213> ORGANISM: Artificial Sequence
<220> FEATURE:
<223> OTHER INFORMATION: Antibody fragment

<400> SEQUENCE: 53

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asn Tyr
            20                  25                  30

Asn Ile His Trp Val Lys Lys Ser Pro Gly Gln Gly Leu Glu Trp Ile
        35                  40                  45

Gly Ala Ile Tyr Pro Gly Asn Gly Asp Ala Pro Tyr Ser Gln Lys Phe
50                  55                  60

Gln Gly Lys Ala Thr Leu Thr Ala Asp Thr Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Val Arg Ala Asn Trp Asp Val Ala Phe Ala Tyr Trp Gly Gln Gly Thr
            100                 105                 110

Leu Val Thr Val Ser Ser
        115
```

<210> SEQ ID NO 54
<211> LENGTH: 118
<212> TYPE: PRT
<213> ORGANISM: Artificial Sequence
<220> FEATURE:
<223> OTHER INFORMATION: Antibody fragment

<400> SEQUENCE: 54

Gln Val Gln Leu Val Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Ile His Trp Val Lys Lys Ser Pro Gly Gln Gly Leu Glu Trp Ile
        35                  40                  45

Gly Ala Ile Tyr Pro Gly Asn Gly Asp Ala Pro Tyr Ser Gln Lys Phe
    50                  55                  60

Gln Asp Arg Ala Thr Leu Thr Ala Asp Thr Ser Ser Thr Thr Tyr
65                  70                  75                  80

Met Glu Leu Ser Ser Leu Thr Ser Glu Asp Ser Ala Val Tyr Tyr Cys
                85                  90                  95

Val Arg Ala Asn Trp Asp Val Ala Phe Ala Tyr Trp Gly Gln Gly Thr
            100                 105                 110

Leu Val Ser Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Antibody fragment

<400> SEQUENCE: 55

Gln Val Gln Leu Val Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Ile His Trp Val Arg Gln Ala Pro Gly Gln Gly Leu Glu Trp Ile
        35                  40                  45

Gly Ala Ile Tyr Pro Gly Asn Gly Asp Ala Pro Tyr Ala Gln Lys Phe
    50                  55                  60

Gln Gly Arg Ala Thr Leu Thr Ala Asp Thr Ser Ser Thr Thr Tyr
65                  70                  75                  80

Met Glu Leu Ser Ser Leu Thr Ser Glu Asp Thr Ala Val Tyr Tyr Cys
                85                  90                  95

Val Arg Ala Asn Trp Asp Val Ala Phe Ala Tyr Trp Gly Gln Gly Thr
            100                 105                 110

Leu Val Thr Val Ser Ser
        115

<210> SEQ ID NO 56
<211> LENGTH: 106
<212> TYPE: PRT
<213> ORGANISM: Artificial Sequence
<220> FEATURE:
<223> OTHER INFORMATION: Antibody fragment

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Arg Tyr
            20                  25                  30

Met Ala Trp Tyr Gln Asp Lys Pro Gly Lys Ala Pro Arg Leu Leu Ile
        35                  40                  45

His Asp Thr Ser Thr Leu Gln Ser Gly Val Pro Ser Arg Phe Ser Gly

```
                50                  55                  60
Ser Gly Ser Gly Arg Asp Tyr Thr Leu Thr Ile Ser Asn Leu Glu Pro
 65                  70                  75                  80

Glu Asp Phe Ala Thr Tyr Tyr Cys Leu Gln Tyr Asp Asn Leu Trp Thr
                    85                  90                  95

Phe Gly Gly Gly Thr Lys Val Glu Ile Lys
                100                 105

<210> SEQ ID NO 57
<211> LENGTH: 106
<212> TYPE: PRT
<213> ORGANISM: Artificial Sequence
<220> FEATURE:
<223> OTHER INFORMATION: Antibody fragment

<400> SEQUENCE: 57

Asp Ile Gln Met Thr Gln Ser Pro Pro Ser Leu Ser Ala Ser Val Gly
  1               5                  10                  15

Gly Lys Val Thr Ile Thr Cys Lys Ala Ser Gln Asp Ile Asp Arg Tyr
                 20                  25                  30

Met Ala Trp Tyr Gln Asp Lys Pro Gly Lys Gly Pro Lys Leu Leu Ile
             35                  40                  45

His Asp Thr Ser Thr Leu Gln Pro Gly Ile Pro Ser Arg Phe Ser Gly
         50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Trp Thr
                    85                  90                  95

Phe Gly Gly Gly Thr Lys Leu Glu Ile Lys
                100                 105

<210> SEQ ID NO 58
<211> LENGTH: 106
<212> TYPE: PRT
<213> ORGANISM: Artificial Sequence
<220> FEATURE:
<223> OTHER INFORMATION: Antibody fragment

<400> SEQUENCE: 58

Asp Ile Gln Met Thr Gln Ser Pro Ser Ser Leu Ser Ala Ser Val Gly
  1               5                  10                  15

Gly Lys Val Thr Ile Thr Cys Lys Ala Ser Gln Asp Ile Asp Arg Tyr
                 20                  25                  30

Met Ala Trp Tyr Gln Gln Lys Pro Gly Lys Gly Pro Lys Leu Leu Ile
             35                  40                  45

His Asp Thr Ser Thr Leu Gln Pro Gly Val Pro Ser Arg Phe Ser Gly
         50                  55                  60

Ser Gly Ser Gly Arg Asp Tyr Ser Leu Thr Ile Ser Ser Leu Glu Pro
 65                  70                  75                  80

Glu Asp Ile Ala Thr Tyr Tyr Cys Leu Gln Tyr Asp Asn Leu Trp Thr
                    85                  90                  95

Phe Gly Gly Gly Thr Lys Leu Glu Ile Lys
                100                 105

<210> SEQ ID NO 59
<211> LENGTH: 213
<212> TYPE: PRT
<213> ORGANISM: Artificial Sequence
<220> FEATURE:
```

<223> OTHER INFORMATION: Antibody fragment

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Arg Tyr
            20                  25                  30

Met Ala Trp Tyr Gln Asp Lys Pro Gly Lys Ala Pro Arg Leu Leu Ile
        35                  40                  45

His Asp Thr Ser Thr Leu Gln Ser Gly Val Pro Ser Arg Phe Ser Gly
    50                  55                  60

Ser Gly Ser Gly Arg Asp Tyr Thr Leu Thr Ile Ser Asn Leu Glu Pro
65                  70                  75                  80

Glu Asp Phe Ala Thr Tyr Tyr Cys Leu Gln Tyr Asp Asn Leu Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 60
<211> LENGTH: 447
<212> TYPE: PRT
<213> ORGANISM: Artificial Sequence
<220> FEATURE:
<223> OTHER INFORMATION: Antibody fragment

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asn Tyr
            20                  25                  30

Asn Ile His Trp Val Lys Lys Ser Pro Gly Gln Gly Leu Glu Trp Ile
        35                  40                  45

Gly Ala Ile Tyr Pro Gly Asn Gly Asp Ala Pro Tyr Ser Gln Lys Phe
    50                  55                  60

Gln Gly Lys Ala Thr Leu Thr Ala Asp Thr Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Val Arg Ala Asn Trp Asp Val Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

```
Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 61
<211> LENGTH: 213
<212> TYPE: PRT
<213> ORGANISM: Artificial Sequence
<220> FEATURE:
<223> OTHER INFORMATION: Antibody fragment

<400> SEQUENCE: 61

Asp Ile Gln Met Thr Gln Ser Pro Pro Ser Leu Ser Ala Ser Val Gly
1               5                   10                  15

Gly Lys Val Thr Ile Thr Cys Lys Ala Ser Gln Asp Ile Asp Arg Tyr
            20                  25                  30

Met Ala Trp Tyr Gln Asp Lys Pro Gly Lys Gly Pro Lys Leu Leu Ile
        35                  40                  45
```

His Asp Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Trp Thr
                 85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 62
<211> LENGTH: 447
<212> TYPE: PRT
<213> ORGANISM: Artificial Sequence
<220> FEATURE:
<223> OTHER INFORMATION: Antibody fragment

<400> SEQUENCE: 62

Gln Val Gln Leu Val Gln Ser Gly Ala Glu Leu Val Lys Pro Gly Ala
 1               5                  10                  15

Ser Val Lys Met Ser Cys Lys Ala Ser Gly Tyr Ile Phe Thr Asn Tyr
             20                  25                  30

Asn Ile His Trp Val Lys Lys Ser Pro Gly Gln Gly Leu Glu Trp Ile
         35                  40                  45

Gly Ala Ile Tyr Pro Gly Asn Gly Asp Ala Pro Tyr Ser Gln Lys Phe
     50                  55                  60

Gln Asp Arg Ala Thr Leu Thr Ala Asp Thr Ser Ser Ser Thr Thr Tyr
 65                  70                  75                  80

Met Glu Leu Ser Ser Leu Thr Ser Glu Asp Ser Ala Val Tyr Tyr Cys
                 85                  90                  95

Val Arg Ala Asn Trp Asp Val Ala Phe Ala Tyr Trp Gly Gln Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 63
<211> LENGTH: 213
<212> TYPE: PRT
<213> ORGANISM: Artificial Sequence
<220> FEATURE:
<223> OTHER INFORMATION: Antibody fragment

<400> SEQUENCE: 63

Asp Ile Gln Met Thr Gln Ser Pro Ser Ser Leu Ser Ala Ser Val Gly
1               5                   10                  15

Gly Lys Val Thr Ile Thr Cys Lys Ala Ser Gln Asp Ile Asp Arg Tyr
            20                  25                  30

Met Ala Trp Tyr Gln Gln Lys Pro Gly Lys Gly Pro Lys Leu Leu Ile
            35                  40                  45

His Asp Thr Ser Thr Leu Gln Pro Gly Val Pro Ser Arg Phe Ser Gly
        50                  55                  60

Ser Gly Ser Gly Arg Asp Tyr Ser Leu Thr Ile Ser Ser Leu Glu Pro
65                  70                  75                  80

Glu Asp Ile Ala Thr Tyr Tyr Cys Leu Gln Tyr Asp Asn Leu Trp Thr
            85                  90                  95

Phe Gly Gly Gly Thr Lys Leu Glu Ile Lys Arg Thr Val Ala Ala Pro
            100                 105                 110
```

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 64
<211> LENGTH: 447
<212> TYPE: PRT
<213> ORGANISM: Homo sapiens

<400> SEQUENCE: 64

Gln Val Gln Leu Val Gln Ser Gly Ala Glu Leu Val Lys Pro Gly Ala
1               5                   10                  15

Ser Val Lys Met Ser Cys Lys Ala Ser Gly Tyr Ile Phe Thr Asn Tyr
            20                  25                  30

Asn Ile His Trp Val Arg Gln Ala Pro Gly Gln Gly Leu Glu Trp Ile
        35                  40                  45

Gly Ala Ile Tyr Pro Gly Asn Gly Asp Ala Pro Tyr Ala Gln Lys Phe
    50                  55                  60

Gln Gly Arg Ala Thr Leu Thr Ala Asp Thr Ser Ser Ser Thr Thr Tyr
65                  70                  75                  80

Met Glu Leu Ser Ser Leu Thr Ser Glu Asp Thr Ala Val Tyr Tyr Cys
                85                  90                  95

Val Arg Ala Asn Trp Asp Val Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
                260               265               270
Glu Val Lys Phe Asn Trp Tyr Val Asp Gly Val Glu Val His Asn Ala
            275               280               285
Lys Thr Lys Pro Arg Glu Glu Gln Tyr Asn Ser Thr Tyr Arg Val Val
        290               295               300
Ser Val Leu Thr Val Leu His Gln Asp Trp Leu Asn Gly Lys Glu Tyr
305               310               315               320
Lys Cys Lys Val Ser Asn Lys Ala Leu Pro Ala Pro Ile Glu Lys Thr
                325               330               335
Ile Ser Lys Ala Lys Gly Gln Pro Arg Glu Pro Gln Val Tyr Thr Leu
            340               345               350
Pro Pro Ser Arg Asp Glu Leu Thr Lys Asn Gln Val Ser Leu Thr Cys
        355               360               365
Leu Val Lys Gly Phe Tyr Pro Ser Asp Ile Ala Val Glu Trp Glu Ser
370               375               380
Asn Gly Gln Pro Glu Asn Asn Tyr Lys Thr Thr Pro Pro Val Leu Asp
385               390               395               400
Ser Asp Gly Ser Phe Phe Leu Tyr Ser Lys Leu Thr Val Asp Lys Ser
                405               410               415
Arg Trp Gln Gln Gly Asn Val Phe Ser Cys Ser Val Met His Glu Ala
            420               425               430
Leu His Asn His Tyr Thr Gln Lys Ser Leu Ser Leu Ser Pro Gly
        435               440               445

<210> SEQ ID NO 65
<211> LENGTH: 213
<212> TYPE: PRT
<213> ORGANISM: Artificial Sequence
<220> FEATURE:
<223> OTHER INFORMATION: Antibody fragment

<400> SEQUENCE: 65

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Ile Asp Arg Tyr
            20                  25                  30
Met Ala Trp Ala Gln Asp Lys Pro Gly Lys Ala Pro Arg Leu Leu Ile
        35                  40                  45
His Asp Thr Ser Thr Leu Gln Ser Gly Val Pro Ser Arg Phe Ser Gly
    50                  55                  60
Ser Gly Ser Gly Arg Asp Tyr Thr Leu Thr Ile Ser Asn Leu Glu Pro
65                  70                  75                  80
Glu Asp Phe Ala Thr Tyr Tyr Cys Leu Gln Tyr Asp Asn Leu Ala Thr
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
```

```
                180             185             190
Cys Glu Val Thr His Gln Gly Leu Ser Ser Pro Val Thr Lys Ser Phe
            195                 200                 205
Asn Arg Gly Glu Cys
    210

<210> SEQ ID NO 66
<211> LENGTH: 447
<212> TYPE: PRT
<213> ORGANISM: Artificial Sequence
<220> FEATURE:
<223> OTHER INFORMATION: Antibody fragment

<400> SEQUENCE: 66

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ile Phe Thr Asn Tyr
            20                  25                  30
Asn Ile His Trp Val Lys Ser Pro Gly Gln Gly Leu Glu Trp Ile
        35                  40                  45
Gly Ala Ile Tyr Pro Gly Asn Gly Asp Ala Pro Tyr Ser Gln Lys Phe
    50                  55                  60
Gln Gly Lys Ala Thr Leu Thr Ala Asp Thr Ser Ser Thr Thr Tyr
65                  70                  75                  80
Met Glu Leu Ser Ser Leu Arg Ser Glu Asp Thr Ala Val Tyr Tyr Cys
                85                  90                  95
Val Arg Ala Asn Ala Asp Val Ala Phe Ala Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
```

```
                    325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
                435                 440                 445

<210> SEQ ID NO 67
<211> LENGTH: 447
<212> TYPE: PRT
<213> ORGANISM: Homo sapiens

<400> SEQUENCE: 67

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ile Phe Thr Asn Tyr
                20                  25                  30
Asn Ile His Trp Val Lys Lys Ser Pro Gly Gln Gly Leu Glu Trp Ile
            35                  40                  45
Gly Ala Ile Tyr Pro Gly Asn Gly Asp Ala Pro Tyr Ser Gln Lys Phe
        50                  55                  60
Gln Gly Lys Ala Thr Leu Thr Ala Asp Thr Ser Thr Ser Thr Thr Tyr
65                  70                  75                  80
Met Glu Leu Ser Ser Leu Arg Ser Glu Asp Thr Ala Val Tyr Tyr Cys
                85                  90                  95
Val Arg Ala Asn Trp Asp Val Ala Phe Ala Tyr Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
```

-continued

Thr Pro Glu Val Thr Cys Val Val Val Ala Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
     290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Arg Asp Glu Leu Thr Lys Asn Gln Val Ser Leu Thr Cys
         355                 360                 365

Leu Val Lys Gly Phe Tyr Pro Ser Asp Ile Ala Val Glu Trp Glu Ser
     370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
             420                 425                 430

Leu His Asn His Tyr Thr Gln Lys Ser Leu Ser Leu Ser Pro Gly
         435                 440                 445

<210> SEQ ID NO 68
<211> LENGTH: 213
<212> TYPE: PRT
<213> ORGANISM: Artificial Sequence
<220> FEATURE:
<223> OTHER INFORMATION: Recombinant Fab LC1

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Arg Tyr
            20                  25                  30

Met Ala Trp Tyr Gln Asp Lys Pro Gly Lys Ala Pro Arg Leu Leu Ile
        35                  40                  45

His Asp Thr Ser Thr Leu Gln Ser Gly Val Pro Ser Arg Phe Ser Gly
    50                  55                  60

Ser Gly Ser Gly Arg Asp Tyr Thr Leu Thr Ile Ser Asn Leu Glu Pro
65                  70                  75                  80

Glu Asp Phe Ala Thr Tyr Tyr Cys Leu Gln Tyr Asp Asn Leu Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210
```

<210> SEQ ID NO 69
<211> LENGTH: 234
<212> TYPE: PRT
<213> ORGANISM: Artificial Sequence
<220> FEATURE:
<223> OTHER INFORMATION: Recombinant Fab HC

<400> SEQUENCE: 69

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asn Tyr
            20                  25                  30

Asn Ile His Trp Val Lys Ser Pro Gly Gln Gly Leu Glu Trp Ile
        35                  40                  45

Gly Ala Ile Tyr Pro Gly Asn Gly Asp Ala Pro Tyr Ser Gln Lys Phe
50                  55                  60

Gln Gly Lys Ala Thr Leu Thr Ala Asp Thr Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Val Arg Ala Asn Trp Asp Val Ala Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Ala Ser His His His His His
225                 230
```

<210> SEQ ID NO 70
<211> LENGTH: 302
<212> TYPE: PRT
<213> ORGANISM: Artificial Sequence
<220> FEATURE:
<223> OTHER INFORMATION: Recombinant TrxA-His-Thr-LAMP1-29-195

<400> SEQUENCE: 70

```
Met Gly Ser Asp Lys Ile Ile His Leu Thr Asp Asp Ser Phe Asp Thr
1               5                   10                  15

Asp Val Leu Lys Ala Asp Gly Ala Ile Leu Val Asp Phe Trp Ala Glu
            20                  25                  30
```

```
Trp Cys Gly Pro Cys Lys Met Ile Ala Pro Ile Leu Asp Glu Ile Ala
        35                  40                  45

Asp Glu Tyr Gln Gly Lys Leu Thr Val Ala Lys Leu Asn Ile Asp Gln
 50                  55                  60

Asn Pro Gly Thr Ala Pro Lys Tyr Gly Ile Arg Gly Ile Pro Thr Leu
 65                  70                  75                  80

Leu Leu Phe Lys Asn Gly Glu Val Ala Ala Thr Lys Val Gly Ala Leu
                 85                  90                  95

Ser Lys Gly Gln Leu Lys Glu Phe Leu Asp Ala Asn Leu Ala Gly Ser
                100                 105                 110

Gly Ser Met Gly Ser Ser His His His His His His Ser Ser Gly Leu
            115                 120                 125

Val Pro Arg Gly Ser His Met Ala Met Phe Met Val Lys Asn Gly Asn
130                 135                 140

Gly Thr Ala Cys Ile Met Ala Asn Phe Ser Ala Ala Phe Ser Val Asn
145                 150                 155                 160

Tyr Asp Thr Lys Ser Gly Pro Lys Asn Met Thr Phe Asp Leu Pro Ser
                165                 170                 175

Asp Ala Thr Val Val Leu Asn Arg Ser Ser Cys Gly Lys Glu Asn Thr
            180                 185                 190

Ser Asp Pro Ser Leu Val Ile Ala Phe Gly Arg Gly His Thr Leu Thr
            195                 200                 205

Leu Asn Phe Thr Arg Asn Ala Thr Arg Tyr Ser Val Gln Leu Met Ser
210                 215                 220

Phe Val Tyr Asn Leu Ser Asp Thr His Leu Phe Pro Asn Ala Ser Ser
225                 230                 235                 240

Lys Glu Ile Lys Thr Val Glu Ser Ile Thr Asp Ile Arg Ala Asp Ile
                245                 250                 255

Asp Lys Lys Tyr Arg Cys Val Ser Gly Thr Gln Val His Met Asn Asn
            260                 265                 270

Val Thr Val Thr Leu His Asp Ala Thr Ile Gln Ala Tyr Leu Ser Asn
            275                 280                 285

Ser Ser Phe Ser Arg Gly Glu Thr Arg Cys Glu Gln Asp Arg
            290                 295                 300

<210> SEQ ID NO 71
<211> LENGTH: 171
<212> TYPE: PRT
<213> ORGANISM: Artificial Sequence
<220> FEATURE:
<223> OTHER INFORMATION: LAMP1-29-195

<400> SEQUENCE: 71

Gly Ser His Met Ala Met Phe Met Val Lys Asn Gly Asn Gly Thr Ala
 1               5                  10                  15

Cys Ile Met Ala Asn Phe Ser Ala Ala Phe Ser Val Asn Tyr Asp Thr
             20                  25                  30

Lys Ser Gly Pro Lys Asn Met Thr Phe Asp Leu Pro Ser Asp Ala Thr
             35                  40                  45

Val Val Leu Asn Arg Ser Ser Cys Gly Lys Glu Asn Thr Ser Asp Pro
 50                  55                  60

Ser Leu Val Ile Ala Phe Gly Arg Gly His Thr Leu Thr Leu Asn Phe
 65                  70                  75                  80

Thr Arg Asn Ala Thr Arg Tyr Ser Val Gln Leu Met Ser Phe Val Tyr
                 85                  90                  95
```

```
Asn Leu Ser Asp Thr His Leu Phe Pro Asn Ala Ser Ser Lys Glu Ile
            100                 105                 110
Lys Thr Val Glu Ser Ile Thr Asp Ile Arg Ala Asp Ile Asp Lys Lys
        115                 120                 125
Tyr Arg Cys Val Ser Gly Thr Gln Val His Met Asn Asn Val Thr Val
    130                 135                 140
Thr Leu His Asp Ala Thr Ile Gln Ala Tyr Leu Ser Asn Ser Ser Phe
145                 150                 155                 160
Ser Arg Gly Glu Thr Arg Cys Glu Gln Asp Arg
                165                 170

<210> SEQ ID NO 72
<211> LENGTH: 10
<212> TYPE: PRT
<213> ORGANISM: Homo sapiens

<400> SEQUENCE: 72

Thr Leu Asn Phe Thr Arg Asn Ala Thr Arg
1               5                   10

<210> SEQ ID NO 73
<211> LENGTH: 14
<212> TYPE: PRT
<213> ORGANISM: Homo sapiens

<400> SEQUENCE: 73

Asp Ile Arg Ala Asp Ile Asp Lys Lys Tyr Arg Cys Val Ser
1               5                   10

<210> SEQ ID NO 74
<211> LENGTH: 15
<212> TYPE: PRT
<213> ORGANISM: Homo sapiens

<400> SEQUENCE: 74

Thr Ile Gln Ala Tyr Leu Ser Asn Ser Ser Phe Ser Arg Gly Glu
1               5                   10                  15

<210> SEQ ID NO 75
<211> LENGTH: 13
<212> TYPE: PRT
<213> ORGANISM: Homo sapiens

<400> SEQUENCE: 75

Ala Met Phe Met Val Lys Asn Gly Asn Gly Thr Ala Cys
1               5                   10

<210> SEQ ID NO 76
<211> LENGTH: 13
<212> TYPE: PRT
<213> ORGANISM: Homo sapiens

<400> SEQUENCE: 76

Pro Ser Asp Ala Thr Val Val Leu Asn Arg Ser Ser Cys
1               5                   10

<210> SEQ ID NO 77
<211> LENGTH: 144
<212> TYPE: PRT
<213> ORGANISM: Homo sapiens

<400> SEQUENCE: 77
```

Ala Met Phe Met Val Lys Asn Gly Asn Gly Thr Ala Cys Ile Met Ala
1               5                   10                  15

Asn Phe Ser Ala Ala Phe Ser Val Asn Tyr Asp Thr Lys Ser Gly Pro
            20                  25                  30

Lys Asn Met Thr Phe Asp Leu Pro Ser Asp Ala Thr Val Val Leu Asn
            35                  40                  45

Arg Ser Ser Cys Gly Lys Glu Asn Thr Ser Asp Pro Ser Leu Val Ile
50                  55                  60

Ala Phe Gly Arg Gly His Thr Leu Ala Met Phe Met Val Lys Asn Gly
65                  70                  75                  80

Asn Gly Thr Ala Cys Ile Met Ala Asn Phe Ser Ala Ala Phe Ser Val
            85                  90                  95

Asn Tyr Asp Thr Lys Ser Gly Pro Lys Asn Met Thr Phe Asp Leu Pro
            100                 105                 110

Ser Asp Ala Thr Val Val Leu Asn Arg Ser Ser Cys Gly Lys Glu Asn
            115                 120                 125

Thr Ser Asp Pro Ser Leu Val Ile Ala Phe Gly Arg Gly His Thr Leu
            130                 135                 140

<210> SEQ ID NO 78
<211> LENGTH: 14
<212> TYPE: PRT
<213> ORGANISM: Homo sapiens

<400> SEQUENCE: 78

Gly His Thr Leu Thr Leu Asn Phe Thr Arg Asn Ala Thr Arg
1               5                   10

<210> SEQ ID NO 79
<211> LENGTH: 17
<212> TYPE: PRT
<213> ORGANISM: Homo sapiens

<400> SEQUENCE: 79

Ala Thr Ile Gln Ala Tyr Leu Ser Asn Ser Ser Phe Ser Arg Gly Glu
1               5                   10                  15

Thr

<210> SEQ ID NO 80
<211> LENGTH: 171
<212> TYPE: PRT
<213> ORGANISM: Homo sapiens

<400> SEQUENCE: 80

Gly Ser His Met Ala Met Phe Met Val Lys Asn Gly Asn Gly Thr Ala
1               5                   10                  15

Cys Ile Met Ala Asn Phe Ser Ala Ala Phe Ser Val Asn Tyr Asp Thr
            20                  25                  30

Lys Ser Gly Pro Lys Asn Met Thr Phe Asp Leu Pro Ser Asp Ala Thr
            35                  40                  45

Val Val Leu Asn Arg Ser Ser Cys Gly Lys Glu Asn Thr Ser Asp Pro
50                  55                  60

Ser Leu Val Ile Ala Phe Gly Arg Gly His Thr Leu Thr Leu Asn Phe
65                  70                  75                  80

Thr Arg Asn Ala Thr Arg Tyr Ser Val Gln Leu Met Ser Phe Val Tyr
            85                  90                  95

Asn Leu Ser Asp Thr His Leu Phe Pro Asn Ala Ser Ser Lys Glu Ile
            100                 105                 110

```
Lys Thr Val Glu Ser Ile Thr Asp Ile Arg Ala Asp Ile Asp Lys Lys
            115                 120                 125

Tyr Arg Cys Val Ser Gly Thr Gln Val His Met Asn Asn Val Thr Val
            130                 135                 140

Thr Leu His Asp Ala Thr Ile Gln Ala Tyr Leu Ser Asn Ser Ser Phe
145                 150                 155                 160

Ser Arg Gly Glu Thr Arg Cys Glu Gln Asp Arg
            165                 170

<210> SEQ ID NO 81
<211> LENGTH: 214
<212> TYPE: PRT
<213> ORGANISM: Artificial Sequence
<220> FEATURE:
<223> OTHER INFORMATION: chimeric

<400> SEQUENCE: 81

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Gly Ile Asn Lys Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
50                  55                  60

Ser Gly Ser Gly Thr Asp Tyr Ser Leu Thr Ile Asn Asn Leu Glu Pro
65                  70                  75                  80

Glu Asp Ile Ala Thr Tyr Tyr Cys Gln Gln Tyr Thr Arg Leu Pro Phe
            85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 82
<211> LENGTH: 16
<212> TYPE: PRT
<213> ORGANISM: Homo sapiens

<400> SEQUENCE: 82

Gln Ala Phe Lys Val Glu Gly Gly Gln Phe Gly Ser Val Glu Glu Cys
1               5                   10                  15

<210> SEQ ID NO 83
<211> LENGTH: 8
```

```
<212> TYPE: PRT
<213> ORGANISM: Mus musculus

<400> SEQUENCE: 83

Gly Tyr Ala Phe Thr Asn Tyr Leu
1               5

<210> SEQ ID NO 84
<211> LENGTH: 8
<212> TYPE: PRT
<213> ORGANISM: Mus musculus

<400> SEQUENCE: 84

Ile Asn Pro Gly Ser Gly Gly Thr
1               5

<210> SEQ ID NO 85
<211> LENGTH: 12
<212> TYPE: PRT
<213> ORGANISM: Mus musculus

<400> SEQUENCE: 85

Ala Arg Tyr Arg Ser Tyr Asp Trp Tyr Phe Asp Val
1               5                   10

<210> SEQ ID NO 86
<211> LENGTH: 6
<212> TYPE: PRT
<213> ORGANISM: Mus musculus

<400> SEQUENCE: 86

Gly Asn Ile His Asn Tyr
1               5

<210> SEQ ID NO 87
<211> LENGTH: 9
<212> TYPE: PRT
<213> ORGANISM: Mus musculus

<400> SEQUENCE: 87

Gln His Phe Trp Ser Asn Pro Tyr Thr
1               5

<210> SEQ ID NO 88
<211> LENGTH: 119
<212> TYPE: PRT
<213> ORGANISM: Mus musculus

<400> SEQUENCE: 88

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Tyr Arg Ser Tyr Asp Trp Tyr Phe Asp Val Trp Gly Ala Gly
```

Thr Thr Val Thr Val Ser Ser
            115

<210> SEQ ID NO 89
<211> LENGTH: 107
<212> TYPE: PRT
<213> ORGANISM: Mus musculus

<400> SEQUENCE: 89

Asp Ile Gln Met Thr Gln Ser Pro Ala Ser Leu Ser Ala Ser Val Gly
1               5                   10                  15

Glu Thr Val Thr Ile Thr Cys Arg Val Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Asn Pro Tyr
                85                  90                  95

Thr Phe Gly Gly Gly Thr Lys Leu Glu Ile Lys
            100                 105

<210> SEQ ID NO 90
<211> LENGTH: 15
<212> TYPE: PRT
<213> ORGANISM: Homo sapiens

<400> SEQUENCE: 90

Ser Ala Ala Phe Ser Val Asn Tyr Asp Thr Lys Ser Gly Pro Lys
1               5                   10                  15

<210> SEQ ID NO 91
<211> LENGTH: 16
<212> TYPE: PRT
<213> ORGANISM: Homo sapiens

<400> SEQUENCE: 91

Glu Ser Ile Thr Asp Ile Arg Ala Asp Ile Asp Lys Lys Tyr Arg Cys
1               5                   10                  15

<210> SEQ ID NO 92
<211> LENGTH: 15
<212> TYPE: PRT
<213> ORGANISM: Homo sapiens

<400> SEQUENCE: 92

Asn Thr Ile Leu Pro Asp Ala Arg Asp Pro Ala Phe Lys Ala Ala
1               5                   10                  15

<210> SEQ ID NO 93
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(2)
<223> OTHER INFORMATION: Xaa is any amino acid
<220> FEATURE:

```
<221> NAME/KEY: MISC_FEATURE
<222> LOCATION: (3)..(3)
<223> OTHER INFORMATION: Xaa is I, L or V

<400> SEQUENCE: 93

Xaa Xaa Xaa Asp Arg Tyr
1               5

<210> SEQ ID NO 94
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (4)..(6)
<223> OTHER INFORMATION: Xaa is any amino acid

<400> SEQUENCE: 94

Leu Gln Tyr Xaa Xaa Xaa Trp Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Y or F.
<220> FEATURE:
<221> NAME/KEY: MISC_FEATURE
<222> LOCATION: (5)..(5)
<223> OTHER INFORMATION: Xaa is any amino acid

<400> SEQUENCE: 95

Xaa Xaa Ile Phe Xaa Asn Tyr Asn
1               5

<210> SEQ ID NO 96
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (6)..(8)
<223> OTHER INFORMATION: Xaa is any amino acid

<400> SEQUENCE: 96

Val Arg Ala Asn Trp Xaa Xaa Xaa Phe Ala Tyr
1               5                   10

<210> SEQ ID NO 97
<211> LENGTH: 50
<212> TYPE: PRT
<213> ORGANISM: Homo sapiens

<400> SEQUENCE: 97

Asn Gly Asn Gly Thr Ala Cys Ile Met Ala Asn Phe Ser Ala Ala Phe
1               5                   10                  15
```

-continued

```
Ser Val Asn Tyr Asp Thr Lys Ser Gly Pro Lys Asn Met Thr Phe Asp
         20                  25                  30

Leu Pro Ser Asp Ala Thr Val Val Leu Asn Arg Ser Ser Cys Gly Lys
         35                  40                  45

Glu Asn
    50

<210> SEQ ID NO 98
<211> LENGTH: 443
<212> TYPE: PRT
<213> ORGANISM: Mus musculus

<400> SEQUENCE: 98

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Tyr Arg Ser Tyr Asp Trp Tyr Phe Asp Val Trp Gly Ala Gly
            100                 105                 110

Thr Thr Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335
```

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 99
<211> LENGTH: 214
<212> TYPE: PRT
<213> ORGANISM: Mus musculus

<400> SEQUENCE: 99

Asp Ile Gln Met Thr Gln Ser Pro Ala Ser Leu Ser Ala Ser Val Gly
1               5                   10                  15

Glu Thr Val Thr Ile Thr Cys Arg Val Ser Gly Asn Ile His Asn Tyr
            20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Asn Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
            210